United States Patent
Nuss et al.

(10) Patent No.: US 8,642,640 B2
(45) Date of Patent: Feb. 4, 2014

(54) 1-PHENYLPYRROLE DERIVATIVES

(75) Inventors: John Nuss, Danville, CA (US); Matthew Williams, San Mateo, CA (US); Raju Mohan, Encinitas, CA (US); Richard Martin, San Diego, CA (US); Tie-Lin Wang, San Diego, CA (US); Hiroyuki Tsuruoka, Tokyo (JP); Kazumasa Aoki, Tokyo (JP); Masatoshi Honzumi, Tokyo (JP); Yusuke Asoh, Tokyo (JP); Keiji Saito, Tokyo (JP); Tsuyoshi Homma, Tokyo (JP)

(73) Assignees: Exelixis, Inc., South San Francisco, CA (US); Daiichi Sankyo Company, Limited, Tokyo (JP)

( * ) Notice: Subject to any disclaimer, the term of this patent is extended or adjusted under 35 U.S.C. 154(b) by 269 days.

(21) Appl. No.: 13/122,239

(22) PCT Filed: Oct. 7, 2009

(86) PCT No.: PCT/US2009/059852
§ 371 (c)(1),
(2), (4) Date: Jul. 15, 2011

(87) PCT Pub. No.: WO2010/042626
PCT Pub. Date: Apr. 15, 2010

(65) Prior Publication Data
US 2011/0263544 A1     Oct. 27, 2011

Related U.S. Application Data

(60) Provisional application No. 61/103,804, filed on Oct. 8, 2008.

(51) Int. Cl.
*A61K 31/40*     (2006.01)
*C07D 207/08*    (2006.01)

(52) U.S. Cl.
USPC .......................................... 514/423; 548/561

(58) Field of Classification Search
None
See application file for complete search history.

(56) References Cited

FOREIGN PATENT DOCUMENTS

WO     2006/012642 A2     2/2006
WO     2008/126831 A1     10/2008

OTHER PUBLICATIONS

Hörig et al., J. Translational Med. 2:44 (2004).*
Millller, A., Vascular Health and Risk Management, 3:605 (2007).*
Eliel, E L. et al., "Stereochemistry of Organic Compounds", John Wiley & Sons, Inc., 1994, pp. 1142-1148, XP002558914.

* cited by examiner

*Primary Examiner* — Michael Barker
(74) *Attorney, Agent, or Firm* — McDonnell Boehnen Hulbert & Berghoff LLP

(57)     ABSTRACT

The present invention comprises a compound for the prevention and/or treatment of cardiovascular diseases, nephropathy, fibrosis, primary aldosteronism or edema. The compound is of the following general formula (I): wherein $R^1$ represents a C1-C3 alkyl group; $R^2$ represents a hydroxy-C1-C4 alkyl group and the like; $R^3$ represents a halogeno group, a halogeno-C1-C3 alkyl group and the like; $R^4$ represents a hydrogen atom, a halogeno group and the like, —$R^5$ represents a sulfamoyl group or a C1-C3 alkylsulfonyl group; $R^6$ represents a hydrogen atom, a halogeno group and the like] or an N-oxide, atropisomer of the foregoing, or pharmaceutically acceptable salt of the foregoing.

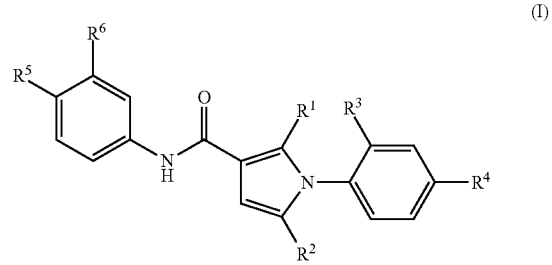

27 Claims, No Drawings

1-PHENYLPYRROLE DERIVATIVES

CROSS-REFERENCE TO RELATED APPLICATIONS

This application is a US national phase of International Application No. PCT/US2009/059852 filed on Oct. 7, 2009, which claims the benefit of U.S. Provisional Application No. 61/103,804 filed on Oct. 8, 2008, the disclosures of which are incorporated herein by reference in their entirety.

BACKGROUND OF THE INVENTION

1. Field of the Invention

The present invention relates to 1-phenylpyrrole compounds, to atropisomers thereof, and to such compounds as preventive or therapeutic drugs and their uses for the prevention or treatment of hypertension, angina pectoris, acute coronary syndrome, congestive heart failure, nephropathy, including diabetic nephropathy, arteriosclerosis, cerebral infarction, fibrosis, primary aldosteronism and edema, which compounds have exceptional mineralocorticoid receptor antagonist activity.

2. Summary of the Related Art

Mineralocorticoid receptor (MR) (aldosterone receptor) is known to play an important role in controlling electrolyte balance in the body and blood pressure (for example, Advances in Physiology Education, 26 (1): 8-20 (2002)), and mineralocorticoid receptor antagonist such as spironolactone and eplerenone having a steroid structure is known to be useful for treating hypertension and heart failure (for example, Clinical Science and molecular medicine. 3 (Suppl), 329s-332s (1976); and Clinical Science and molecular medicine. 45 (Suppl 1), 219s-224s (1973)).

Hypertension is not only a primary cause of the development of cardiovascular, cardiac and renal diseases, but a risk factor for the progression of these diseases initiated by other mechanisms such as atherosclerosis, cardiovascular disease, ischemic heart disease, diabetes, diabetic nephropathy, chronic glomerulonephritis and polycystic kidney disease (J. Am. Soc. Nephrol., 14:2395-2401 (2003)).

In renal failure, as with the case of chronic heart failure, a number of clinical trials have established that interruption of the RAAS cascade with ACE inhibitors is beneficial in limiting renal disease (Am. J. Kid. Dis., 37 (4): 677-688 (2001). Additional studies have also established that aldosterone antagonists can attenuate proteinuria and renal damage typically observed in progressive renal disease and offer further therapeutic benefit compared to ACE inhibitors alone (Hypertension., 31:451-458 (1998)).

However, spironolactone has low selectivity for MR, and side effects such as menstrual irregularity in women and gynecomastia in men are reported (e.g., Circulation, 107, 2512-2518 (2003)). In contrast, since eplerenone has relatively weak effect against MR (for example, Nature Reviews, 2, 177-178 (2003)) and thus induces hyperkalemia, it is not suitable for patients having renal failure.

Here, as a mineralocorticoid receptor antagonist having a non-steroidal skeleton, pyrrole derivatives described in pamphlet of International Publication No. WO 2006/012642 have been known; however, atropisomers of a compound represented by the general formula (I) of the present invention have not been known.

SUMMARY OF THE INVENTION

As a result of conducting extensive studies on various 1-phenylpyrrole compounds for the intension to develop a superior preventive drug or a therapeutic drug for cardiovascular disease, the present inventors have found that there are atropisomers of the compound represented by the general formula (I), and that one of them in particular is extremely effective in sustention of mineralocorticoid receptor antagonistic action (both in vitro and in vivo) and drug efficacy. Furthermore, it was found that it has good solubility, oral absorbability, blood concentration, metabolic stability and safety and the like, and it is useful as a medicament, preferably as a preventive drug or a therapeutic drug (especially a therapeutic drug) for diseases such as hypertension, angina pectoris, acute coronary syndrome, congestive heart failure, nephropathy, including diabetic nephropathy, arteriosclerosis, cerebral infarction, fibrosis, primary aldosteronism, heart disease or edema, more preferably for congestive heart failure, nephropathy, including diabetic nephropathy, hypertension and the like, particularly preferably for hypertension, and particularly preferably for diabetic nephropathy, thereby completing the invention.

DETAILED DESCRIPTION OF THE INVENTION

The present invention provides compounds represented by the general formula (I) (including an atropisomer thereof), pharmaceutical composition comprising it (e.g., and a medicament as a preventive or therapeutic drug (especially a therapeutic drug)), and their uses for prevention or treatment of hypertension, angina pectoris, acute coronary syndrome, congestive heart failure, nephropathy, including diabetic nephropathy, arteriosclerosis, cerebral infarction, fibrosis, primary aldosteronism or heart disease (more preferably for congestive heart failure, nephropathy, including diabetic nephropathy, and hypertension; particularly preferably for hypertension). The compounds of the invention have excellent mineralocorticoid receptor antagonist activity. Preferred compounds/compositions comprise the atropisomer of the compound of the invention having superior mineralocorticoid receptor antagonist activity compared to the other atropisomer(s) of that structure.

The present invention comprises, (1): a compound represented by the following general formula (I):

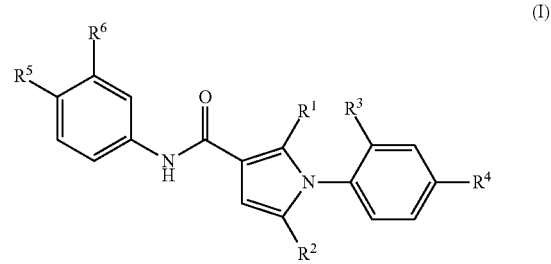

an N-oxide thereof; diastereomer, compound enriched in a diastereomer, or racemate thereof; an atropisomer, compound enriched in an atropisomer, or an equal mixture of atropisomers; or a pharmaceutically acceptable salt of the foregoing, wherein, $R^1$ represents a C1-C3 alkyl group;

$R^2$ represents a hydroxy-C1-C4 alkyl group, a fluoro-C1-C4 alkyl group, a carbamoyl-C1-C2 alkyl group, a N-mono (C1-C3 alkyl)carbamoyl-C1-C2 alkyl group or a N,N-di(C1-C3 alkyl)carbamoyl-C1-C2 alkyl group;

R³ represents a halogeno group, a C1-C3 alkyl group, a C1-C3 alkoxy group, a halogeno-C1-C3 alkyl group, a halogeno-C1-C3 alkoxy group, a 4-halogenophenyl group or a 4-halogenophenoxy group;

R⁴ represents a hydrogen atom, a halogeno group or a C1-C3 alkyl group;

R⁵ represents a sulfamoyl group or a C1-C3 alkylsulfonyl group;

R⁶ represents a hydrogen atom, a halogeno group, a C1-C3 alkyl group or a C1-C3 alkoxy group], or atropisomers thereof.

In addition, the present invention comprises, (2): the compound according to the aforementioned (1), wherein R¹ is a methyl group or an ethyl group;

(3): the compound according to the aforementioned (1), wherein R¹ is a methyl group;

(4): the compound according to any one of the aforementioned (1) through (3), wherein R² is a 2-hydroxyethyl group, a 2-hydroxypropyl group, a 2-fluoropropyl group or a 2-fluoroethyl group;

(5): the compound according to any one of the aforementioned (1) through (3), wherein R² is a 2-hydroxypropyl group;

(6): the compound according to any one of the aforementioned (1) through (5), wherein R³ is a methyl group, a chlorine atom, a halogenomethyl group or a halogenomethoxy group;

(7): the compound according to any one of the aforementioned (1) through (5), wherein R³ is a methyl group, a chlorine atom, a difluoromethyl group, a trifluoromethyl group, a difluoromethoxy group or a trifluoromethoxy group;

(8): the compound according to any one of the aforementioned (1) through (5), wherein R³ is a trifluoromethyl group, a difluoromethoxy group or a trifluoromethoxy group;

(9): the compound according to any one of the aforementioned (1) through (8), wherein R⁴ is a halogeno group;

(10): the compound according to any one of the aforementioned (1) through (8), wherein R⁴ is a fluorine atom;

(11): the compound according to any one of the aforementioned (1) through (10), wherein R⁵ is a sulfamoyl group or a methylsulfonyl group;

(12): the compound according to any one of the aforementioned (1) through (10), wherein R⁵ is a methylsulfonyl group;

(13): the compound according to any one of the aforementioned (1) through (12), wherein R⁶ is a hydrogen atom, a chlorine atom or a methyl group; and (14): the compound according to any one of the aforementioned (1) through (12), wherein R⁶ is a hydrogen atom.

Furthermore, the present invention comprises (15): the following compounds:

1-[4-chloro-2-(trifluoromethyl)phenyl]-5-(2-hydroxyethyl)-2-methyl-N-[4-(methylsulfonyl)phenyl]-1H-pyrrole-3-carboxamide;

1-[4-fluoro-2-(trifluoromethyl)phenyl]-5-[(2S)-2-hydroxypropyl]-2-methyl-N-[4-(methylsulfonyl)phenyl]-1H-pyrrole-3-carboxamide;

1-[4-chloro-2-(trifluoromethyl)phenyl]-5-[(2S)-2-hydroxypropyl]-2-methyl-N-[4-(methylsulfonyl)phenyl]-1H-pyrrole-3-carboxamide;

1-(4-fluoro-2-methylphenyl)-5-[(2S)-2-hydroxypropyl]-2-methyl-N-[4-(methylsulfonyl)phenyl]-1H-pyrrole-3-carboxamide;

1-[2-(difluoromethoxy)-4-fluorophenyl]-5-[(2S)-2-hydroxypropyl]-2-methyl-N-[4-(methylsulfonyl)phenyl]-1H-pyrrole-3-carboxamide;

N-[4-(aminosulfonyl)-3-methylphenyl]-1-[4-fluoro-2-(trifluoromethyl)phenyl]-5-[(2S)-2-hydroxypropyl]-2-methyl-1H-pyrrole-3-carboxamide;

1-[4-chloro-2-(difluoromethoxy)phenyl]-5-[(2S)-2-hydroxypropyl]-2-methyl-N-[4-(methylsulfonyl)phenyl]-1H-pyrrole-3-carboxamide;

N-[4-(aminosulfonyl)-3-chlorophenyl]-1-[4-fluoro-2-(trifluoromethyl)phenyl]-5-[(2S)-2-hydroxypropyl]-2-methyl-1H-pyrrole-3-carboxamide;

1-[4-fluoro-2-(trifluoromethoxy)phenyl]-5-[(2S)-2-hydroxypropyl]-2-methyl-N-[4-(methylsulfonyl)phenyl]-1H-pyrrole-3-carboxamide;

1-[2-(difluoromethoxy)-4-fluorophenyl]-5-[(2S)-2-hydroxypropyl]-2-methyl-N-[3-methyl-4-(methylsulfonyl)phenyl]-1H-pyrrole-3-carboxamide;

1-[2-(difluoromethyl)-4-fluorophenyl]-5-[(2S)-2-hydroxypropyl]-2-methyl-N-[4-(methylsulfonyl)phenyl]-1H-pyrrole-3-carboxamide;

1-(4-fluoro-2-methylphenyl)-5-[(2S)-2-hydroxypropyl]-2-methyl-N-[3-methyl-4-(methylsulfonyl)phenyl]-1H-pyrrole-3-carboxamide;

1-[2-(difluoromethoxy)-4-fluorophenyl]-2-ethyl-5-[(2S)-2-hydroxypropyl]-N-[4-(methylsulfonyl)phenyl]-1H-pyrrole-3-carboxamide;

1-(2-chloro-4-fluorophenyl)-5-[(2S)-2-hydroxypropyl]-2-methyl-N-[4-(methylsulfonyl)phenyl]-1H-pyrrole-3-carboxamide;

1-(4-chloro-2-methylphenyl)-5-[(2S)-2-hydroxypropyl]-2-methyl-N-[4-(methylsulfonyl)phenyl]-1H-pyrrole-3-carboxamide;

1-[4-chloro-2-(trifluoromethoxy)phenyl]-5-[(2S)-2-hydroxypropyl]-2-methyl-N-[4-(methylsulfonyl)phenyl]-1H-pyrrole-3-carboxamide;

1-(2,4-dichlorophenyl)-5-[(2S)-2-hydroxypropyl]-2-methyl-N-[4-(methylsulfonyl)phenyl]-1H-pyrrole-3-carboxamide;

1-(2-chloro-4-fluorophenyl)-2-ethyl-5-[(2S)-2-hydroxypropyl]-N-[4-(methylsulfonyl)phenyl]-1H-pyrrole-3-carboxamide;

1-(2,4-dichlorophenyl)-2-ethyl-5-[(2S)-2-hydroxypropyl]-N-[4-(methylsulfonyl)phenyl]-1H-pyrrole-3-carboxamide;

1-(4-chloro-2-methylphenyl)-5-(2-fluoroethyl)-2-methyl-N-[4-(methylsulfonyl)phenyl]-1H-pyrrole-3-carboxamide;

5-(2-fluoroethyl)-1-(4-fluoro-2-methylphenyl)-2-methyl-N-[4-(methylsulfonyl)phenyl]-1H-pyrrole-3-carboxamide;

1-[2-(difluoromethoxy)-4-fluorophenyl]-5-(2-fluoroethyl)-2-methyl-N-[4-(methylsulfonyl)phenyl]-1H-pyrrole-3-carboxamide;

1-[4-chloro-2-(trifluoromethyl)phenyl]-5-[(2R)-2-fluoropropyl]-2-methyl-N-[4-(methylsulfonyl)phenyl]-1H-pyrrole-3-carboxamide;

1-[4-chloro-2-(difluoromethoxy)phenyl]-5-[(2R)-2-fluoropropyl]-2-methyl-N-[4-(methylsulfonyl)phenyl]-1H-pyrrole-3-carboxamide;

and 1-[4-chloro-2-(trifluoromethyl)phenyl]-5-[2-(dimethylamino)-2-oxoethyl]-2-methyl-N-[4-(methylsulfonyl)phenyl]-1H-pyrrole-3-carboxamide;

N-oxides thereof; diastereomers, racemates, and compounds enriched in a diastereomer thereof; atropisomers, equal mixtures of atropisomers, and compounds enriched in an atropisomer thereof; and pharmaceutically acceptable salts of any of the foregoing.

In addition, the present invention comprises (16): the following compounds:

1-[4-fluoro-2-(trifluoromethyl)phenyl]-5-[(2S)-2-hydroxypropyl]-2-methyl-N-[4-(methylsulfonyl)phenyl]-1H-pyrrole-3-carboxamide;

1-[4-chloro-2-(trifluoromethyl)phenyl]-5-[(2S)-2-hydroxypropyl]-2-methyl-N-[4-(methylsulfonyl)phenyl]-1H-pyrrole-3-carboxamide;

1-[2-(difluoromethoxy)-4-fluorophenyl]-5-[(2S)-2-hydroxypropyl]-2-methyl-N-[4-(methylsulfonyl)phenyl]-1H-pyrrole-3-carboxamide;

1-[4-chloro-2-(difluoromethoxy)phenyl]-5-[(2S)-2-hydroxypropyl]-2-methyl-N-[4-(methylsulfonyl)phenyl]-1H-pyrrole-3-carboxamide;

1-[4-fluoro-2-(trifluoromethoxy)phenyl]-5-[(2S)-2-hydroxypropyl]-2-methyl-N-[4-(methylsulfonyl)phenyl]-1H-pyrrole-3-carboxamide;

1-[2-(difluoromethyl)-4-fluorophenyl]-5-[(2S)-2-hydroxypropyl]-2-methyl-N-[4-(methylsulfonyl)phenyl]-1H-pyrrole-3-carboxamide;

1-(2-chloro-4-fluorophenyl)-5-[(2S)-2-hydroxypropyl]-2-methyl-N-[4-(methylsulfonyl)phenyl]-1H-pyrrole-3-carboxamide;

1-[4-chloro-2-(trifluoromethoxy)phenyl]-5-[(2S)-2-hydroxypropyl]-2-methyl-N-[4-(methylsulfonyl)phenyl]-1H-pyrrole-3-carboxamide;

and 1-(2,4-dichlorophenyl)-5-[(2S)-2-hydroxypropyl]-2-methyl-N-[4-(methylsulfonyl)phenyl]-1H-pyrrole-3-carboxamide;

and N-oxides; diastereomers, racemates, and compounds enriched in a diastereomer, and racemates thereof; atropisomers, compounds enriched in an atropisomer, and equal mixtures of atropisomers thereof; and pharmaceutically acceptable salts of any of the foregoing.

Further, the present invention comprises (17): the atropisomers of the compound according to any one of the aforementioned (1) through (16) having a greater mineralocorticoid receptor antagonistic activity than the other atropisomer of the compound.

In addition, the present invention comprises (18): a medicament comprising the compound according to any one of the aforementioned (1) through (17) as an active ingredient;

(19): a preventive drug or a therapeutic drug for a cardiovascular disease, comprising the compound according to any one of the aforementioned (1) through (17) as an active ingredient;

(20): a preventive drug or a therapeutic drug for hypertension, angina pectoris, acute coronary syndrome, congestive heart failure, nephropathy, including diabetic nephropathy, arteriosclerosis, cerebral infarction, fibrosis, primary aldosteronism or edema, comprising the compound according to any one of the aforementioned (1) through (17) as an active ingredient;

(21): a preventive drug or a therapeutic drug for nephropathy, comprising the compound according to any one of the aforementioned (1) through (17) as an active ingredient;

(22): a preventive drug or a therapeutic drug for hypertension, comprising the compound according to any one of the aforementioned (1) through (17) as an active ingredient; and (23): a preventive drug or a therapeutic drug for diabetic nephropathy, comprising the atropisomer according to any one of the aforementioned (1) through (17) as an active ingredient.

Furthermore, the present invention comprises (24): a pharmaceutical composition comprising the compound according to any one of the aforementioned (1) through (17) and a pharmacologically/pharmaceutically acceptable carrier.

Because one of the atropisomers of the 1-phenylpyrrole compounds of the present invention shows stronger mineralocorticoid receptor antagonistic activity than the other, it is useful as a preventive drug or a therapeutic drug (especially a therapeutic drug) for diseases such as hypertension, angina pectoris, acute coronary syndrome, congestive heart failure, nephropathy, including diabetic nephropathy, arteriosclerosis, cerebral infarction, fibrosis, primary aldosteronism, heart disease or edema, more preferably for congestive heart failure, nephropathy, including diabetic nephropathy, hypertension and the like, particularly preferably for hypertension, and particularly preferably diabetic nephropathy.

The atropisomers of the compound represented by the general formula (I) of the present invention have excellent mineralocorticoid receptor antagonistic activity, show high oral absorbability, plasma concentration levels, and long half-life in the blood, and have excellent pharmacological properties. In addition, the atropisomers of the compound represented by general formula (I) of the present invention have superior internal pharmacokinetic properties, such as body distribution, retention in blood and the like, and low toxicity in organs such as the kidney and liver. Furthermore, the atropisomers of the compound represented by the general formula (I) of the present invention are extremely stable; for example, no racemization was observed after letting it stand in methanol at room temperature for 7 days, and in acetonitrile-phthalic acid buffer at 60° C. for 4 hours.

Therefore, the atropisomers of the compound represented by the general formula (I) of the present invention are, for example, useful as a medicament, particularly as a medicament to prevent or treat various cardiovascular diseases (preferably hypertension, angina pectoris, acute coronary syndrome, congestive heart failure, nephropathy, including diabetic nephropathy, arteriosclerosis, cerebral infarction, fibrosis, primary aldosteronism, heart disease or edema).

DEFINITIONS (1) A "halogeno group" is a fluoro group, a chloro group or a bromo group, and preferably a fluoro group or a chloro group.

(2) A "C1-C4 alkyl group" is a linear or branched alkyl group having 1 to 4 carbon atoms such as a methyl group, an ethyl group, a n-propyl group, an isopropyl group, a n-butyl group, an isobutyl group and a tert-butyl group, preferably a methyl group and an ethyl group, and particularly preferably a methyl group.

(3) A "C1-C3 alkoxy group" is a C1-C3 alkyloxy group structured from the "C1-C3 alkyl group", and represents for example, a linear or branched alkoxy group having 1 to 3 carbon atoms such as a methoxy group, an ethoxy group, a n-propoxy group and an isopropoxy group, and preferably represents a methoxy group.

(4) A "hydroxy C1-C4 alkyl group" is a group in which the aforementioned "C1-C4 alkyl group" is substituted with one hydroxy group, including, for example, a 2-hydroxyethyl group, a 2-hydroxy-1-methylethyl group, a 2-hydroxypropyl group, a 3-hydroxypropyl group and a 3-hydroxybutyl group, preferably a 2-hydroxyethyl group and a 2-hydroxypropyl group, and more preferably a 2-hydroxypropyl group.

(5) A "halogeno-C1-C3 alkyl group" is a group in which the aforementioned "C1-C3 alkyl group" is substituted with 1 to 5 of the same or different halogeno groups, including, for example, a fluoromethyl group, a difluoromethyl group, a trifluoromethyl group, a chlorodifluoromethyl group, a 2-fluoroethyl group, a 2-fluoro-1-methylethyl group, a 2,2,2-trifluoroethyl group, a pentafluoroethyl group and a 3-fluoropropyl group, preferably a difluoromethyl group, a trifluoromethyl group, a 2-fluoroethyl group, a 2-fluoropropyl group and a 2-fluoro-1-methylethyl group and the like.

(6) A "halogeno-C1-C3 alkoxy group" is a group in which the aforementioned "C1-C3 alkoxy group" is substituted with 1 to 5 of the same or different halogeno groups, including for example, a fluoromethoxy group, a difluoromethoxy group, a trifluoromethoxy group, a 2-fluoroethoxy group, a 1,1-difluoroethoxy group, a pentafluoroethoxy group and a 3-fluoropropoxy group, preferably a difluoromethoxy group, a trifluoromethoxy group and the like.

(7) A "carbamoyl-C1-C2 alkyl group" is a group in which a methyl group or an ethyl group is substituted with one carbamoyl group, including, for example, a carbamoylmethyl group, a 2-carbamoylethyl group and a 1-carbamoylethyl group, preferably a carbamoylmethyl group.

(8) A "N-mono(C1-C3 alkyl)carbamoyl-C1-C2 alkyl group" is a group in which the nitrogen atom of the carbamoyl group of the aforementioned "carbamoyl-C1-C2 alkyl group" is substituted with one C1-C3 alkyl group, including, for example, a (N-methylcarbamoyl)methyl group and a (N-ethylcarbamoyl)methyl group.

(9) A "N,N-di(C1-C3 alkyl)carbamoyl-C1-C2 alkyl group" is a group in which the nitrogen atom of the carbamoyl group of the aforementioned "carbamoyl-C1-C2 alkyl group" is substituted with two of the same or different C1-C3 alkyl groups, including, for example, a (N,N-dimethylcarbamolyl)methyl group and a (N-ethyl-N-methylcarbamoyl)methyl group.

Hereinafter, the present invention will be explained in greater detail.

$R^1$, $R^2$, $R^3$, $R^4$, $R^5$ and $R^6$ in the general formula (I) will be explained.

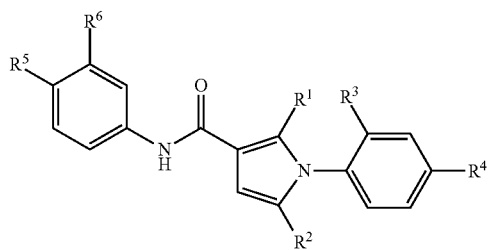

(I)

$R^1$ in the general formula (I) represents:
(a) C1-C3 alkyl;
(b) methyl or ethyl; or
(c) methyl.

$R^2$ in the general formula (I) represents:
(a) hydroxy-C1-C4 alkyl, fluoro-C1-C4 alkyl, carbamoyl-C1-C2 alkyl, N-mono(C1-C3 alkyl)carbamoyl-C1-C2 alkyl or N,N-di(C1-C3 alkyl)carbamoyl-C1-C2 alkyl;
(b) hydroxy-C1-C4 alkyl or fluoro-C1-C4 alkyl group;
(c) 2-hydroxyethyl or 2-hydroxypropyl;
(d) 2-hydroxypropyl; or
(e) 2-fluoroethyl or 2-fluoropropyl.

$R^3$ in the general formula (I) represents:
(a) halogeno, C1-C3 alkyl, C1-C3 alkoxy, halogeno-C1-C3 alkyl, halogeno-C1-C3 alkoxy, halogeno-C1-C3 alkyl, halogeno-C1-C3 alkoxy, 4-halogenophenyl, or 4-halogenophenoxy;

(b) as the halogeno group, a chloro group is preferable; as the C1-C3 alkyl group, a methyl group is preferable; as the C1-C3 alkoxy group, a methoxy group is preferable; as the halogeno-C1-C3 alkyl group, difluoromethyl, and trifluoromethyl groups are preferable; as the halogeno-C1-C3 alkoxy group, difluoromethoxy and trifluoromethoxy groups are preferable; as the 4-halogenophenyl group, 4-fluorophenyl, and 4-chlorophenyl groups are preferable; or and as the 4-halogenophenoxy group, a 4-fluorophenoxy group is preferable;

(b) chloro, methyl, difluoromethyl, trifluoromethyl, difluoromethoxy, or trifluoromethoxy; or (c) difluoromethyl, trifluoromethyl, difluoromethoxy, or trifluoromethoxy.

$R^4$ in the general formula (I) represents:
(a) hydrogen, halogeno, or C1-C3 alkyl;
(b) halogeno; or
(c) fluoro.

$R^5$ in the general formula (I) represents:
(a) sulfamoyl or C1-C3 alkyl sulfonyl;
(b) sulfamoyl or methylsulfonyl; or
(c) methylsulfonyl.

$R^6$ in the general formula (I) represents:
(a) hydrogen, halogeno, C1-C3 alkyl, or C1-C3 alkoxy;
(b) hydrogen, chloro, or methyl; or
(c) a hydrogen atom.

All combinations of definitions of each of the forgoing substituents are contemplated.

Preferable compounds represented by the general formula (I), include, (a) racemic mixtures, diastereomers, and compounds enriched in a diastereomer, (b) atropisomers, equal mixtures of atropisomers, and compounds enriched in an atropisomer (preferably the atropisomer having stronger mineralocorticoid receptor antagonist activity than the other atropisomer), and (c) pharmaceutically acceptable salts of any of the foregoing, of one of the following:

1-[4-chloro-2-(trifluoromethyl)phenyl]-5-(2-hydroxyethyl)-2-methyl-N-[4-(methylsulfonyl)phenyl]-1H-pyrrole-3-carboxamide;

1-[4-fluoro-2-(trifluoromethyl)phenyl]-5-[(2S)-2-hydroxypropyl]-2-methyl-N-[4-(methylsulfonyl)phenyl]-1H-pyrrole-3-carboxamide;

1-[4-chloro-2-(trifluoromethyl)phenyl]-5-[(2S)-2-hydroxypropyl]-2-methyl-N-[4-(methylsulfonyl)phenyl]-1H-pyrrole-3-carboxamide;

1-(4-fluoro-2-methylphenyl)-5-[(2S)-2-hydroxypropyl]-2-methyl-N-[4-(methylsulfonyl)phenyl]-1H-pyrrole-3-carboxamide;

1-[2-(difluoromethoxy)-4-fluorophenyl]-5-[(2S)-2-hydroxypropyl]-2-methyl-N-[4-(methylsulfonyl)phenyl]-1H-pyrrole-3-carboxamide;

N-[4-(aminosulfonyl)-3-methylphenyl]-1-[4-fluoro-2-(trifluoromethyl)phenyl]-5-[(2S)-2-hydroxypropyl]-2-methyl-1H-pyrrole-3-carboxamide;

1-[4-chloro-2-(difluoromethoxy)phenyl]-5-[(2S)-2-hydroxypropyl]-2-methyl-N-[4-(methylsulfonyl)phenyl]-1H-pyrrole-3-carboxamide;

N-[4-(aminosulfonyl)-3-chlorophenyl]-1-[4-fluoro-2-(trifluoromethyl)phenyl]-5-[(2S)-2-hydroxypropyl]-2-methyl-1H-pyrrole-3-carboxamide;

1-[4-fluoro-2-(trifluoromethoxy)phenyl]-5-[(2S)-2-hydroxypropyl]-2-methyl-N-[4-(methylsulfonyl)phenyl]-1H-pyrrole-3-carboxamide;

1-[2-(difluoromethoxy)-4-fluorophenyl]-5-[(2S)-2-hydroxypropyl]-2-methyl-N-[3-methyl-4-(methylsulfonyl)phenyl]-1H-pyrrole-3-carboxamide;

1-[2-(difluoromethyl)-4-fluorophenyl]-5-[(2S)-2-hydroxypropyl]-2-methyl-N-[4-(methylsulfonyl)phenyl]-1H-pyrrole-3-carboxamide;

1-(4-fluoro-2-methylphenyl)-5-[(2S)-2-hydroxypropyl]-2-methyl-N-[3-methyl-4-(methylsulfonyl)phenyl]-1H-pyrrole-3-carboxamide;

1-[2-(difluoromethoxy)-4-fluorophenyl]-2-ethyl-5-[(2S)-2-hydroxypropyl]-N-[4-(methylsulfonyl)phenyl]-1H-pyrrole-3-carboxamide;

1-(2-chloro-4-fluorophenyl)-5-[(2S)-2-hydroxypropyl]-2-methyl-N-[4-(methylsulfonyl)phenyl]-1H-pyrrole-3-carboxamide;

1-(4-chloro-2-methylphenyl)-5-[(2S)-2-hydroxypropyl]-2-methyl-N-[4-(methylsulfonyl)phenyl]-1H-pyrrole-3-carboxamide;

1-[4-chloro-2-(trifluoromethoxy)phenyl]-5-[(2S)-2-hydroxypropyl]-2-methyl-N-[4-(methylsulfonyl)phenyl]-1H-pyrrole-3-carboxamide;

1-(2,4-dichlorophenyl)-5-[(2S)-2-hydroxypropyl]-2-methyl-N-[4-(methylsulfonyl)phenyl]-1H-pyrrole-3-carboxamide;

1-(2-chloro-4-fluorophenyl)-2-ethyl-5-[(2S)-2-hydroxypropyl]-N-[4-(methylsulfonyl)phenyl]-1H-pyrrole-3-carboxamide;

1-(2,4-dichlorophenyl)-2-ethyl-5-[(2S)-2-hydroxypropyl]-N-[4-(methylsulfonyl)phenyl]-1H-pyrrole-3-carboxamide;

1-(4-chloro-2-methylphenyl)-5-(2-fluoroethyl)-2-methyl-N-[4-(methylsulfonyl)phenyl]-1H-pyrrole-3-carboxamide;

5-(2-fluoroethyl)-1-(4-fluoro-2-methylphenyl)-2-methyl-N-[4-(methylsulfonyl)phenyl]-1H-pyrrole-3-carboxamide;

1-[2-(difluoromethoxy)-4-fluorophenyl]-5-(2-fluoroethyl)-2-methyl-N-[4-(methylsulfonyl)phenyl]-1H-pyrrole-3-carboxamide;

1-[4-chloro-2-(trifluoromethyl)phenyl]-5-[(2R)-2-fluoropropyl]-2-methyl-N-[4-(methylsulfonyl)phenyl]-1H-pyrrole-3-carboxamide;

1-[4-chloro-2-(difluoromethoxy)phenyl]-5-[(2R)-2-fluoropropyl]-2-methyl-N-[4-(methylsulfonyl)phenyl]-1H-pyrrole-3-carboxamide;

1-[4-chloro-2-(trifluoromethyl)phenyl]-5-[2-(dimethylamino)-2-oxoethyl]-2-methyl-N-[4-(methylsulfonyl)phenyl]-1H-pyrrole-3-carboxamide;

an N-oxide thereof, or a pharmaceutically acceptable salt of any of the foregoing.

Preferable compounds represented by the general formula (I) include (a) racemic mixtures, diastereomers, and compounds enriched in a diastereomer, (b) atropisomers, equal mixtures of atropisomers, and compounds enriched in an atropisomer (preferably the atropisomer having stronger mineralocorticoid receptor antagonist activity than the other atropisomer), and (c) pharmaceutically acceptable salts of any of the foregoing, of one of the following (Table 1):

TABLE 1

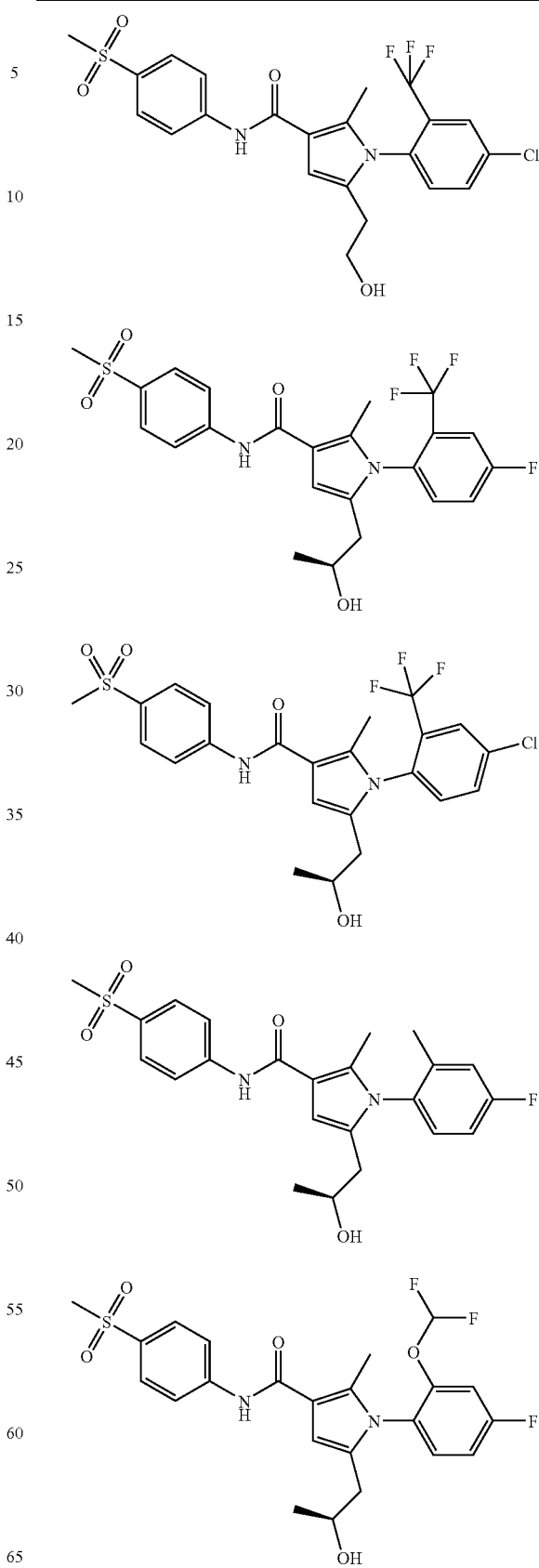

TABLE 1-continued
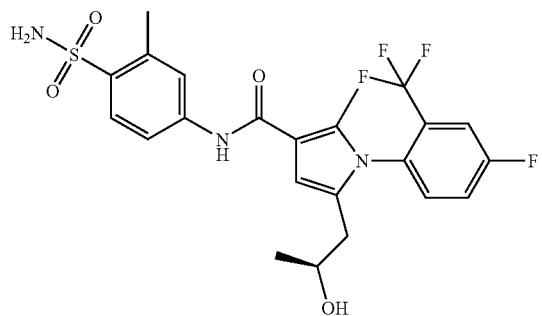 [SMILES: Cc1cc(NC(=O)c2cc(C[C@H](C)O)n(-c3ccc(F)cc3C(F)(F)F)c2C)ccc1S(N)(=O)=O]
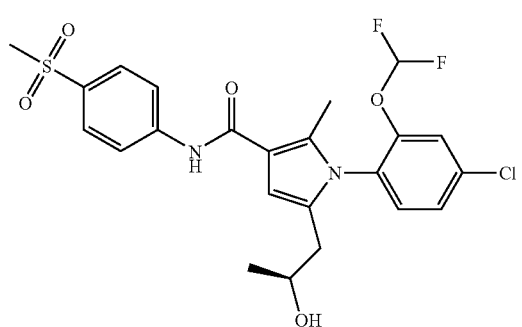 [SMILES: Cc1c(C(=O)Nc2ccc(S(C)(=O)=O)cc2)cc(C[C@H](C)O)n1-c1ccc(Cl)cc1OC(F)F]
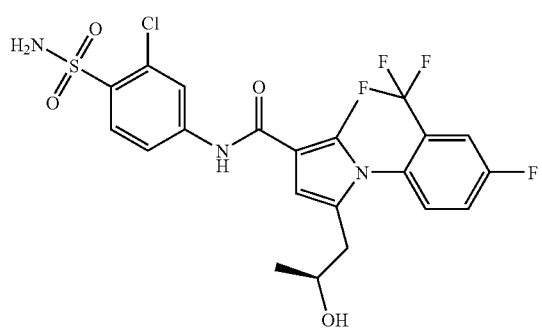 [SMILES: Cc1c(C(=O)Nc2ccc(S(N)(=O)=O)c(Cl)c2)cc(C[C@H](C)O)n1-c1ccc(F)cc1C(F)(F)F]
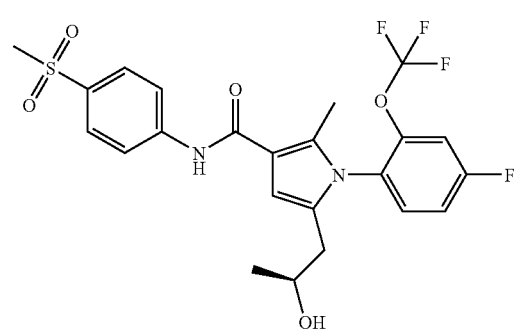 [SMILES: Cc1c(C(=O)Nc2ccc(S(C)(=O)=O)cc2)cc(C[C@H](C)O)n1-c1ccc(F)cc1OC(F)(F)F]
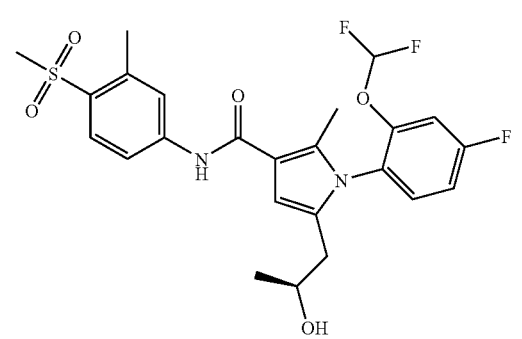 [SMILES: Cc1cc(NC(=O)c2cc(C[C@H](C)O)n(-c3ccc(F)cc3OC(F)F)c2C)ccc1S(C)(=O)=O]
TABLE 1-continued
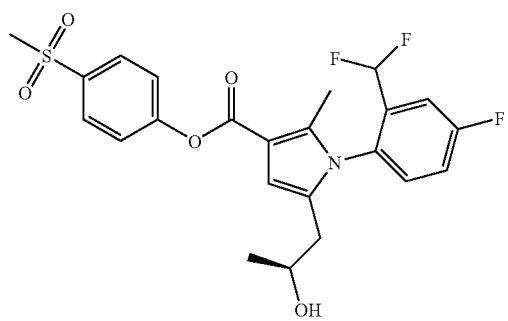 [SMILES: Cc1c(C(=O)Oc2ccc(S(C)(=O)=O)cc2)cc(C[C@H](C)O)n1-c1ccc(F)cc1C(F)F]
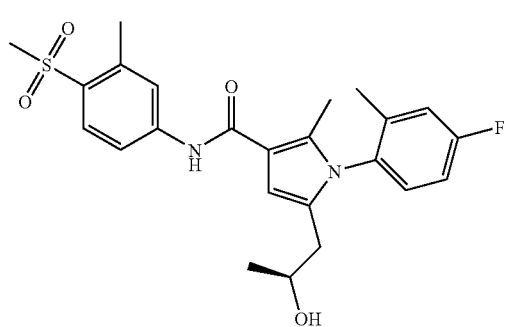 [SMILES: Cc1cc(F)ccc1-n1c(C[C@H](C)O)cc(C(=O)Nc2ccc(S(C)(=O)=O)c(C)c2)c1C]
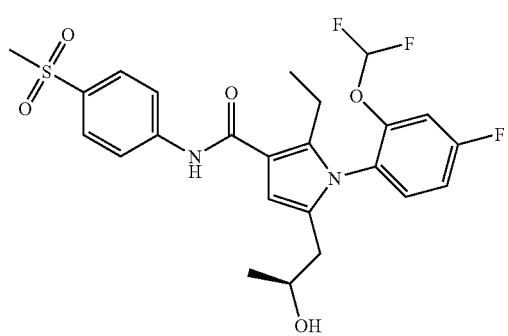 [SMILES: CCc1c(C(=O)Nc2ccc(S(C)(=O)=O)cc2)cc(C[C@H](C)O)n1-c1ccc(F)cc1OC(F)F]
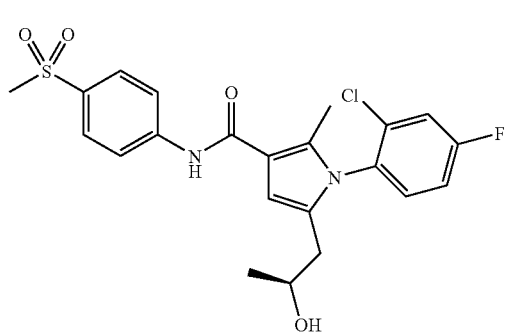 [SMILES: Cc1c(C(=O)Nc2ccc(S(C)(=O)=O)cc2)cc(C[C@H](C)O)n1-c1ccc(F)cc1Cl]
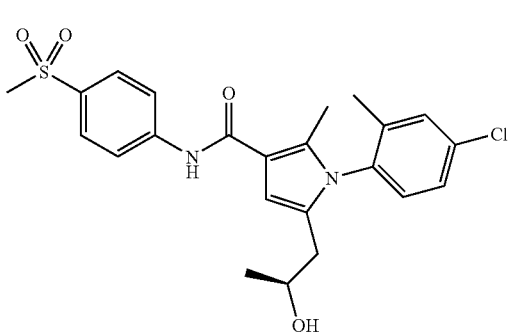 [SMILES: Cc1cc(Cl)ccc1-n1c(C[C@H](C)O)cc(C(=O)Nc2ccc(S(C)(=O)=O)cc2)c1C]

TABLE 1-continued
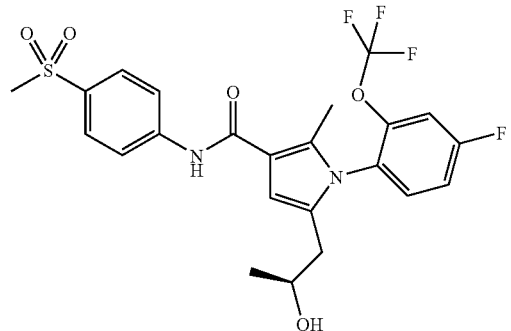 [SMILES: Cc1c(C(=O)Nc2ccc(S(C)(=O)=O)cc2)cc(C[C@H](C)O)n1-c1ccc(F)cc1OC(F)(F)F]
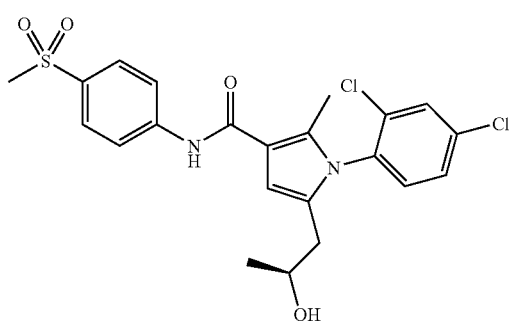 [SMILES: Cc1c(C(=O)Nc2ccc(S(C)(=O)=O)cc2)cc(C[C@H](C)O)n1-c1ccc(Cl)cc1Cl]
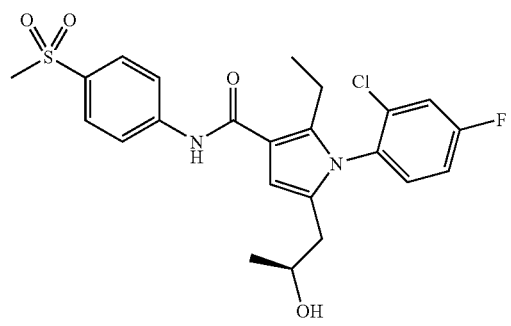 [SMILES: CCc1c(C(=O)Nc2ccc(S(C)(=O)=O)cc2)cc(C[C@H](C)O)n1-c1ccc(F)cc1Cl]
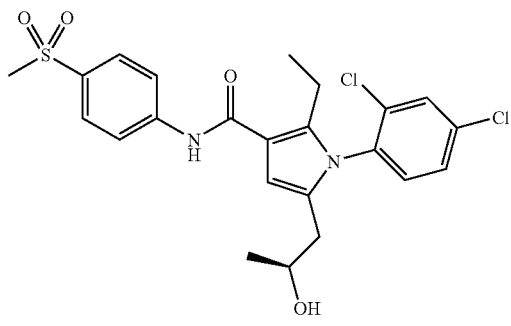 [SMILES: CCc1c(C(=O)Nc2ccc(S(C)(=O)=O)cc2)cc(C[C@H](C)O)n1-c1ccc(Cl)cc1Cl]
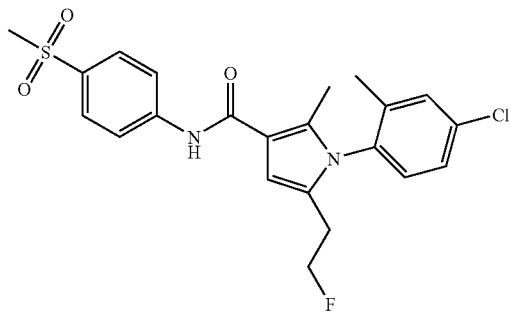 [SMILES: Cc1cc(Cl)ccc1-n1c(CCF)cc(C(=O)Nc2ccc(S(C)(=O)=O)cc2)c1C]
TABLE 1-continued
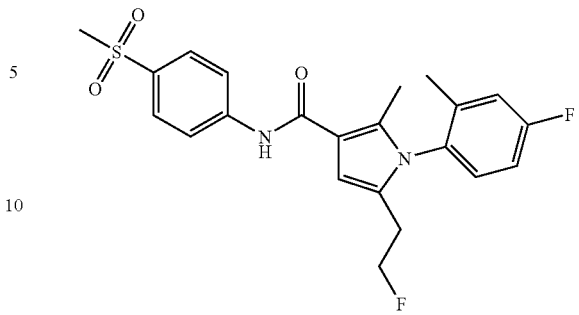
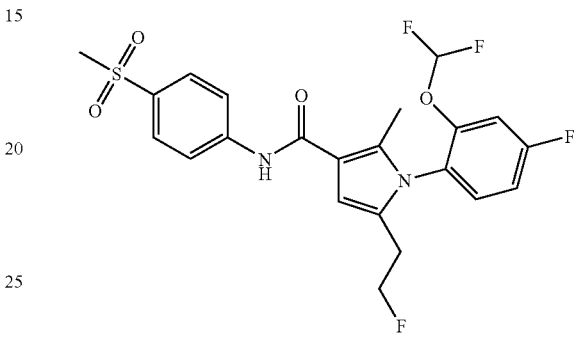
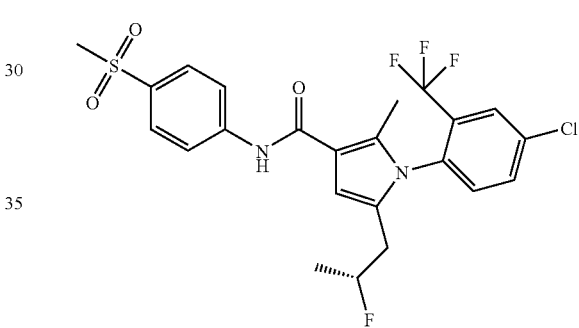
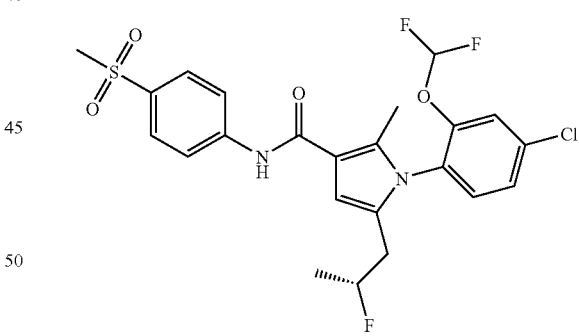
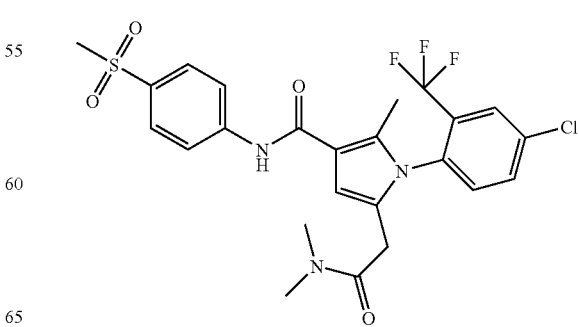

an N-oxide thereof, or a pharmaceutically acceptable salt of any of the foregoing.

Preferable compounds represented by the general formula (I) include (a) racemic mixtures, diastereomers, and compounds enriched in a diastereomer, (b) atropisomers, equal mixtures of atropisomers, and compounds enriched in an atropisomer (preferably the atropisomer having stronger mineralocorticoid receptor antagonist activity than the other atropisomer), and (c) pharmaceutically acceptable salts of any of the foregoing, of one of the following of the following compounds:

1-[4-fluoro-2-(trifluoromethyl)phenyl]-5-[(2S)-2-hydroxypropyl]-2-methyl-N-[4-(methylsulfonyl)phenyl]-1H-pyrrole-3-carboxamide;

1-[4-chloro-2-(trifluoromethyl)phenyl]-5-[(2S)-2-hydroxypropyl]-2-methyl-N-[4-(methylsulfonyl)phenyl]-1H-pyrrole-3-carboxamide;

1-[2-(difluoromethoxy)-4-fluorophenyl]-5-[(2S)-2-hydroxypropyl]-2-methyl-N-[4-(methylsulfonyl)phenyl]-1H-pyrrole-3-carboxamide;

1-[4-chloro-2-(difluoromethoxy)phenyl]-5-[(2S)-2-hydroxypropyl]-2-methyl-N-[4-(methylsulfonyl)phenyl]-1H-pyrrole-3-carboxamide;

1-[4-fluoro-2-(trifluoromethoxy)phenyl]-5-[(2S)-2-hydroxypropyl]-2-methyl-N-[4-(methylsulfonyl)phenyl]-1H-pyrrole-3-carboxamide;

1-[2-(difluoromethyl)-4-fluorophenyl]-5-[(2S)-2-hydroxypropyl]-2-methyl-N-[4-(methylsulfonyl)phenyl]-1H-pyrrole-3-carboxamide;

1-(2-chloro-4-fluorophenyl)-5-[(2S)-2-hydroxypropyl]-2-methyl-N-[4-(methylsulfonyl)phenyl]-1H-pyrrole-3-carboxamide;

1-[4-chloro-2-(trifluoromethoxy)phenyl]-5-[(2S)-2-hydroxypropyl]-2-methyl-N-[4-(methylsulfonyl)phenyl]-1H-pyrrole-3-carboxamide;

1-(2,4-dichlorophenyl)-5-[(2S)-2-hydroxypropyl]-2-methyl-N-[4-(methylsulfonyl)phenyl]-1H-pyrrole-3-carboxamide;

an N-oxide thereof, or a pharmaceutically acceptable salt of any of the foregoing.

Preferable compounds represented by the general formula (I) include (a) racemic mixtures, diastereomers, and compounds enriched in a diastereomer, (b) atropisomers, equal mixtures of atropisomers, and compounds enriched in an atropisomer (preferably the atropisomer having stronger mineralocorticoid receptor antagonist activity than the other atropisomer), and (c) pharmaceutically acceptable salts of any of the foregoing, of one of the following (Table 2):

TABLE 2

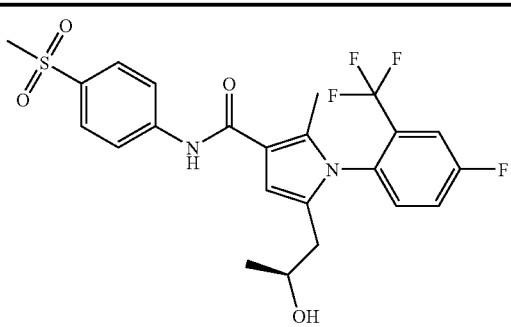

TABLE 2-continued

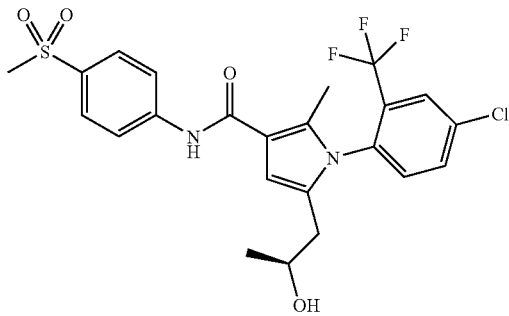 [SMILES: Cc1c(C(=O)Nc2ccc(S(C)(=O)=O)cc2)cc(C[C@H](C)O)n1-c1ccc(Cl)cc1C(F)(F)F]

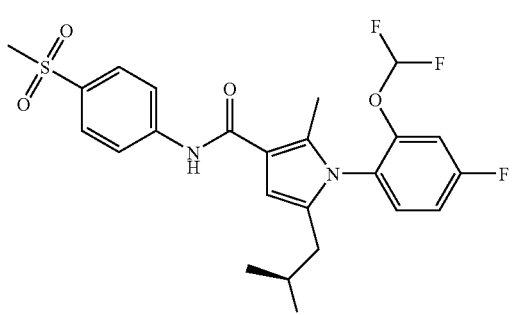

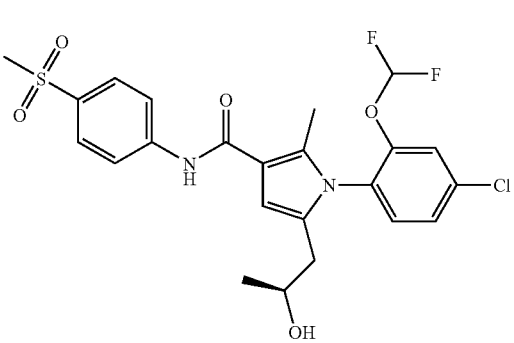 [SMILES: Cc1c(C(=O)Nc2ccc(S(C)(=O)=O)cc2)cc(C[C@H](C)O)n1-c1ccc(Cl)cc1OC(F)F]

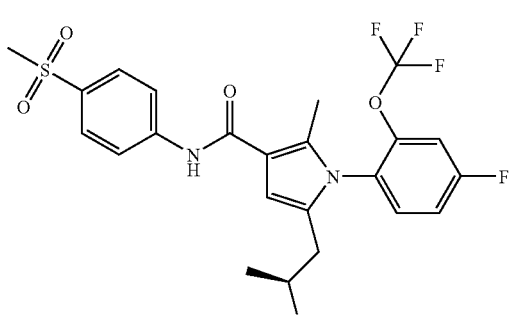

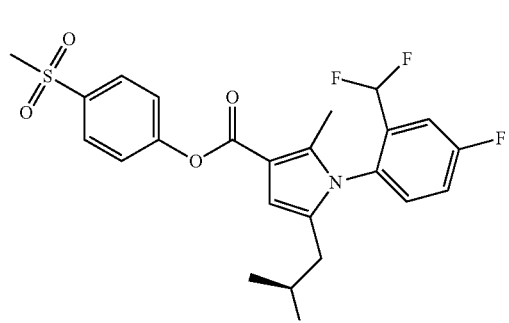

TABLE 2-continued

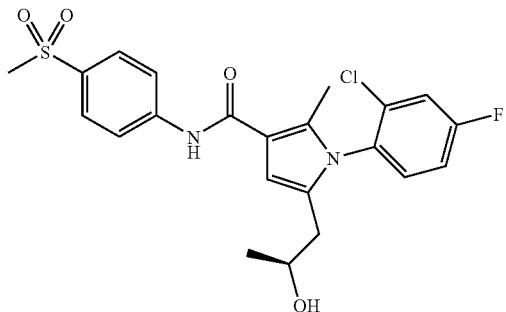 [SMILES: Cc1c(C(=O)Nc2ccc(S(C)(=O)=O)cc2)cc(C[C@H](C)O)n1-c1ccc(F)cc1Cl]

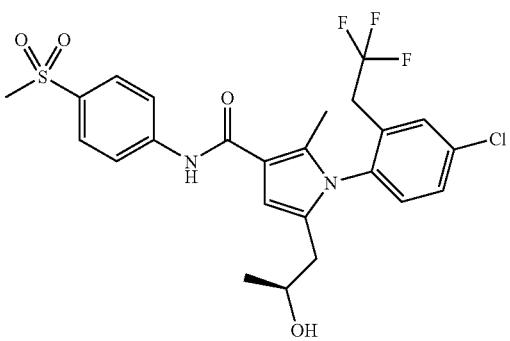 [SMILES: Cc1c(C(=O)Nc2ccc(S(C)(=O)=O)cc2)cc(C[C@H](C)O)n1-c1ccc(Cl)cc1CC(F)(F)F]

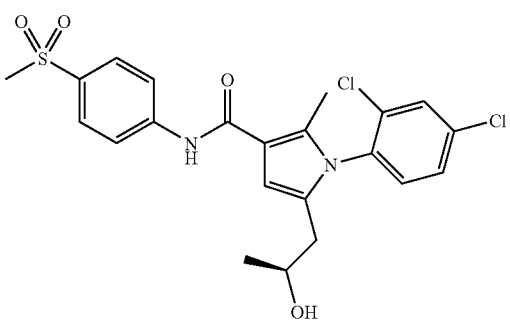

an N-oxide thereof, or a pharmaceutically acceptable salt of any of the foregoing.

Here, "congestive heart failure" in the present specification includes "chronic cardiac failure" and "CHF (chronic heart failure)".

Specific examples of "fibrosis" in the present specification, include endocardial fibrosis, vascular fibrosis, kidney fibrosis and hepatic fibrosis.

"Heart disease" in the present specification means ischemic heart disease, heart failure, heart systolic dysfunction, cardiac dilatation dysfunction, myocardial necrosis, pulmonary venous congestion, atrial fibrillation, myocardial infarction, myocardial fibrosis and chronic heart failure.

"Renal disease" or "kidney disease" or "nephropathy" in the present specification include diabetic nephropathy, chronic glomerulonephritis, polycystic kidney, non-diabetic nephropathy and chronic renal disease.

Hereinafter, the production process for the compound represented by the formula (I) of the present invention will be explained.

The compound of formula (I) of the present invention can be produced by the method shown in the following [Scheme 1].

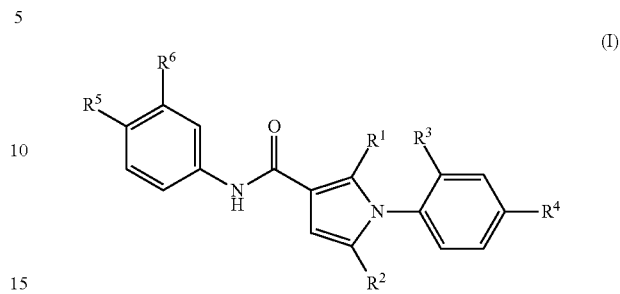

The compound of formula (I) can be produced by preparing a pyrrole carboxylic acid ester derivative (3) by a cyclization reaction of a diketone derivative (1) and an aniline derivative or a salt thereof, and then condensing the pyrrole carboxylic acid ester derivative (3) with an aniline derivative (4). During such production, in a case where the compound has isomers stemming from an asymmetric atom, axial asymmetry and the like, (I-isomer), which is a single isomer, can be obtained by carrying out an optical resolution as necessary.

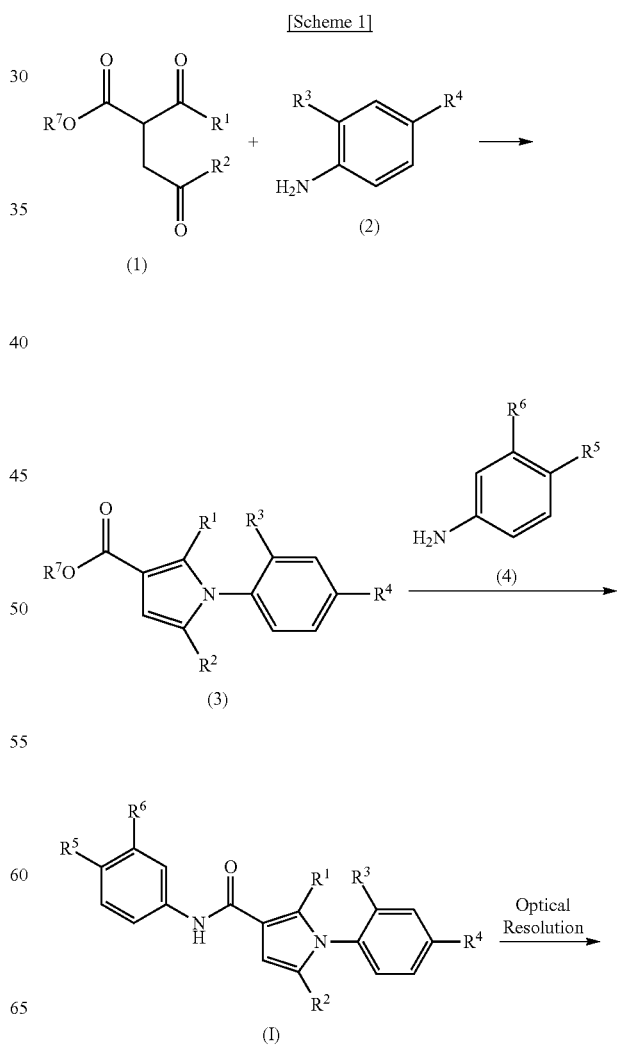

-continued

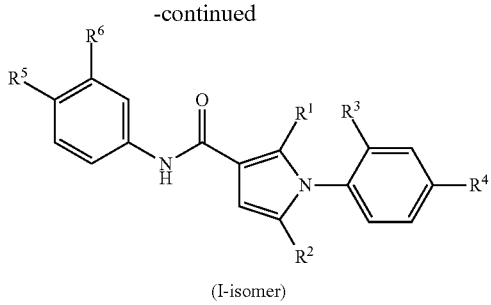
(I-isomer)

(Here, $R^7$ represents a C1-C4 alkyl group or an aryl group; and $R^1$, $R^2$, $R^3$, $R^4$, $R^5$ and $R^6$ represent the same as described above.)

In the cyclization reaction of the diketone derivative (1) and the aniline derivative (2) or a salt thereof, a cyclization method carried out under an acidic condition such as the one described in a patent document (WO 2006/012642) can be used. As an acid catalyst, inorganic acids such as hydrochloric acid, sulfuric acid, sodium bisulfate and the like, and organic acids such as acetic acid, tosyl acid and camphorsulfonic acid can be used. Further, Lewis acids such as scandium (III) triflate and tin (II) chloride that are described in the method of Chen, J. et al [Tetrahedron Lett., 47, 5358-5387 (2006)] can also be used. Preferably, it is acetic acid, tosyl acid or scandium (III) triflate. With respect to the reaction solvent, the reaction can also be carried out in the absence of a solvent, while halogenohydrocarbon solvents such as methylene chloride, hydrocarbon solvents such as toluene, ether solvents such as tetrahydrofuran, or polar solvents such as N,N-dimethylformamide and the like can be used. Preferably, it is carried out in the absence of a solvent or in toluene and the like. As the reaction temperature, it is in the range of 0° C. to boiling point of the solvent, preferably room temperature to boiling point of the solvent. As the reaction time, it is usually from about 0.5 to about 24 hours.

[Scheme 1A]

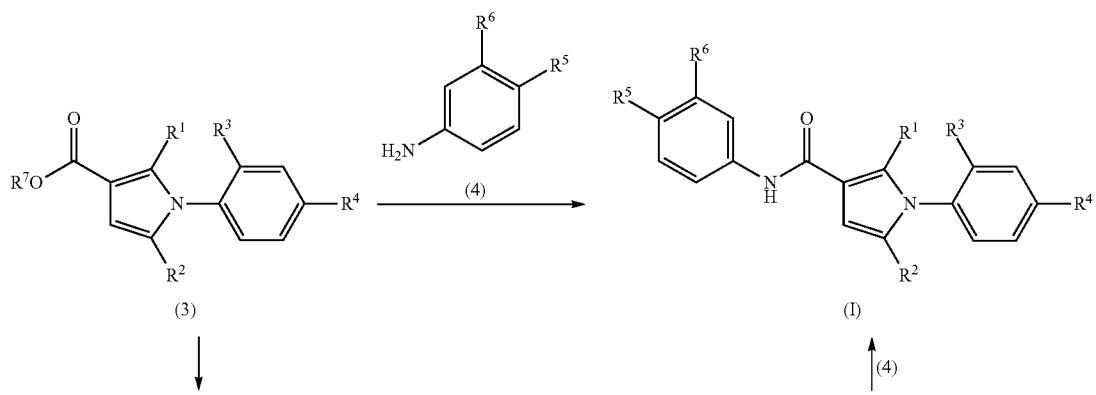

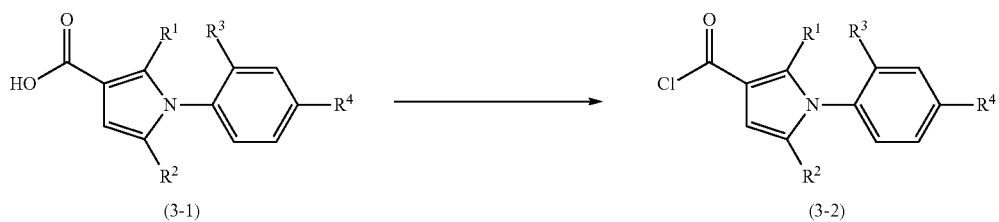

(Here, $R^1$, $R^2$, $R^3$, $R^4$, $R^5$, $R^6$ and $R^7$ represent the same as described above.)

In the production of compound of formula (I), the method described in Patent Document (WO 2006/012642) can be used as the amide formation reaction of the pyrrolecarboxylic acid ester derivative (3) with the aniline derivative (4).

That is, when producing the compound of formula (I) directly by an ester-amide exchange reaction from the pyrrolecarboxylic acid ester derivative (3) and the aniline derivative (4) as in [Scheme 1A], trialkyl aluminum, n-butyl lithium, potassium t-butoxide and the like can be used as the reagent, and trimethyl aluminum can be mentioned preferably. As a solvent for reaction, hydrocarbon solvents such as toluene, benzene and hexane, ether solvents such as tetrahydrofuran, or polar solvents such as N,N-dimethylformamide and the like can be used. Preferably, toluene and tetrahydrofuran can be mentioned. As the reaction temperature, it is in the range of 0° C. to boiling point of the solvent, preferably in the range of room temperature to boiling point of the solvent. As the reaction time, it is usually from about 0.5 to about 24 hours.

In addition, the compound of the formula (I) can be produced by converting a pyrrolecarboxylic acid (3-1), which is obtained from alkaline hydrolysis treatment of the pyrrolecarboxylic acid ester derivative (3), to an acid chloride (3-2), and then carrying out a condensation reaction of the acid chloride (3-2) with the aniline (4). As the method for converting the pyrrolecarboxylic acid (3-1) to the acid chloride (3-2), a known production process may be used. As a condensation agent, the one described in a patent document (WO 2006/012642) may be used. As a solvent for the condensation reaction, halogenohydrocarbon solvents such as methylene chloride, hydrocarbon solvents such as toluene, and ether solvents such as tetrahydrofuran are preferable. As the reaction temperature, it is in the range of −20° C. to the boiling point of the solvent, and is preferably in the range of room temperature to the boiling point of the solvent. In the condensation reaction, organic bases such as triethylamine can be used. The reaction time is usually from about 2 to about 24 hours.

The compound of the formula (I) has two atropisomers that stem from axial asymmetry which arises from restriction of the rotation of the bond connecting the phenyl group having a $R^3$ group as a substituent and the substituted pyrrole ring, due to steric hindrance. Regarding a method for optical resolution of the atropisomers, direct resolution can be conducted by high performance liquid chromatography using a chiral column. As the chiral column, there can be mentioned for example, CHIRALPAK AD-H, AS-H, CHIRALCEL OJ-RH (DAICEL), etc.

Hereinafter, a production process for a diketone derivative (1), an aniline derivative (2), and a pyrrole carboxylic acid ester derivative (3) and their intermediates, which are the compounds used in [Scheme 1], will be described.

The diketone (1) used in [Scheme 1] can be produced by the following method.

[Scheme 2]

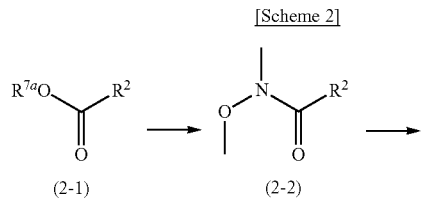

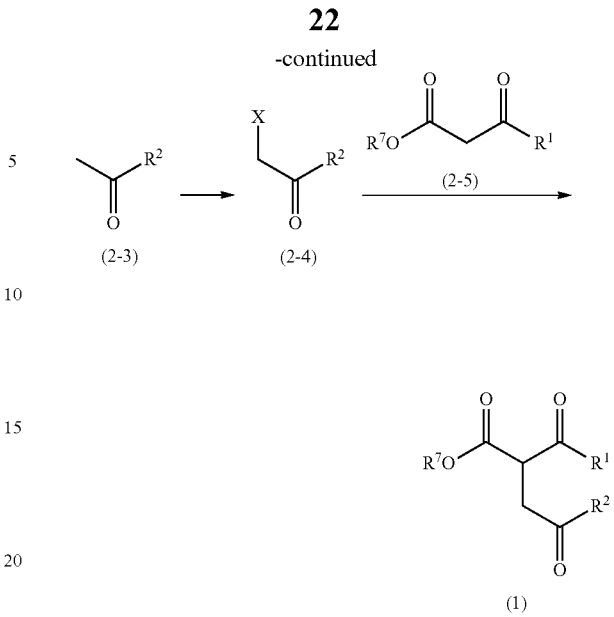

(Here, $R^7$ and $R^{7a}$ are the same or different from each other, and represent a C1-C4 alkyl group or an aryl group; X represents a halogeno group; $R^1$ and $R^2$ represent the same as described above.)

Diketone (1) can be produced from an ester (2-1), by preparing a N-methoxyamide (2-2) by the method of Weinreb et. al [Tetrahedron Lett., 22, 3815 (1981), J., Am. Chem. Soc., 112, 2998 (1990), J. Org. Chem., 56, 2911 (1991)], followed by reaction with Grignard reagent, alkyl lithium and the like to give a methylketone (2-3), continued with preparation of a halogenomethylketone (2-4) by a halogenating agent, and then carrying out an alkylation reaction of the halogenomethylketone (2-4) and a β-ketoester (2-5). As the halogenating agent, N-bromosuccinimide, N-chlorosuccinimide, bromine, chlorine and the like can be used, and bromine is preferable. As a reaction solvent for the aforementioned alkylation reaction, alcohol solvents such as ethanol and methanol, ether solvents such as tetrahydrofuran, or polar solvents such as N,N-dimethylformamide can be used, and ethanol and methanol are preferable. In addition, with respect to the present alkylation reaction, it is preferable to carry it out in the presence of a base, and preferable as a base are sodium ethoxide, sodium methoxide, and sodium hydride.

The aniline derivative (2) used in [Scheme 1] is a commercialized product, or can be produced by each of the routes shown in the following [Scheme 3].

[Scheme 3]

(Route 3A)

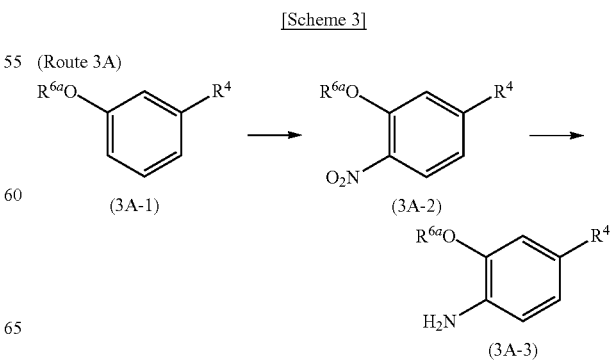

(Route 3B)

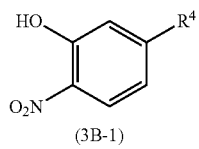
(3B-1)

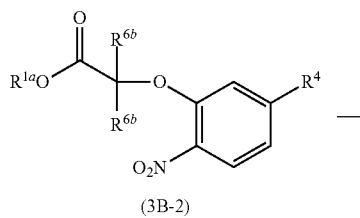
(3B-2)

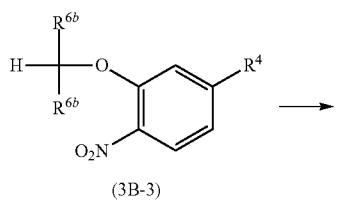
(3B-3)

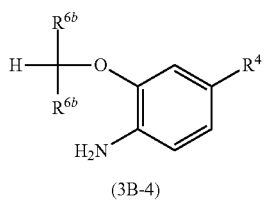
(3B-4)

(Route 3C)

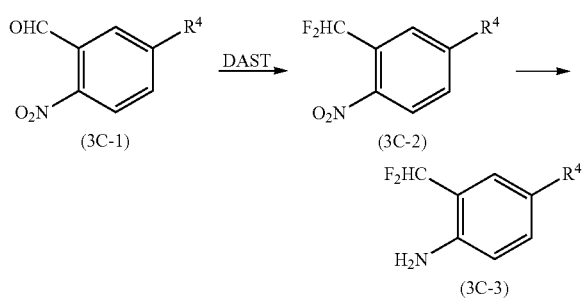
(3C-1) (3C-2) (3C-3)

(Here, $R^{6a}$ represents a C1-C3 alkyl group or a halogeno-C1-C3 alkyl group; $R^{6b}$ represents a halogeno group; $R^{7a}$ represents a C1-C4 alkyl group or an aryl group; and $R^4$ represents the same as described above.)

As shown in (Route 3A) of [Scheme 3], compound (3A-3) which is an aniline derivative can be produced by nitrating compound (3A-1) with a known method, followed by catalytic reduction. As a catalyst used for the catalytic reduction, palladium-carbon, platinum oxide, or palladium hydroxide can be mentioned, and palladium-carbon or palladium hydroxide is preferable. As a reaction solvent for the catalytic reduction, alcohol solvents such as ethanol and methanol, ether solvents such as tetrahydrofuran can be mentioned, and ethanol or methanol is preferable. As the hydrogen pressure, it is in the range of normal pressure to 10 Mpa, and normal pressure to 1.5 Mpa is preferable. As the reaction temperature for the catalytic reduction, it is in the range of 0 to 100° C., and preferably in the range of 20 to 60° C. As the reaction time, it is usually from about 3 to about 24 hours.

As shown in (Route 3B) of [Scheme 3], compound (3B-4) which is an aniline derivative can be produced by alkylation and decarboxylation of compound (3B-1) by the method described in the patent document (WO 1996/23754) to give compound (3B-3), and then conducting catalytic reduction of compound (3B-3). As the alkylating agent, α-haloacetic acid esters can be used, and preferably, bromoacetic acid ethyl ester, bromoacetic acid methyl ester, chlorodifluoroacetic acid methyl ester can be mentioned. In the catalytic reduction, the catalyst, reaction solvent and reaction conditions described in aniline (3A-3) of (Route 3A) can be applied correspondingly.

As shown in (Route 3C) of [Scheme 3], compound (3C-3) which is an aniline derivative can be produced by preparation of difluoromethyl derivative (3C-2) by benzaldehyde (3C-1) and a fluorinating agent, followed by catalytic reduction of the nitro group of the difluoromethyl derivative (3C-2). As a fluorinating agent, dimethylaminosulfur trifluoride (DAST), bis(2-methoxyethyl)aminosulfur trifluoride (BAST) and the like can be used, and DAST is preferable. In the catalytic reduction, the catalyst, reaction solvent and reaction conditions described in aniline (3A-3) of (Route 3A) can be applied correspondingly.

The aniline derivative (4) used in [Scheme 1] is a commercialized product, or can be produced by the method shown in the following [Scheme 4].

[Scheme 4]

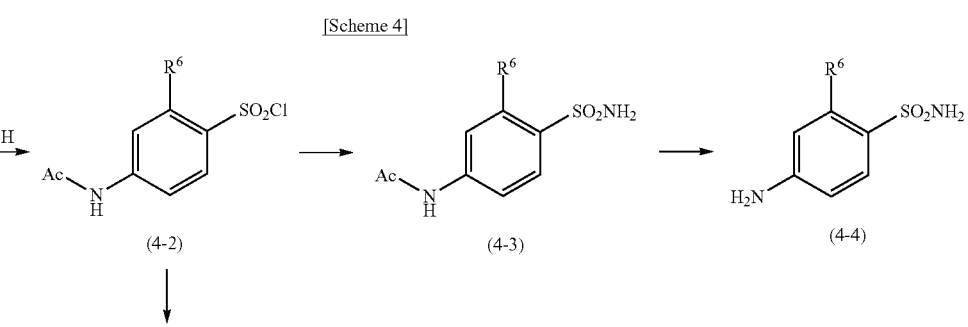
(4-1) (4-2) (4-3) (4-4)

-continued

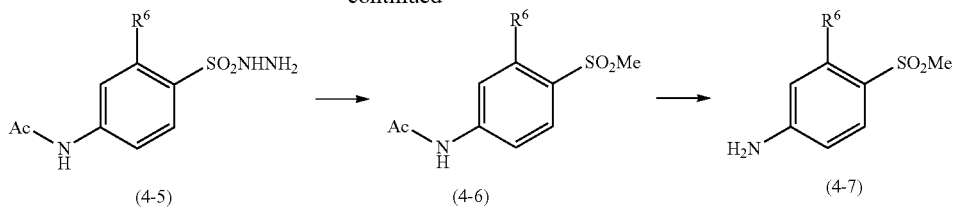

(4-5)    (4-6)    (4-7)

(Here, Ac represents an acetyl group; and $R^6$ represents the same as described above.)

A sulfonamide derivative (4-4) can be produced from compound (4-1) in accordance with the method described in Scheme 23 of the patent document (WO 2006/012642). In addition, compound (4-7) which is an alkylsulfonylaniline derivative can be produced from compound (4-2) which is a chlorosulfonyl derivative, via compound (4-5) and compound (4-6) in accordance with the method of Ballini, R. et al [Tetrahedron, 45, 6791 (1989)].

Compound (5-1) shown in [Scheme 1], which is a derivative of formula (I), can be converted into an alcohol derivative (5-2) by conducting a deprotection reaction if necessary.

[Scheme 5]

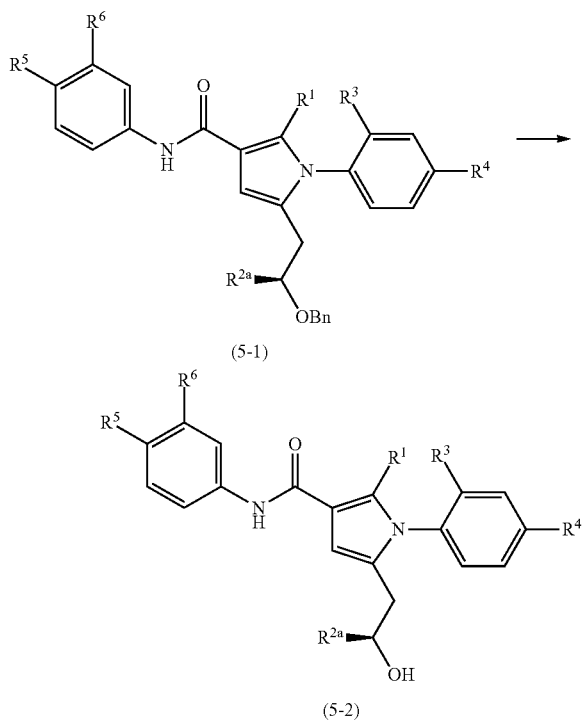

(5-1)

(5-2)

(Here, Bn represents a benzyl group; $R^{2a}$ represents a hydrogen atom or a C1-C2 alkyl group; and $R^1$, $R^3$, $R^4$, $R^5$ and $R^6$ represent the same as described above.)

As a protecting group used for compound (5-1) which is a protected alcohol derivative, a protecting group generally used when protecting alcohols can be used, and a benzyl group can be mentioned preferably. In addition, regarding the selection of a protecting group, and the conditions for introduction and cleavage of the protecting group, documents described in the review books such as Protective Groups in Organic Synthesis (T. W. Greene and P. G. M. Wuts, John Wiley & Sons, Inc., New York, 1999) can be referred to.

For the deprotection of the benzyl group, general deprotection conditions for the benzyl group can be used, and is preferably catalytic reduction, acid treatment, and boron tribromide. As a catalyst, reaction solvent and reaction conditions used in the catalytic reduction, the catalyst, reaction solvent and reaction conditions described in the aforementioned (Route 3A) of [Scheme 3] can be applied correspondingly. As an acid used in the acid treatment, acids such as hydrochloric acid, sulfuric acid, trifluoromethanesulfonic acid can be used, and is preferably trifluoromethanesulfonic acid. As a reaction solvent, the reaction can also be carried out in the absence of a solvent, while halogenohydrocarbon solvents such as methylene chloride, hydrocarbon solvents such as toluene, ether solvents such as tetrahydrofuran, and the like can be used, and is preferably methylene chloride. As the reaction temperature, it is in the range of 0° C. to the boiling point of the solvent, preferably in the range of room temperature to boiling point of the solvent. As the reaction time, it is usually from about 0.5 to about 24 hours. In the case of the reaction with boron tribromide, halogenohydrocarbon solvents such as methylene chloride are preferable as the reaction solvent. As the reaction temperature, it is in the range of −70° C. to room temperature, preferably −40° C. to room temperature. As the reaction time, it is usually from about 0.5 to about 24 hours.

[Scheme 6] shows a production process of a compound of formula (I) having a fluoro-C1-C4 alkyl group as $R^2$.

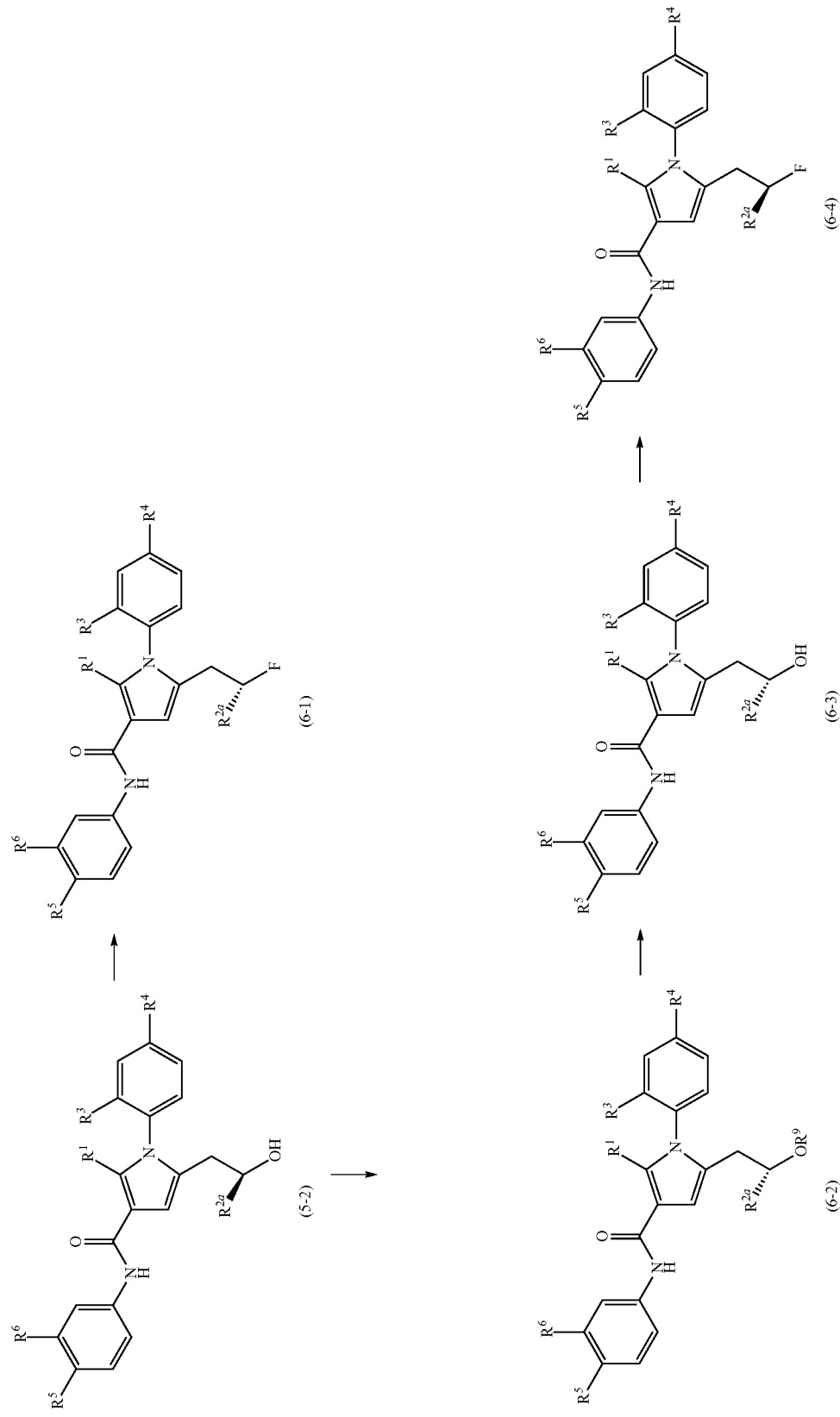

(Here, $R^1$, $R^{2a}$, $R^3$, $R^4$, $R^5$ and $R^6$ represent the same as described above.)

Compound (6-1), which is a fluoroalkylpyrrole derivative having an asymmetric carbon, can be produced by fluorination of compound (5-2) which is an alcohol derivative. In addition, compound (6-4), which is a stereoisomer of compound (6-1), can be produced via Mitsunobu Reaction of compound (5-2).

As a fluorinating agent, dimethylaminosulfur trifluoride (DAST) and bis(2-methoxyethyl)aminosulfur trifluoride (BAST) are preferable.

In the Mitsunobu Reaction, a combination of trialkylphosphine, triarylphosphine and azodicarboxylic acid ester, or Tsunoda reagent and the like can be used, and is preferably a combination of triphenylphosphine and diisopropyl azodicarboxylate. In such case, the carboxylic acid used is preferably 4-nitrobenzoic acid and the like. As a reaction solvent, ether solvents such as tetrahydrofuran are preferable.

[Scheme 7] shows a production process of a compound of formula (I) having a carbamoyl-C1-C2 alkyl group as $R^2$.

which a carboxylic acid is produced by sodium dihydrogenphosphate, 2-methyl-2-butene and sodium chlorite, after producing an aldehyde derivative by Dess-Martin oxidation [J. Am. Chem. Soc. 100, 300 (1978), J. Am. Chem. Soc. 101, 5294 (1979)], can be mentioned.

In the condensation reaction, a condensation agent used in general amide-forming reaction can be used, and a combination of 1-(3-dimethyl-aminopropyl)-3-ethylcarbodiimide hydrochloride salt (water soluble carbodiimide) and 1-hydroxybenzotriazole monohydrate is preferable.

The atropisomers in the present invention are structural isomers based on an axial or facial chirality, arising from constrained intramolecular rotation. The compound having the general formula (I) of the present invention has two atropisomers that stem from axial asymmetry which arises from restriction of the rotation of the bond connecting the phenyl group having $R^3$ group as a substituent and the substituted pyrrole ring, due to steric hindrance. With respect to the atropisomers of the present invention, in a case where the compound having the general formula (I) has isomers arising

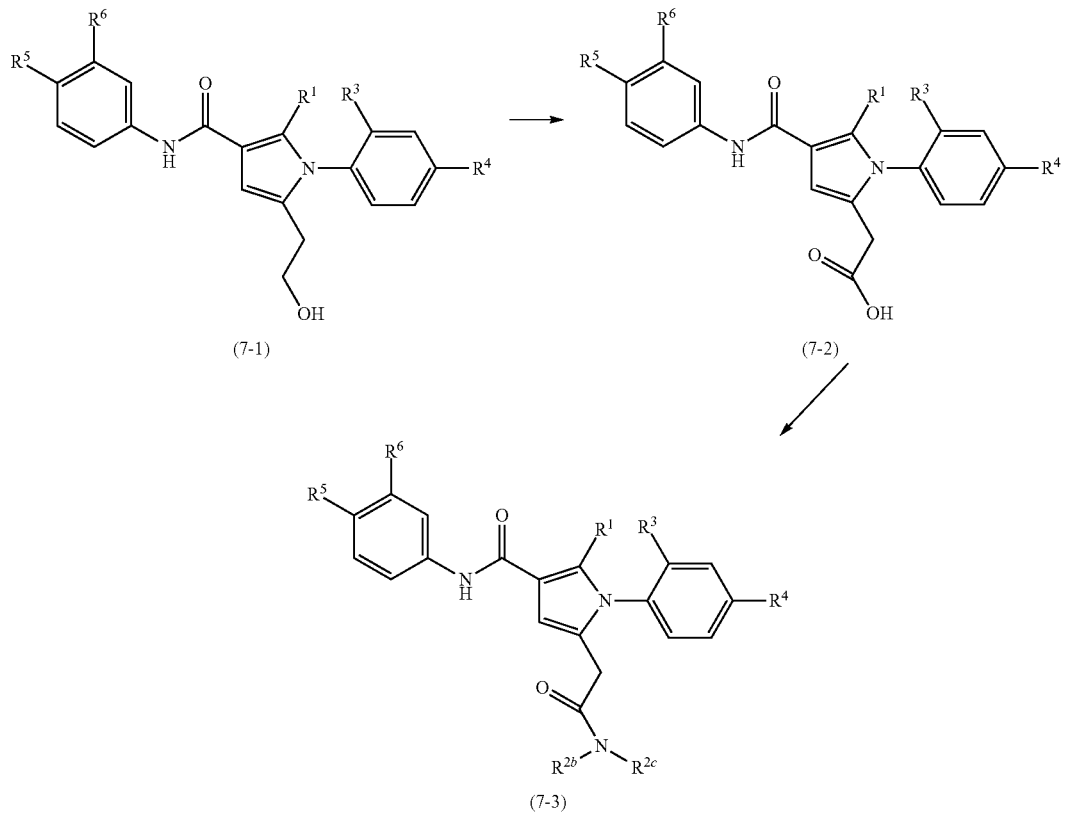

(Here, $R^{2b}$ and $R^{2c}$ are the same or different from one another, and represent a hydrogen atom or a C1-C3 alkyl group; and $R^1$, $R^3$, $R^4$, $R^5$, and $R^6$ represent the same as described above.)

Compound (7-3), which is a carbamoyl-C1-C2 alkyl derivative, can be produced by oxidation of compound (7-1) to give compound (7-2) which is a carboxylic acid derivative, and then conducting condensation with amines or salts thereof. As the oxidation reaction, a one-step or two-step oxidation reaction known to produce a carboxylic acid from an alcohol derivative can be used. Preferably, a method in from an asymmetric carbon and the like, it means either one of a pair of atropisomers that exist for each of such isomeric compounds. The atropisomer which has superior pharmacological/pharmacokinetic activity, stability, internal kinetics, safety and the like, and has preferable properties as a medicament is preferred.

Here, the present invention comprises, among the atropisomers existing for the compound of the general formula (I), the atropisomer having superior or preferred pharmacological and/or pharmacokinetic activity, stability, internal kinetics, safety and the like, and has preferable properties as a medicament. However, the present invention also comprises compounds/compositions enriched in the atropisomer having the preferable properties as a major component, or also includes a mixture with the other atropisomer at any ratio, so long as it demonstrates such preferable properties. In compounds/compositions enriched in the atropisomer having superior and/or preferred properties, the atropisomer having such properties is present in greater concentration than the other atropisomer(s). Preferably, the preferred atropisomer comprises greater than 50%, 60%, 70%, 80%, 90%, 95%, 98%, or 99% of the atropisomers of the same structure. In a preferred embodiment, atropisomers of the same structure other than the preferred atropisomer are undetectable.

As separation and purification methods for the atropisomers produced by the aforementioned methods include, for example, chromatography, although the method is not limited thereto. Hereinafter, details of a general optical resolution method by chromatography will be described.

In the optical resolution method using chromatography, when a stationary phase which incorporates an asymmetric element bonded with a derivative such as sugar is used as a carrier, the retention time of the chromatography becomes differentiated, thereby allowing resolution. By utilizing this property, direct resolution can be conducted by using the high performance liquid chromatography. Chiral columns include, for example, CHIRALPAK AD-H, CHIRALCEL OJ-RH (DAICEL), etc.

In a case where the atropisomer of the present invention is used as a medicament, the atropisomer of the compound having the aforementioned general formula (I) can be administered as itself (or a composition enriched in that atropisomer), or it (or a compound/composition enriched in it) can be mixed with an appropriate excipient, diluent and the like that are pharmacologically acceptable, and be administered orally as a tablet, a capsule, granules, powders, syrup and the like, or can be administered parenterally as injection, suppository, adhesive preparation or external preparation.

These pharmaceutical preparations are produced through known methods by using additives such as excipients, lubricants, binders, disintegrants, emulsifiers, stabilizers, correctives and diluents.

The present invention also comprises methods of inhibiting mineralocorticoid receptor activity, both in vitro and in vivo, the method comprising contacting the mineralocorticoid receptor with an effective inhibiting amount of compound of the invention. In one preferred embodiment, the receptor is in a cell. Preferably, the cell is within an animal body, preferably a human body. Such methods are useful, irrespective of any therapeutic effect, to study the role of the mineralocorticoid receptor in biological processes in vitro and in vivo.

The present invention also comprises a method of preventing or treating a mineralocorticoid receptor mediated condition or disease. Such conditions or diseases including, for example, hypertension, angina pectoris, acute coronary syndrome, congestive heart failure, nephropathy, including diabetic nephropathy, arteriosclerosis, cerebral infarction, fibrosis, primary aldosteronism and edema. The methods of prevention and/or treatment comprise administering to the animal (preferably human) an effective amount of a compound of the invention (alone or in a pharmaceutical composition). As used herein, "treatment" encompasses both curative as well as palliative treatments.

The dosage amount varies depending on the symptom, age and the like, the dose in the case of oral administration for a human adult is from 0.02 mg/kg (preferably 0.1 mg/kg) per dosage as a lower limit to 100 mg/kg (preferably 10 mg/kg) per dosage as an upper limit, and the dose in the case of parental administration is from 0.002 mg/kg (preferably 0.01 mg/kg) per dosage as a lower limit to 10 mg/kg (preferably 1 mg/kg) per dosage as an upper limit, and the dosage can be administered from one to six times per day depending on the symptoms.

The atropisomer of the compounds of the invention having preferred pharmacological and/or pharmacokinetic activity can be routinely determined and identified using the methods described herein and/or known to those skilled in the art.

All publications (patent and non-patent) referenced herein are hereby incorporated by reference.

EXAMPLES

Hereinafter, the present invention will be specifically explained with reference to Comparative Examples, Examples and Test Examples; however, the present invention is by no means limited to these. As used herein, "referential" and "comparative" are used interchangeably.

Here, the symbols "NMR" and "MS" in the Examples respectively mean "nuclear magnetic resonance" and "mass spectroscopy". The ratio of solvent for elution described in the portion of separation and purification using chromatography refers to volume ratio, unless otherwise noted. "NMR" means $^1$H-NMR unless otherwise noted, content of the parenthesis shows the solvent for measurement, and TMS (tetramethylsilane) was used as internal standard for all cases. Further, "Anal. Calcd for RATIONAL FORMULA" and "required" respectively means a calculated value for elemental analysis and high resolution mass spectroscopy (HRMS), and the measured value was provided following "found". In addition, in high performance liquid chromatography, analysis and purification were carried out by using either one of the following conditions of LC1 to LC10.

LC1: (Analytical)
Instrument: SHIMADZU CLASS-VP system (LC-10ADVP/SCL-10AVP/SPD-M10AVP/CTO10ACVP/DGU12A);
chiral column: CHIRALPAK AS-H (0.46 cm×25 cm), oven: 40° C., flow rate: 1.0 mL/min, detection: UV (254 nm).

LC2: (Analytical)
Instrument: SHIMADZU CLASS-VP system (LC-10ADVP/SCL-10AVP/SPD-M10AVP/CTO10ACVP/DGU12A);
chiral column: CHIRALPAK AD-H (0.46 cm×25 cm), oven: 40° C., flow rate: 1.0 mL/min, detection: UV (254 nm).

LC3: (Preparative)
Instrument: SHIMADZU CLASS-VP system (LC-8A/SCL-10AVP/SIL-10AP/SPD-10AVP/FRC-10A);
chiral column: CHIRALPAK AS-H (2 cm×25 cm), oven: ambient temperature, flow rate: 20.0 mL/min, detection: UV (254 nm).

LC4: (Preparative)
Instrument: SHIMADZU CLASS-VP system (LC-8A/SCL-10AVP/SIL-10AP/SPD-10AVP/FRC-10A);
chiral column: CHIRALPAK AD-H (2 cm×25 cm), oven: ambient temperature, flow rate: 20.0 mL/min, detection: UV (254 nm).

LC5: (Analytical)
Instrument: SHIMADZU CLASS-VP system (LC-20AD/SCL-10AVP/SPD-M20A/FCV-14AH/DGU-20A5);
chiral column: CHIRALPAK AD-H (0.46 cm×25 cm), oven: ambient temperature, flow rate: 0.5-0.8 mL/min, detection: UV (254 nm).

LC6: (Preparative)
Instrument: SHIMADZU CLASS-VP system (LC-8A/SCL-10AVP/SIL-10AVP/SPD-10AVP/FRC-10A);

chiral column: CHIRALPAK AD-H (2 cm×25 cm), oven: ambient temperature, flow rate: 7.0 mL/min, detection: UV (254 nm).

LC7: (Analytical)
Instrument: SHIMADZU CLASS-VP system (LC-20AD/SCL-10AVP/SPD-M20A/FCV-14AH/DGU-20A5);
chiral column: CHIRALPAK OJ-H (0.46 cm×25 cm), oven: ambient temperature, flow rate: 0.5 mL/min, detection: UV (254 nm).

LC8: (Preparative)
Instrument: SHIMADZU CLASS-VP system (LC-8A/SCL-10AVP/SIL-10AVP/SPD-10AVP/FRC-10A);
chiral column: CHIRALPAK OJ-H (2 cm×25 cm), oven: ambient temperature, flow rate: 7.0 mL/min, detection: UV (254 nm).

LC9: (Analytical)
Instrument: SHIMADZU CLASS-VP system (LC-20AD/SCL-10AVP/SPD-M20A/FCV-14AH/DGU-20A5);
chiral column: CHIRALPAK AS-H (0.46 cm×25 cm), oven: ambient temperature, flow rate: 0.5 mL/min, detection: UV (254 nm).

LC10: (Preparative)
Instrument: SHIMADZU CLASS-VP system (LC-8A/SCL-10AVP/SIL-10AVP/SPD-10AVP/FRC-10A);
chiral column: CHIRALPAK AS-H (2 cm×25 cm), oven: ambient temperature, flow rate: 7.0 mL/min, detection: UV (254 nm).

Comparative Example 1

(4S)-4-(Benzyloxy)pentan-2-one

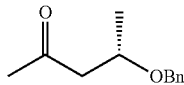

Under a nitrogen atmosphere, to a solution of (S)-(+)-3-hydroxybutyric acid ethyl ester (100 g, 0.76 mol) in methylene chloride (1.0 L), benzyl 2,2,2-trichloroacetoimidate (381 g, 1.5 mol) and trifluoromethanesulfonic acid (6.7 mL, 76 mmol) were gradually added, and the mixture was stirred at room temperature overnight. The precipitated solid was filtered, and after the mother liquid was successively washed with a saturated aqueous sodium hydrogencarbonate solution, water and saturated brine, it was dried with sodium sulfate and the solvent was distilled off under reduced pressure. Hexane was added to the residue, and after the solid was filtered again, the solvent of the mother liquid was distilled off under reduced pressure to give (3S)-3-(benzyloxy)butanoic acid ethyl ester (339 g) as a mixture. The present compound was used for the subsequent reaction without further purification.

To a solution of the above ethyl (3S)-3-(benzyloxy)butanoic acid ethyl ester (339 g) in 1,4-dioxane (1.5 L), 2N aqueous sodium hydroxide solution (0.75 L, 1.5 mol) was added, and the mixture was stirred at room temperature for 3 hours. After the reaction, the solvent was distilled off under reduced pressure, and after the aqueous phase was washed with diethyl ether, concentrated hydrochloric acid (0.14 L) was added to acidify it. After it was extracted with ethyl acetate, it was successively washed with water and saturated brine, and then it was dried with sodium sulfate and the solvent was distilled off under reduced pressure to give (3S)-3-(benzyloxy)butanoic acid (254 g) as a mixture. The present compound was used for the subsequent reaction without further purification.

Under a nitrogen atmosphere, to a solution of the above (3S)-3-(benzyloxy)butanoic acid (225 g) in DMF (1.5 L), N,O-dimethylhydroxylamine hydrochloride (111 g, 1.1 mol) and triethylamine (0.32 mL, 2.3 mol) were added, and the mixture was stirred at room temperature for 40 minutes. Subsequently, 1-hydroxybenzotriazole (112 g, 0.83 mol) and 1-ethyl-3-(3'-dimethylaminopropyl)carbodiimide hydrochloride (160 g, 0.83 mol) were successively added, and the mixture was stirred at room temperature for 5 hours. After the reaction, the reaction mixture was poured to ice-water, and it was extracted with diethyl ether. After it was successively washed with 1N hydrochloric acid, water, a saturated aqueous sodium hydrogencarbonate solution and saturated brine, it was dried with sodium sulfate and the solvent was distilled off under reduced pressure to give (3S)-3-(benzyloxy)-N-methoxy-N-methylbutanamide (196 g) as a mixture. The present compound was used for the subsequent reaction without further purification.

Under a nitrogen atmosphere, to a solution of the above (3S)-3-(benzyloxy)-N-methoxy-N-methylbutanamide (196 g) in THF (1.5 L), a 3M methyl magnesium bromide/diethyl ether solution (0.38 mL, 1.1 mol) was gradually added under ice-cooling, and the mixture was stirred at the same temperature for 3 hours. After the reaction, the reaction mixture was poured to 2N hydrochloric acid, and after THF was distilled off under reduced pressure, it was extracted with diethyl ether. After it was successively washed with water, a saturated aqueous sodium hydrogencarbonate solution and saturated brine, it was dried with sodium sulfate and the solvent was distilled off under reduced pressure to give a crude product. This was purified by reduced pressure distillation to give a title compound (44 g) as an oil.

$^1$H-NMR (400 MHz, CDCl$_3$) δ: 7.38-7.25 (5H, m), 4.57 (1H, d, J=11.4 Hz), 4.46 (1H, d, J=11.7 Hz), 4.08-4.00 (1H, m), 2.80 (1H, dd, J=15.8, 7.2 Hz), 2.49 (1H, dd, J=15.9, 5.4 Hz), 2.16 (3H, s), 1.24 (3H, d, J=6.2 Hz).

Comparative Example 2

(6S)-2-Acetyl-6-(benzyloxy)-4-oxoheptanoic acid ethyl ester

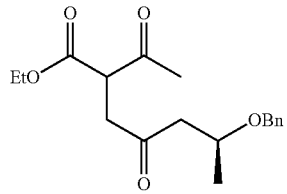 [SMILES: CCOC(=O)C(CC(=O)C[C@H](C)OCc1ccccc1)C(C)=O]

Under a nitrogen atmosphere, to a solution of the compound (54 g, 0.28 mol) of Comparative Example 1 in methanol (0.28 L), a solution of bromine (14 mL, 0.28 mmol) in methanol (45 mL) was gradually added under ice-cooling, and the mixture was stirred at room temperature for 1 hour. A 1M aqueous sodium hydrogencarbonate solution was added to stop the reaction and after methanol was distilled off under reduced pressure, it was extracted with diethyl ether. After it was successively washed with water and saturated brine, it was dried with sodium sulfate and the solvent was distilled off under reduced pressure. Subsequently, 1M sulfuric acid (0.42 L, 0.42 mol) was added to a solution of the residue in THF (0.84 L), and the mixture was heated under reflux for 2 hours. After the reaction, THF was distilled off under reduced pressure and it was extracted with diethyl ether. After it was successively washed with water, a saturated aqueous sodium hydrogencarbonate solution and saturated brine, it was dried with sodium sulfate, and the solvent was distilled off under reduced pressure to give (4S)-4-(benzyloxy)-1-bromopentan-2-one (75 g, 99%) as a mixture.

$^1$H-NMR (400 MHz, CDCl$_3$) δ: 7.38-7.28 (5H, m), 4.58 (1H, d, J=11.3 Hz), 4.43 (1H, d, J=11.4 Hz), 4.08-4.03 (1H, m), 3.93 (2H, s), 2.94 (1H, dd, J=15.7, 7.9 Hz), 2.70 (1H, dd, J=15.5, 4.9 Hz), 1.27 (3H, d, J=6.3 Hz).

Under a nitrogen atmosphere, to a solution of ethyl acetoacetate (1.0 g, 7.7 mmol) in ethanol (30 mL), 20% sodium ethoxide/ethanol solution (3.1 mL, 7.7 mmol) was gradually added under ice-cooling, and the mixture was stirred at room temperature for 30 minutes. Thereafter, under ice-cooling, a solution of the above (4S)-4-(benzyloxy)-1-bromopentan-2-one (2.1 g, 7.7 mmol) in ethanol (6.0 mL) was gradually added, and the mixture was stirred at room temperature for 3 hours. After the reaction, ethanol was distilled off under reduced pressure and 1N hydrochloric acid (0.20 L) was added to acidify it. After it was extracted with ethyl acetate and successively washed with water, a saturated aqueous sodium hydrogencarbonate solution and saturated brine, it was dried with sodium sulfate and the solvent was distilled off under reduced pressure. It was purified by silica gel column chromatography (ethyl acetate/hexane, 1:3, v/v) to give the title compound (1.6 g, 65%) as an oil.

$^1$H-NMR (400 MHz, CDCl$_3$) δ: 7.38-7.25 (5H, m), 4.55 (1H, dd, J=9.4, 1.6 Hz), 4.44 (1H, dd, J=11.8, 3.5 Hz), 4.21-4.16 (2H, m), 4.05-3.98 (2H, m), 3.18-3.10 (1H, m), 2.98-2.91 (1H, m), 2.84-2.78 (1H, m), 2.55-2.49 (1H, m), 2.34 (3H, d, J=6.3 Hz), 1.29-1.23 (6H, m).

Comparative Example 3

(6S)-6-(Benzyloxy)-4-oxo-2-propionylheptanoic acid methyl ester

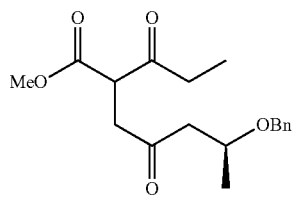 [SMILES: CCC(=O)C(CC(=O)C[C@H](C)OCc1ccccc1)C(=O)OC]

After (4S)-4-(benzyloxy)-1-bromopentan-2-one (15 g, 52 mmol) was prepared from the compound of Comparative Example 1 in the process similar to Comparative Example 2, it was reacted with 3-oxopentanoic acid methyl ester (6.5 mL, 52 mmol) to give the title compound (7.8 g, 47%).

$^1$H-NMR (400 MHz, CDCl$_3$) δ: 7.38-7.25 (5H, m), 4.55 (1H, d, J=11.3 Hz), 4.44 (1H, dd, J=11.3, 3.4 Hz), 4.04-3.99 (2H, m), 3.72 (3H, d, J=2.4 Hz), 3.22-3.11 (1H, m), 3.00-2.93 (1H, m), 2.84-2.60 (3H, m), 2.55-2.47 (1H, m), 1.23 (3H, d, J=6.3 Hz), 1.09-1.05 (3H, m).

MS (FAB) m/z: 321 [M+H]$^+$.

Comparative Example 4

(6S)-6-(Benzyloxy)-4-oxo-2-propionylheptanoic acid ethyl ester

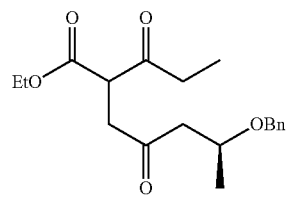 [SMILES: CCOC(=O)C(CC(=O)C[C@H](C)OCc1ccccc1)C(=O)CC]

The title compound was obtained from the compound of Comparative Example 1 in the process similar to Comparative Example 2.

$^1$H NMR (400 MHz, CDCl$_3$) δ: 7.35-7.25 (5H m), 4.55 (1H, dd, J=0.8, 11.2), 4.44 (1H, dd, J=4.0, 11.2), 4.21-4.14 (2H, m), 4.04-3.98 (2H, m), 3.20-3.10 (1H, m), 2.99-2.92 (1H, m), 2.84-2.60 (3H, m), 2.55-2.48 (1H, m), 1.28-1.22 (6H, m), 1.09-1.05 (3H, m).

Comparative Example 5

2-Acetyl-6-(benzyloxy)-4-oxohexanoic acid ethyl ester

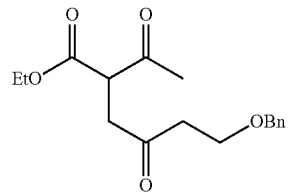 [SMILES: CCOC(=O)C(CC(=O)CCOCc1ccccc1)C(C)=O]

After 4-(benzyloxy)-1-bromobutan-2-one [$^1$H-NMR (400 MHz, CDCl$_3$) δ: 7.38-7.29 (5H, m), 4.51 (2H, s), 3.95 (2H, s), 3.77 (2H, t, J=6.1 Hz), 2.92 (2H, t, J=6.1 Hz).] was prepared in the process similar to Comparative Example 2 using 4-(benzyloxy)butan-2-one (61 g, 0.34 mol) as a starting material, the title compound (61 g, 67%) was obtained as an oil.

$^1$H-NMR (400 MHz, CDCl$_3$) δ: 7.38-7.28 (5H, m), 4.50 (2H, s), 4.19 (2H, q, J=7.0 Hz), 4.04 (1H, dd, J=8.2, 5.9 Hz), 3.76-3.70 (2H, m), 3.16 (1H, dd, J=18.4, 8.2 Hz), 2.97 (1H, dd, J=18.4, 5.9 Hz), 2.75 (2H, td, J=6.3, 2.0 Hz), 2.35 (3H, s), 1.27 (3H, t, J=7.0 Hz).

Comparative Example 6

4-Fluoro-1-nitro-2-(trifluoromethoxy)benzene

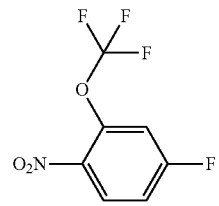

Fuming nitric acid (20 mL) was added dropwise to concentrated sulfuric acid (40 ml) under cooling (−10° C.), and subsequently, 1-fluoro-3-(trifluoromethoxy)benzene (15 g, 83 mmol) was added to the mixture at −10° C., and the mixture was stirred for 0.5 hours. After the mixture was added into ice-water to stop the reaction, it was extracted with dichloromethane. After the obtained organic layer was washed with a 1N aqueous sodium hydroxide solution and water, it was dried with anhydrous sodium sulfate. After filtration, the solution was concentrated and the residue was purified by silica gel column chromatography (100:0-97:3, hexane:ethyl acetate) to give the title compound (3.1 g, 16%) as an oil.

$^1$H-NMR (400 MHz, CDCl$_3$) δ: 8.10 (1H, dd, J=5.5, 9.4 Hz), 7.23-7.15 (2H, m).

Comparative Example 7

4-Fluoro-2-(trifluoromethoxy)aniline

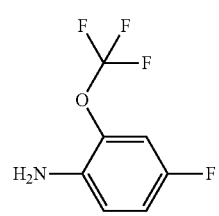 [SMILES: O=[N+]([O-])c1ccc(F)cc1OC(F)(F)F]

To a solution of the compound of Comparative Example 6 (3.1 g, 14 mmol) in ethanol (80 ml), 10% palladium-carbon (1.0 g) was added, and the mixture was stirred under a hydrogen atmosphere at room temperature for 6 hours. After the reaction, it was filtered by Celite and the solution was concentrated. Thereafter, the residue was purified by silica gel column chromatography (5:1-2:3, hexane:ethyl acetate) to give the title compound (1.9 g, 71%) as an oil.

$^1$H-NMR (500 MHz, CDCl$_3$) δ: 6.93 (1H, d, J=8.8 Hz), 6.85 (1H, dt, J=2.9, 8.8 Hz), 6.75 (1H, dd, J=5.4, 8.8 Hz), 3.87-3.57 (2H, brs).

Comparative Example 8

2-(Difluoromethoxy)-4-fluoro-1-nitrobenzene

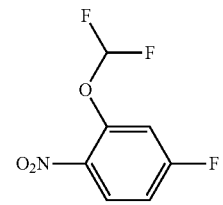 [SMILES: O=[N+]([O-])c1ccc(F)cc1OC(F)F]

To a solution of 5-fluoro-2-nitrophenol (3.1 g, 20 mmol) in DMF (40 mL), potassium carbonate (4.2 g, 30 mmol) and chlorodifluoroacetic acid methyl ester (3.2 mL, 30 mmol) were successively added at room temperature. Subsequently, the temperature of the mixture was raised to 100° C., and the mixture was stirred for 2 hours. The mixture was cooled to room temperature, and water (100 mL) was added to the reaction mixture, followed by extraction with diethyl ether (200 mL) once. The organic layer was successively washed with water (100 mL) and a saturated aqueous sodium chloride solution (100 mL), and after it was dried with sodium sulfate, the solvent was distilled off under reduced pressure. The obtained residue was purified by silica gel column chromatography to give the title compound (3.1 g, yield: 75%).

$^1$H-NMR (400 MHz, CDCl$_3$) δ: 8.03 (1H, dd, J=9.0, 5.9 Hz), 7.17-7.06 (2H, m), 6.65 (1H, t, J=72.3 Hz).

Comparative Example 9

2-(Difluoromethoxy)-4-fluoroaniline

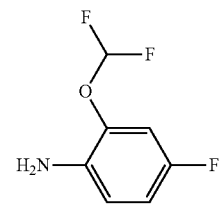

To a solution of the compound (1.0 g, 4.8 mmol) of Comparative Example 8 in ethanol (25 mL), palladium-carbon (0.51 g) was added. The inside of the system was made to be a hydrogen atmosphere, and the mixture was stirred at room temperature for 4 hours. The reaction mixture was filtered by Celite, and the filtrate was concentrated. The obtained residue was purified by silica gel column chromatography to give the title compound (0.79 g, yield: 92%).

$^1$H-NMR (400 MHz, CDCl$_3$) δ: 6.86-6.69 (3H, m), 6.47 (1H, t, J=73.5 Hz), 3.71 (2H, s).

Comparative Example 10

4-Chloro-2-(difluoromethyl)aniline

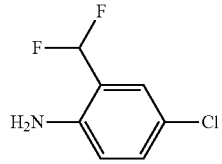 [SMILES: Nc1ccc(Cl)cc1C(F)F]

Under a nitrogen atmosphere, to a solution of 5-chloro-2-nitrobenzaldehyde (6.0 g, 32 mmol) in methylene chloride (40 mL), diethylaminosulfur trifluoride (5.0 mL, 38 mmol) was gradually added under ice-cooling, and the mixture was stirred at the same temperature for 1 hour. Saturated brine was added to stop the reaction, and after the precipitated solid was filtered, the mother liquid was extracted with methylene chloride. After it was dried with sodium sulfate, the solvent was distilled off under reduced pressure to give 4-chloro-2-(difluoromethyl)-1-nitrobenzene (6.0 g) as a crude product. The present compound was used for the subsequent reaction without further purification. Under a nitrogen atmosphere, to a solution of the above 4-chloro-2-(difluoromethyl)-1-nitrobenzene (6.0 g) in ethanol (0.10 L), stannous chloride dihydrate (28 g, 0.13 mol) and concentrated hydrochloric acid (20 mL) were successively added under ice-cooling, and the mixture was stirred at room temperature for 40 minutes. After the reaction, ethanol was distilled off under reduced pressure and a 5M aqueous sodium hydroxide solution was added under ice-cooling to make it basic. Thereafter, it was extracted with ethyl acetate and after it was successively washed with water and saturated brine, it was dried with sodium sulfate and the solvent was distilled off under reduced pressure. The residue was purified by silica gel column chromatography (ethyl acetate/hexane, 1:3, v/v) to give the title compound (4.2 g, 76%) as a solid.

$^1$H-NMR (400 MHz, CDCl$_3$) δ: 7.24-7.18 (2H, m), 6.67 (1H, d, J=8.6 Hz), 6.57 (1H, t, J=55.1 Hz), 4.06 (2H, brs).

Comparative Example 11

2-(Difluoromethyl)-4-fluoroaniline

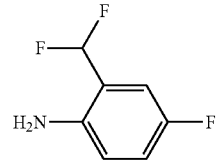 [SMILES: Nc1ccc(F)cc1C(F)F]

Under a nitrogen atmosphere, to a solution of 5-fluoro-2-nitrobenzaldehyde (6.0 g, 36 mmol) in methylene chloride (40 mL), diethylaminosulfur trifluoride (5.6 mL, 43 mmol) was gradually added under ice-cooling, and the mixture was stirred at the same temperature for 1 hour. Saturated brine was added to stop the reaction, and after the precipitated solid was filtered, the mother liquid was extracted with methylene chloride. After it was dried with sodium sulfate, the solvent was distilled off under reduced pressure. The residue was purified by silica gel column chromatography (ethyl acetate/hexane, 1:6, v/v) to give 2-(difluoromethyl)-4-fluoro-1-nitrobenzene (5.9 g, 87%) as an oil.

$^1$H-NMR (400 MHz, CDCl$_3$) δ: 8.26 (1H, dd, J=9.0, 4.7 Hz), 7.60 (1H, dd, J=8.6, 2.7 Hz), 7.41 (1H, t, J=54.7 Hz), 7.37-7.33 (1H, m).

LRMS (EI) m/z: 191 [M]$^+$.

Under a nitrogen atmosphere, to a solution of the above 2-(difluoromethyl)-4-fluoro-1-nitrobenzene (5.9 g, 31 mmol) in ethanol (0.10 L), stannous chloride dihydrate (28 g, 0.12 mol) and concentrated hydrochloric acid (20 mL) were successively added under ice-cooling, and the mixture was stirred at room temperature for 1 hour. After the reaction, ethanol was distilled off under reduced pressure and a 5M aqueous sodium hydroxide solution was added under ice-cooling to make it basic. Thereafter, it was extracted with diethyl ether and after it was successively washed with water and saturated brine, it was dried with sodium sulfate and the solvent was distilled off under reduced pressure. The residue was purified by silica gel column chromatography (ethyl acetate/hexane, 1:4, v/v) to give the title compound (3.0 g, 60%) as an oil.

$^1$H-NMR (400 MHz, CDCl$_3$) δ: 7.04-6.95 (2H, m), 6.70 (1H, dd, J=9.0, 4.3 Hz), 6.60 (1H, t, J=55.3 Hz), 3.89 (2H, br s).

MS (EI) m/z: 161 [M]$^+$.

Comparative Example 12

4-Amino-2-methylbenzenesulfonamide

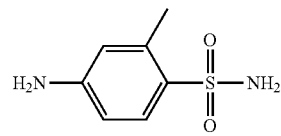

To chlorosulfuric acid (20 mL, 302 mmol), m-acetotoluidine (10 g, 67 mmol) was added at room temperature over 20 minutes, and subsequently, the mixture was heated to 70° C. and stirred for 8 hours. The mixture was cooled to room temperature, ice (50 g) was added to the reaction mixture, and the produced solid was collected by removing an aqueous layer by decantation. Subsequently, the obtained solid was washed with water (50 mL) to obtain a crude product. A solution of the obtained crude product in THF (50 mL) was cooled to 0° C., and concentrated ammonia water (20 mL) was added. Subsequently, the temperature of the mixture was raised to room temperature and the mixture was stirred for 2 hours. The reaction mixture was concentrated, water (100 mL) was added to the obtained solid, and filtration was carried out to give a crude product. To a solution of the obtained crude product in ethanol (200 mL), 6N hydrochloric acid (200 mL) was added at room temperature, and the mixture was heated under reflux and stirred for 3 hours. The reaction mixture was concentrated, methylene chloride (200 mL) was added to the obtained solid, and filtration was carried out to give the title compound (7.1 g, yield: 48%).

¹H-NMR (400 MHz, CD₃OD) δ: 8.07 (1H, d, J=8.2 Hz), 7.34-7.27 (2H, m), 2.70 (3H, s).

Comparative Example 13

N-[4-(Hydrazinosulfonyl)-3-methylphenyl]acetamide

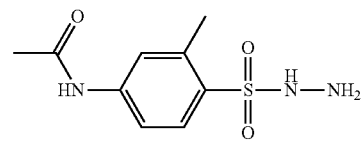 [SMILES: CC(=O)Nc1ccc(S(=O)(=O)NN)c(C)c1]

Under a nitrogen atmosphere, to 3-acetotoluidine (5.0 g, 34 mmol), chlorosulfuric acid (10 mL, 0.15 mol) was gradually added at room temperature, and the mixture was stirred at 70° C. for 10 hours. After the reaction, ice was added to the mixture to stop the reaction under ice-cooling and an aqueous phase was removed. To a suspension of the residue in THF (0.10 L), hydrazine monohydrate (5.1 mL, 0.10 mol) was gradually added, and the mixture was stirred at room temperature for 1.5 hours. After the reaction, THF was distilled off under reduced pressure. Thereafter, the produced solid was washed with water and diisopropyl ether, and it was dried to give the title compound (3.5 g, 43%) as an oil.

¹H-NMR (400 MHz, DMSO-d₆) δ: 10.22 (1H, s), 8.25-8.24 (1H, m), 7.75 (1H, d, J=4.7 Hz), 7.57-7.55 (2H, m), 4.07 (2H, d, J=2.7 Hz), 2.52 (3H, s), 2.07 (3H, s).

LRMS (FAB) m/z: 244 [M+H]⁺.

Comparative Example 14

N-[3-Methyl-4-(methylsulfonyl)phenyl]acetamide

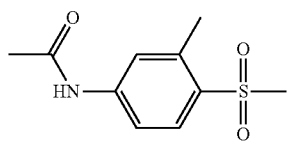

Under a nitrogen atmosphere, to a solution of the compound (3.5 g, 14 mmol) of Comparative Example 13 in ethanol (40 mL), methyl iodide (4.5 mL, 72 mmol) and sodium acetate (12 g, 0.14 mol) were added at room temperature, and the mixture was heated under reflux overnight. After the reaction, ethanol was distilled off under reduced pressure, ethyl acetate was added, and it was successively washed with water and saturated brine. Thereafter, it was dried with sodium sulfate and the solvent was distilled off under reduced pressure. The residue was purified by silica gel column chromatography (ethyl acetate/hexane, 4:1, v/v) to give the title compound (2.6 g, 79%) as a solid. (Reference literature: Tetrahedron, 45, 679 (1989)).

¹H-NMR (400 MHz, CDCl₃) δ: 7.96 (1H, d, J=8.6 Hz), 7.60 (1H, s), 7.50 (1H, s), 7.44 (1H, dd, J=8.6, 2.2 Hz), 3.06 (3H, s), 2.68 (3H, s), 2.22 (3H, s).

LRMS (EI) m/z: 227 [M]⁺.

Comparative Example 15

3-Methyl-4-(methylsulfonyl)aniline

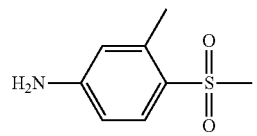

Under a nitrogen atmosphere, to a solution of the compound (2.6 g, 11 mmol) of Comparative Example 14 in ethanol (30 mL), concentrated hydrochloric acid (1.1 mL) was added, and the mixture was heated under reflux for 5 hours. After the reaction, ethanol was distilled off under reduced pressure and a 1N aqueous sodium hydroxide solution was added to make it basic. Thereafter, after the produced solid was washed with water and diisopropyl ether, it was dried to give the title compound (1.8 g, 84%) as a solid.

¹H-NMR (400 MHz, CDCl₃) δ: 7.80 (1H, d, J=8.2 Hz), 6.56-6.53 (2H, m), 4.09 (2H, br s), 3.03 (3H, s), 2.59 (3H, s).

LRMS (FAB) m/z: 186 [M+H]⁺.

Comparative Example 16

N-[3-Chloro-4-(hydrazinosulfonyl)phenyl]acetamide

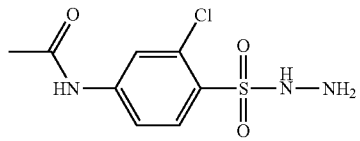 [SMILES: CC(=O)Nc1ccc(S(=O)(=O)NN)c(Cl)c1]

The title compound (3.5 g, 43%) was prepared as an oil from 3'-chloroacetoanilide (5.2 g, 31 mmol) in the process similar to Comparative Example 13.

¹H-NMR (400 MHz, DMSO-d₆) δ: 10.46 (1H, s), 8.48 (1H, br s), 7.97 (1H, d, J=2.0 Hz), 7.89 (1H, d, J=8.6 Hz), 7.57 (1H, dd, J=8.6, 2.0 Hz), 4.22 (2H, s), 2.10 (3H, s).

LRMS (FAB) m/z: 264 [M+H]⁺.

Comparative Example 17

N-[3-Chloro-4-(methylsulfonyl)phenyl]acetamide

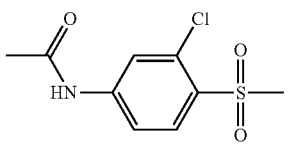

The title compound (2.7 g, 81%) was prepared as an oil from the compound (3.5 g, 13 mmol) of Comparative Example 16 in the process similar to Comparative Example 14.

¹H-NMR (400 MHz, CDCl₃) δ: 8.01 (1H, d, J=8.6 Hz), 7.93 (1H, d, J=2.0 Hz), 7.87 (1H, br s), 7.47 (1H, dd, J=8.6, 2.0 Hz), 3.27 (3H, s), 2.23 (3H, s).

LRMS (EI) m/z: 247 [M]⁺.

Comparative Example 18

3-Chloro-4-(methylsulfonyl)aniline

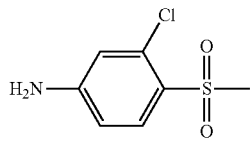

The title compound (2.0 g, 90%) was prepared as a solid from the compound (2.7 g, 11 mmol) of Comparative Example 17 in the process similar to Comparative Example 15.

$^1$H-NMR (400 MHz, CDCl$_3$) δ: 7.87 (1H, d, J=8.6 Hz), 6.75 (1H, d, J=2.4 Hz), 6.60 (1H, dd, J=8.6, 2.4 Hz), 4.27 (2H, br s), 3.21 (3H, s).

LRMS (EI) m/z: 205 [M]$^+$.

Comparative Example 19

N-[3-Fluoro-4-(hydrazinosulfonyl)phenyl]acetamide

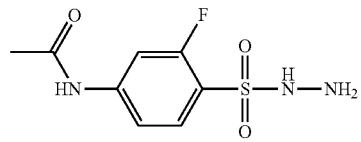

The title compound (2.5 g, 32%) was prepared from 3'-chloroacetoanilide (5.0 g, 31 mmol) in the process similar to Comparative Example 13.

$^1$H-NMR (400 MHz, DMSO-d$_6$) δ: 10.51 (1H, s), 8.49 (1H, s), 7.75 (1H, dd, J=13.3, 2.0 Hz), 7.70 (1H, t, J=8.6 Hz), 7.38 (1H, dd, J=8.6, 2.0 Hz), 4.23 (2H, s), 2.10 (3H, s).

Comparative Example 20

N-[3-Fluoro-4-(methylsulfonyl)phenyl]acetamide

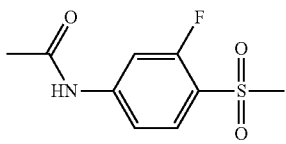

The title compound (1.8 g, 77%) was prepared from the compound (2.5 g, 10 mmol) of Comparative Example 19 in the process similar to Comparative Example 14.

$^1$H-NMR (400 MHz, CDCl$_3$) δ: 7.86-7.79 (2H, m), 7.73 (1H, s), 7.18 (1H, dd, J=9.0, 2.4 Hz), 3.22 (3H, s), 2.23 (3H, s).

Comparative Example 21

3-Fluoro-4-(methylsulfonyl)aniline

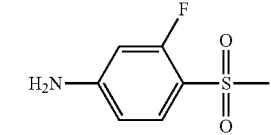

The title compound (1.4 g, 80%) was prepared from the compound (1.8 g, 7.7 mmol) of Comparative Example 20 in the process similar to Comparative Example 15.

$^1$H-NMR (400 MHz, CDCl$_3$) δ: 7.67 (1H, t, J=8.6 Hz), 6.47 (1H, dd, J=8.6, 2.0 Hz), 6.41 (1H, dd, J=8.6, 2.0 Hz), 4.34 (2H, s), 3.16 (3H, s).

Comparative Example 22

4-Chloro-2-(4-fluorophenoxy)aniline

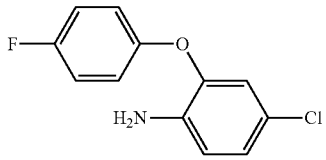 [SMILES: Nc1ccc(Cl)cc1Oc1ccc(F)cc1]

To a solution of 4-chloro-2-fluoronitrobenzene (3.0 g, 17.0 mmol) in DMF (8.7 mL), 4-fluorophenol (2.0 g, 17.9 mmol) and potassium carbonate (2.46 g, 17.9 mmol) were successively added, and the mixture was stirred at 70° C. for 2 hours. After the reaction, the mixture was cooled to room temperature and ethyl acetate was added to the mixture. After the organic phase was washed with water (30 mL), 1N sodium hydroxide (aq., 30 mL) and saturated brine (20 mL), it was dried with sodium sulfate. The solvent was distilled off under reduced pressure to give 4-chloro-2-(4-fluorophenoxy)-1-nitrobenzene as a crude product. The obtained compound was used for the subsequent reaction without further purification.

To a solution of 4-chloro-2-(4-fluorophenoxy)-1-nitrobenzene (4.56 g, 17.0 mmol) and iron powder (3.07 g, 55.0 mmol) in ethanol (20 mL), a saturated aqueous ammonium chloride solution (aq., 8.0 mL) was added, and the mixture was stirred at 90° C. for 30 minutes. After the reaction, the reaction mixture was cooled to room temperature, and ethyl acetate (30 mL) was added. After the organic phase was washed with water (30 mL), 1N sodium hydroxide (aq., 30 mL) and saturated brine (20 mL), it was dried with sodium sulfate. The solvent was distilled off under reduced pressure to give the title compound (3.62 g, 90%). The obtained compound was used for the subsequent reaction without further purification.

¹H-NMR (400 MHz, CDCl₃) δ: 7.15-6.89 (m, 5H), 6.75-6.73 (m, 2H), 3.85 (br. s, 2H).
MS (EI) for C₁₂H₉ClFNO, found 238.1 [M+H]⁺.

Comparative Example 23

5-Chloro-4'-fluorobiphenyl-2-amine

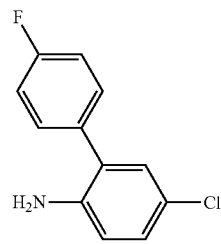 [SMILES: Nc1ccc(Cl)cc1-c1ccc(F)cc1]

To water (2 mL) and dimethoxyethane (20 mL), 5-chloro-2-nitrophenylboronic acid (3.27 g, 16.4 mmol), 1-fluoro-4-iodobenzene (3.65 g, 16.4 mmol), tetrakis(triphenylphosphine)palladium (0.95 g, 0.82 mmol) and potassium carbonate (6.81 g, 49.3 mmol) were added, and the mixture was stirred under a nitrogen atmosphere at 60° C. for 2 hours. After the reaction, the reaction mixture was cooled to room temperature and ethyl acetate (30 mL) was added. After the organic phase was washed with water (30 mL) and saturated brine (20 mL), it was dried with sodium sulfate. The solvent was distilled off under reduced pressure to give 5-chloro-4'-fluoro-2-nitrobiphenyl as a crude product. The obtained compound was used for the subsequent reaction without further purification.

To a solution of the above 5-chloro-4'-fluoro-2-nitrobiphenyl (4.20 g, 15.7 mmol) and iron powder (2.75 g, 49.3 mmol) in ethanol (20 mL), a saturated aqueous ammonium chloride solution (aq., 8.0 mL) was added, and the mixture was stirred at 90° C. for 30 minutes. After the reaction, the reaction mixture was cooled to room temperature and ethyl acetate (30 mL) was added. After the organic phase was washed with water (30 mL), it was dried with sodium sulfate. After the filtration and concentration, the residue was purified by silica gel column chromatography (ethyl acetate/hexane, 1:20-1:3, v/v) to give the title compound (2.43 g, 11.0 mmol, 67%).

¹H-NMR (400 MHz, DMSO-d₆) δ: 7.45 (dd, J=8.4, 6.0 Hz, 2H), 7.27 (t, J=8.8 Hz, 2H), 7.07 (dd, J=8.8, 2.8 Hz, 1H), 6.97 (d, J=2.4 Hz, 1H), 6.75 (d, J=8.4 Hz, 1H), 4.98 (br. s, 2H). MS (EI) for C₁₂H₉ClFN, found 222.1 (M+H⁺).

Comparative Example 28

5-[2-(Benzyloxy)ethyl]-1-(4-fluoro-2-methylphenyl)-2-methyl-1H-pyrrole-3-carboxylic acid ethyl ester

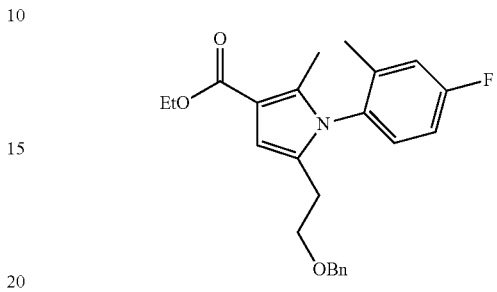

To a solution of the compound (1.0 g, 3.3 mmol) of Comparative Example 5 in acetic acid (5 ml), 4-fluoro-2-methylaniline (0.38 ml, 3.4 mmol) was added, and the mixture was stirred at 100° C. for 10 hours. 10 ml of water was poured to the reaction mixture, and after the organic layer was extracted with diethyl ether, it was washed with a 1N aqueous sodium hydroxide solution, water, a saturated aqueous ammonium chloride solution and saturated brine, and dried with sodium sulfate. The solvent was distilled off under reduced pressure and the residue was purified by silica gel column chromatography (hexane-hexane:ethyl acetate=1:1) to give the title compound (0.87 g, 67%) as an oil.

MS (ES+) m/z: 396 [M+H]⁺.

The compounds in the following (Table 3) were prepared similarly to (Comparative Example 28).

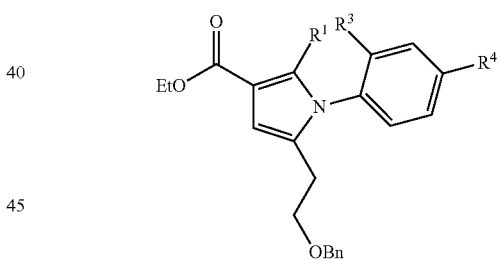

TABLE 3

| R<sub>Comparative</sub> Example Number | R¹ | R³ | R⁴ | Compound Name | MS and/or ¹H-NMR spectrum |
|---|---|---|---|---|---|
| 29 | Me | Me | Cl | 5-[2-(benzyloxy)ethyl]-1-(4-chloro-2-methylphenyl)-2-methyl-1H-pyrrole-3-carboxylic acid ethyl ester | MS (ES+) m/z: 412 [M + H]⁺. |
| 30 | Me | Cl | F | 5-[2-(benzyloxy)ethyl]-1-(2-chloro-4-fluorophenyl)-2-methyl-1H-pyrrole-3-carboxylic acid ethyl ester | MS (ESI) m/z: 416 [M + H]⁺. |
| 31 | Me | Cl | Cl | 5-[2-(benzyloxy)ethyl]-1-(2,4-dichlorophenyl)-2-methyl-1H-pyrrole-3-carboxylic acid ethyl ester | MS (ESI) m/z: 432 [M + H]⁺. |

TABLE 3-continued

| Comparative Example Number | R¹ | R³ | R⁴ | Compound Name | MS and/or ¹H-NMR spectrum |
|---|---|---|---|---|---|
| 32 | Me | CF₃ | H | 5-[2-(benzyloxy)ethyl]-2-methyl-1-[2-(trifluoromethyl)phenyl]-1H-pyrrole-3-carboxylic acid ethyl ester | MS (FAB) m/z: 432 [M + H]⁺. |
| 33 | Me | CF₃ | F | 5-[2-(benzyloxy)ethyl]-1-[4-fluoro-2-(trifluoromethyl)phenyl]-2-methyl-1H-pyrrole-3-carboxylic acid ethyl ester | MS (ES+) m/z: 450 [M + H]⁺. |
| 34 | Me | CF₃ | Cl | 5-[2-(benzyloxy)ethyl]-1-[4-chloro-2-(trifluoromethyl)phenyl]-2-methyl-1H-pyrrole-3-carboxylic acid ethyl ester | ¹H-NMR (400 MHz, CDCl₃) d 7.80 (1H, d, J = 2.3 Hz), 7.55 (1H, dd, J = 8.6, 2.4 Hz), 7.40-7.24 (5H, m), 7.11 (1H, d, J = 8.2 Hz), 6.44 (1H, s), 4.45 (2H, s), 4.28 (2H, q, J = 7.2 Hz), 3.59 (2H, t, J = 7.2 Hz), 2.62-2.55 (1H, m), 2.41-2.33 (1H, m), 2.17 (3H, s), 1.35 (3H, t, J = 7.2 Hz). |
| 35 | Me | OCF₂H | F | 5-[2-(benzyloxy)ethyl]-1-[2-(difluoromethoxy)-4-fluorophenyl]-2-methyl-1H-pyrrole-3-carboxylic acid ethyl ester | MS (ES+) m/z: 448 [M + H]⁺. |

Comparative Example 36

5-[(2S)-2-Benzyloxypropyl]-1-(2-chloro-4-methylphenyl)-2-methyl-1H-pyrrole-3-carboxylic acid ethyl ester

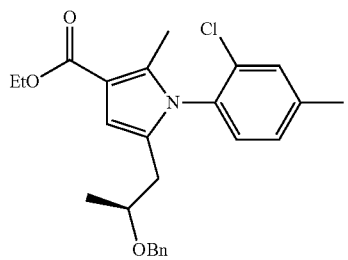 [SMILES: CCOC(=O)c1cc(C[C@H](C)OCc2ccccc2)n(-c2ccc(C)cc2Cl)c1C]

The title compound (1.2 g, 61%) was obtained from the compound (1.5 g, 4.7 mmol) of Comparative Example 2 and 2-chloro-4-methylaniline (0.64 g, 4.6 mmol) in the process similar to Comparative Example 28.

¹H-NMR (400 MHz, CDCl₃) δ: 7.37-7.09 (7H, m), 7.05 (0.5H, d, J=8.2 Hz), 6.97 (0.5H, d, J=8.2 Hz), 6.47 (0.5H, s), 6.46 (0.5H, s), 4.41-4.24 (4H, m), 3.64-3.55 (0.5H, m), 3.50-3.41 (0.5H, m), 2.72 (0.5H, dd, J=15.3, 5.5 Hz), 2.55 (0.5H, dd, J=15.3, 5.9 Hz), 2.42 (1.5H, s), 2.41 (1.5H, s), 2.37 (0.5H, dd, J=15.3, 7.4 Hz), 2.30 (0.5H, dd, J=14.9, 8.2 Hz), 2.22 (1.5H, s), 2.21 (1.5H, s), 1.36 (3H, t, J=7.0 Hz), 1.16 (1.5H, d, J=6.3 Hz), 1.13 (1.5H, d, J=6.3 Hz).

MS (ESI) m/z: 426 [M+H]⁺.

The compounds in the following (Table 4) were prepared, if necessary, using the compound of Comparative Example 4 instead of the compound of Comparative Example 2 in the process similar to (Comparative Example 36).

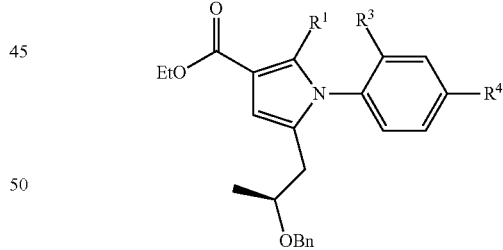

TABLE 4

| Comparative Example Number | R¹ | R³ | R⁴ | Compound Name | MS and/or ¹H-NMR spectrum |
|---|---|---|---|---|---|
| 37 | Me | Cl | F | 5-[(2S)-2-benzyloxypropyl]-1-(2-chloro-4-fluorophenyl)-2-methyl-1H-pyrrole-3-carboxylic acid ethyl ester | MS (FAB) m/z: 430 [M + H]⁺. |
| 38 | Me | Cl | Cl | 5-[(2S)-2-benzyloxypropyl]-1-(2,4-dichlorophenyl)-2-methyl-1H-pyrrole-3-carboxylic acid ethyl ester | MS (ESI) m/z: 446 [M + H]⁺. |

TABLE 4-continued

| Comparative Example Number | R¹ | R³ | R⁴ | Compound Name | MS and/or ¹H-NMR spectrum |
|---|---|---|---|---|---|
| 39 | Me | Me | F | 5-[(2S)-2-benzyloxypropyl]-1-(4-fluoro-2-methylphenyl)-2-methyl-1H-pyrrole-3-carboxylic acid ethyl ester | ¹H-NMR (400 MHz, CDCl₃) δ: 7.33-7.22 (3H, m), 7.21-7.15 (2H, m), 7.05-6.87 (3H, m), 6.48 (0.6H, s), 6.46 (0.4H, s), 4.42 (0.6H, d, J = 11.7 Hz), 4.37 (0.4H, d, J = 11.1 Hz), 4.34-4.25 (3H, m), 3.58-3.42 (1H, m), 2.61 (0.6H, dd, J = 14.9, 5.9 Hz), 2.46 (0.4H, dd, J = 14.9, 5.5 Hz), 2.35 (0.4H, dd, J = 14.9, 7.4 Hz), 2.24 (0.6H, dd, J = 14.9, 7.4 Hz), 2.17 (1.2H, s), 2.16 (1.8H, s), 1.88 (1.2H, s), 1.85 (1.8H, s), 1.36 (3H, t, J = 7.0 Hz), 1.17 (1.2H, d, J = 5.9 Hz), 1.12 (1.8H, d, J = 5.9 Hz). MS (ESI) m/z: 410 [M + H]⁺. |
| 40 | Me | Me | Cl | 5-[(2S)-2-benzyloxypropyl]-1-(4-chloro-2-methylphenyl)-2-methyl-1H-pyrrole-3-carboxylic acid ethyl ester | MS (ESI) m/z: 426 [M + H]⁺. |
| 41 | Me | CF₂H | F | 5-[(2S)-2-benzyloxypropyl]-1-[2-(difluoromethyl)-4-fluorophenyl]-2-methyl-1H-pyrrole-3-carboxylic acid ethyl ester | MS (FAB) m/z: 446 [M + H]⁺. |
| 42 | Me | CF₂H | Cl | 5-[(2S)-2-benzyloxypropyl]-1-[4-chloro-2-(difluoromethyl)phenyl]-2-methyl-1H-pyrrole-3-carboxylic acid ethyl ester | MS (FAB) m/z: 462 [M + H]⁺. |
| 43 | Me | CF₃ | H | 5-[(2S)-2-benzyloxypropyl]-2-methyl-1-[2-(trifluoromethyl)phenyl]-1H-pyrrole-3-carboxylic acid ethyl ester | MS (FAB) m/z: 446 [M + H]⁺. |
| 44 | Me | CF₃ | F | 5-[(2S)-2-benzyloxypropyl]-1-[4-fluoro-2-(trifluoromethyl)phenyl]-2-methyl-1H-pyrrole-3-carboxylic acid ethyl ester | ¹H-NMR (400 MHz, CDCl₃) δ: 7.52-7.47 (1H, m), 7.33-7.16 (6H, m), 7.09 (0.3H, dd, J = 9.0, 5.1 Hz), 6.98 (0.7H, dd, J = 8.6, 5.1 Hz), 6.47 (0.7H, s), 6.45 (0.3H, s), 4.50 (0.7H, d, J = 11.9 Hz), 4.46 (0.3H, d, J = 11.8 Hz), 4.35 (0.7H, d, J = 11.9 Hz), 4.31 (0.3H, d, J = 11.8 Hz), 4.29 (2H, q, J = 7.1 Hz), 3.68-3.52 (1H, m), 2.68 (0.7H, dd, J = 15.2, 5.5 Hz), 2.43 (0.3H, dd, J = 15.4, 6.5 Hz), 2.32 (0.3H, dd, J = 15.3, 6.6 Hz), 2.19-2.13 (3.7H, m), 1.36 (3H, t, J = 7.1 Hz), 1.18 (1H, d, J = 6.3 Hz), 1.13 (2H, d, J = 5.9 Hz). |
| 45 | Me | CF₃ | Cl | 5-[(2S)-2-benzyloxypropyl]-1-[4-chloro-2-(trifluoromethyl)phenyl]-2-methyl-1H-pyrrole-3-carboxylic acid ethyl ester | MS (FAB) m/z: 480 [M + H]⁺. |
| 46 | Me | OCF₂H | Me | 5-[(2S)-2-benzyloxypropyl]-1-[2-(difluoromethoxy)-4-methylphenyl]-2-methyl-1H-pyrrole-3-carboxylic acid ethyl ester | ¹H-NMR (400 MHz, CDCl₃) δ: 7.33-7.04 (7.5H, m), 6.94 (0.5H, d, J = 8.6 Hz), 6.45 (0.5H, s), 6.44 (0.5H, s), 6.26 (0.5H, d, J = 73.5 Hz), 6.16 (0.5H, d, J = 73.5 Hz), 4.38 (0.5H, d, J = 12.1 Hz), 4.36 (0.5H, d, J = 12.1 Hz), 4.34-4.25 (3H, m), 3.62-3.53 (0.5H, m), 3.50-3.40 (0.5H, m), 2.69 (0.5H, dd, J = 15.3, 5.5 Hz), 2.58 (0.5H, dd, J = 15.3, 5.5 Hz), 2.44 (3H, s), 2.40 (0.5H, dd, J = 15.3, 7.4 Hz), 2.32 (0.5H, dd, J = 15.3, 7.8 Hz), 2.23 (1.5H, s), 2.21 (1.5H, s), 1.36 (3H, t, J = 7.0 Hz), 1.14 |

TABLE 4-continued

| Comparative Example Number | R¹ | R³ | R⁴ | Compound Name | MS and/or ¹H-NMR spectrum |
|---|---|---|---|---|---|
| | | | | | (1.5H, d, J = 5.9 Hz), 1.11 (1.5H, d, J = 5.9 Hz).<br>MS (ESI) m/z: 458 [M + H]⁺. |
| 47 | Me | OCF₂H | F | 5-[(2S)-2-benzyloxypropyl]-1-[2-(difluoromethoxy)-4-flurophenyl]-2-methyl-1H-pyrrole-3-carboxylic acid ethyl ester | ¹H-NMR (400 MHz, CDCl₃) δ: 7.38-7.23 (3H, m), 7.21-7.06 (3H, m), 7.05-6.91 (2H, m), 6.46 (0.5H, s), 6.45 (0.5H, s), 6.27 (0.5H, t, J = 72.0 Hz), 6.17 (0.5H, t, J = 72.0 Hz), 4.42 (0.5H, d, J = 12.1 Hz), 4.41 (0.5H, d, J = 12.1 Hz), 4.35-4.25 (3H, m), 3.62-3.32 (0.5H, m), 3.46-3.36 (0.5H, m), 2.65 (0.5H, dd, J = 15.3, 5.9 Hz), 2.51 (0.5H, dd, J = 15.3, 6.3 Hz), 2.41 (0.5H, dd, J = 15.3, 6.7 Hz), 2.32 (0.5H, dd, J = 15.3, 7.4 Hz), 2.21 (1.5H, s), 2.20 (1.5H, s), 1.36 (3H, t, J = 7.0 Hz), 1.14 (1.5H, d, J = 5.9 Hz), 1.11 (1.5H, d, J = 5.9 Hz).<br>MS (ESI) m/z: 462 [M + H]⁺. |
| 48 | Me | OCF₂H | Cl | 5-[(2S)-2-benzyloxypropyl]-1-[4-chloro-2-(difluoro-methoxy)phenyl]-2-methyl-1H-pyrrole-3-carboxylic acid ethyl ester | ¹H-NMR (400 MHz, CDCl₃) δ: 7.37-7.14 (7H, m), 7.08 (0.5H, d, J = 8.2 Hz), 6.97 (0.5H, d, J = 8.2 Hz), 6.47 (0.5H, s), 6.46 (0.5H, s), 6.25 (0.5H, t, J = 72.0 Hz), 6.13 (0.5H, t, J = 72.0 Hz), 4.42 (0.5H, d, J = 12.1 Hz), 4.40 (0.5H, d, J = 12.1 Hz), 4.35-4.25 (3H, m), 3.62-3.52 (0.5H, m), 3.46-3.36 (0.5H, m), 2.65 (0.5H, dd, J = 15.3, 5.9 Hz), 2.51 (0.5H, dd, J = 15.3, 6.3 Hz), 2.42 (0.5H, dd, J = 15.3, 6.3 Hz), 2.32 (0.5H, dd, J = 15.3, 7.4 Hz), 2.22 1.5H, s), 2.20 (1.5H, s), 1.36 (3H, t, J = 7.0 Hz), 1.14 (1.5H, d, J = 6.3 Hz), 1.11 (1.5H, d, J = 6.3 Hz.<br>MS (ESI) m/z: 478 [M + H]⁺. |
| 49 | Me | OCF₃ | F | 5-[(2S)-2-benzyloxypropyl]-1-[4-fluoro-2-(trifluoro-methoxy)phenyl]-2-methyl-1H-pyrrole-3-carboxylic acid ethyl ester | ¹H-NMR (500 MHz, CDCl₃) δ: 7.34-6.98 (8H, m), 6.47 (0.5H, s), 6.45 (0.5H, s), 4.48-4.40 (1H, m), 4.35-4.24 (3H, m), 3.64-3.56 (0.5H, m), 3.48-3.41 (0.5H, m), 2.68 (0.5H, dd, J = 5.4, 15.1 Hz), 2.50-2.36 (1H, m), 2.29 (0.5H, dd, J = 7.3, 15.1 Hz), 2.21 (1.5H, s), 2.20 (1.5H, s), 1.36 (3H, d, J = 7.3 Hz), 1.15 (1.5H, d, J = 5.9 Hz), 1.11 (1.5H, d, J = 5.9 Hz). |

TABLE 4-continued

| Comparative Example Number | R¹ | R³ | R⁴ | Compound Name | MS and/or ¹H-NMR spectrum |
|---|---|---|---|---|---|
| 50 | Me | OCF₃ | Cl | 5-[(2S)-2-benzyloxypropyl]-1-[4-chloro-2-(trifluoromethoxy)phenyl]-2-methyl-1H-pyrrole-3-carboxylic acid ethyl ester | MS (ESI) m/z: 496 [M + H]⁺. |
| 51 | Me | 4-F—PhO | Cl | 5-[(2S)-2-benzyloxypropyl]-1-[4-chloro-2-(4-fluorophenoxy)phenyl]-2-methyl-1H-pyrrole-3-carboxylic acid ethyl ester | MS (ESI) m/z: 522 [M + H]⁺. |
| 52 | Et | Cl | F | 5-[(2S)-2-benzyloxypropyl]-1-(2-chloro-4-fluorophenyl)-2-ethyl-1H-pyrrole-3-carboxylic acid ethyl ester | MS (ESI) m/z: 444 [M + H]⁺. |

Comparative Example 53

5-[(2S)-2-Benzyloxypropyl]-1-[2-(difluoromethoxy)-4-fluorophenyl]-2-ethyl-1H-pyrrole-3-carboxylic acid methyl ester

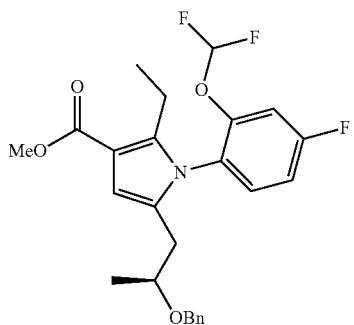 [SMILES: CCc1c(C(=O)OC)cc(C[C@H](C)OCc2ccccc2)n1-c1ccc(F)cc1OC(F)F]

The title compound (0.58 g, 10%) was obtained from the compound (3.8 g, 12 mmol) of Comparative Example 3 and the compound (1.9 g, 12 mmol) of Comparative Example 9 in the process similar to Comparative Example 28.

MS (FAB) m/z: 462 [M+H]⁺.

Comparative Example 54

5-[(2S)-2-Benzyloxypropyl]-1-[4-chloro-2-(trifluoromethyl)phenyl]-2-ethyl-1H-pyrrole-3-carboxylic acid ethyl ester

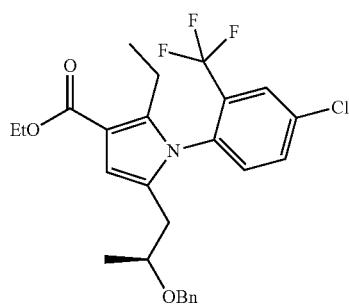 [SMILES: CCOC(=O)c1cc(C[C@H](C)OCc2ccccc2)n(-c2ccc(Cl)cc2C(F)(F)F)c1CC]

To a neat mixture of diketone (2.02 g, 6 mmol) and 2-trifluoromethyl-4-chloroaniline (0.85 mL, 6 mmol) was added Sc(OTf)₃ (148 mg, 0.3 mmol). The reaction was stirred at room temperature for 15 h, and then was evaporated from CH₃CN (2×10 mL) to remove water. The crude residue was purified by chromatography on silica gel (2% diethyl ether in 1/1—hexane/CH₂Cl₂) to afford the pyrrole product (1.48 g, 49%) as a pale yellow oil.

¹H-NMR (400 MHz, CDCl₃) δ: 7.77 (1H, m), 7.51 (0.5H, dd, J=8.4, 2.0 Hz), 7.45 (0.5H, dd, J=8.4, 2.0 Hz), 7.33-7.21 (4H, m), 7.17 (1H, m), 7.09 (0.5H, d, J=8.4 Hz), 6.98 (0.5H, d, J=8.4), 6.47 (0.5H, s), 6.45 (0.5H, s), 4.50 (0.5H, d, J=12.0 Hz), 4.46 (0.5H, d, J=11.6 Hz), 4.37-4.25 (3H, m), 3.68-3.54 (1H, m), 3.04-2.93 (1H, m), 2.66 (0.5H, dd, J=15.6, 5.6 Hz), 2.42 (0.5H, dd, J=15.2, 6.0 Hz), 2.26 (0.5H, dd, J=15.2, 6.8 Hz), 2.19-2.06 (1.5H, m), 1.36 (3H, t, J=7.2 Hz), 1.18 (1.5H, d, J=6.4 Hz), 1.13 (1.5H, d, J=6.0 Hz), 1.00-0.96 (3H, m).

The compounds in the following (Table 5) were prepared, if necessary, using the compound of Comparative Example 2 instead of the compound of Comparative Example 4 in the process similar to (Comparative Example 54).

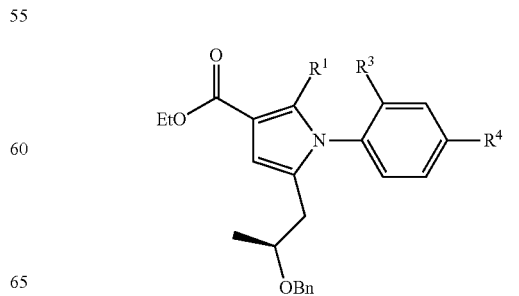

TABLE 5

| Comparative Example Number | R¹ | R³ | R⁴ | Compound Name | MS and/or ¹H-NMR spectrum |
|---|---|---|---|---|---|
| 55 | Et | Cl | Cl | 5-[(2S)-2-benzyloxypropyl]-1-(2,4-dichlorophenyl)-2-ethyl-1H-pyrrole-3-carboxylic acid ethyl ester | ¹H-NMR (400 MHz, CDCl₃) δ: 7.55 (0.5H, d, J = 2.4 Hz), 7.50 (0.5H, d, J = 2.0 Hz), 7.33-7.24 (4H, m), 7.18 (2H, m), 7.12 (0.5H, d, J = 8.4 Hz), 6.99 (0.5H, d, J = 8.4 Hz), 6.50 (0.5H, s), 6.48 (0.5H, s), 4.42 (1H, dd, J = 5.2, 12.0 Hz), 4.33-4.26 (3H, m), 3.60-3.55 (0.5H, m), 3.46-3.43 (0.5H, m), 2.79-2.64 (1.5H, m), 2.53-2.40 (2H, m), 2.25 (0.5H, dd, J = 7.6, 14.8 Hz), 1.36 (3H, t, 7.0 Hz), 1.17 (1.5H, d, J = 6.0 Hz), 1.13 (1.5H, d, J = 6.0 Hz), 0.99-0.94 (3H, m). |
| 56 | Et | CF₃ | F | 5-[(2S)-2-benzyloxypropyl]-2-ethyl-1-[4-fluoro-2-(trifluoromethyl)phenyl]-1H-pyrrole-3-carboxylic acid ethyl ester | ¹H-NMR (400 MHz, CDCl₃) δ: 7.51-7.48 (1H, m), 7.33-7.14 (6.4H, m), 7.05 (0.6H, dd, J = 8.8, 8.4 Hz), 6.47 (0.6H, s), 6.45 (0.4H, s), 4.50 (0.6H, d, J = 11.6.0 Hz), 4.46 (0.4H, d, J = 11.6 Hz), 4.35 (0.6H, d, J = 11.6 Hz), 4.33-4.25 (2.4H, m), 3.68-3.54 (1H, m), 3.02-2.93 (1H, m), 2.67 (0.6H, dd, J = 14.8, 5.2 Hz), 2.42 (0.4H, dd, J = 15.2, 6.0 Hz), 2.27 (0.4H, dd, J = 15.2, 6.8 Hz), 2.20-2.08 (1.6H, m), 1.37 (3H, t, J = 7.2 Hz), 1.18 (1.2H, d, J = 6.4 Hz), 1.13 (1.8H, d, J = 6.0 Hz), 1.00-0.96 (3H, m). |
| 57 | Me | 4-F—Ph | Cl | 5-[(2S)-2-benzyloxypropyl]-1-(5-chloro-4'-fluorobiphenyl-2-yl)-2-methyl-1H-pyrrole-3-carboxylic acid ethyl ester | MS (ESI) m/z: 506 [M + H]⁺. |

Comparative Example 58

1-(4-Chloro-2-methylphenyl)-5-[(2S)-2-benzyloxypropyl]-2-methyl-1H-pyrrole-3-carboxylic acid

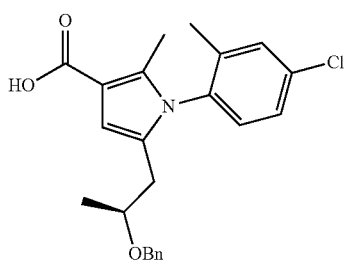 [SMILES: Cc1cc(Cl)ccc1-n1c(C[C@H](C)OCc2ccccc2)cc(C(=O)O)c1C]

To a solution of (6S)-2-acetyl-6-(benzyloxy)-4-oxoheptanoic acid ethyl ester (2.5 g, 7.8 mmol) in acetic acid (8 ml), 4-chloro-2-methylaniline (1.1 g, 7.8 mmol) was added, and the mixture was stirred at 110° C. for 15 hours. 15 ml of water was poured to the reaction mixture, and after the organic layer was extracted with diethyl ether, it was washed with 1N aqueous sodium hydroxide solution, water, a saturated aqueous ammonium chloride solution and saturated brine, and dried with sodium sulfate. The solvent was distilled off under reduced pressure and the residue was crudely purified by silica gel column chromatography. Subsequently, the product was dissolved in a 5M aqueous sodium hydroxide solution (30 mL) and methanol (40 mL), and the mixture was stirred at 100° C. for 4 hours. After the reaction, 2M hydrochloric acid (80 mL) was added under ice-cooling to neutralize it, and it was extracted with ethyl acetate. The obtained organic layer was washed with water and saturated brine and dried with sodium sulfate. The solvent was distilled off under reduced pressure and the residue was purified by silica gel column chromatography to give the title compound (2.3 g, 73%).

¹H-NMR (400 MHz, CDCl₃) δ: 7.35-7.13 (7H, m), 6.98 (0.4H, d, J=8.2 Hz), 6.86 (0.6H, d, J=8.2 Hz), 6.53 (1H, d, J=7.8 Hz), 4.45-4.25 (2H, m), 3.60-3.40 (1H, m), 2.60 (0.6H, dd, J=6.3, 15.3 Hz), 2.46 (0.4H, dd, J=5.5, 14.9 Hz), 2.37 (0.4H, dd, J=7.4, 15.3 Hz), 2.25 (0.6H, d, J=6.7 Hz), 2.20-2.18 (3H, m), 1.88 (1.2H, s), 1.84 (1.8H, s), 1.17 (1.2H, d, J=5.9 Hz), 1.12 (1.8H, d, J=6.3 Hz).

Comparative Example 59

1-(4-Fluoro-2-methylphenyl)-5-[(2S)-2-benzyloxypropyl]-2-methyl-1H-pyrrole-3-carboxylic acid

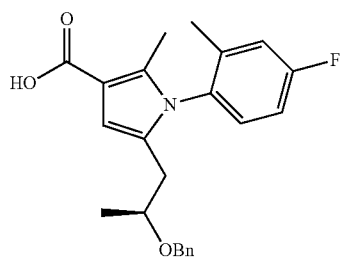 [SMILES: Cc1cc(F)ccc1-n1c(C[C@H](C)OCc2ccccc2)cc(C(=O)O)c1C]

The compound (2.8 g, 6.8 mmol) of Comparative Example 39 was dissolved in a 5M aqueous sodium hydroxide solution (30 mL) and methanol (45 mL), and the mixture was stirred at 100° C. for 4 hours. After the reaction, 2M hydrochloric acid (75 mL) was added under ice-cooling to neutralize it, and it was extracted with ethyl acetate. The obtained organic layer was washed with water and saturated brine and dried with sodium sulfate. The solvent was distilled off under reduced pressure and the residue was purified by silica gel column chromatography to give the title compound (2.6 g, 99%).

MS (ESI) m/z: 382 [M+H]⁺

Abbreviations of aniline reagents used in the following Comparative Examples and Examples are shown in the following.
Aniline A: 4-methylsulfonylaniline
Aniline B: 4-aminosulfonylaniline
Aniline C: 4-aminosulfonyl-3-chloroaniline [Synthesized by the method described in Patent document (WO2006/012642)].

Comparative Example 60

5-[2-(Benzyloxy)ethyl]-1-[4-chloro-2-(trifluoromethyl)phenyl]-2-methyl-N-[4-(methylsulfonyl)phenyl]-1H-pyrrole-3-carboxamide

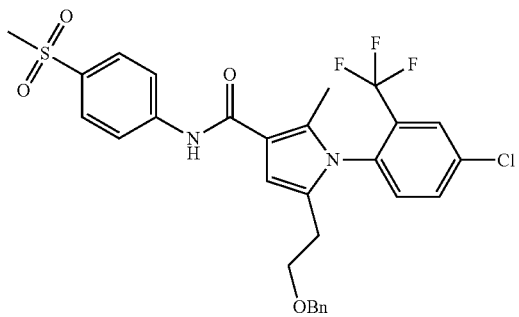 [SMILES: Cc1c(C(=O)Nc2ccc(S(C)(=O)=O)cc2)cc(CCOCc2ccccc2)n1-c1ccc(Cl)cc1C(F)(F)F]

To a solution of the compound (75 g, 0.16 mol) of Comparative Example 34 in methanol (0.95 L), a 5N aqueous sodium hydroxide solution (0.64 L, 3.2 mol) was added, and the mixture was heated under reflux for 4 hours. After the reaction, methanol was distilled off under reduced pressure, and after 5N hydrochloric acid was added to acidify it, it was extracted with ethyl acetate. After it was successively washed with water and saturated brine, it was dried with sodium sulfate and the solvent was distilled off under reduced pressure. The residue was purified by silica gel column chromatography (ethyl acetate/hexane, 1:2, v/v) to give pyrrolecarboxylic acid (63 g, 89%). Under a nitrogen atmosphere, to a solution of pyrrolecarboxylic acid (63 g, 0.14 mol) in methylene chloride, oxalyl chloride (15 mL, 0.17 mol) was added, and after the mixture was stirred at room temperature for 2 hours, methylene chloride was distilled off under reduced pressure. Tetrahydrofuran (0.43 L) was added to the residue, aniline A (31 g, 0.15 mol) and diisopropylethylamine (75 mL, 0.43 mol) were successively added, and the mixture was stirred at 70° C. overnight. After the reaction, tetrahydrofuran was distilled off under reduced pressure. After 5N hydrochloric acid was added to acidify it, it was extracted with diethyl ether. After it was successively washed with water, a saturated aqueous sodium hydrogencarbonate solution and saturated brine, it was dried with sodium sulfate and the solvent was distilled off under reduced pressure. The residue was purified by silica gel column chromatography (ethyl acetate/hexane, 1:1, v/v) to give the desired compound (77 g, 81%) as a solid.

¹H-NMR (400 MHz, CDCl₃) δ: 7.91 (2H, d, J=8.6 Hz), 7.81 (2H, d, J=8.6 Hz), 7.67 (1H, s), 7.59 (1H, dd, J=8.2, 2.4 Hz), 7.37-7.25 (6H, m), 7.13 (1H, d, J=8.2 Hz), 6.28 (1H, s), 4.48 (2H, s), 3.62-3.57 (2H, m), 3.05 (3H, s), 2.66-2.59 (1H, m), 2.46-2.38 (1H, m), 2.24 (3H, s).

The compounds in the following (Table 6) were prepared by reacting them with aniline B in the process similar to (Comparative Example 60).

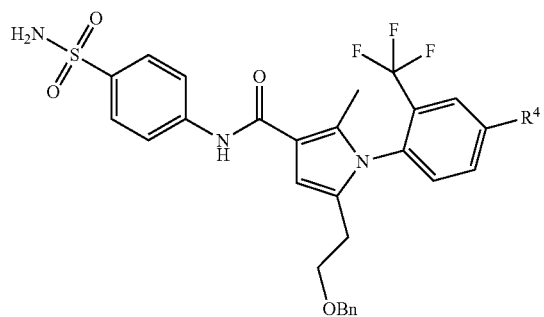

TABLE 6

| Comparative Example Number | R⁴ | Compound Name | MS and/or ¹H-NMR spectrum |
|---|---|---|---|
| 61 | F | N-[4-(aminosulfonyl)phenyl]-5-[2-(benzyloxy)ethyl]-1-[4-fluoro-2-(trifluoromethyl)phenyl]-2-methyl-1H-pyrrole-3-carboxamide | MS (ES+) m/z: 576 [M + H]⁺. |
| 62 | Cl | N-[4-(aminosulfonyl)phenyl]-1-[4-chloro-2-(trifluoromethyl)phenyl]-5-[2-(benzyloxy)ethyl]-2-methyl-1H-pyrrole-3-carboxamide | MS (ES+) m/z: 592 [M + H]⁺. |

Comparative Example 63

5-[2-(Benzyloxy)ethyl]-2-methyl-N-[4-(methylsulfonyl)phenyl]-1-[2-(trifluoromethyl)phenyl]-1H-pyrrole-3-carboxamide

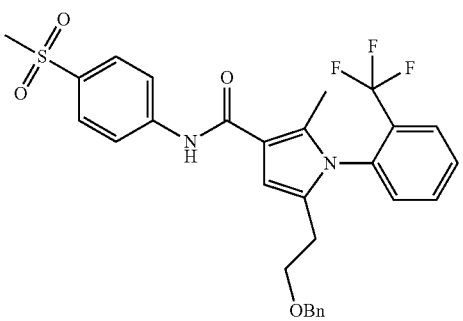 [SMILES: Cc1c(C(=O)Nc2ccc(S(C)(=O)=O)cc2)cc(CCOCc2ccccc2)n1-c1ccccc1C(F)(F)F]

Under a nitrogen atmosphere, to a suspension of the compound (0.17 g, 0.39 mmol) of Comparative Example 32 and aniline A (71 mg, 0.41 mmol) in toluene (3 mL), trimethyl aluminum (1.8M toluene solution, 0.43 mL, 0.77 mmol) was added. Subsequently, after the temperature of the mixture was raised to 110° C., the mixture was stirred for 1 hour. After the reaction, 2M hydrochloric acid (0.5 mL) was added under ice-cooling and it was extracted once with ethyl acetate (10 mL). The organic layer was successively washed with water (10 mL) and a saturated aqueous sodium chloride solution (10 mL). After it was dried with sodium sulfate, the solvent was distilled off under reduced pressure. The obtained residue was purified by silica gel column chromatography to give the title desired compound (0.16 g, yield: 75%).

MS (FAB) m/z: 557 [M+H]$^+$.

The compounds in the following (Table 7) were prepared by reacting them with aniline A in the process similar to (Comparative Example 63).

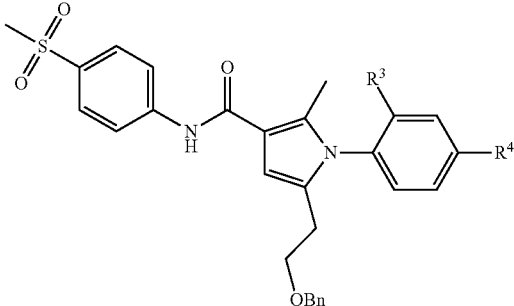

TABLE 7

| Comparative Example Number | R$^3$ | R$^4$ | Compound Name | MS and/or $^1$H-NMR spectrum |
|---|---|---|---|---|
| 64 | Cl | F | 5-[2-(benzyloxy)ethyl]-1-(2-chloro-4-fluorophenyl)-2-methyl-N-[4-(methylsulfonyl)phenyl]-1H-pyrrole-3-carboxamide | MS (ESI) m/z: 541 [M + H]$^+$. |
| 65 | Cl | Cl | 5-[2-(benzyloxy)ethyl]-1-(2,4-dichlorophenyl)-2-methyl-N-[4-(methylsulfonyl)phenyl]-1H-pyrrole-3-carboxamide | MS (ESI) m/z: 557 [M + H]$^+$. |
| 66 | Me | F | 5-[2-(benzyloxy)ethyl]-1-(4-fluoro-2-methylphenyl)-2-methyl-N-[4-(methylsulfonyl)phenyl]-1H-pyrrole-3-carboxamide | MS (FAB+) m/z: 521 [M + H]$^+$. |
| 67 | Me | Cl | 5-[2-(benzyloxy)ethyl]-1-(4-chloro-2-methylphenyl)-2-methyl-N-[4-(methylsulfonyl)phenyl]-1H-pyrrole-3-carboxamide | MS (FAB+) m/z: 535 [M − H]$^+$. |
| 68 | OCF$_2$H | F | 5-[2-(benzyloxy)ethyl]-1-[2-(difluoromethoxy)-4-fluorophenyl]-2-methyl-N-[4-(methylsulfonyl)phenyl]-1H-pyrrole-3-carboxamide | MS (FAB+) m/z: 572 [M]$^+$. |

Comparative Example 69

5-[(2S)-2-(Benzyloxy)propyl]-1-[4-chloro-2-(trifluoromethyl)phenyl]-2-methyl-N-[4-(methylsulfonyl)phenyl]-1H-pyrrole-3-carboxamide

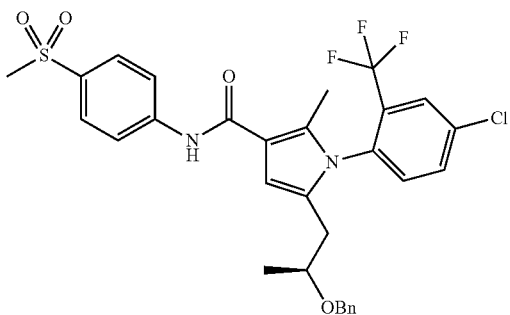 [SMILES: Cc1c(C(=O)Nc2ccc(S(C)(=O)=O)cc2)cc(C[C@H](C)OCc2ccccc2)n1-c1ccc(Cl)cc1C(F)(F)F]

The title compound (37 g, 75%) was obtained from the compound (39 g, 81 mmol) of Comparative Example 45 and aniline A (14 g, 69 mmol) in the process of Comparative Example 60.
MS (FAB) m/z: 605 [M+H]+.

Comparative Example 70

5-[(2S)-2-(Benzyloxy)propyl]-1-(4-fluoro-2-methylphenyl)-2-methyl-N-[3-methyl-4-(methylsulfonyl)phenyl]-1H-pyrrole-3-carboxamide

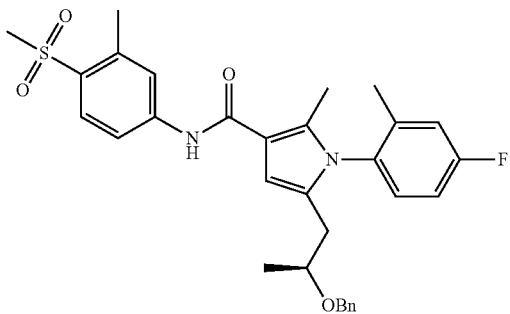 [SMILES: Cc1cc(F)ccc1-n1c(C[C@H](C)OCc2ccccc2)cc(C(=O)Nc2ccc(S(C)(=O)=O)c(C)c2)c1C]

Under a nitrogen atmosphere, to a solution of the compound (0.55 g, 1.5 mmol) of Comparative Example 59 in methylene chloride (4.0 mL), oxalyl chloride (0.15 mL, 1.7 mmol) was added, and after the mixture was stirred at room temperature, methylene chloride was distilled off under reduced pressure. Tetrahydrofuran (4.0 mL) was added to the residue, and the compound (0.28 g, 1.5 mmol) of Comparative Example 15 and diisopropylethylamine (0.63 mL, 3.6 mmol) were successively added, and the mixture was stirred at 70° C. overnight. After the reaction, tetrahydrofuran was distilled off under reduced pressure. After 5N hydrochloric acid was added to acidify it, it was extracted with diethyl ether. After it was successively washed with water, a saturated aqueous sodium hydrogen carbonate solution and saturated brine, it was dried with sodium sulfate and the solvent was distilled off under reduced pressure. The residue was purified by silica gel column chromatography (ethyl acetate/hexane) to give the desired compound (0.50 g, 63%) as a solid.
MS (FAB) m/z: 549 [M+H]+.

Comparative Example 71

5-[(2S)-2-(Benzyloxy)propyl]-N-[3-chloro-4-(methylsulfonyl)phenyl]-1-(4-fluoro-2-methylphenyl)-2-methyl-1H-pyrrole-3-carboxamide

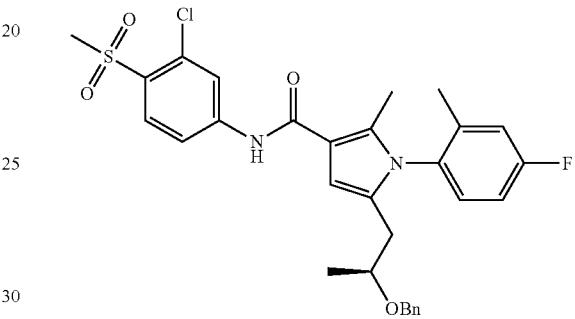

The desired compound (0.58 g, 78%) was obtained as a solid from the compound (0.55 g, 1.5 mol) of Comparative Example 59 and the compound (0.28 g, 1.4 mmol) of Comparative Example 17 in the process similar to Comparative Example 70.
MS (FAB) m/z: 569 [M+H]+.

The compounds in the following (Table 8) were prepared by reacting them with the compound of Comparative Example 12 in the process similar to (Comparative Example 60).

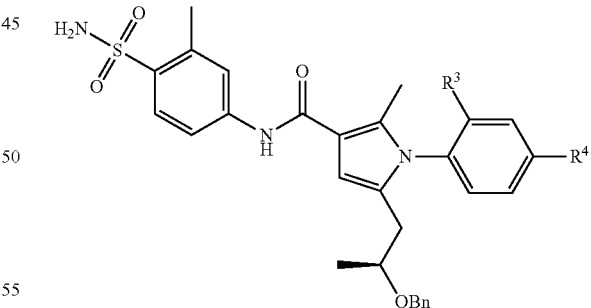

TABLE 8

| Comparative Example Number | $R^3$ | $R^4$ | Compound Name | MS and/or $^1$H-NMR spectrum |
|---|---|---|---|---|
| 72 | CF$_3$ | F | N-[4-(aminosulfonyl)-3-methylphenyl]-5-[(2S)- | $^1$H-NMR (400 MHz, CDCl$_3$) δ: 7.97 (1H, d, J = 8.6 Hz), 7.68 (1H, s), 7.60 (0.6H, s), 7.56-7.45 (2.4H, m), 7.35-7.19 (6H, |

TABLE 8-continued

| Comparative Example Number | R³ | R⁴ | Compound Name | MS and/or ¹H-NMR spectrum |
|---|---|---|---|---|
| | | | 2-(benzyloxy)propyl]-1-[4-fluoro-2-(trifluoromethyl)phenyl]-2-methyl-1H-pyrrole-3-carboxamide | m), 7.15 (0.4H, dd, J = 8.6, 5.1 Hz), 6.90 (0.6H, dd, J = 8.6, 5.1 Hz), 6.30 (0.6H, s), 6.24 (0.4H, s), 4.79 (2H, s), 4.57 (0.6H, d, J = 12.1 Hz), 4.52 (0.4H, d, J = 12.1 Hz), 4.35 (0.6H, d, J = 12.1 Hz), 4.34 (0.4H, d, J = 12.1 Hz), 3.71-3.62 (0.4H, m), 3.58-3.49 (0.6H, m), 2.68 (3H, s), 2.65 (0.6H, dd, J = 15.6, 6.7 Hz), 2.49 (0.4H, dd, J = 15.6, 5.5 Hz), 2.33 (0.4H, dd, J = 15.6, 7.4 Hz), 2.23 (3H, s), 2.21 (0.6H, dd, J = 15.6, 5.9 Hz), 1.20 (1.2H, d, J = 5.9 Hz), 1.15 (1.8H, d, J = 5.9 Hz), MS (ESI) m/z: 604 [M + H]⁺. |
| 73 | CF₃ | Cl | N-[4-(aminosulfonyl)-3-methylphenyl]-5-[(2S)-2-(benzyloxy)propyl]-1-[4-chloro-2-(trifluoromethyl)phenyl]-2-methyl-1H-pyrrole-3-carboxamide | ¹H-NMR (400 MHz, CDCl₃) δ: 7.97 (1H, d, J = 8.6 Hz), 7.81 (1H, dd, J = 6.3, 2.4 Hz), 7.69-7.67 (1H, m), 7.60 (0.6H, s), 7.56-7.44 (2.4H, m), 7.36-7.18 (5H, m), 7.09 (0.4H, d, J = 8.6 Hz), 6.83 (0.6H, d, J = 8.6 Hz), 6.31 (0.6H, s), 6.24 (0.4H, s), 4.78 (2H, s), 4.57 (0.6H, d, J = 12.1 Hz), 4.52 (0.4H, d, J = 12.1 Hz), 4.34 (0.6H, d, J = 12.1 Hz), 4.33 (0.4H, d, J = 12.1 Hz), 3.71-3.62 (0.4H, m), 3.57-3.47 (0.6H, m), 2.68 (3H, s), 2.66 (0.6H, dd, J = 15.6, 6.7 Hz), 2.49 (0.4H, dd, J = 15.6, 5.5 Hz), 2.32 (0.4H, dd, J = 15.6, 7.0 Hz), 2.23 (3H, s), 2.22 (0.6H, dd, J = 15.6, 5.5 Hz), 1.20 (1.2H, d, J = 6.3 Hz), 1.15 (1.8H, d, J = 6.3 Hz), MS (ESI) m/z: 620 [M + H]⁺ |
| 74 | OCF₃ | Cl | N-[4-(aminosulfonyl)-3-methylphenyl]-5-[(2S)-2-(benzyloxy)propyl]-1-[4-chloro-2-(trifluoromethoxy)phenyl]-2-methyl-1H-pyrrole-3-carboxamide | ¹H-NMR (400 MHz, CDCl₃) δ: 7.96 (1H, d, J = 8.6 Hz), 7.70-7.66 (1H, m), 7.60 (0.5H, s), 7.54 (0.5H, s), 7.51-7.44 (1.5H, m), 7.43-7.40 (0.5H, m), 7.35-7.26 (4H, m), 7.23-7.15 (2.5H, m), 6.90 (0.5H, d, J = 8.6 Hz), 6.31 (0.5H, s), 6.24 (0.5H, s), 4.79 (2H, s), 4.52 (0.5H, d, J = 12.1 Hz), 4.51 (0.5H, d, J = 12.1 Hz), 4.33 (0.5H, d, J = 12.1 Hz), 4.32 (0.5H, d, J = 12.1 Hz), 3.67-3.53 (0.5H, m), 3.50-3.41 (0.5H, m), 2.68 (3H, s), 2.66 (0.5H, dd, J = 15.6, 7.0 Hz), 2.46 (1H, d, J = 6.3 Hz), 2.38-2.30 (0.5H, m), 2.28 (1.5H, s), 2.27 (1.5H, s), 1.17 (1.5H, d, J = 5.9 Hz), 1.13 (1.5H, d, J = 5.9 Hz) MS (ESI) m/z: 636 [M + H]⁺ |
| 75 | Me | Cl | N-[4-(aminosulfonyl)-3-methylphenyl]-5-[(2S)-2-(benzyloxy)propyl]-1-(4-chloro-2-methylphenyl)-2-methyl-1H-pyrrole-3-carboxamide | ¹H-NMR (400 MHz, CDCl₃) δ: 7.97 (1H, d, J = 8.6 Hz), 7.71-7.67 (1H, m), 7.57 (0.6H, s), 7.54 (0.4H, s), 7.50-7.45 (1H, m), 7.36-7.17 (7H, m), 7.01 (0.4H, d, J = 8.2 Hz), 6.80 (0.6H, d, J = 8.2 Hz), 6.28 (0.6H, s), 6.25 (0.4H, s), 4.76 (2H, s), 4.50 (0.6H, d, J = 12.1 Hz), 4.46 (0.4H, d, J = 12.1 Hz), 4.34 (0.6H, d, J = 12.1 Hz), 4.32 (0.4H, d, J = 12.1 Hz), 3.61-3.52 (0.4H, m), 3.51-3.43 (0.6H, m), 2.69 (3H, s), 2.59 (0.6H, dd, J = 15.2, 7.0 Hz), 2.51-2.38 (0.8H, m), 2.28 (0.6H, dd, J = 15.2, 5.9 Hz), 2.24 (1.2H, s), 2.23 (1.8H, s), 1.89 (1.2H, s), 1.87 (1.8H, s), 1.18 (1.2H, d, J = 6.3 Hz), 1.14 (1.8H, d, J = 6.3 Hz) MS (ESI) m/z: 566 [M + H]⁺ |

The compounds in the following (Table 9) were prepared by reacting them with aniline C in the process similar to (Comparative Example 60).

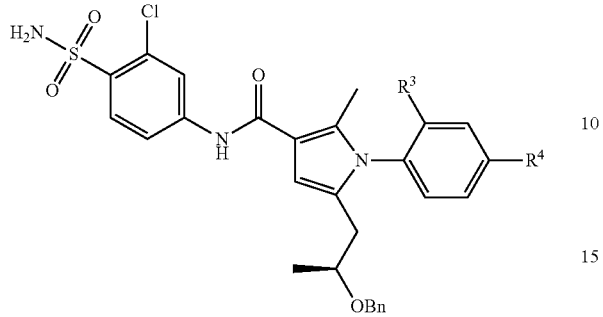

TABLE 9

| Comparative Example Number | R³ | R⁴ | Compound Name | MS and/or ¹H-NMR spectrum |
|---|---|---|---|---|
| 76 | OCF₃ | Cl | N-[4-(aminosulfonyl)-3-chlorophenyl]-5-[(2S)-2-(benzyloxy)propyl]-1-[4-chloro-2-(trifluoromethoxy)phenyl]-2-methyl-1H-pyrrole-3-carboxamide | ¹H-NMR (400 MHz, CDCl₃) δ: 8.10-7.73 (3H, m), 7.50-7.39 (3H, m), 7.37-7.15 (5.5H, m), 6.90 (0.5H, d, J = 8.6 Hz), 6.39 (0.5H, s), 6.32 (0.5H, s), 5.35-5.15 (2H, brs), 4.55-4.45 (1H, m), 4.36-4.28 (1H, m), 3.68-3.58 (0.5H, m), 3.50-3.40 (0.5H, m), 2.65 (0.5H, dd, J = 6.7, 15.3 Hz), 2.46 (1H, d, J = 6.3 Hz), 2.33 (0.5H, dd, J = 5.5, 15.3 Hz), 2.27 (1.5H, s), 2.26 (1.5H, s), 1.17 (1.5H, d, J = 5.9 Hz), 1.13 (1.5H, d, J = 5.9 Hz). |
| 77 | OCF₃ | F | N-[4-(aminosulfonyl)-3-chlorophenyl]-5-[(2S)-2-(benzyloxy)propyl]-1-[4-fluoro-2-(trifluoromethoxy)phenyl]-2-methyl-1H-pyrrole-3-carboxamide | ¹H-NMR (400 MHz, CDCl₃) δ: 8.10 (0.6H, d, J = 2.4 Hz), 8.08 (0.4H, d, J = 2.0 Hz), 8.03 (1H, d, J = 8.6 Hz), 7.62 (0.6H, s), 7.56 (0.4H, s), 7.48-7.42 (1H, m), 7.36-7.25 (4H, m), 7.25-6.92 (4H, m), 6.29 (0.6H, s), 6.22 (0.4H, s), 5.09 (2H, s), 4.56-4.49 (1H, m), 4.36-4.29 (1H, m), 3.67-3.58 (0.4H, m), 3.51-3.40 (0.6H, m), 2.65 (0.6H, dd, J = 6.3, 15.6 Hz), 2.46 (0.8H, d, J = 6.3 Hz), 2.34 (0.6H, dd, J = 5.6, 15.6 Hz), 2.28 (1.2H, s), 2.27 (1.8H, s), 1.18 (1.2H, d, J = 6.3 Hz), 1.14 (1.8H, d, J = 5.9 Hz). |
| 78 | Cl | F | N-[4-(aminosulfonyl)-3-chlorophenyl]-5-[(2S)-2-(benzyloxy)propyl]-1-(2-chloro-4-fluorophenyl)-2-methyl-1H-pyrrole-3-carboxamide | MS (ESI) m/z: 590 [M + H]⁺. |
| 79 | CF₃ | F | N-[4-(aminosulfonyl)-3-chlorophenyl]-5-[(2S)-2-(benzyloxy)propyl]-1-[4-fluoro-2-(trifluoromethyl)phenyl]-2-methyl-1H-pyrrole-3-carboxamide | ¹H-NMR (400 MHz, CDCl₃) δ: 8.08 (0.6H, d, J = 2.0 Hz), 8.07 (0.4H, d, J = 2.0 Hz), 8.02 (1H, d, J = 8.6 Hz), 7.64 (0.6H, s), 7.58 (0.4H, s), 7.56-7.50 (1H, m), 7.48-7.43 (1H, m), 7.36-7.19 (6H, m), 7.18-7.13 (0.4H, m), 6.94-6.88 (0.6H, m), 6.30 (0.6H, s), 6.23 (0.4H, s), 5.10 (2H, s), 4.60-4.50 (1H, m), 4.38-4.28 (1H, m), 3.71-3.62 (0.4H, m), 3.59-3.47 (0.6H, m), 2.65 (0.6H, dd, J = 7.4, 15.3 Hz), 2.48 (0.4H, dd, J = 5.1, 15.3 Hz), 2.32 (0.4H, dd, J = 7.4, 15.3 Hz), 2.26-2.18 (3.6H, m), 1.19 (1.2H, d, J = 5.9 Hz), 1.15 (1.8H, d, J = 5.9 Hz). |
| 80 | CF₃ | Cl | N-[4-(aminosulfonyl)-3-chlorophenyl]-5-[(2S)-2-(benzyloxy)propyl]-1-[4-fluoro-2-(trifluoromethyl)phenyl]-2-methyl-1H-pyrrole-3-carboxamide | ¹H-NMR (400 MHz, CDCl₃) δ: 8.08 (0.6H, d, J = 2.0 Hz), 8.07 (0.4H, d, J = 2.0 Hz), 8.03 (0.6H, s), 8.02 (0.4H, s), 7.83-7.77 (1H, m), 7.62 (0.6H, s), 7.57 (0.4H, s), 7.55-7.42 (2H, m), 7.32-7.22 (5H, m), 7.10 (0.4H, d, J = 8.3 Hz), |

TABLE 9-continued

| Comparative Example Number | R³ | R⁴ | Compound Name | MS and/or ¹H-NMR spectrum |
|---|---|---|---|---|
| | | | | 6.84 (0.6H, d, J = 8.3 Hz), 6.30 (0.6H, s), 6.23 (0.4H, s), 5.09 (2H, s), 4.60-4.50 (1H, m), 4.37-4.30 (1H, m), 3.71-3.63 (0.4H, m), 3.58-3.48 (0.6H, m), 2.65 (0.6H, dd, J = 6.8, 15.6 Hz), 2.48 (0.4H, dd, J = 5.4, 15.6 Hz), 2.32 (0.4H, dd, J = 7.3, 15.6 Hz), 2.27-2.18 (3.6H, m), 1.20 (1.2H, d, J = 5.9 Hz), 1.15 (1.8H, d, J = 6.4 Hz). |

The compounds in the following (Table 10) were prepared by reacting them with aniline A in the process similar to (Comparative Example 63).

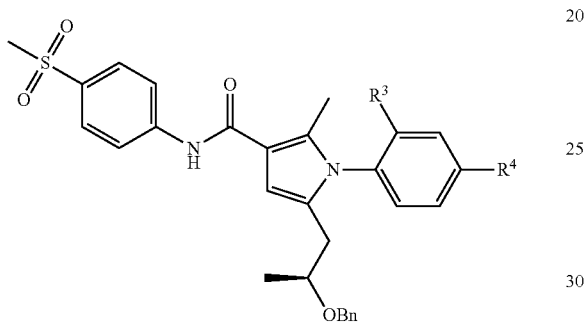

TABLE 10

| Comparative Example Number | R³ | R⁴ | Compound Name | MS and/or ¹H-NMR spectrum |
|---|---|---|---|---|
| 81 | CF₃ | F | 5-[(2S)-2-(benzyloxy)propyl]-1-[4-fluoro-2-(trifluoromethyl)phenyl]-2-methyl-N-[4-(methylsulfonyl)phenyl]-1H-pyrrole-3-carboxamide | ¹H-NMR (400 MHz, CDCl₃) δ: 7.91 (2H, d, J = 8.6 Hz), 7.83-7.79 (2H, m), 7.68 (0.7H, s), 7.62 (0.3H, s), 7.55-7.51 (1H, m), 7.35-7.20 (6H, m), 7.16 (0.3H, dd, J = 8.8, 4.9 Hz), 6.90 (0.7H, dd, J = 8.6, 5.0 Hz), 6.31 (0.7H, s), 6.24 (0.3H, s), 4.57 (0.7H, d, J = 12.1 Hz), 4.53 (0.3H, d, J = 12.1 Hz), 4.35 (0.7H, d, J = 11.7 Hz), 4.33 (0.3H, d, J = 11.8 Hz), 3.70-3.62 (0.3H, m), 3.57-3.49 (0.7H, m), 3.06 (3H, s), 2.67 (0.7H, dd, J = 15.5, 6.9 Hz), 2.49 (0.3H, dd, J = 16.4, 5.3 Hz), 2.33 (0.3H, d, J = 15.4, 7.2 Hz), 2.25-2.20 (3.7H, m), 1.20 (0.9H, d, J = 5.9 Hz), 1.15 (2.1H, d, J = 6.3 Hz). |
| 82 | CF₃ | H | 5-[(2S)-2-(benzyloxy)propyl]-2-methyl-N-[4-(methylsulfonyl)phenyl]-1-[2-(trifluoromethyl)phenyl]-1H-pyrrole-3-carboxamide | MS (FAB) m/z: 571 [M + H]⁺. |
| 83 | Me | F | 5-[(2S)-2-(benzyloxy)propyl]-1-(4-fluoro-2-methylphenyl)-2-methyl-N-[4-(methylsulfonyl)phenyl]-1H-pyrrole-3-carboxamide | ¹H-NMR (400 MHz, CDCl₃) δ: 7.91 (2H, d, J = 9.0 Hz), 7.81 (2H, d, J = 9.0 Hz), 7.66 (0.5H, s), 7.64 (0.5H, s), 7.35-7.25 (3H, m), 7.24-7.18 (2H, m), 7.08-6.99 (1.5H, m), 6.98-6.92 (1H, m), 6.87-6.82 (0.5H, m), 6.29 (0.5H, s), 6.26 (0.5H, s), 4.50 (0.5H, d, J = 12.1 Hz), 4.46 (0.5H, d, J = 12.1 Hz), 4.33 (0.5H, d, J = 12.1 Hz), 4.31 (0.5H, d, J = 12.1 Hz), 3.61-3.53 (0.5H, m), 3.52-3.44 (0.5H, m), 3.06 (3H, s), |

TABLE 10-continued

| Comparative Example Number | R³ | R⁴ | Compound Name | MS and/or ¹H-NMR spectrum |
|---|---|---|---|---|
| | | | | 2.60 (0.5H, dd, J = 15.3, 7.0 Hz), 2.48 (0.5H, dd, J = 15.3, 6.3 Hz), 2.42 (0.5H, dd, J = 15.3, 6.7 Hz), 2.29 (0.5H, dd, J = 15.3, 6.3 Hz), 2.25 (1.5H, s), 2.24 (1.5H, s), 1.91 (1.5H, s), 1.89 (1.5H, s), 1.19 (1.5H, d, J = 5.9 Hz), 1.15 (1.5H, d, J = 5.9 Hz) MS (ESI) m/z: 535 [M + H]⁺. |
| 84 | OCF₂H | F | 5-[(2S)-2-(benzyloxy)propyl]-1-[2-(difluoromethoxy)-4-fluorophenyl]-2-methyl-N-[4-(methylsulfonyl)phenyl]-1H-pyrrole-3-carboxamide | ¹H-NMR (400 MHz, CDCl₃) δ: 7.91 (2H, d, J = 9.0 Hz), 7.81 (1H, d, J = 9.0 Hz), 7.79 (1H, d, J = 9.0 Hz), 7.66 (0.5H, s), 7.63 (0.5H, s), 7.35-7.26 (3H, m), 7.23-7.16 (2.5H, m), 7.11 (0.5H, d, J = 9.0 Hz), 7.06 (0.5H, d, J = 9.0 Hz), 7.02-6.96 (1.5H, m), 6.32 (0.5H, t, J = 72.0 Hz), 6.28 (0.5H, s), 6.25 (0.5H, t, J = 72.0 Hz), 6.24 (0.5H, s), 4.49 (0.5H, d, J = 12.1 Hz), 4.48 (0.5H, d, J = 12.1 Hz), 4.33 (0.5H, d, J = 12.1 Hz), 4.31 (0.5H, d, J = 12.1 Hz), 3.65-3.55 (0.5H, m), 3.48-3.38 (0.5H, m), 3.05 (3H, s), 2.65 (0.5H, dd, J = 15.3, 6.7 Hz), 2.53 (0.5H, dd, J = 15.3, 6.7 Hz), 2.46 (0.5H, dd, J = 15.3, 6.3 Hz), 2.37 (0.5H, dd, J = 15.3, 6.3 Hz), 2.29 (1.5H, s), 2.27 (1.5H, s), 1.17 (1.5H, d, J = 6.3 Hz), 1.14 (1.5H, d, J = 6.3 Hz) MS (ESI) m/z: 587 [M + H]⁺. |
| 85 | OCF₂H | Cl | 5-[(2S)-2-(benzyloxy)propyl]-1-[4-chloro-2-(difluoromethoxy)phenyl]-2-methyl-N-[4-(methylsulfonyl)phenyl]-1H-pyrrole-3-carboxamide | ¹H-NMR (500 MHz, CDCl₃) δ: 7.91 (2H, d, J = 8.8 Hz), 7.81 (1H, d, J = 8.8 Hz), 7.79 (1H, d, J = 8.8 Hz), 7.67 (0.5H, s), 7.63 (0.5H, s), 7.38 (0.5H, d, J = 2.0 Hz), 7.34-7.23 (4.5H, m), 7.22-7.15 (2H, m), 7.13 (0.5H, d, J = 8.3 Hz), 6.91 (0.5H, d, J = 8.3 Hz), 6.31 (0.5H, t, J = 72.0 Hz), 6.29 (0.5H, s), 6.25 (0.5H, s), 6.22 (0.5H, t, J = 72.0 Hz), 4.50 (0.5H, d, J = 12.2 Hz), 4.49 (0.5H, d, J = 12.2 Hz), 4.33 (0.5H, d, J = 12.2 Hz), 4.31 (0.5H, d, J = 12.2 Hz), 3.64-3.56 (0.5H, m), 3.47-3.39 (0.5H, m), 3.05 (3H, s), 2.65 (0.5H, dd, J = 15.1, 6.8 Hz), 2.51 (0.5H, dd, J = 15.6, 6.4 Hz), 2.47 (0.5H, dd, J = 15.6, 5.9 Hz), 2.38 (0.5H, dd, J = 1.51, 6.4 Hz), 2.29 (1.5H, s), 2.27 (1.5H, s), 1.17 (1.5H, d, J = 6.4 Hz), 1.14 (1.5H, d, J = 6.4 Hz) MS (ESI) m/z: 603 [M + H]⁺. |
| 86 | OCF₃ | F | 5-[(2S)-2-(benzyloxy)propyl]-1-[4-fluoro-2-(trifluoromethoxy)phenyl]-2-methyl-N-[4-(methylsulfonyl)phenyl]-1H-pyrrole-3-carboxamide | ¹H-NMR (400 MHz, CDCl₃) δ: 7.91 (2H, d, J = 8.6 Hz), 7.84-7.77 (2H, m), 7.65 (0.5H, s), 7.60 (0.5H, s), 7.35-7.25 (3H, m), 7.24-7.12 (3.5H, m), 7.10-7.01 (1H, m), 6.96 (0.5H, dd, J = 5.5, 8.6 Hz), 6.30 (0.5H, s), 6.24 (0.5H, s), 4.55-4.48 (1H, m), 4.35-4.30 (1H, m), 3.66-3.57 (0.5H, m), 3.50-3.41 (0.5H, m), 3.06 (3H, s), 2.66 (0.5H, dd, J = 6.7, 15.6 Hz), 2.46 (1H, d, J = 6.3 Hz), 2.34 (0.5H, dd, J = 5.9, 15.6 Hz), 2.28 (1.5H, s), 2.27 (1.5H, s), 1.18 (1.5H, d, J = 5.9 Hz), 1.14 (1.5H, d, J = 5.9 Hz). |
| 87 | Cl | Me | 5-[(2S)-2-(benzyloxy)propyl]-1-(2-chloro-4-methylphenyl)-2-methyl-N-[4-(methylsulfonyl)phenyl]-1H-pyrrole-3-carboxamide | ¹H-NMR (400 MHz, CDCl₃) δ: 7.90 (2H, d, J = 9.0 Hz), 7.81 (1H, d, J = 9.0 Hz), 7.80 (1H, s), 7.69 (0.5H, s), 7.64 (0.5H, s), 7.40-7.08 (7.5H, m), 6.90 (0.5H, d, J = 8.6 Hz), 6.31 (0.5H, s), 6.25 (0.5H, s), 4.47 (0.5H, d, J = 12.1 Hz), 4.46 (0.5H, d, J = 12.1 Hz), 4.36 (0.5H, d, J = 12.1 Hz), 4.32 (0.5H, d, J = 12.1 Hz), 3.67-3.57 (0.5H, m), |

TABLE 10-continued

| Comparative Example Number | R³ | R⁴ | Compound Name | MS and/or ¹H-NMR spectrum |
|---|---|---|---|---|
| | | | | 3.53-3.43 (0.5H, m), 3.05 (3H, s), 2.70 (0.5H, dd, J = 15.2, 6.3 Hz), 2.54 (0.5H, dd, J = 15.2, 6.7 Hz), 2.45 (0.5H, dd, J = 15.2, 6.3 Hz), 2.43 (1.5H, s), 2.42 (1.5H, s), 2.35 (0.5H, dd, J = 15.2, 6.3 Hz), 2.29 (1.5H, s), 2.28 (1.5H, s), 1.17 (1.5H, d, J = 5.9 Hz), 1.15 (1.5H, d, J = 5.9 Hz); MS (ESI) m/z: 551 [M + H]⁺. |
| 88 | OCF₂H | Me | 5-[(2S)-2-(benzyloxy)propyl]-1-[2-(difluoromethoxy)-4-methylphenyl]-2-methyl-N-[4-(methylsulfonyl)phenyl]-1H-pyrrole-3-carboxamide | ¹H-NMR (400 MHz, CDCl₃) δ: 7.90 (2H, d, J = 9.0 Hz), 7.81 (1H, d, J = 9.0 Hz), 7.80 (1H, d, J = 9.0 Hz), 7.66 (0.5H, s), 7.62 (0.5H, s), 7.34-7.14 (5.5H, m), 7.12-7.06 (2H, m), 6.88 (0.5H, d, J = 7.8 Hz), 6.31 (0.5H, t, J = 72.7 Hz), 6.27 (0.5H, s), 6.24 (0.5H, s), 6.24 (0.5H, t, J = 72.7 Hz), 4.47 (0.5H, d, J = 12.1 Hz), 4.46 (0.5H, d, J = 12.1 Hz), 4.34 (0.5H, d, J = 12.1 Hz), 4.33 (0.5H, d, J = 12.1 Hz), 3.65-3.56 (0.5H, m), 3.51-3.42 (0.5H, m), 3.05 (3H, s), 2.68 (0.5H, dd, J = 15.2, 6.3 Hz), 2.57 (0.5H, dd, J = 15.2, 6.3 Hz), 2.47 (0.5H, dd, J = 15.2, 6.3 Hz), 2.46 (1.5H, s), 2.45 (1.5H, s), 2.38 (0.5H, dd, J = 15.2, 6.3 Hz), 2.30 (1.5H, s), 2.28 (1.5H, s), 1.17 (1.5H, d, J = 6.3 Hz), 1.14 (1.5H, d, J = 6.3 Hz); MS (ESI) m/z: 583 [M + H]⁺. |
| 89 | CF₂H | Cl | 5-[(2S)-2-(benzyloxy)propyl]-1-[4-chloro-2-(difluoromethyl)phenyl]-2-methyl-N-[4-(methylsulfonyl)phenyl]-1H-pyrrole-3-carboxamide | MS (FAB) m/z: 587 [M + H]⁺. |
| 90 | CF₂H | F | 5-[(2S)-2-(benzyloxy)propyl]-1-[2-(difluoromethyl)-4-fluorophenyl]-2-methyl-N-[4-(methylsulfonyl)phenyl]-1H-pyrrole-3-carboxamide | MS (FAB) m/z: 571 [M + H]⁺. |
| 91 | Cl | F | 5-[(2S)-2-(benzyloxy)propyl]-1-(2-chloro-4-fluorophenyl)-2-methyl-N-[4-(methylsulfonyl)phenyl]-1H-pyrrole-3-carboxamide | MS (ESI) m/z: 555 [M + H]⁺. |
| 92 | Me | Cl | 5-[(2S)-2-(benzyloxy)propyl]-1-(4-chloro-2-methylphenyl)-2-methyl-N-[4-(methylsulfonyl)phenyl]-1H-pyrrole-3-carboxamide | MS (ESI) m/z: 551 [M + H]⁺. |
| 93 | OCF₃ | Cl | 5-[(2S)-2-(benzyloxy)propyl]-1-[4-chloro-2-(trifluoromethoxy)phenyl]-2-methyl-N-[4-(methylsulfonyl)phenyl]-1H-pyrrole-2-carboxamide | MS (ESI) m/z: 621 [M + H]⁺. |
| 94 | Cl | Cl | 5-[(2S)-2-(benzyloxy)propyl]-1-(2,4-dichlorophenyl)-2-methyl-N-[4-(methylsulfonyl)phenyl]-1H-pyrrole-3-carboxamide | MS (ESI) m/z: 571 [M + H]⁺. |
| 95 | 4-F—PhO | Cl | 5-[(2S)-2-(benzyloxy)propyl]-1-[4-chloro-2-(4-fluorophenoxy)phenyl]-2-methyl-N-[4-(methylsulfonyl)phenyl]-1H-pyrrole-3-carboxamide | MS (ESI) m/z: 647 [M + H]⁺. |
| 96 | 4-F—Ph | Cl | 5-[(2S)-2-(benzyloxy)propyl]-1-(5-chloro-4'-fluorobiphenyl-2-yl)-2-methyl-N-[4-(methylsulfonyl)phenyl]-1H-pyrrole-3-carboxamide | MS (ESI) m/z: 631 [M + H]⁺. |

The compounds in the following (Table 11) were prepared by reacting them with the compound of Comparative Example 15 in the process similar to (Comparative Example 63).

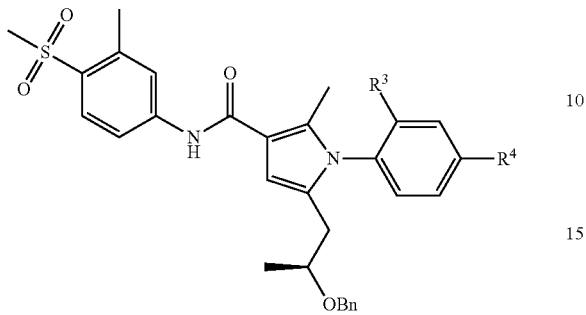

TABLE 11

| Comparative Example Number | R³ | R⁴ | Compound Name | MS and/or ¹H-NMR spectrum |
|---|---|---|---|---|
| 97 | CF$_3$ | Cl | 5-[(2S)-2-(benzyloxy)propyl]-1-[4-chloro-2-(trifluoromethyl)phenyl]-2-methyl-N-[3-methyl-4-(methylsulfonyl)phenyl]-1H-pyrrole-3-carboxamide | ¹H-NMR (400 MHz, CDCl$_3$) δ: 7.99 (1H, d, J = 8.6 Hz), 7.80 (1H, d, J = 2.4 Hz), 7.74 (1H, d, J = 1.6 Hz), 7.60 (1H, s), 7.51 (1H, d, J = 8.6 Hz), 7.36-7.18 (5H, m), 6.82 (1H, d, J = 8.2 Hz), 6.30 (1H, s), 4.56 (1H, d, J = 12.1 Hz), 4.34 (1H, d, J = 12.1 Hz), 3.57-3.48 (1H, m), 3.08 (3H, s), 2.71 (3H, s), 2.66 (1H, dd, J = 15.6, 7.0 Hz), 2.23 (3H, s), 2.22 (1H, dd, J = 15.6, 5.9 Hz), 1.15 (3H, d, J = 6.3 Hz) MS (ESI) m/z: 619 [M + H]⁺. |
| 98 | OCF$_3$ | Cl | 5-[(2S)-2-(benzyloxy)propyl]-1-[4-chloro-2-(trifluoromethoxy)phenyl]-2-methyl-N-[3-methyl-4-(methylsulfonyl)phenyl]-1H-pyrrole-3-carboxamide | ¹H-NMR (400 MHz, CDCl$_3$) δ: 7.99 (1H, d, J = 9.0 Hz), 7.75 (1H, d, J = 2.4 Hz), 7.60 (1H, s), 7.52 (1H, dd, J = 8.6, 2.0 Hz), 7.44-7.40 (1H, m), 7.35-7.26 (4H, m), 7.23-7.16 (2H, m), 6.88 (1H, d, J = 8.6 Hz), 6.30 (1H, s), 4.52 (1H, d, J = 12.1 Hz), 4.32 (1H, d, J = 12.1 Hz), 3.50-3.39 (1H, m), 3.08 (3H, s), 2.71 (3H, s), 2.66 (1H, dd, J = 15.6, 7.0 Hz), 2.34 (1H, dd, J = 15.6, 5.9 Hz), 2.27 (3H, s), 1.13 (3H, d, J = 5.9 Hz) MS (ESI) m/z: 635 [M + H]⁺. |
| 99 | Cl | F | 5-[(2S)-2-(benzyloxy)propyl]-1-(2-chloro-4-fluorophenyl)-2-methyl-N-[3-methyl-4-(methylsulfonyl)phenyl]-1H-pyrrole-3-carboxamide | MS (FAB) m/z: 569 [M + H]⁺. |
| 100 | CF$_2$H | F | 5-[(2S)-2-(benzyloxy)propyl]-1-[2-(difluoromethyl)-4-fluorophenyl]-2-methyl-N-[3-methyl-4-(methylsulfonyl)phenyl]-1H-pyrrole-3-carboxamide | MS (FAB) m/z: 585 [M + H]⁺. |
| 101 | OCF$_2$H | F | 5-[(2S)-2-(benzyloxy)propyl]-1-[2-(difluoromethoxy)-4-fluorophenyl]-2-methyl-N-[3-methyl-4-(methylsulfonyl)phenyl]-1H-pyrrole-3-carboxamide | MS (FAB) m/z: 601 [M + H]⁺. |
| 102 | CF$_3$ | F | 5-[(2S)-2-(benzyloxy)propyl]-1-[4-fluoro-2-(trifluoromethyl)phenyl]-2-methyl-N-[3-methyl-4-(methylsulfonyl)phenyl]-1H-pyrrole-3-carboxamide | MS (FAB) m/z: 603 [M + H]⁺. |

The compounds in the following (Table 12) were prepared by reacting them with the compound of Comparative Example 18 in the process similar to (Comparative Example 63).

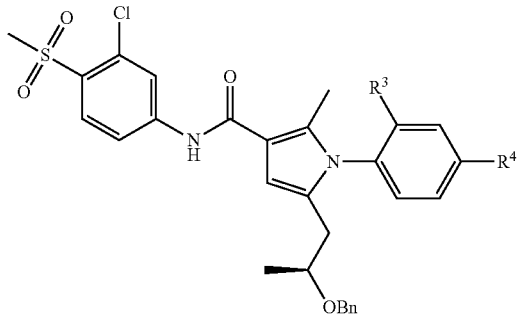

TABLE 12

| Comparative Example Number | R³ | R⁴ | Compound Name | MS and/or ¹H-NMR spectrum |
|---|---|---|---|---|
| 103 | OCF₂H | F | 5-[(2S)-2-(benzyloxy)propyl]-N-[3-chloro-4-(methylsulfonyl)phenyl]-1-[2-(difluoromethoxy)-4-fluorophenyl]-2-methyl-1H-pyrrole-3-carboxamide | MS (FAB) m/z: 621 [M + H]⁺. |
| 104 | CF₃ | F | 5-[(2S)-2-(benzyloxy)propyl]-N-[3-chloro-4-(methylsulfonyl)phenyl]-1-[4-fluoro-2-(trifluoromethyl)phenyl]-2-methyl-1H-pyrrole-3-carboxamide | MS (FAB) m/z: 623 [M + H]⁺. |
| 105 | Cl | F | 5-[(2S)-2-(benzyloxy)propyl]-1-(2-chloro-4-fluorophenyl)-N-[3-chloro-4-(methylsulfonyl)phenyl]-2-methyl-1H-pyrrole-3-carboxamide | MS (FAB) m/z: 589 [M + H]⁺. |

The compounds in the following (Table 13) were prepared by reacting them with the compound of Comparative Example 21 in the process similar to (Comparative Example 63).

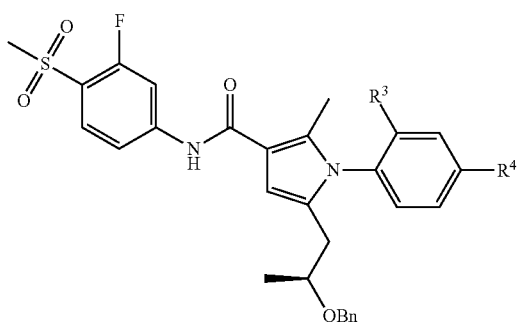

TABLE 13

| Comparative Example Number | R³ | R⁴ | Compound Name | MS and/or ¹H-NMR spectrum |
|---|---|---|---|---|
| 106 | CF₂H | F | 5-[(2S)-2-(benzyloxy)propyl]-1-[2-(difluoromethyl)-4-(fluorophenyl)-N-[3-fluoro-4-(methylsulfonyl)phenyl]-2-methyl-1H-pyrrole-3-carboxamide | MS (FAB) m/z: 589 [M + H]⁺. |
| 107 | OCF₂H | F | 5-[(2S)-2-(benzyloxy)propyl]-1-[2-(difluoromethoxy)-4-(fluorophenyl)-N-[3-fluoro-4-(methylsulfonyl)phenyl]-2-methyl-1H-pyrrole-3-carboxamide | MS (FAB) m/z: 605 [M + H]⁺. |
| 108 | CF₃ | F | 5-[(2S)-2-(benzyloxy)propyl]-N-[3-fluoro-4-(methylsulfonyl)phenyl]-1-[4-fluoro-2-(trifluoromethyl)phenyl]-2-methyl-1H-pyrrole-3-carboxamide | MS (ESI) m/z: 607 [M + H]⁺ |
| 109 | Cl | F | 5-[(2S)-2-(benzyloxy)propyl]-1-(2-chloro-4-fluorophenyl)-N-[3-fluoro-4-(methylsulfonyl)phenyl]-2-methyl-1H-pyrrole-3-carboxamide | MS (FAB) m/z: 573 [M + H]⁺. |

The compounds in the following (Table 14) were prepared by reacting them with aniline A in the process similar to (Comparative Example 63).

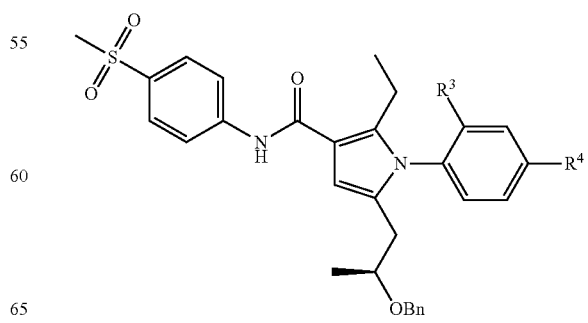

TABLE 14

| Comparative Example Number | R³ | R⁴ | Compound Name | MS and/or ¹H-NMR spectrum |
|---|---|---|---|---|
| 110 | OCF₂H | F | 5-[(2S)-2-(benzyloxy)propyl]-1-[2-(difluoromethoxy)-4-fluorophenyl]-2-ethyl-N-[4-(methylsulfonyl)phenyl]-1H-pyrrole-3-carboxamide | MS (FAB) m/z: 601 [M + H]⁺. |
| 111 | Cl | F | 5-[(2S)-2-(benzyloxy)propyl]-1-(2-chloro-4-fluorophenyl)-2-ethyl-N-[4-(methylsulfonyl)phenyl]-1H-pyrrole-3-carboxamide | MS (ESI) m/z: 569 [M + H]⁺. |
| 112 | Cl | Cl | 5-[(2S)-2-(benzyloxy)propyl]-1-(2,4-dichlorophenyl)-2-ethyl-N-[4-(methylsulfonyl)phenyl]-1H-pyrrole-3-carboxamide | ¹H-NMR (400 MHz, CDCl₃) δ: 7.91 (2H, m), 7.82-7.79 (2H, m), 7.68 (0.4H, s), 7.63 (0.6H, s), 7.58 (0.6H, d, J = 2.4 Hz), 7.53 (0.4H, d, J = 2.4 Hz), 7.32-7.28 (4H, m), 7.22-7.16 (2.6H, m), 6.91 (0.4H, d, J = 8.8 Hz), 6.32 (0.4H, s), 6.25 (0.6H, s), 4.51 (0.4H, d, J = 12.0 Hz), 4.49 (0.6H, d, J = 12.0 Hz), 4.35 (0.6H, d, J = 12.0 Hz), 4.32 (0.4H, d, J = 12.0 Hz), 3.64-3.59 (0.6H, m), 3.48-3.43 (0.4H, m), 3.06 (3H, s), 2.86-2.75 (1H, m), 2.68-2.53 (1.6H, m), 2.49-2.39 (1H, m), 2.30 (0.4H, dd, J = 5.6, 15.2 Hz), 1.19 (0.6H, d, J = 6.0 Hz), 1.15 (0.6H, d, J = 6.4 Hz), 1.04-0.99 (3H, m). |
| 113 | CF₃ | Cl | 5-[(2S)-2-(benzyloxy)propyl]-1-[4-chloro-2-(trifluoromethyl)phenyl]-2-ethyl-N-[4-(methylsulfonyl)phenyl]-1H-pyrrole-3-carboxamide | ¹H-NMR (400 MHz, CDCl₃) δ: 7.91 (2H, d, J = 8.4 Hz), 7.81-7.79 (3H, m), 7.67 (0.5H, s), 7.62 (0.5H, s), 7.53-7.50 (1H, m), 7.34-7.15 (5.5H, m), 6.91 (0.5H, d, J = 8.4), 6.30 (0.5H, s), 6.22 (0.5H, s), 4.55 (0.5H, d, J = 12.4 Hz), 4.53 (0.5H, d, J = 11.6 Hz), 4.34 (0.5H, d, J = 12.4 Hz), 4.31 (0.5H, d, J = 12.0 Hz), 3.69-3.64 (0.5H, m), 3.55-3.51 (0.5H, m), 3.10-2.97 (1H, m), 3.05 (3H, s), 2.64 (0.5H, dd, J = 15.6, 7.2 Hz), 2.47 (0.5H, dd, J = 15.6, 5.2 Hz), 2.30-2.04 (2H, m), 1.19 (1.5H, d, J = 6.0 Hz), 1.15 (1.5H, d, J = 6.4 Hz), 1.06-1.00 (3H, m). |
| 114 | CF₃ | F | 5-[(2S)-2-(benzyloxy)propyl]-2-ethyl-1-[4-fluoro-2-(trifluoromethyl)phenyl]-N-[4-(methylsulfonyl)phenyl]-1H-pyrrole-3-carboxamide | ¹H-NMR (400 MHz, CDCl₃) δ: 7.91 (2H, d, J = 8.8 Hz), 7.83-7.79 (2H, m), 7.68 (0.5H, s), 7.63 (0.5H, s), 7.54-7.51 (1H, m), 7.36-7.18 (6.5H, m), 6.91 (0.5H, d, J = 8.4), 6.30 (0.5H, s), 6.22 (0.5H, s), 4.58 (0.5H, d, J = 12.0 Hz), 4.54 (0.5H, d, J = 12.0 Hz), 4.36 (0.5H, d, J = 12.0 Hz), 4.32 (0.5H, d, J = 12.0 Hz), 3.70-3.65 (0.5H, m), 3.57-3.52 (0.5H, m), 3.11-2.99 (1H, m), 3.06 (3H, s), 2.65 (0.5H, dd, J = 15.6, 6.8 Hz), 2.48 (0.5H, dd, J = 15.6, 5.2 Hz), 2.31-2.15 (2H, m), 1.20 (1.5H, d, J = 6.0 Hz), 1.16 (1.5H, d, J = 6.4 Hz), 1.07-1.02 (3H, m). |

Example 1

1-[4-Chloro-2-(trifluoromethyl)phenyl]-5-(2-hydroxyethyl)-2-methyl-N-[4-(methylsulfonyl)phenyl]-1H-pyrrole-3-carboxamide

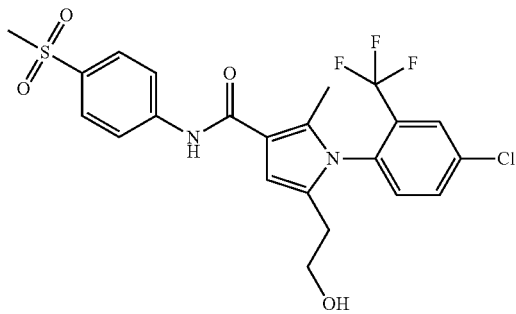 [SMILES: Cc1c(C(=O)Nc2ccc(S(C)(=O)=O)cc2)cc(CCO)n1-c1ccc(Cl)cc1C(F)(F)F]

Under a nitrogen atmosphere, to a solution of the compound (77 g, 0.13 mmol) of Comparative Example 60 in chloroform (0.68 L), methanesulfonic acid (0.33 L, 5.0 mol) was gradually added, and the mixture was stirred at room temperature for 2 hours. After the reaction, the mixture was poured into an ice bath, and it was extracted with chloroform. After the obtained organic phase was successively washed with water and saturated brine, it was dried with sodium sulfate and the solvent was distilled off under reduced pressure. The residue was purified by silica gel column chromatography (ethyl acetate/hexane, 3:1, v/v) to give the desired compound (44 g, 67%) as a solid.

$^1$H-NMR (400 MHz, CDCl$_3$) δ: 7.91 (2H, d, J=9.0 Hz), 7.86 (1H, d, J=2.3 Hz), 7.83 (2H, dt, J=9.0, 2.2 Hz), 7.73-7.70 (2H, m), 7.28-7.25 (1H, m), 6.37 (1H, s), 3.81-3.74 (2H, m), 3.05 (3H, s), 2.59 (1H, dt, J=15.7, 6.4 Hz), 2.42 (1H, dt, J=15.7, 6.5 Hz), 2.27 (3H, s), 1.50 (1H, br s).

MS (FAB) m/z: 501 [M+H]$^+$.

Retention time: 9.0 (Example 1—isomer A), 12.5 min (Example 1—isomer B)

chiral HPLC condition: LC1, eluent: hexane-EtOH-MeOH [80:16:4 (v/v/v), isocratic]

Resolution was carried out under the following condition.
chiral HPLC condition: LC3, eluent: hexane-EtOH-MeOH [80:16:4 (v/v/v), isocratic Example 1—Isomer A $^1$H-NMR (400 MHz, CDCl$_3$) δ: 7.90 (2H, d, J=9.0 Hz), 7.85 (1H, d, J=2.3 Hz), 7.83 (2H, dt, J=9.0, 2.0 Hz), 7.78 (1H, s), 7.71 (1H, dd, J=8.4, 2.5 Hz), 7.26 (1H, d, J=8.5 Hz), 6.38 (1H, s), 3.81-3.72 (2H, m), 3.06 (3H, s), 2.59 (1H, dt, J=15.6, 6.6 Hz), 2.41 (1H, dt, J=15.6, 6.4 Hz), 2.26 (3H, s), 1.61 (1H, t, J=5.6 Hz).

HRMS (ESI) calcd for C$_{22}$H$_{21}$ClF$_3$N$_2$O$_4$S [M+H]$^+$, required m/z: 501.0863, found 501.0857.

Retention time: 9.0 min chiral HPLC condition: LC1, eluent: hexane-EtOH-MeOH [80:16:4 (v/v/v), isocratic].

[α]$_D^{22}$: +3.8 (c=1.0, EtOH).

Example 1—Isomer B $^1$H-NMR (400 MHz, CDCl$_3$) δ: 7.91 (2H, d, J=9.0 Hz), 7.86 (1H, d, J=2.3 Hz), 7.83 (2H, dt, J=9.0, 2.0 Hz), 7.74 (1H, s), 7.71 (1H, dd, J=8.5, 2.3 Hz), 7.27 (1H, d, J=8.2 Hz), 6.37 (1H, s), 3.81-3.71 (2H, m), 3.06 (3H, s), 2.59 (1H, dt, J=15.6, 6.4 Hz), 2.41 (1H, dt, J=15.6, 6.4 Hz), 2.27 (3H, s), 1.54 (1H, t, J=5.7 Hz).

HRMS (ESI) calcd for C$_{22}$H$_{21}$ClF$_3$N$_2$O$_4$S [M+H]$^+$, required m/z: 501.0863, found 501.0863.

Retention time: 12.5 min chiral HPLC condition: LC1, eluent: hexane-EtOH-MeOH [80:16:4 (v/v/v), isocratic].

Example 2

5-(2-Hydroxyethyl)-2-methyl-N-[4-(methylsulfonyl)phenyl]-1-[2-(trifluoromethyl)phenyl]-1H-pyrrole-3-carboxamide

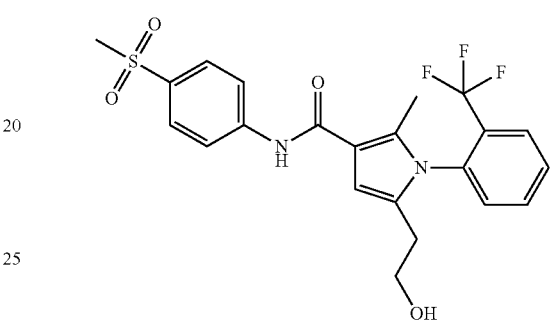

To a solution of the compound (1.0 g, 1.8 mmol) of Comparative Example 63 in methanol (20 mL), 20% palladium hydroxide-carbon (50% Wet, 0.5 g) was added, the inside of the system was made to a hydrogen atmosphere, and the mixture was stirred at room temperature for 5 hours. After the reaction, the reaction mixture was filtered by Celite, and the filtrate was concentrated. The obtained residue was purified by silica gel column chromatography to give the title desired compound (0.83 g, 99%).

MS (FAB) m/z: 467 [M+H]$^+$.

Retention time: 5.6 min (Example 2—isomer A), 6.6 min (Example 2—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [80:16:4 (v/v/v), isocratic]

Example 2—Isomer A $^1$H-NMR (400 MHz, CDCl$_3$) δ: 7.92-7.82 (5H, m), 7.77-7.73 (2H, m), 7.68 (1H, t, J=7.6 Hz), 7.31 (1H, d, J=7.4 Hz), 6.37 (1H, s), 3.80-3.72 (2H, m), 3.06 (3H, s), 2.60 (1H, dt, J=15.6, 6.6 Hz), 2.43 (1H, dt, J=15.6, 6.4 Hz), 2.26 (3H, s), 1.57-1.55 (1H, m).

HRMS (ESI) calcd for C$_{22}$H$_{22}$F$_3$N$_2$O$_4$S [M+H]$^+$, required m/z: 467.1252, found 467.1217.

Retention time: 5.6 min chiral HPLC condition: LC1, eluent: hexane-EtOH-MeOH [70:24:6 (v/v/v), isocratic]

[α]$_D^{20}$: +4.3 (c=1.1, EtOH).

Example 2—Isomer B $^1$H-NMR (400 MHz, CDCl$_3$) δ: 7.92-7.82 (5H, m), 7.76-7.66 (3H, m), 7.30 (1H, d, J=7.8 Hz), 6.39 (1H, s), 3.81-3.71 (2H, m), 3.06 (3H, s), 2.69 (1H, dt, J=15.6, 6.6 Hz), 2.42 (1H, dt, J=15.6, 6.3 Hz), 2.26 (3H, s), 1.65 (1H, br s).

HRMS (ESI) calcd for $C_{22}H_{22}F_3N_2O_4S$ [M+H]$^+$, required m/z: 467.1252, found 467.1256.

Retention time: 6.6 min chiral HPLC condition: LC1, eluent: hexane-EtOH-MeOH [70:24:6 (v/v/v), isocratic].

Example 3

1-(2-Chloro-4-fluorophenyl)-5-(2-hydroxyethyl)-2-methyl-N-[4-(methylsulfonyl)phenyl]-1H-pyrrole-3-carboxamide

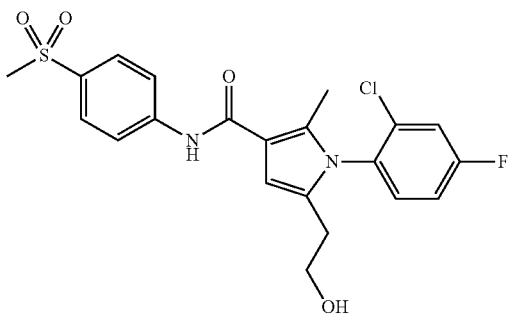 [SMILES: Cc1c(C(=O)Nc2ccc(S(C)(=O)=O)cc2)cc(CCO)n1-c1ccc(F)cc1Cl]

Under a nitrogen atmosphere, to a solution of the compound (0.60 g, 1.1 mmol) of Comparative Example 64 in methylene chloride (4 mL), boron tribromide (1.0M methylene chloride solution, 3.3 mL, 3.3 mmol) was added at −40° C., and the mixture was stirred at the same temperature for 1 hour. After the reaction, water (5 mL) was added, and the mixture was extracted with ethyl acetate. The organic layer was successively washed with a saturated aqueous sodium hydrogencarbonate solution, water and a saturated aqueous sodium chloride solution and after it was dried with sodium sulfate, the solvent was distilled off under reduced pressure. The obtained residue was purified by silica gel column chromatography to give the title desired compound (0.38 g, 76%) as a solid.

$^1$H-NMR (400 MHz, CDCl$_3$) δ: 7.91 (2H, d, J=8.8 Hz), 7.83 (2H, d, J=8.8 Hz), 7.75 (1H, s), 7.36 (1H, dd, J=8.8, 2.8 Hz), 7.31 (1H, dd, J=8.8, 5.6 Hz), 7.20-7.15 (1H, m), 6.39 (1H, s), 3.72 (2H, t, J=6.2 Hz), 3.06 (3H, s), 2.61-2.52 (2H, m), 2.30 (3H, s)

MS (ESI) m/z: 451 [M+H]$^+$.

Retention time: 13.7 min (Example 3—isomer A), 16.3 min (Example 3—isomer B)

chiral HPLC condition: LC5, eluent: EtOH-MeOH [50:50 (v/v), isocratic]

Resolution of the isomer was carried out under the following condition.

chiral HPLC condition: LC6, eluent: EtOH-MeOH [50:50 (v/v), isocratic]

Example 3—Isomer A

MS (ESI) m/z: 451 [M+H]$^+$.

Retention time: 13.7 min chiral HPLC condition: LC5, eluent: EtOH-MeOH [50:50 (v/v), isocratic].

Example 3—Isomer B

MS (ESI) m/z: 451 [M+H]$^+$.

Retention time: 16.3 min chiral HPLC condition: LC5, eluent: EtOH-MeOH [50:50 (v/v), isocratic].

Example 4

1-(2,4-Dichlorophenyl)-5-(2-hydroxyethyl)-2-methyl-N-[4-(methylsulfonyl)phenyl]-1H-pyrrole-3-carboxamide

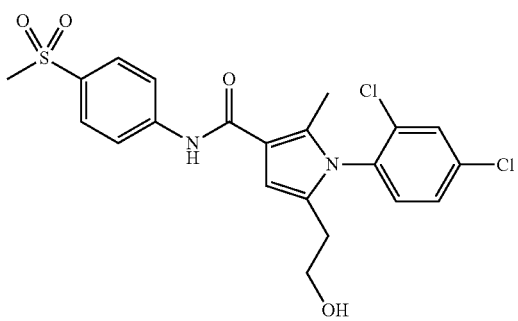 [SMILES: Cc1c(C(=O)Nc2ccc(S(C)(=O)=O)cc2)cc(CCO)n1-c1ccc(Cl)cc1Cl]

The title compound (0.38 g, 90%) was obtained from the compound (0.50 g, 0.90 mmol) of Comparative Example 65 in the process similar to Example 3.

MS (ESI) m/z: 467 [M+H]$^+$.

Retention time: 8.0 min (Example 4—isomer A), 11.1 min (Example 4—isomer B)

chiral HPLC condition: LC5, eluent: EtOH-MeOH [50:50 (v/v), isocratic]

Resolution of the isomer was carried out under the following condition.

chiral HPLC condition: LC6, eluent: EtOH-MeOH [50:50 (v/v), isocratic]

Example 4—Isomer A

MS (ESI) m/z: 467 [M+H]$^+$.

Retention time: 8.0 min chiral HPLC condition: LC5, eluent: EtOH-MeOH [50:50 (v/v), isocratic].

Example 4—Isomer B

MS (ESI) m/z: 467 [M+H]$^+$.

Retention time: 11.4 min

Example 5

1-[4-Fluoro-2-(trifluoromethyl)phenyl]-5-[(2S)-2-hydroxypropyl]-2-methyl-N-[4-(methylsulfonyl)phenyl]-1H-pyrrole-3-carboxamide

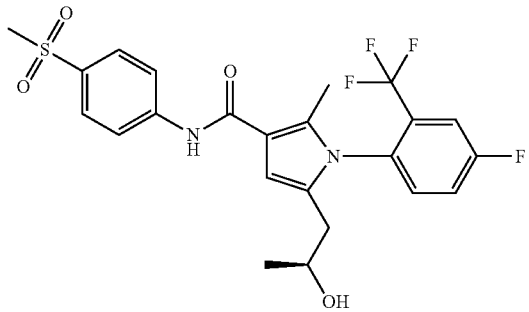 [SMILES: Cc1c(C(=O)Nc2ccc(S(C)(=O)=O)cc2)cc(C[C@H](C)O)n1-c1ccc(F)cc1C(F)(F)F]

The title compound (0.55 g, 88%) was obtained from the compound (0.74 g, 1.3 mmol) of Comparative Example 81 in the process similar to Example 2.

$^1$H-NMR (400 MHz, CDCl$_3$) δ: 7.91 (2H, d, J=9.0 Hz), 7.83 (2H, d, J=9.0 Hz), 7.74 (0.7H, s), 7.74 (0.3H, s), 7.61-7.57 (1H, m), 7.47-7.42 (1H, m), 7.34-7.30 (1H, m), 6.39 (0.7H, s), 6.38 (0.3H, s), 4.07-3.98 (0.3H, m), 3.88-3.79 (0.7H, m), 3.08 (3H, s), 2.52-2.43 (1H, m), 2.33-2.19 (4H, m), 1.71 (0.7H, d, J=3.5 Hz), 1.62 (0.3H, d, J=3.9 Hz), 1.20 (0.9H, d, J=5.9 Hz), 1.16 (2.1H, d, J=6.3 Hz).

HRMS (ESI) calcd for C$_{23}$H$_{23}$F$_4$N$_2$O$_4$S [M+H]$^+$, required m/z: 499.1315, found 499.1319.

Retention time: 6.3 min (Example 5—isomer A), 9.7 min (Example 5—isomer B)

chiral HPLC condition: LC1, eluent: hexane-EtOH-MeOH [80:16:4 (v/v/v), isocratic]

Resolution of the isomer was carried out under the following condition.

chiral HPLC condition: LC3, eluent: hexane-EtOH-MeOH [80:16:4 (v/v/v), isocratic]

Example 5—Isomer A $^1$H-NMR (400 MHz, CDCl$_3$) δ: 7.91 (2H, d, J=9.0 Hz), 7.83 (2H, dt, J=9.0, 2.0 Hz), 7.78 (1H, s), 7.59 (1H, dd, J=8.2, 3.1 Hz), 7.47-7.41 (1H, m), 7.32 (1H, dd, J=8.8, 4.9 Hz), 6.40 (1H, s), 3.89-3.79 (1H, m), 3.06 (3H, s), 2.46 (1H, dd, J=15.6, 8.6 Hz), 2.29 (1H, dd, J=15.3, 3.9 Hz), 2.26 (3H, s), 1.75 (1H, d, J=3.5 Hz), 1.16 (3H, d, J=5.9 Hz).

HRMS (ESI) calcd for C$_{23}$H$_{23}$F$_4$N$_2$O$_4$S [M+H]$^+$, required m/z: 499.1315, found 499.1300.

Retention time: 6.3 min chiral HPLC condition: LC1, eluent: hexane-EtOH-MeOH [80:16:4 (v/v/v), isocratic]

[α]$_D^{22}$: −3.9° (c=1.1, EtOH).

Example 5—Isomer B $^1$H-NMR (400 MHz, CDCl$_3$) δ: 7.90 (2H, d, J=8.8 Hz), 7.83 (2H, dt, J=8.8, 2.0 Hz), 7.78 (1H, s), 7.58 (1H, dd, J=8.2, 2.7 Hz), 7.47-7.41 (1H, m), 7.32 (1H, dd, J=8.6, 4.7 Hz), 6.40 (1H, s), 4.06-3.98 (1H, m), 3.06 (3H, s), 2.48 (1H, dd, J=15.8, 4.1 Hz), 2.26 (3H, s), 2.22 (1H, dd, J=15.6, 8.6 Hz), 1.69 (1H, d, J=3.9 Hz), 1.19 (3H, d, J=6.3 Hz).

HRMS (ESI) calcd for C$_{23}$H$_{23}$F$_4$N$_2$O$_4$S [M+H]$^+$, required m/z: 499.1315, found 499.1286.

Retention time: 9.7 min chiral HPLC condition: LC1, eluent: hexane-EtOH-MeOH [80:16:4 (v/v/v), isocratic].

Example 6

1-[4-Chloro-2-(trifluoromethyl)phenyl]-5-[(2S)-2-hydroxypropyl]-2-methyl-N-[4-(methylsulfonyl)phenyl]-1H-pyrrole-3-carboxamide

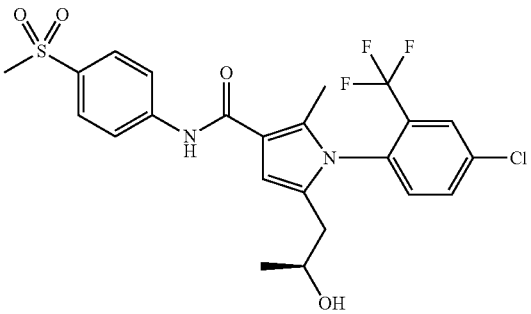 [SMILES: Cc1c(C(=O)Nc2ccc(S(C)(=O)=O)cc2)cc(C[C@H](C)O)n1-c1ccc(Cl)cc1C(F)(F)F]

The title compound (0.13 g, 68%) was obtained from the compound (0.22 g, 0.37 mmol) of Comparative Example 69 in the process similar to Example 1.

$^1$H-NMR (400 MHz, CDCl$_3$) δ: 7.91 (2H, d, J=8.8 Hz), 7.87-7.81 (3H, m), 7.73-7.70 (2H, m), 7.28-7.25 (1H, m), 6.39 (0.6H, s), 6.38 (0.4H, s), 4.06-3.99 (0.4H, m), 3.87-3.81 (0.6H, m), 3.05 (3H, s), 2.51-2.44 (1H, m), 2.32-2.20 (4H, m), 1.69-1.63 (1H, m), 1.20 (1.2H, d, J=6.3 Hz), 1.17 (1.8H, d, J=3.6 Hz).

MS (FAB) m/z: 515 [M+H]$^+$

Retention time: 6.4 min (Example 6—isomer A), 10.0 min (Example 6—isomer B)

chiral HPLC condition: LC1, eluent: hexane-EtOH-MeOH [80:16:4 (v/v/v), isocratic]

Resolution of the isomer was carried out under the following condition.

chiral HPLC condition: LC3, eluent: hexane-EtOH-MeOH [80:16:4 (v/v/v), isocratic]

Example 6—Isomer A $^1$H-NMR (400 MHz, CDCl$_3$) δ: 7.91-7.81 (6H, m), 7.71 (1H, dd, J=8.2, 2.3 Hz), 7.28-7.25 (1H, m), 6.43 (1H, s), 3.88-3.79 (1H, m), 3.05 (3H, s), 2.46 (1H, dd, J=15.5, 8.8 Hz), 2.29 (1H, dd, J=15.6, 3.9 Hz), 2.25 (3H, s), 1.84 (1H, d, J=3.5 Hz), 1.15 (3H, d, J=6.3 Hz).

HRMS (ESI) calcd for C$_{23}$H$_{23}$ClF$_3$N$_2$O$_4$S [M+H]$^+$, required m/z: 515.1019, found 515.1001.

Retention time: 6.4 min chiral HPLC condition: LC1, eluent: hexane-EtOH-MeOH [80:16:4 (v/v/v), isocratic]

[α]$_D^{22}$: −2.0 (c=1.0, EtOH).

Example 6—Isomer B $^1$H-NMR (400 MHz, CDCl$_3$) δ: 7.90 (2H, dt, J=9.0, 2.1 Hz), 7.86-7.81 (3H, m), 7.78 (1H, s), 7.71 (1H, dd, J=8.6, 2.3 Hz), 7.28-7.25 (1H, m), 6.40 (1H, s), 4.06-3.98 (1H, m), 3.06 (3H, s), 2.48 (1H, dd, J=15.4, 4.1 Hz), 2.26 (3H, s), 2.21 (1H, dd, J=15.6, 8.6 Hz), 1.68 (1H, d, J=3.9 Hz), 1.19 (3H, d, J=6.3 Hz).

HRMS (ESI) calcd for $C_{23}H_{23}ClF_3N_2O_4S$ [M+H]$^+$, required m/z: 515.1019, found 515.1002.

Retention time: 10.0 min chiral HPLC condition: LC1, eluent: hexane-EtOH-MeOH [80:16:4 (v/v/v), isocratic].

Example 7

5-[(2S)-2-Hydroxypropyl]-2-methyl-N-[4-(methylsulfonyl)phenyl]-1-[2-(trifluoromethyl)phenyl]-1H-pyrrole-3-carboxamide

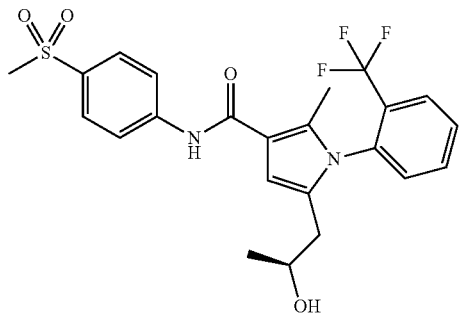 [SMILES: Cc1c(C(=O)Nc2ccc(S(C)(=O)=O)cc2)cc(C[C@H](C)O)n1-c1ccccc1C(F)(F)F]

The title compound (1.1 g, 89%) was obtained from the compound (1.4 g, 2.5 mmol) of Comparative Example 82 in the process similar to Example 2.

MS (FAB) m/z: 481 [M+H]$^+$.

Retention time: 4.7 min (Example 7—isomer A), 6.0 min (Example 7—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [80:16:4 (v/v/v), isocratic]

Example 7—Isomer A $^1$H-NMR (400 MHz, CDCl$_3$) δ: 7.93-7.88 (3H, m), 7.84 (2H, d, J=9.0 Hz), 7.78-7.67 (3H, m), 7.31 (1H, d, J=7.4 Hz), 6.40 (1H, s), 3.86-3.79 (1H, m), 3.06 (3H, s), 2.46 (1H, dd, J=15.4, 8.8 Hz), 2.33-2.26 (4H, m), 1.75 (1H, d, J=3.5 Hz), 1.14 (3H, d, J=6.3 Hz).

HRMS (ESI) calcd for $C_{23}H_{24}F_3N_2O_4S$ [M+H]$^+$, required m/z: 481.1409, found 481.1393.

Retention time: 4.7 min.

chiral HPLC condition: LC1, eluent: hexane-EtOH-MeOH [70:24:6 (v/v/v), isocratic]

$[α]_D^{20}$: −3.2 (c=1.1, EtOH).

Example 7—Isomer B $^1$H-NMR (400 MHz, CDCl$_3$) δ: 7.92-7.80 (6H, m), 7.77-7.72 (1H, m), 7.68 (1H, t, J=7.6 Hz), 7.30 (1H, d, J=7.4 Hz), 6.40 (1H, s), 4.05-3.98 (1H, m), 3.06 (3H, s), 2.48 (1H, dd, J=15.2, 4.3 Hz), 2.27-2.21 (4H, m), 1.70 (1H, br s), 1.18 (3H, d, J=6.3 Hz).

HRMS (ESI) calcd for $C_{23}H_{24}F_3N_2O_4S$ [M+H]$^+$, required m/z: 481.1409, found 481.1401.

Retention time: 6.0 min chiral HPLC condition: LC1, eluent: hexane-EtOH-MeOH [70:24:6 (v/v/v), isocratic].

Example 8

1-(4-Fluoro-2-methylphenyl)-5-[(2S)-2-hydroxypropyl]-2-methyl-N-[4-(methylsulfonyl)phenyl]-1H-pyrrole-3-carboxamide

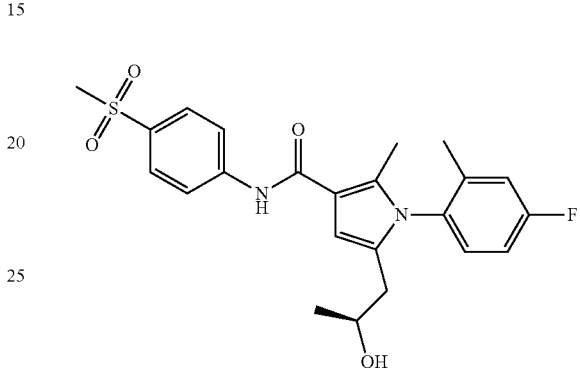

The title compound (1.2 g, 99%) was obtained from the compound (1.4 g, 2.7 mmol) of Comparative Example 83 in the process similar to Example 2.

MS (FAB) m/z: 445 [M+H]$^+$

Retention time: 5.8 min (Example 8—isomer A), 7.5 min (Example 8—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [70:24:6 (v/v/v), isocratic]

Example 8—Isomer A $^1$H-NMR (500 MHz, CDCl$_3$) δ: 7.90 (2H, d, J=8.6 Hz), 7.84 (2H, d, J=8.6 Hz), 7.77 (1H, s), 7.16-7.01 (3H, m), 6.40 (1H, s), 3.87-3.78 (1H, m), 3.06 (3H, s), 2.40 (1H, dd, J=15.2, 8.8 Hz), 2.32 (1H, dd, J=15.2, 4.4 Hz), 2.26 (3H, s), 1.94 (1H, s), 1.72 (1H, brs), 1.15 (3H, d, J=5.9 Hz).

HRMS (ESI) calcd for $C_{23}H_{26}FN_2O_4S$ [M+H]$^+$, required m/z: 445.1597, found 445.1593.

Retention time: 5.8 min chiral HPLC condition: LC1, eluent: hexane-EtOH-MeOH [70:24:6 (v/v/v), isocratic]

$[α]_D^{22}$: −9.7° (c=1.0, EtOH).

Example 8—Isomer B $^1$H-NMR (400 MHz, CDCl$_3$) δ: 7.90 (2H, d, J=8.6 Hz), 7.84 (2H, d, J=8.6 Hz), 7.77 (1H, s), 7.16-7.00 (3H, m), 6.40 (1H, s), 3.89-3.78 (1H, m), 3.06 (3H, s), 2.45 (1H, dd, J=15.2, 4.4 Hz), 2.34 (1H, dd, J=15.2, 8.6 Hz), 2.26 (3H, s), 1.95 (1H, s), 1.66 (1H, brs), 1.17 (3H, d, J=5.9 Hz).

HRMS (ESI) calcd for $C_{23}H_{26}FN_2O_4S$ [M+H]$^+$, required m/z: 445.1597, found 445.1605.

Retention time: 7.5 min chiral HPLC condition: LC1, eluent: hexane-EtOH-MeOH [70:24:6 (v/v/v), isocratic].

Example 9

1-[2-(Difluoromethoxy)-4-fluorophenyl]-5-[(2S)-2-hydroxypropyl]-2-methyl-N-[4-(methylsulfonyl)phenyl]-1H-pyrrole-3-carboxamide

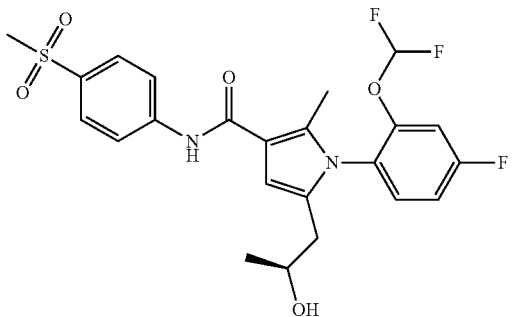 [SMILES: Cc1c(C(=O)Nc2ccc(S(C)(=O)=O)cc2)cc(C[C@H](C)O)n1-c1ccc(F)cc1OC(F)F]

The title compound (1.1 g, 97%) was obtained from the compound (1.4 g, 2.3 mmol) of Comparative Example 84 in the process similar to Example 2.

MS (FAB) m/z: 497 [M+H]$^+$

Retention time: 4.6 min (Example 9—isomer A), 6.3 min (Example 9—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [70:24:6 (v/v/v), isocratic]

Example 9—Isomer A $^1$H-NMR (500 MHz, CDCl$_3$) δ: 7.91 (2H, d, J=8.6 Hz), 7.83 (2H, d, J=8.6 Hz), 7.76 (1H, s), 7.29-7.24 (1H, m), 7.20-7.15 (1H, m), 7.13-7.07 (1H, m), 6.41 (1H, t, J=72.3 Hz), 6.38 (1H, s), 3.88-3.79 (1H, m), 3.05 (3H, s), 2.41 (2H, d, J=6.4 Hz), 2.30 (3H, s), 1.67 (1H, brs), 1.15 (3H, d, J=6.4 Hz).

HRMS (ESI) calcd for $C_{23}H_{24}F_3N_2O_5S$ [M+H]$^+$, required m/z: 497.1358, found 497.1350.

Retention time: 4.6 min chiral HPLC condition: LC1, eluent: hexane-EtOH-MeOH [70:24:6 (v/v/v), isocratic]

$[α]_D^{22}$: −12.6° (c=1.0, EtOH).

Example 9—Isomer B $^1$H-NMR (400 MHz, CDCl$_3$) δ: 7.91 (2H, d, J=8.6 Hz), 7.83 (2H, d, J=8.6 Hz), 7.76 (1H, s), 7.31-7.27 (1H, m), 7.20-7.14 (1H, m), 7.13-7.07 (1H, m), 6.42 (1H, t, J=72.0 Hz), 6.39 (1H, s), 3.94-3.84 (1H, m), 3.05 (3H, s), 2.50 (1H, dd, J=15.2, 4.3 Hz), 2.38 (1H, dd, J=15.2, 8.6 Hz), 2.38 (3H, s), 1.66 (1H, brs), 1.16 (3H, d, J=6.4 Hz).

HRMS (ESI) calcd for $C_{23}H_{24}F_3N_2O_5S$ [M+H]$^+$, required m/z: 497.1358, found 497.1374.

Retention time: 6.3 min chiral HPLC condition: LC1, eluent: hexane-EtOH-MeOH [70:24:6 (v/v/v), isocratic].

Example 10

N-[4-(Aminosulfonyl)-3-methylphenyl]-1-[4-fluoro-2-(trifluoromethyl)phenyl]-5-[(2S)-2-hydroxypropyl]-2-methyl-1H-pyrrole-3-carboxamide

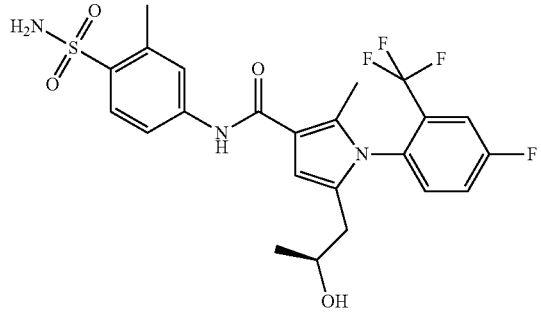 [SMILES: Cc1cc(NC(=O)c2cc(C[C@H](C)O)n(-c3ccc(F)cc3C(F)(F)F)c2C)ccc1S(N)(=O)=O]

The title compound (0.29 g, 72%) was obtained from the compound (0.47 g, 0.78 mmol) of Comparative Example 72 in the process similar to Example 2.

MS (FAB) m/z: 514 [M+H]$^+$

Retention time: 3.4 min (Example 10—isomer A), 5.0 min (Example 10—isomer B)

chiral HPLC condition: LC1, eluent: hexane-EtOH-MeOH [50:40:10 (v/v/v), isocratic]

Resolution of the isomer was carried out under the following condition.

chiral HPLC condition: LC3, eluent: hexane-EtOH-MeOH [50:40:10 (v/v/v), isocratic]

Example 10—Isomer A $^1$H-NMR (400 MHz, CDCl$_3$) δ: 7.92 (1H, d, J=8.6 Hz), 7.78 (1H, s), 7.67 (1H, d, J=2.0 Hz), 7.59 (1H, dd, J=8.2, 3.1 Hz), 7.51-7.40 (2H, m), 7.35-7.30 (1H, m), 6.42 (1H, s), 4.91 (2H, s), 3.88-3.78 (1H, m), 2.65 (3H, s), 2.45 (1H, dd, J=15.6, 9.0 Hz), 2.29 (1H, dd, J=15.6, 3.9 Hz), 2.25 (3H, s), 1.67 (1H, brs), 1.15 (3H, d, J=6.4 Hz).

HRMS (ESI) calcd for $C_{23}H_{24}F_4N_3O_4S$ [M+H]$^+$, required m/z: 514.1424, found 514.1432.

Retention time: 3.4 min chiral HPLC condition: LC1, eluent: hexane-EtOH-MeOH [50:40:10 (v/v/v), isocratic].

Example 10—Isomer B $^1$H-NMR (400 MHz, CDCl$_3$) δ: 7.98 (1H, d, J=8.6 Hz), 7.72 (1H, d, J=2.0 Hz), 7.63 (1H, s), 7.58 (1H, dd, J=8.6, 3.1 Hz), 7.50 (1H, dd, J=8.6, 2.0 Hz), 7.47-7.41 (1H, m), 7.35-7.30 (1H, m), 6.37 (1H, s), 4.74 (2H, s), 4.07-3.97 (1H, m), 2.69 (3H, s), 2.49 (1H, dd, J=15.6, 4.3 Hz), 2.26 (3H, s), 2.22 (1H, dd, J=15.6, 8.6 Hz), 1.62 (1H, brs), 1.19 (3H, d, J=6.4 Hz).

HRMS (ESI) calcd for $C_{23}H_{24}F_4N_3O_4S$ [M+H]$^+$, required m/z: 514.1424, found 514.1441.

Retention time: 5.0 min chiral HPLC condition: LC1, eluent: hexane-EtOH-MeOH [50:40:10 (v/v/v), isocratic].

Example 11

1-[4-Chloro-2-(difluoromethoxy)phenyl]-5-[(2S)-2-hydroxypropyl]-2-methyl-N-[4-(methylsulfonyl)phenyl]-1H-pyrrole-3-carboxamide

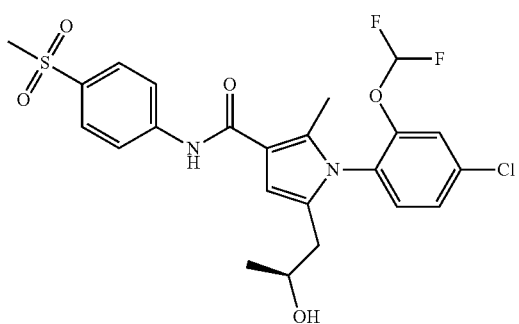 [SMILES: Cc1c(C(=O)Nc2ccc(S(C)(=O)=O)cc2)cc(C[C@H](C)O)n1-c1ccc(Cl)cc1OC(F)F]

The title compound (0.31 g, 80%) was obtained from the compound (0.57 g, 0.94 mmol) of Comparative Example 85 in the process similar to Example 1.

MS (FAB) m/z: 513 [M+H]$^+$

Retention time: 4.8 min (Example 11—isomer A), 6.6 min (Example 11—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [70:24:6 (v/v/v), isocratic]

Example 11—Isomer A $^1$H-NMR (500 MHz, CDCl$_3$) δ: 7.91 (2H, d, J=8.6 Hz), 7.83 (2H, d, J=8.6 Hz), 7.76 (1H, s), 7.45-7.42 (1H, m), 7.37 (1H, dd, J=8.3, 2.4 Hz), 7.22 (1H, d, J=8.8 Hz), 6.40 (1H, t, J=72.0 Hz), 6.39 (1H, s), 3.88-3.79 (1H, m), 3.05 (3H, s), 2.43 (2H, d, J=6.4 Hz), 2.31 (3H, s), 1.67 (1H, brs), 1.15 (3H, d, J=6.4 Hz).

HRMS (ESI) calcd for $C_{23}H_{24}ClF_2N_2O_5S$ [M+H]$^+$, required m/z: 513.1063, found 513.1071.

Retention time: 4.8 min chiral HPLC condition: LC1, eluent: hexane-EtOH-MeOH [70:24:6 (v/v/v), isocratic]

$[α]_D^{22}$: −11.0° (c=1.0, EtOH).

Example 11—Isomer B $^1$H-NMR (400 MHz, CDCl$_3$) δ: 7.91 (2H, d, J=8.6 Hz), 7.83 (2H, d, J=8.6 Hz), 7.76 (1H, s), 7.44-7.41 (1H, m), 7.37 (1H, dd, J=8.3, 2.4 Hz), 7.24 (1H, d, J=8.2 Hz), 6.41 (1H, t, J=72.0 Hz), 6.39 (1H, s), 3.95-3.84 (1H, m), 3.05 (3H, s), 2.50 (1H, dd, J=15.2, 4.3 Hz), 2.38 (1H, dd, J=15.2, 8.6 Hz), 2.31 (3H, s), 1.66 (1H, brs), 1.16 (3H, d, J=5.9 Hz).

HRMS (ESI) calcd for $C_{23}H_{24}ClF_2N_2O_5S$ [M+H]$^+$, required m/z: 513.1081, found 513.1071.

Retention time: 6.6 min chiral HPLC condition: LC1, eluent: hexane-EtOH-MeOH [70:24:6 (v/v/v), isocratic].

Example 12

N-[4-(Aminosulfonyl)-3-chlorophenyl]-1-[4-fluoro-2-(trifluoromethyl)phenyl]-5-[(2S)-2-hydroxypropyl]-2-methyl-1H-pyrrole-3-carboxamide

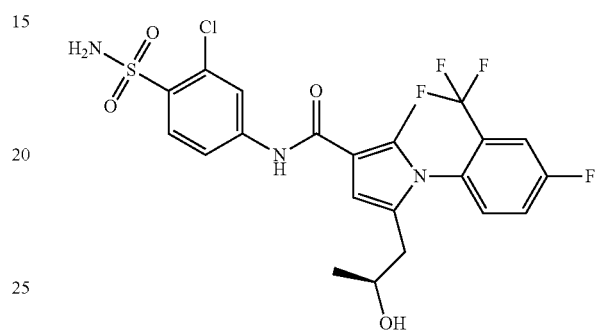

The title compound (0.19 g, 67%) was obtained from the compound (0.31 g, 0.52 mmol) of Comparative Example 79 in the process similar to Example 3.

$^1$H-NMR (500 MHz, DMSO-d$_6$) δ: 9.89 (1H, d, J=5.9 Hz), 8.13 (1H, s), 7.95 (1H, dd, J=2.4, 8.3 Hz), 7.91 (0.4H, s), 7.90 (0.6H, s), 7.87 (0.6H, s), 7.85 (0.4H, s), 7.83-7.77 (1H, m), 7.62 (1H, dd, J=4.9, 8.8 Hz), 7.46 (2H, s), 6.73 (1H, s), 4.57 (0.6H, d, J=4.9 Hz), 4.55 (0.4H, d, J=4.4 Hz), 3.75-3.68 (1H, m), 2.43 (0.6H, dd, J=5.9, 15.1 Hz), 2.28-2.16 (0.8H, m), 2.15 (1.8H, s), 2.14 (1.2H, s), 2.03 (0.6H, dd, J=6.8, 15.1 Hz), 1.05 (1.2H, d, J=6.4 Hz), 0.99 (1.8H, d, J=6.4 Hz).

MS (ESI) m/z: 534 [M+H]$^+$

Retention time: 3.4 min (Example 12—isomer A), 4.9 min (Example 12—isomer B)

chiral HPLC condition: LC1, eluent: hexane-EtOH-MeOH [50:40:10 (v/v/v), isocratic]

Resolution of the isomer was carried out under the following condition.

chiral HPLC condition: LC3, eluent: hexane-EtOH-MeOH [50:40:10 (v/v/v), isocratic]

Example 12—Isomer A $^1$H-NMR (500 MHz, CDCl$_3$) δ: 8.03 (2H, d, J=9.3 Hz), 7.91 (1H, d, J=8.3 Hz), 7.58 (1H, dd, J=2.9, 8.3 Hz), 7.48-7.40 (2H, m), 7.33 (1H, dd, J=4.9, 8.3 Hz), 6.49 (1H, s), 5.37 (2H, s), 3.87-3.78 (1H, brs), 2.43 (1H, dd, J=8.8, 15.6 Hz), 2.30-3.20 (4H, m), 2.13 (1H, s), 1.13 (3H, d, J=5.9 Hz).

MS (ESI) m/z: 534 [M+H]$^+$

HRMS (ESI) calcd for $C_{22}H_{20}ClF_4N_3NaO_4S$ [M+Na]$^+$, required m/z: 556.0697, found 556.0719

Retention time: 3.3 min chiral HPLC condition: LC1, eluent: hexane-EtOH-MeOH [50:40:10 (v/v/v), isocratic]

$[α]_D^{22}$: −3.8° (c=1.0, EtOH).

Example 12—Isomer B $^1$H-NMR (500 MHz, CDCl$_3$) δ: 8.05 (2H, d, J=9.3 Hz), 7.97-7.88 (2H, m), 7.56 (1H, dd, J=2.9, 8.3 Hz), 7.49-7.40 (2H, m), 7.33 (1H, dd, J=4.9, 8.3 Hz), 6.45 (1H, s), 5.31 (2H, s), 4.08-3.98 (1H, brs), 2.45 (1H, dd, J=3.9, 15.6 Hz), 2.27-2.15 (4H, m), 1.96 (1H, s), 1.17 (3H, d, J=5.9 Hz).

MS (ESI) m/z: 534 [M+H]$^+$
HRMS (ESI) calcd for $C_{22}H_{20}ClF_4N_3NaO_4S$ [M+Na]$^+$, required m/z: 556.0697, found 556.0716
Retention time: 4.9 min
chiral HPLC condition: LC1, eluent: hexane-EtOH-MeOH [50:40:10 (v/v/v), isocratic]
$[\alpha]_D^{22}$: +3.3° (c=0.75, EtOH).

Example 13

N-[4-(Aminosulfonyl)-3-chlorophenyl]-1-[4-chloro-2-(trifluoromethyl)phenyl]-5-[(2S)-2-hydroxypropyl]-2-methyl-1H-pyrrole-3-carboxamide

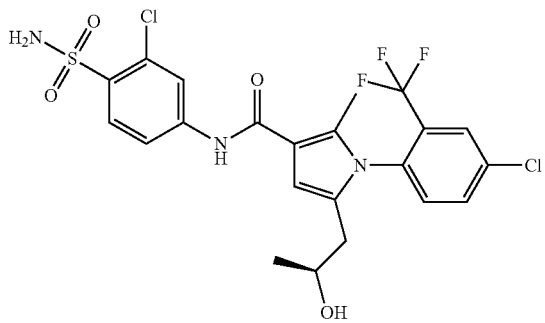 [SMILES: Cc1c(C(=O)Nc2ccc(S(N)(=O)=O)c(Cl)c2)cc(C[C@H](C)O)n1-c1ccc(Cl)cc1C(F)(F)F]

The title compound (0.26 g, 88%) was obtained from the compound (0.25 g, 0.39 mmol) of Comparative Example 80 in the process similar to Example 3.

$^1$H-NMR (500 MHz, DMSO-d$_6$) δ: 9.89 (0.6H, s), 9.88 (0.4H, s), 8.15-8.08 (2H, m), 8.03-7.98 (1H, m), 7.93-7.84 (2H, m), 7.58 (1H, d, J=8.3 Hz), 7.48-7.44 (2H, brs), 6.74 (1H, s), 4.57 (0.6H, d, J=4.4 Hz), 4.55 (0.4H, d, J=4.4 Hz), 3.76-3.65 (1H, m), 2.43 (0.6H, dd, J=5.9, 15.1 Hz), 2.30-2.17 (0.8H, m), 2.15 (1.8H, s), 2.14 (1.2H, s), 2.04 (0.6H, dd, J=6.8, 15.1 Hz), 1.05 (1.2H, d, J=5.4 Hz), 0.99 (1.8H, d, J=6.4 Hz).
MS (ESI) m/z: 550 [M+H]$^+$
Retention time: 3.4 min (Example 13—isomer A), 5.0 min (Example 13—isomer B)
chiral HPLC condition: LC1, eluent: hexane-EtOH-MeOH [50:40:10 (v/v/v), isocratic]
Resolution of the isomer was carried out under the following condition.
chiral HPLC condition: LC3, eluent: hexane-EtOH-MeOH [50:40:10 (v/v/v), isocratic]
Example 13—Isomer A
$^1$H-NMR (500 MHz, DMSO-d$_6$) δ: 9.89 (1H, s), 8.13 (1H, d, J=2.4 Hz), 8.11 (1H, d, J=2.4 Hz), 8.01 (1H, dd, J=2.4, 8.8 Hz), 7.93-7.83 (2H, m), 7.58 (1H, d, J=8.3 Hz), 7.50-7.41 (2H, brs), 6.74 (1H, s), 4.57 (1H, d, J=4.4 Hz), 3.75-3.65 (1H, m), 2.43 (1H, dd, J=5.9, 15.1 Hz), 2.15 (3H, s), 2.04 (1H, dd, J=6.8, 15.1 Hz), 0.99 (3H, d, J=6.4 Hz).
MS (ESI) m/z: 550 [M+H]$^+$
HRMS (ESI) calcd for $C_{22}H_{20}Cl_2F_3N_3NaO_4S$ [M+Na]$^+$, required m/z: 572.04014, found 572.0414
Retention time: 3.4 min
chiral HPLC condition: LC1, eluent: hexane-EtOH-MeOH [50:40:10 (v/v/v), isocratic].
Example 13—Isomer B
$^1$H-NMR (500 MHz, DMSO-d$_6$) δ: 9.88 (1H, s), 8.13 (1H, d, J=2.0 Hz), 8.10 (1H, d, J=2.4 Hz), 8.00 (1H, dd, J=2.0, 8.8 Hz), 7.93-7.83 (2H, m), 7.58 (1H, d, J=8.8 Hz), 7.49-7.41 (2H, brs), 6.74 (1H, s), 4.55 (1H, d, J=4.4 Hz), 3.76-3.67 (1H, m), 2.30-2.17 (2H, m), 2.14 (3H, s), 1.05 (3H, d, J=5.4 Hz).
MS (ESI) m/z: 550 [M+H]$^+$
HRMS (ESI) calcd for $C_{22}H_{20}Cl_2F_3N_3NaO_4S$ [M+Na]$^+$, required m/z: 572.04014, found 572.0392
Retention time: 5.0 min
chiral HPLC condition: LC1, eluent: hexane-EtOH-MeOH [50:40:10 (v/v/v), isocratic].

Example 14

N-[4-(Aminosulfonyl)-3-methylphenyl]-1-[4-chloro-2-(trifluoromethyl)phenyl]-5-[(2S)-2-hydroxypropyl]-2-methyl-1H-pyrrole-3-carboxamide

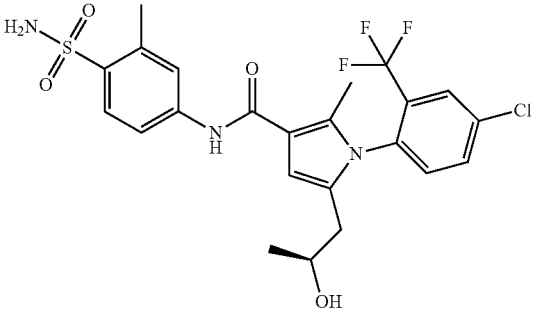 [SMILES: Cc1cc(NC(=O)c2cc(C[C@H](C)O)n(-c3ccc(Cl)cc3C(F)(F)F)c2C)ccc1S(N)(=O)=O]

The title compound (0.36 g, 73%) was obtained from the compound (0.67 g, 0.92 mmol) of Comparative Example 73 in the process similar to Example 3.
MS (FAB) m/z: 530 [M+H]$^+$
Retention time: 3.4 min (Example 14—isomer A), 5.0 min (Example 14—isomer B)
chiral HPLC condition: LC1, eluent: hexane-EtOH-MeOH [50:40:10 (v/v/v), isocratic]
Resolution of the isomer was carried out under the following condition.
chiral HPLC condition: LC3, eluent: hexane-EtOH-MeOH [50:40:10 (v/v/v), isocratic]
Example 14—Isomer A
$^1$H-NMR (400 MHz, CDCl$_3$) δ: 7.92 (1H, s), 7.84 (2H, dd, J=5.5, 3.1 Hz), 7.70 (1H, dd, J=8.6, 2.4 Hz), 7.62 (1H, d, J=2.0 Hz), 7.48-7.42 (1H, m), 7.27 (1H, d, J=8.2 Hz), 6.47 (1H, s), 5.10 (2H, s), 3.87-3.74 (1H, m), 2.59 (3H, s), 2.43 (1H, dd, J=15.6, 9.0 Hz), 2.30-2.21 (1H, m), 2.24 (3H, s), 2.16 (1H, brs), 1.13 (3H, d, J=6.3 Hz).
HRMS (ESI) calcd for $C_{23}H_{24}ClF_3N_3O_4S$ [M+H]$^+$, required m/z: 530.1128, found 530.1141.
Retention time: 3.4 min
chiral HPLC condition: LC1, eluent: hexane-EtOH-MeOH [50:40:10 (v/v/v), isocratic]
$[\alpha]_D^{22}$: −2.7° (c=1.0, EtOH).
Example 14—Isomer B
$^1$H-NMR (400 MHz, CDCl$_3$) δ: 7.91 (1H, d, J=8.6 Hz), 7.84 (1H, d, J=2.4 Hz), 7.76 (1H, s), 7.71 (1H, dd, J=8.6, 2.4 Hz), 7.66 (1H, d, J=2.0 Hz), 7.50-7.44 (1H, m), 7.26 (1H, d, J=8.6 Hz), 6.42 (1H, s), 4.92 (2H, s), 4.07-3.97 (1H, m), 2.64 (3H, s), 2.46 (1H, dd, J=15.6, 3.9 Hz), 2.25 (3H, s), 2.20 (1H, dd, J=15.6, 9.0 Hz), 1.85 (1H, brs), 1.18 (3H, d, J=6.3 Hz).

HRMS (ESI) calcd for $C_{23}H_{24}ClF_3N_3O_4S$ [M+H]+, required m/z: 530.1128, found 530.1130.

Retention time: 5.0 min chiral HPLC condition: LC1, eluent: hexane-EtOH-MeOH [50:40:10 (v/v/v), isocratic].

Example 15

N-[4-(Aminosulfonyl)-3-methylphenyl]-1-[4-chloro-2-(trifluoromethoxy)phenyl]-5-[(2S)-2-hydroxypropyl]-2-methyl-1H-pyrrole-3-carboxamide

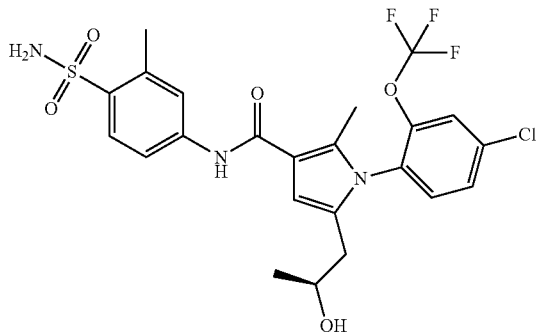 [SMILES: Cc1cc(NC(=O)c2cc(C[C@H](C)O)n(-c3ccc(Cl)cc3OC(F)(F)F)c2C)ccc1S(N)(=O)=O]

The title compound (0.54 g, 88%) was obtained from the compound (0.72 g, 1.1 mmol) of Comparative Example 74 in the process similar to Example 3.

MS (FAB) m/z: 546 [M+H]+

Retention time: 3.3 min (Example 15—isomer A), 4.7 min (Example 15 isomer B)

chiral HPLC condition: LC1, eluent: hexane-EtOH-MeOH [50:40:10 (v/v/v), isocratic]

Resolution of the isomer was carried out under the following condition.

chiral HPLC condition: LC3, eluent: hexane-EtOH-MeOH [50:40:10 (v/v/v), isocratic]

Example 15—Isomer A $^1$H-NMR (400 MHz, CDCl$_3$) δ: 7.91 (1H, d, J=8.6 Hz), 7.78 (1H, s), 7.67 (1H, d, J=2.0 Hz), 7.51-7.43 (3H, m), 7.28 (1H, d, J=8.6 Hz), 6.43 (1H, s), 4.93 (2H, s), 3.86-3.75 (1H, m), 2.64 (3H, s), 2.40 (1H, dd, J=15.6, 8.2 Hz), 2.37 (1H, dd, J=15.6, 4.3 Hz), 2.30 (3H, s), 1.88 (1H, brs), 1.15 (3H, d, J=6.3 Hz).

HRMS (ESI) calcd for $C_{23}H_{24}ClF_3N_3O_5S$ [M+H]+, required m/z: 546.1077, found 546.1089.

Retention time: 3.3 min chiral HPLC condition: LC1, eluent: hexane-EtOH-MeOH [50:40:10 (v/v/v), isocratic]

$[α]_D^{22}$: −7.6° (c=1.0, EtOH).

Example 15—Isomer B $^1$H-NMR (400 MHz, CDCl$_3$) δ: 7.92 (1H, d, J=8.6 Hz), 7.74 (1H, s), 7.67 (1H, d, J=2.0 Hz), 7.51-7.43 (3H, m), 7.29 (1H, d, J=8.6 Hz), 6.42 (1H, s), 4.90 (2H, s), 4.02-3.90 (1H, m), 2.65 (3H, s), 2.47 (1H, dd, J=15.6, 4.3 Hz), 2.32 (1H, dd, J=15.6, 8.6 Hz), 2.30 (3H, s), 1.83 (1H, brs), 1.17 (3H, d, J=6.3 Hz).

HRMS (ESI) calcd for $C_{23}H_{24}ClF_3N_3O_5S$ [M+H]+, required m/z: 546.1077, found 546.1088.

Retention time: 4.7 min chiral HPLC condition: LC1, eluent: hexane-EtOH-MeOH [50:40:10 (v/v/v), isocratic].

Example 16

1-[4-Fluoro-2-(trifluoromethoxy)phenyl]-5-[(2S)-2-hydroxypropyl]-2-methyl-N-[4-(methylsulfonyl)phenyl]-1H-pyrrole-3-carboxamide

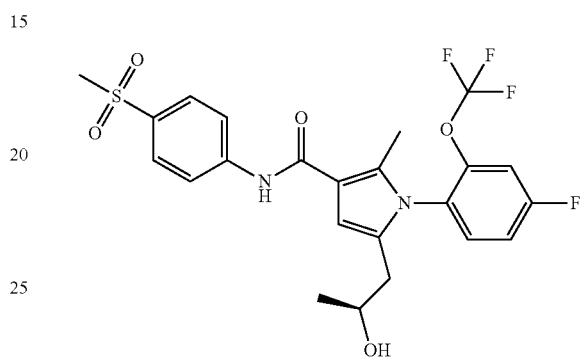

The title compound (0.10 g, 79%) was obtained from the compound (0.15 g, 0.25 mmol) of Comparative Example 86 in the process similar to Example 3.

$^1$H-NMR (400 MHz, CDCl$_3$) δ: 7.90 (2H, d, J=8.8 Hz), 7.83 (2H, d, J=8.8 Hz), 7.77 (1H, s), 7.37-7.29 (1H, m), 7.26-7.16 (2H, m), 6.41 (1H, s), 4.00-3.91 (0.5H, m), 3.87-3.77 (0.5H, m), 3.05 (3H, s), 2.51-2.28 (5H, m), 1.73-1.65 (1H, m), 1.17 (1.5H, d, J=6.4 Hz), 1.15 (1.5H, d, J=6.4 Hz).

MS (AP) m/z: 515 [M+H]+

Retention time: 3.9 min (Example 16—isomer A), 5.1 min (Example 16—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [70:24:6 (v/v/v), isocratic]"

Example 16—Isomer A $^1$H-NMR (500 MHz, CDCl$_3$) δ: 7.90 (2H, d, J=8.8 Hz), 7.86-7.81 (3H, m), 7.32 (1H, dd, J=5.4, 8.8 Hz), 7.26-7.16 (2H, m), 6.42 (1H, s), 3.87-3.77 (1H, m), 3.05 (3H, s), 2.46 (1H, dd, J=8.3, 15.6 Hz), 2.38 (1H, dd, J=3.9, 15.6 Hz), 2.30 (3H, s), 1.77 (1H, s), 1.15 (3H, d, J=6.4 Hz).

MS (ESI) m/z: 515 [M+H]+

Retention time: 3.9 min chiral HPLC condition: LC1, eluent: hexane-EtOH-MeOH [70:24:6 (v/v/v), isocratic]

$[α]_D^{22}$: −3.6° (c=1.0, EtOH).

Example 16—Isomer B $^1$H-NMR (500 MHz, CDCl$_3$) δ: 7.90 (2H, d, J=8.8 Hz), 7.85-7.78 (3H, m), 7.33 (1H, dd, J=5.9, 8.8 Hz), 7.25-7.16 (2H, m), 6.41 (1H, s), 4.00-3.91 (1H, m), 3.05 (3H, s), 2.47 (1H, dd, J=4.4, 15.6 Hz), 2.34 (1H, dd, J=8.8, 15.6 Hz), 2.30 (3H, s), 1.75 (1H, d, J=3.9 Hz), 1.17 (3H, d, J=6.4 Hz)

Example 17

N-[4-(Aminosulfonyl)-3-methylphenyl]-1-(4-chloro-2-methylphenyl)-5-[(2S)-2-hydroxypropyl]-2-methyl-1H-pyrrole-3-carboxamide

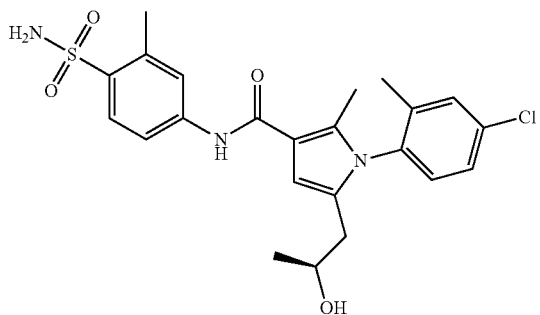 [SMILES: Cc1cc(Cl)ccc1-n1c(C[C@H](C)O)cc(C(=O)Nc2ccc(S(N)(=O)=O)c(C)c2)c1C]

The title compound (0.48 g, 79%) was obtained from the compound (0.75 g, 1.3 mmol) of Comparative Example 75 in the process similar to Example 3.

MS (FAB) m/z: 476 [M+H]$^+$

Retention time: 5.1 min (Example 17—isomer A), 8.3 min (Example 17—isomer B)

chiral HPLC condition: LC1, eluent: hexane-EtOH-MeOH [50:40:10 (v/v/v), isocratic]

Resolution of the isomer was carried out under the following condition.

chiral HPLC condition: LC3, eluent: hexane-EtOH-MeOH [50:40:10 (v/v/v), isocratic]

Example 17—Isomer A $^1$H-NMR (400 MHz, CDCl$_3$) δ: 7.94 (1H, d, J=8.6 Hz), 7.71 (1H, s), 7.69 (1H, d, J=2.0 Hz), 7.49 (1H, dd, J=8.6, 2.4 Hz), 7.38 (1H, d, J=2.4 Hz), 7.35-7.30 (1H, m), 7.09 (1H, d, J=8.2 Hz), 6.40 (1H, s), 4.85 (2H, s), 3.87-3.77 (1H, m), 2.67 (3H, s), 2.39 (1H, dd, J=15.6, 8.6 Hz), 2.31 (1H, dd, J=15.6, 4.3 Hz), 2.26 (3H, s), 1.93 (3H, s), 1.82 (1H, brs), 1.14 (3H, d, J=6.3 Hz).

HRMS (ESI) calcd for C$_{23}$H$_{27}$ClN$_3$O$_4$S [M+H]$^+$, required m/z: 476.1411, found 476.1425.

Retention time: 5.1 min chiral HPLC condition: LC1, eluent: hexane-EtOH-MeOH [50:40:10 (v/v/v), isocratic]

[α]$_D^{22}$: −6.9° (c=1.0, EtOH).

Example 17—Isomer B $^1$H-NMR (400 MHz, CDCl$_3$) δ: 7.88 (1H, d, J=8.6 Hz), 7.81 (1H, s), 7.65 (1H, d, J=2.0 Hz), 7.47 (1H, dd, J=8.6, 2.0 Hz), 7.37 (1H, d, J=2.4 Hz), 7.31 (1H, dd, J=8.2, 2.4 Hz), 7.08 (1H, d, J=8.2 Hz), 6.44 (1H, s), 5.01 (2H, s), 3.89-3.78 (1H, m), 2.62 (3H, s), 2.43 (1H, dd, J=15.6, 4.3 Hz), 2.31 (1H, dd, J=15.6, 8.6 Hz), 2.25 (3H, s), 1.94 (3H, s), 1.61 (1H, brs), 1.14 (3H, d, J=5.9 Hz).

HRMS (ESI) calcd for C$_{23}$H$_{27}$ClN$_3$O$_4$S [M+H]$^+$, required m/z: 476.1411, found 476.1425.

Retention time: 8.3 min chiral HPLC condition: LC1, eluent: hexane-EtOH-MeOH [50:40:10 (v/v/v), isocratic].

Example 18

N-[4-(Aminosulfonyl)-3-chlorophenyl]-1-[4-chloro-2-(trifluoromethoxy)phenyl]-5-[(2S)-2-hydroxypropyl]-2-methyl-1H-pyrrole-3-carboxamide

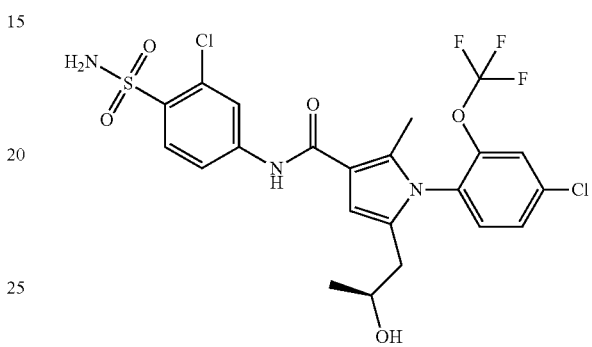

The title compound (0.27 g, 83%) was obtained from the compound (0.38 g, 0.58 mmol) of Comparative Example 76 in the process similar to Example 3.

$^1$H-NMR (500 MHz, CDCl$_3$) δ: 8.05 (1H, s), 7.95 (1H, d, J=8.6 Hlz), 7.91 (0.5H, s), 7.89 (0.5H, s), 7.51-7.44 (3H, m), 7.32-7.27 (1H, m), 5.28 (2H, s), 4.03-3.93 (0.5H, m), 3.86-3.77 (0.5H, m), 2.50-2.44 (5H, m), 2.00-1.86 (1H, m), 1.17 (1.5H, d, J=6.3 Hz), 1.14 (1.5H, d, J=6.3 Hz).

MS (ESI) m/z: 566 [M+H]$^+$

Retention time: 3.3 min (Example 18—isomer A), 4.7 min (Example 18—isomer B)

chiral HPLC condition: LC1, eluent: hexane-EtOH-MeOH [50:40:10 (v/v/v), isocratic]

Resolution of the isomer was carried out under the following condition.

chiral HPLC condition: LC3, eluent: hexane-EtOH-MeOH [50:40:10 (v/v/v), isocratic]

Example 18—Isomer A $^1$H-NMR (400 MHz, CDCl$_3$) δ: 8.07 (1H, d, J=2.4 Hz), 7.96 (1H, d, J=8.6 Hz), 7.85 (1H, s), 7.47 (1H, dd, J=2.4, 8.6 Hz), 7.38 (1H, d, J=2.4 Hz), 7.32 (1H, dd, J=2.4, 8.2 Hz), 7.09 (1H, d, J=8.2 Hz), 6.44 (1H, s), 5.29-5.18 (2H, brs), 3.89-3.77 (1H, m), 2.43-2.17 (5H, m), 1.90 (1H, s), 1.14 (3H, d, J=6.3 Hz).

MS (ESI) m/z: 566 [M+H]$^+$

HRMS (ESI) calcd for C$_{22}$H$_{20}$Cl$_2$F$_3$N$_3$NaO$_5$S [M+Na]$^+$, required m/z: 588.0351, found 588.0374

Retention time: 3.3 min chiral HPLC condition: LC1, eluent: hexane-EtOH-MeOH [50:40:10 (v/v/v), isocratic].

Example 18—Isomer B $^1$H-NMR (400 MHz, CDCl$_3$) δ: 8.07 (1H, d, J=2.0 Hz), 7.96 (1H, d, J=8.6 Hz), 7.86 (1H, s), 7.51-7.43 (3H, m), 7.29 (1H, d, J=8.6 Hz), 6.44 (1H, s), 5.30 (2H, s), 4.02-3.92 (1H, m), 2.46 (1H, dd, J=4.3, 15.6 Hz), 2.37-2.26 (4H, m), 1.88 (1H, d, J=3.5 Hz), 1.17 (3H, d, J=6.3 Hz).

MS (ESI) m/z: 566 [M+H]$^+$

HRMS (ESI) calcd for $C_{22}H_{20}Cl_2F_3N_3NaO_5S$ [M+Na]$^+$, required m/z: 588.0351, found 588.0364

Retention time: 4.7 min chiral HPLC condition: LC1, eluent: hexane-EtOH-MeOH [50:40:10 (v/v/v), isocratic].

Example 19

1-(2-Chloro-4-methylphenyl)-5-[(2S)-2-hydroxypropyl]-2-methyl-N-[4-(methylsulfonyl)phenyl]-1H-pyrrole-3-carboxamide

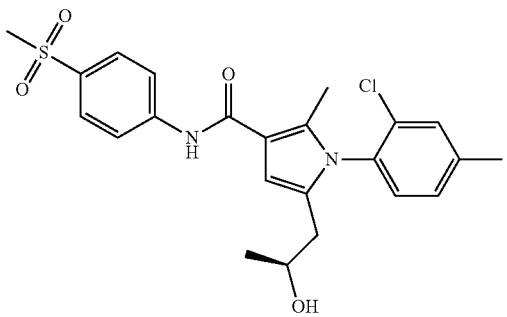

The title compound (0.56 g, 80%) was obtained from the compound (0.84 g, 1.5 mmol) of Comparative Example 87 in the process similar to Example 3.

MS (ESI) m/z: 461 [M+H]$^+$

Retention time: 5.6 min (Example 19—isomer A), 7.0 min (Example 19—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [70:24:6 (v/v/v), isocratic]

Example 19—Isomer A $^1$H-NMR (400 MHz, CDCl$_3$) δ: 7.91 (2H, d, J=8.6 Hz), 7.83 (2H, d, J=8.6 Hz), 7.77 (1H, s), 7.40 (1H, s), 7.25-7.21 (1H, m), 7.16 (1H, d, J=7.8 Hz), 6.39 (1H, s), 3.86-3.76 (1H, m), 3.06 (3H, s), 2.48 (1H, dd, J=15.6, 8.2 Hz), 2.45 (3H, s), 2.40 (1H, dd, J=15.6, 4.7 Hz), 2.29 (3H, s), 1.73 (1H, brs), 1.15 (3H, d, J=6.3 Hz).

HRMS (ESI) calcd for $C_{23}H_{26}ClN_2O_4S$ [M+H]$^+$, required m/z: 461.1302, found 461.1284.

Retention time: 5.6 min chiral HPLC condition: LC1, eluent: hexane-EtOH-MeOH [70:24:6 (v/v/v), isocratic]

[α]$_D^{22}$: −26.6° (c=1.0, EtOH).

Example 19—Isomer B $^1$H-NMR (400 MHz, CDCl$_3$) δ: 7.91 (2H, d, J=8.6 Hz), 7.83 (2H, d, J=8.6 Hz), 7.77 (1H, s), 7.40 (1H, s), 7.25-7.21 (1H, m), 7.16 (1H, d, J=7.8 Hz), 6.39 (1H, s), 3.89-3.77 (1H, m), 3.06 (3H, s), 2.49 (1H, dd, J=15.3, 4.3 Hz), 2.45 (3H, s), 2.38 (1H, dd, J=15.3, 8.6 Hz), 2.30 (3H, s), 1.74 (1H, brs), 1.14 (3H, d, J=5.9 Hz).

HRMS (ESI) calcd for $C_{23}H_{26}ClN_2O_4S$ [M+H]$^+$, required m/z: 461.1302, found 461.1296.

Retention time: 7.0 min chiral HPLC condition: LC1, eluent: hexane-EtOH-MeOH [70:24:6 (v/v/v), isocratic].

Example 20

1-[2-(Difluoromethoxy)-4-methylphenyl]-5-[(2S)-2-hydroxypropyl]-2-methyl-N-[4-(methylsulfonyl)phenyl]-1H-pyrrole-3-carboxamide

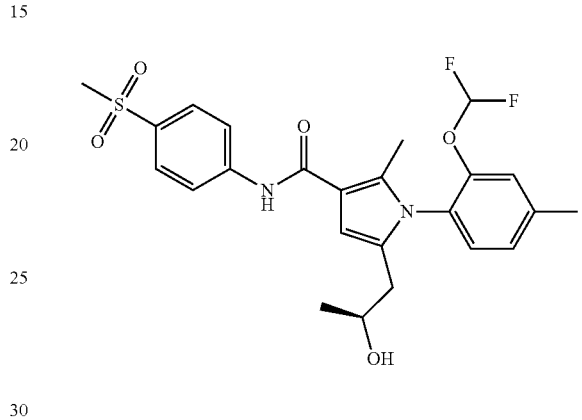

The title compound (0.87 g, 98%) was obtained from the compound (1.0 g, 0.78 mmol) of Comparative Example 88 in the process similar to Example 2.

MS (ESI) m/z: 493 [M+H]$^+$

Retention time: 4.7 min (Example 20—isomer A), 6.1 min (Example 20—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [70:24:6 (v/v/v), isocratic]

Example 20—Isomer A $^1$H-NMR (400 MHz, CDCl$_3$) δ: 7.91 (2H, d, J=9.0 Hz), 7.83 (2H, d, J=9.0 Hz), 7.76 (1H, s), 7.20-7.15 (2H, m), 7.13 (1H, d, J=7.8 Hz), 6.38 (1H, t, J=72.7 Hz), 6.37 (1H, s), 3.88-3.76 (1H, m), 3.06 (3H, s), 2.47 (3H, s), 2.44 (2H, d, J=6.7 Hz), 2.30 (3H, s), 1.73 (1H, brs), 1.14 (3H, d, J=6.3 Hz).

HRMS (ESI) calcd for $C_{24}H_{27}F_2N_2O_5S$ [M+H]$^+$, required m/z: 493.1609, found 493.1587.

Retention time: 4.7 min chiral HPLC condition: LC1, eluent: hexane-EtOH-MeOH [70:24:6 (v/v/v), isocratic]

[α]$_D^{22}$: −13.4° (c=1.0, EtOH).

Example 20—Isomer B $^1$H-NMR (400 MHz, CDCl$_3$) δ: 7.91 (2H, d, J=9.0 Hz), 7.83 (2H, d, J=9.0 Hz), 7.76 (1H, s), 7.20-7.11 (3H, m), 6.39 (1H, t, J=72.7 Hz), 6.38 (1H, s), 3.92-3.82 (1H, m), 3.05 (3H, s), 2.50 (1H, dd, J=15.6, 4.3 Hz), 2.47 (3H, s), 2.39 (1H, dd, J=15.6, 8.6 Hz), 2.30 (3H, s), 1.73 (1H, brs), 1.15 (3H, d, J=5.9 Hz).

HRMS (ESI) calcd for $C_{24}H_{27}F_2N_2O_5S$ [M+H]$^+$, required m/z: 493.1609, found 493.1598.

Retention time: 6.1 min chiral HPLC condition: LC1, eluent: hexane-EtOH-MeOH [70:24:6 (v/v/v), isocratic].

Example 21

1-[4-Chloro-2-(difluoromethyl)phenyl]-5-[(2S)-2-hydroxypropyl]-2-methyl-N-[4-(methylsulfonyl)phenyl]-1H-pyrrole-3-carboxamide

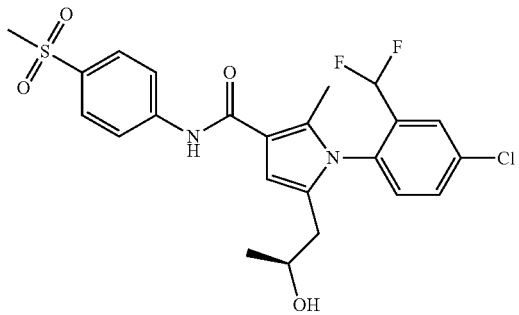 [SMILES: Cc1c(C(=O)Nc2ccc(S(C)(=O)=O)cc2)cc(C[C@H](C)O)n1-c1ccc(Cl)cc1C(F)F]

The title compound (0.50 g, 80%) was obtained from the compound (0.74 g, 1.3 mmol) of Comparative Example 89 in the process similar to Example 1.

MS (FAB) m/z: 497 [M+H]$^+$.

Retention time: 5.5 min (Example 21—isomer A), 7.8 min (Example 21—isomer B)

chiral HPLC condition: LC1, eluent: hexane-EtOH-MeOH [75:20:5 (v/v/v), isocratic]

Resolution of the isomer was carried out under the following condition.

chiral HPLC condition: LC3, eluent: hexane-EtOH-MeOH [75:20:5 (v/v/v), isocratic]

Example 21—Isomer A $^1$H-NMR (400 MHz, CDCl$_3$) δ: 7.90 (2H, d, J=9.0 Hz), 7.85-7.81 (4H, m), 7.63 (1H, dd, J=8.4, 2.2 Hz), 7.22 (1H, d, J=8.2 Hz), 6.45 (1H, s), 6.10 (1H, t, J=54.4 Hz), 3.89-3.81 (1H, m), 3.06 (3H, s), 2.39-2.36 (2H, m), 2.27 (3H, s), 1.75 (1H, d, J=3.5 Hz), 1.16 (3H, d, J=6.3 Hz).

HRMS (ESI) calcd for $C_{23}H_{24}ClF_2N_2O_4S$ [M+H]$^+$, required m/z: 497.1113, found 497.1109

Retention time: 5.5 min chiral HPLC condition: LC1, eluent: hexane-EtOH-MeOH [75:20:5 (v/v/v), isocratic]

$[α]_D^{21}$: +16° (c=1.0, EtOH).

Example 21—Isomer B $^1$H-NMR (400 MHz, CDCl$_3$) δ: 7.90 (2H, d, J=8.6 Hz), 7.85-7.79 (4H, m), 7.65-7.62 (1H, m), 7.23 (1H, d, J=8.6 Hz), 6.43 (1H, s), 6.07 (1H, t, J=54.4 Hz), 3.96-3.88 (1H, m), 3.06 (3H, s), 2.47 (1H, dd, J=15.6, 4.3 Hz), 2.31 (1H, dd, J=15.2, 8.2 Hz), 2.27 (3H, s), 1.65 (1H, br s), 1.18 (3H, d, J=6.3 Hz).

HRMS (ESI) calcd for $C_{23}H_{24}ClF_2N_2O_4S$ [M+H]$^+$, required m/z: 497.1113, found 497.1126.

Retention time: 7.8 min chiral HPLC condition: LC1, eluent: hexane-EtOH-MeOH [75:20:5 (v/v/v), isocratic].

Example 22

1-[2-(Difluoromethoxy)-4-fluorophenyl]-5-[(2S)-2-hydroxypropyl]-2-methyl-N-[3-methyl-4-(methylsulfonyl)phenyl]-1H-pyrrole-3-carboxamide

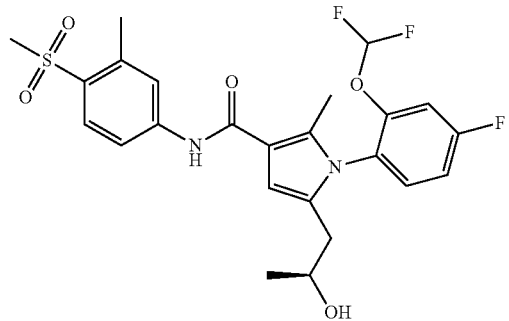 [SMILES: Cc1cc(NC(=O)c2cc(C[C@H](C)O)n(-c3ccc(F)cc3OC(F)F)c2C)ccc1S(C)(=O)=O]

The title compound (0.27 g, 86%) was obtained from the compound (0.37 g, 0.62 mmol) of Comparative Example 101 in the process similar to Example 2.

MS (FAB) m/z: 511 [M+H]$^+$.

Retention time: 4.5 min (Example 22—isomer A), 7.0 min (Example 22—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [70:24:6 (v/v/v), isocratic]

Example 22—Isomer A $^1$H-NMR (400 MHz, CDCl$_3$) δ: 8.00 (1H, d, J=8.6 Hz), 7.75 (1H, s), 7.63 (1H, s), 7.53 (1H, d, J=8.6 Hz), 7.29-7.24 (1H, m), 7.17 (1H, d, J=9.0 Hz), 7.13-7.07 (1H, m), 6.41 (1H, t, J=71.9 Hz), 6.36 (1H, s), 3.86-3.79 (1H, m), 3.08 (3H, s), 2.71 (3H, s), 2.43 (2H, d, J=6.3 Hz), 2.30 (3H, s), 1.65 (1H, d, J=3.1 Hz), 1.15 (3H, d, J=6.3 Hz).

HRMS (ESI) calcd for $C_{24}H_{26}F_3N_2O_5S$ [M+H]$^+$, required m/z: 511.1515, found 511.1489.

Retention time: 4.5 min chiral HPLC condition: LC3, eluent: hexane-EtOH-MeOH [70:24:6 (v/v/v), isocratic].

Example 22—Isomer B $^1$H-NMR (400 MHz, CDCl$_3$) δ: 7.99 (1H, d, J=8.6 Hz), 7.75 (1H, d, J=2.0 Hz), 7.67 (1H, s), 7.53 (1H, dd, J=8.6, 2.0 Hz), 7.28 (1H, dd, J=9.0, 5.9 Hz), 7.17 (1H, dd, J=9.0, 2.0 Hz), 7.12-7.07 (1H, m), 6.42 (1H, t, J=71.7 Hz), 6.37 (1H, s), 3.92-3.84 (1H, m), 3.07 (3H, s), 2.70 (3H, s), 2.49 (1H, dd, J=15.2, 4.3 Hz), 2.37 (1H, dd, J=15.4, 8.4 Hz), 2.30 (3H, s), 1.66 (1H, d, J=3.5 Hz), 1.16 (3H, d, J=6.3 Hz).

Example 23

N-[3-Chloro-4-(methylsulfonyl)phenyl]-1-[2-(difluoromethoxy)-4-fluorophenyl]-5-[(2S)-2-hydroxypropyl]-2-methyl-1H-pyrrole-3-carboxamide

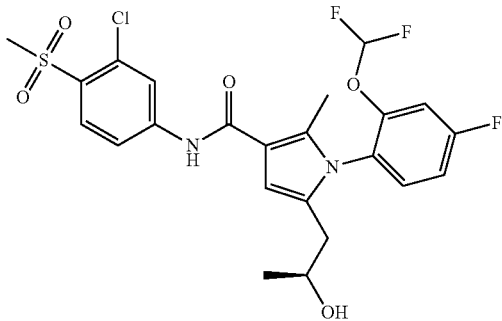 [SMILES: Cc1c(C(=O)Nc2ccc(S(C)(=O)=O)c(Cl)c2)cc(C[C@H](C)O)n1-c1ccc(F)cc1OC(F)F]

The title compound (0.11 g, 42%) was obtained from the compound (0.30 g, 0.48 mmol) of Comparative Example 103 in the process similar to Example 2.

MS (FAB) m/z: 531 [M+H]$^+$.

Retention time: 4.4 min (Example 23—isomer A), 7.1 min (Example 23—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [70:24:6 (v/v/v), isocratic].

Example 23—Isomer A $^1$H-NMR (400 MHz, CDCl$_3$) δ: 8.11 (1H, d, J=2.0 Hz), 8.07 (1H, d, J=8.6 Hz), 7.74 (1H, s), 7.55 (1H, dd, J=8.6, 2.0 Hz), 7.29-7.25 (1H, m), 7.17 (1H, dd, J=9.0, 2.7 Hz), 7.13-7.07 (1H, m), 6.41 (1H, t, J=71.7 Hz), 6.37 (1H, s), 3.87-3.81 (1H, m), 3.27 (3H, s), 2.42 (2H, d, J=6.3 Hz), 2.30 (3H, s), 1.67 (1H, d, J=3.5 Hz), 1.15 (3H, d, J=6.3 Hz).

HRMS (ESI) calcd for C$_{23}$H$_{23}$ClF$_3$N$_2$O$_5$S [M+H]$^+$, required m/z: 531.0968, found 531.0960.

Retention time: 4.4 min chiral HPLC condition: LC1, eluent: hexane-EtOH-MeOH [70:24:6 (v/v/v), isocratic]

[α]$_D^{21}$: −12° (c=0.53, EtOH).

Example 23—Isomer B $^1$H-NMR (400 MHz, CDCl$_3$) δ: 8.11 (1H, d, J=2.0 Hz), 8.07 (1H, d, J=9.0 Hz), 7.78 (1H, s), 7.56 (1H, dd, J=8.9, 2.0 Hz), 7.31-7.26 (1H, m), 7.17 (1H, dd, J=8.8, 2.5 Hz), 7.13-7.07 (1H, m), 6.42 (1H, t, J=71.7 Hz), 6.38 (1H, s), 3.93-3.85 (1H, m), 3.27 (3H, s), 2.48 (1H, dd, J=15.2, 4.3 Hz), 2.37 (1H, dd, J=15.4, 8.4 Hz), 2.30 (3H, s), 1.69 (1H, d, J=3.9 Hz), 1.16 (3H, d, J=5.9 Hz).

HRMS (ESI) calcd for C$_{24}$H$_{26}$F$_3$N$_2$O$_5$S [M+H]$^+$, required m/z: 511.1515, found 511.1504.

Retention time: 7.0 min chiral HPLC condition: LC3, eluent: hexane-EtOH-MeOH [70:24:6 (v/v/v), isocratic].

Example 24

1-[2-(Difluoromethyl)-4-fluorophenyl]-5-[(2S)-2-hydroxypropyl]-2-methyl-N-[4-(methylsulfonyl)phenyl]-1H-pyrrole-3-carboxamide

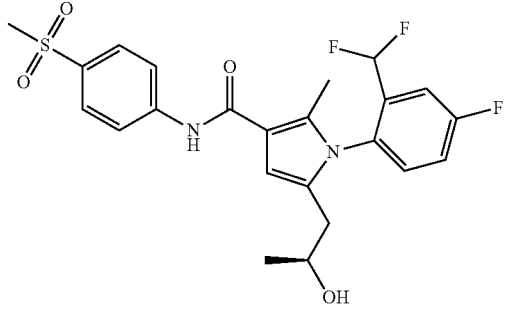 [SMILES: Cc1c(C(=O)Nc2ccc(S(C)(=O)=O)cc2)cc(C[C@H](C)O)n1-c1ccc(F)cc1C(F)F]

The title compound (0.29 g, 90%) was obtained from the compound (0.38 g, 0.67 mmol) of Comparative Example 90 in the process similar to Example 2.

MS (FAB) m/z: 481 [M+H]$^+$.

Retention time: 4.5 min (Example 24—isomer A), 6.0 min (Example 24—isomer B)

chiral HPLC condition: LC1, eluent: hexane-EtOH-MeOH [75:20:5 (v/v/v), isocratic]

Resolution of the isomer was carried out under the following condition.

chiral HPLC condition: LC3, eluent: hexane-EtOH-MeOH [75:20:5 (v/v/v), isocratic]

Example 24—Isomer A $^1$H-NMR (400 MHz, CDCl$_3$) δ: 7.90 (2H, d, J=9.0 Hz), 7.85-7.81 (3H, m), 7.54 (1H, dd, J=8.2, 2.7 Hz), 7.39-7.33 (1H, m), 7.29-7.25 (1H, m), 6.44 (1H, s), 6.10 (1H, t, J=53.6 Hz), 3.90-3.81 (1H, m), 3.06 (3H, s), 2.39-2.36 (2H, m), 2.27 (3H, s), 1.71 (1H, d, J=3.5 Hz), 1.16 (3H, d, J=6.3 Hz).

HRMS (ESI) calcd for C$_{23}$H$_{24}$F$_3$N$_2$O$_4$S [M+H]$^+$, required m/z: 481.1409, found 481.1416.

Retention time: 4.5 min chiral HPLC condition: LC1, eluent: hexane-EtOH-MeOH [75:20:5 (v/v/v), isocratic]

[α]$_D^{21}$: +14° (c=1.0, EtOH).

Example 24—Isomer B $^1$H-NMR (400 MHz, CDCl$_3$) δ: 7.91 (2H, d, J=8.8 Hz), 7.83 (2H, d, J=8.8 Hz), 7.77 (1H, s), 7.54 (1H, dd, J=8.2, 2.7 Hz), 7.39-7.34 (1H, m), 7.30-7.26 (1H, m), 6.42 (1H, s), 6.06 (1H, t, J=53.2 Hz), 3.97-3.89 (1H, m), 3.06 (3H, s), 2.47 (1H, dd, J=15.6, 4.3 Hz), 2.31 (1H, dd, J=15.4, 8.4 Hz), 2.27 (3H, s), 1.62 (1H, d, J=4.3 Hz), 1.18 (3H, d, J=6.3 Hz).

HRMS (ESI) calcd for $C_{23}H_{24}F_3N_2O_4S$ [M+H]$^+$, required m/z: 481.1409, found 481.1421.

Retention time: 6.0 min chiral HPLC condition: LC1, eluent: hexane-EtOH-MeOH [75:20:5 (v/v/v), isocratic].

Example 25

N-[4-(Aminosulfonyl)-3-chlorophenyl]-1-[4-fluoro-2-(trifluoromethoxy)phenyl]-5-[(2S)-2-hydroxypropyl]-2-methyl-1H-pyrrole-3-carboxamide

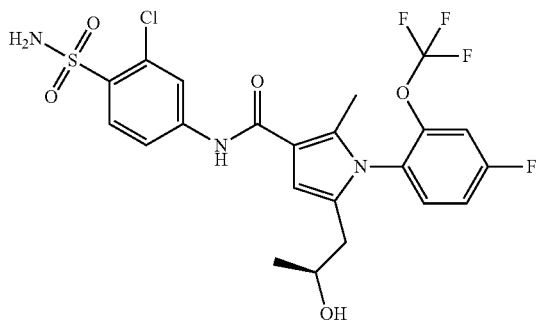 [SMILES: Cc1c(C(=O)Nc2ccc(S(N)(=O)=O)c(Cl)c2)cc(C[C@H](C)O)n1-c1ccc(F)cc1OC(F)(F)F]

The title compound (0.14 g, 78%) was obtained from the compound (0.22 g, 0.36 mmol) of Comparative Example 77 in the process similar to Example 3.

$^1$H-NMR (400 MHz, CD$_3$OD) δ: 8.12 (1H, d, J=2.4 Hz), 7.99 (1H, d, J=9.0 Hz), 7.74 (0.6H, d, J=2.0 Hz), 7.72 (0.4H, d, J=2.4 Hz), 7.57-7.51 (1H, m), 7.48-7.43 (1H, m), 7.40-7.34 (1H, m), 6.66 (0.4H, s), 6.65 (0.6H, s), 3.90-3.75 (1H, m), 2.58 (0.4H, dd, J=6.7, 15.3 Hz), 2.41 (0.6H, d, J=6.7 Hz), 2.34-2.23 (4H, m), 1.14 (1.2H, d, J=6.3 Hz), 1.10 (1.8H, d, J=6.3 Hz).

MS (ESI) m/z: 550 [M+H]$^+$

Retention time: 3.3 min (Example 25—isomer A), 4.5 min (Example 25—isomer B)

chiral HPLC condition: LC1, eluent: hexane-EtOH-MeOH [50:40:10 (v/v/v), isocratic]

Resolution of the isomer was carried out under the following condition.

chiral HPLC condition: LC3, eluent: hexane-EtOH-MeOH [50:40:10 (v/v/v), isocratic]

Example 25—Isomer A $^1$H-NMR (500 MHz, CDCl$_3$) δ: 8.05 (1H, s), 7.99-7.90 (2H, m), 7.46 (1H, d, J=8.8 Hz), 7.34 (1H, dd, J=5.3, 8.3 Hz), 7.25-7.16 (2H, m), 6.48 (1H, s), 5.34 (2H, s), 3.58-3.55 (1H, m), 2.49-2.32 (2H, m), 2.28 (3H, s), 2.02 (1H, s), 1.13 (3H, d, J=5.9 Hz).

MS (ESI) m/z: 550 [M+H]$^+$

HRMS (ESI) calcd for $C_{22}H_{20}ClF_4N_3NaO_5S$ [M+Na]$^+$, required m/z: 572.0646, found 572.0675

Retention time: 3.3 min chiral HPLC condition: LC-1, eluent: hexane-EtOH-MeOH [50:40:10 (v/v/v), isocratic]

$[α]_D^{22}$: −3.8° (c=0.75, EtOH).

Example 25—Isomer B $^1$H-NMR (500 MHz, CDCl$_3$) δ: 8.06 (1H, s), 8.02 (1H, s), 7.88 (1H, d, J=8.8 Hz), 7.45 (1H, d, J=8.8 Hz), 7.33 (1H, dd, J=5.9, 8.8 Hz), 7.24-7.15 (2H, m), 6.50 (1H, s), 5.48 (2H, s), 4.03-3.92 (1H, m), 2.42 (1H, dd, J=3.9, 15.6 Hz), 2.35-2.15 (5H, m), 1.14 (3H, d, J=5.9 Hz).

MS (ESI) m/z: 550 [M+H]$^+$

HRMS (ESI) calcd for $C_{22}H_{20}ClF_4N_3NaO_5S$ [M+Na]$^+$, required m/z: 572.0646, found 572.0674

Retention time: 4.6 min chiral HPLC condition: LC-1, eluent: hexane-EtOH-MeOH [50:40:10 (v/v/v), isocratic]

$[α]_D^{22}$: +0.14° (c=0.50, EtOH).

Example 26

1-[4-Fluoro-2-(trifluoromethyl)phenyl]-5-[(2S)-2-hydroxypropyl]-2-methyl-N-[3-methyl-4-(methylsulfonyl)phenyl]-1H-pyrrole-3-carboxamide

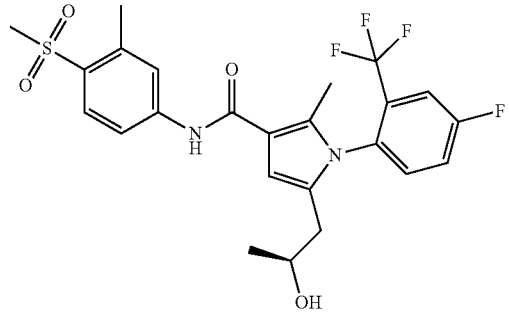 [SMILES: Cc1cc(NC(=O)c2cc(C[C@H](C)O)n(-c3ccc(F)cc3C(F)(F)F)c2C)ccc1S(C)(=O)=O]

The title compound (0.11 g, 51%) was obtained from the compound (0.25 g, 0.42 mmol) of Comparative Example 102 in the process similar to Example 2.

MS (FAB) m/z: 513 [M+H]$^+$.

Retention time: 5.6 min (Example 26—isomer A), 8.4 min (Example 26—isomer B)

chiral HPLC condition: LC1, eluent: hexane-EtOH-MeOH [75:20:5 (v/v/v), isocratic]

Resolution of the isomer was carried out under the following condition.

chiral HPLC condition: LC3, eluent: hexane-EtOH-MeOH [75:20:5 (v/v/v), isocratic]

Example 26—Isomer A $^1$H-NMR (400 MHz, CDCl$_3$) δ: 7.99 (1H, d, J=8.6 Hz), 7.75 (1H, d, J=1.6 Hz), 7.71 (1H, s), 7.59 (1H, dd, J=8.2, 2.7 Hz), 7.54 (1H, dd, J=8.8, 2.2 Hz), 7.47-7.41 (1H, m), 7.32 (1H, dd, J=8.6, 5.1 Hz), 6.39 (1H, s), 3.88-3.79 (1H, m), 3.08 (3H, s), 2.70 (3H, s), 2.46 (1H, dd, J=15.6, 8.6 Hz), 2.32-2.25 (4H, m), 1.76 (1H, br s), 1.16 (3H, d, J=6.3 Hz).

HRMS (ESI) calcd for $C_{24}H_{25}F_4N_2O_4S$ [M+H]$^+$, required m/z: 513.1471, found 513.1458.

Retention time: 5.6 min chiral HPLC condition: LC1, eluent: hexane-EtOH-MeOH [75:20:5 (v/v/v), isocratic]

$[α]_D^{20}$: −5.5° (c=1.1, EtOH).

Example 26—Isomer B $^1$H-NMR (400 MHz, CDCl$_3$) δ: 7.99 (1H, d, J=8.6 Hz), 7.76 (1H, d, J=2.0 Hz), 7.67 (1H, s), 7.58 (1H, dd, J=8.2, 2.7 Hz), 7.53 (1H, dd, J=8.6, 2.0 Hz), 7.47-7.41 (1H, m), 7.32 (1H, dd, J=8.6, 5.1 Hz), 6.37 (1H, s), 4.06-3.99 (1H, m), 3.08

(3H, s), 2.71 (3H, s), 2.48 (1H, dd, J=15.6, 4.3 Hz), 2.26 (3H, s), 2.22 (1H, dd, J=15.6, 8.6 Hz), 1.64 (1H, d, J=3.5 Hz), 1.19 (3H, d, J=6.3 Hz).

HRMS (ESI) calcd for $C_{24}H_{25}F_4N_2O_4S$ [M+H]$^+$, required m/z: 513.1471, found 513.1472.

Retention time: 8.4 min chiral HPLC condition: LC1, eluent: hexane-EtOH-MeOH [75:20:5 (v/v/v), isocratic].

Example 27

N-[3-Chloro-4-(methylsulfonyl)phenyl]-1-[4-fluoro-2-(trifluoromethyl)phenyl]-5-[(2S)-2-hydroxypropyl]-2-methyl-1H-pyrrole-3-carboxamide

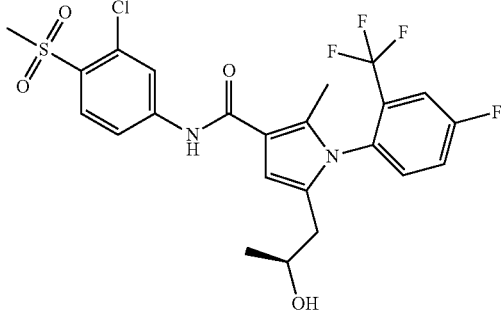 [SMILES: Cc1c(C(=O)Nc2ccc(S(C)(=O)=O)c(Cl)c2)cc(C[C@H](C)O)n1-c1ccc(F)cc1C(F)(F)F]

The title compound (0.48 g, 87%) was obtained from the compound (0.64 g, 1.0 mmol) of Comparative Example 104 in the process similar to Example 3.

MS (FAB) m/z: 533 [M+H]$^+$.

Retention time: 4.8 min (Example 27—isomer A), 7.8 min (Example 27—isomer B)

chiral HPLC condition: LC1, eluent: hexane-EtOH-MeOH [75:20:5 (v/v/v), isocratic]

Resolution of the isomer was carried out under the following condition.

chiral HPLC condition: LC3, eluent: hexane-EtOH-MeOH [75:20:5 (v/v/v), isocratic]

Example 27—Isomer A $^1$H-NMR (400 MHz, CDCl$_3$) δ: 8.10 (1H, d, J=2.0 Hz), 8.05 (1H, d, J=8.6 Hz), 7.89 (1H, s), 7.61-7.56 (2H, m), 7.47-7.42 (1H, m), 7.32 (1H, dd, J=8.8, 4.9 Hz), 6.43 (1H, s), 3.88-3.80 (1H, m), 3.26 (3H, s), 2.46 (1H, dd, J=15.6, 8.6 Hz), 2.31-2.24 (4H, m), 1.86 (1H, br s), 1.15 (3H, d, J=6.3 Hz).

HRMS (ESI) calcd for $C_{23}H_{22}ClF_4N_2O_4S$ [M+H]$^+$, required m/z: 533.0925, found 533.0973.

Retention time: 4.8 min chiral HPLC condition: LC1, eluent: hexane-EtOH-MeOH [75:20:5 (v/v/v), isocratic]

$[α]_D^{20}$: −4.4° (c=0.93, EtOH).

Example 27—Isomer B $^1$H-NMR (400 MHz, CDCl$_3$) δ: 8.10 (1H, d, J=2.3 Hz), 8.06 (1H, d, J=9.0 Hz), 7.80 (1H, s), 7.60-7.54 (2H, m), 7.47-7.41 (1H, m), 7.32 (1H, dd, J=8.8, 4.9 Hz), 6.40 (1H, s), 4.07-3.99 (1H, m), 3.27 (3H, s), 2.48 (1H, dd, J=15.6, 3.9 Hz), 2.25 (3H, s), 2.21 (1H, dd, J=15.6, 8.6 Hz), 1.71 (1H, d, J=3.5 Hz), 1.19 (3H, d, J=5.9 Hz).

HRMS (ESI) calcd for $C_{23}H_{22}ClF_4N_2O_4S$ [M+H]$^+$, required m/z: 533.0925, found 533.0945.

Retention time: 7.8 min chiral HPLC condition: LC1, eluent: hexane-EtOH-MeOH [75:20:5 (v/v/v), isocratic].

Example 28

1-(4-Fluoro-2-methylphenyl)-5-[(2S)-2-hydroxypropyl]-2-methyl-N-[3-methyl-4-(methylsulfonyl)phenyl]-1H-pyrrole-3-carboxamide

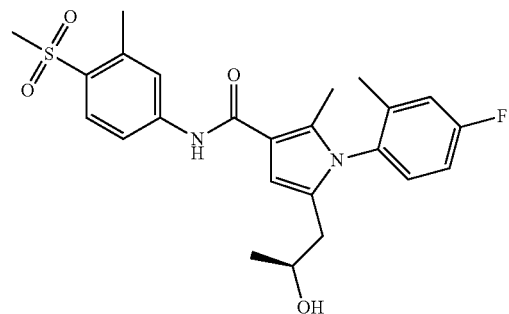 [SMILES: Cc1cc(F)ccc1-n1c(C[C@H](C)O)cc(C(=O)Nc2ccc(S(C)(=O)=O)c(C)c2)c1C]

The title compound (0.21 g, 50%) was obtained from the compound (0.50 g, 0.91 mmol) of Comparative Example 70 in the process similar to Example 2.

MS (FAB) m/z: 459 [M+H]$^+$.

Retention time: 8.3 min (Example 28—isomer A), 9.7 min (Example 28—isomer B)

chiral HPLC condition: LC2, eluent: hexane-EtOH [50:50 (v/v), isocratic]

Resolution of the isomer was carried out under the following condition.

chiral HPLC condition: LC3, eluent: hexane-EtOH-MeOH [65:28:7 (v/v/v), isocratic]

Example 28—Isomer A $^1$H-NMR (400 MHz, CDCl$_3$) δ: 7.99 (1H, d, J=8.6 Hz), 7.76 (1H, d, J=2.0 Hz), 7.69 (1H, s), 7.54 (1H, dd, J=8.6, 2.0 Hz), 7.15-7.01 (3H, m), 6.39 (1H, s), 3.87-3.78 (1H, m), 3.08 (3H, s), 2.71 (3H, s), 2.40 (1H, dd, J=15.2, 8.6 Hz), 2.32 (1H, dd, J=15.2, 4.3 Hz), 2.27 (3H, s), 1.94 (3H, s), 1.75 (1H, d, J=2.7 Hz), 1.15 (3H, d, J=6.3 Hz).

HRMS (ESI) calcd for $C_{24}H_{28}FN_2O_4S$ [M+H]$^+$, required m/z: 459.1754, found 459.1742.

Retention time: 8.3 min chiral HPLC condition: LC2, eluent: hexane-EtOH [50:50 (v/v), isocratic]

$[α]_D^{21}$: −8.8° (c=1.1, EtOH).

Example 28—Isomer B $^1$H-NMR (400 MHz, CDCl$_3$) δ: 7.99 (1H, d, J=9.0 Hz), 7.76 (1H, d, J=2.0 Hz), 7.69 (1H, s), 7.54 (1H, dd, J=8.6, 2.0 Hz), 7.15-7.01 (3H, m), 6.38 (1H, s), 3.88-3.80 (1H, m), 3.08 (3H, s), 2.70 (3H, s), 2.45 (1H, dd, J=15.2, 4.3 Hz), 2.33 (1H, dd, J=15.2, 8.2 Hz), 2.26 (3H, s), 1.95 (3H, s), 1.66 (1H, d, J=3.5 Hz), 1.16 (3H, d, J=6.3 Hz).

HRMS (ESI) calcd for $C_{24}H_{28}FN_2O_4S$ [M+H]$^+$, required m/z: 459.1754, found 459.1774.

Retention time: 9.7 min chiral HPLC condition: LC2, eluent: hexane-EtOH [50:50 (v/v), isocratic].

Example 29

N-[3-chloro-4-(methylsulfonyl)phenyl]-1-(4-fluoro-2-methylphenyl)-5-[(2S)-2-hydroxypropyl]-2-methyl-1H-pyrrole-3-carboxamide

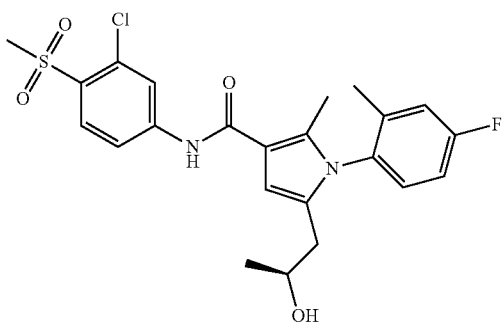

The title compound (0.37 g, 76%) was obtained from the compound (0.58 g, 1.0 mmol) of Comparative Example 71 in the process similar to Example 3.

MS (FAB) m/z: 479 [M+H]$^+$.

Retention time: 9.1 min (Example 29—isomer A), 10.3 min (Example 29—isomer B)

chiral HPLC condition: LC2, eluent: hexane-EtOH [60:40 (v/v), isocratic]

Resolution of the isomer was carried out under the following condition.

chiral HPLC condition: LC4, eluent: hexane-EtOH [60:40 (v/v), isocratic]

Example 29—Isomer A $^1$H-NMR (400 MHz, CDCl$_3$) δ: 8.12 (1H, d, J=2.0 Hz), 8.07 (1H, d, J=8.6 Hz), 7.76 (1H, s), 7.56 (1H, dd, J=8.6, 2.2 Hz), 7.15-7.01 (3H, m), 6.39 (1H, s), 3.87-3.79 (1H, m), 3.27 (3H, s), 2.39 (1H, dd, J=15.2, 8.6 Hz), 2.32 (1H, dd, J=15.2, 4.1 Hz), 2.26 (3H, s), 1.94 (3H, s), 1.74 (1H, d, J=3.1 Hz), 1.15 (3H, d, J=6.3 Hz).

HRMS (ESI) calcd for $C_{23}H_{25}ClFN_2O_4S$ [M+H]$^+$, required m/z: 479.1208, found 479.1198.

Retention time: 9.1 min chiral HPLC condition: LC2, eluent: hexane-EtOH [60:40 (v/v), isocratic]

$[α]_D^{21}$: −9.0° (c=1.1, EtOH).

Example 29—Isomer B $^1$H-NMR (400 MHz, CDCl$_3$) δ: 8.11 (1H, d, J=2.3 Hz), 8.07 (1H, d, J=8.6 Hz), 7.79 (1H, s), 7.56 (1H, dd, J=8.6, 2.3 Hz), 7.15-7.01 (3H, m), 6.39 (1H, s), 3.89-3.80 (1H, m), 3.27 (3H, s), 2.45 (1H, dd, J=15.3, 4.3 Hz), 2.33 (1H, dd, J=15.2, 8.2 Hz), 2.26 (3H, s), 1.94 (3H, s), 1.68 (1H, d, J=3.5 Hz), 1.16 (3H, d, J=6.3 Hz).

HRMS (ESI) calcd for $C_{23}H_{25}ClFN_2O_4S$ [M+H]$^+$, required m/z: 479.1208, found 479.1210.

Retention time: 10.3 min chiral HPLC condition: LC2, eluent: hexane-EtOH [60:40 (v/v), isocratic].

Example 30

1-[2-(Difluoromethyl)-4-fluorophenyl]-5-[(2S)-2-hydroxypropyl]-2-methyl-N-[3-methyl-4-(methylsulfonyl)phenyl]-1H-pyrrole-3-carboxamide

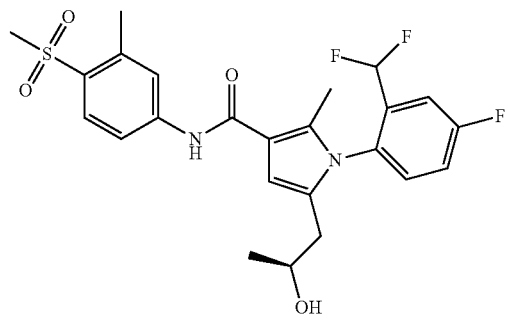 [SMILES: Cc1cc(NC(=O)c2cc(C[C@H](C)O)n(-c3ccc(F)cc3C(F)F)c2C)ccc1S(C)(=O)=O]

The title compound (0.30 g, 96%) was obtained from the compound (0.37 g, 0.64 mmol) of Comparative Example 100 in the process similar to Example 2.

MS (FAB) m/z: 495 [M+H]$^+$.

Retention time: 4.6 min (Example 30—isomer A), 6.9 min (Example 30—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [70:24:6 (v/v/v), isocratic]

Example 30—Isomer A $^1$H-NMR (400 MHz, CDCl$_3$) δ: 7.99 (1H, d, J=8.6 Hz), 7.75 (1H, d, J=2.0 Hz), 7.72 (1H, s), 7.56-7.52 (2H, m), 7.39-7.33 (1H, m), 7.29-7.25 (1H, m), 6.42 (1H, s), 6.09 (1H, t, J=54.4 Hz), 3.89-3.81 (1H, m), 3.08 (3H, s), 2.70 (3H, s), 2.39-2.35 (2H, m), 2.27 (3H, s), 1.69 (1H, d, J=3.9 Hz), 1.16 (3H, d, J=6.3 Hz).

HRMS (ESI) calcd for $C_{24}H_{26}F_3N_2O_4S$ [M+H]$^+$, required m/z: 495.1565, found 495.1550.

Retention time: 4.6 min chiral HPLC condition: LC1, eluent: hexane-EtOH-MeOH [70:24:6 (v/v/v), isocratic]

$[α]_D^{22}$: +13° (c=1.3, EtOH).

Example 30—Isomer B $^1$H-NMR (400 MHz, CDCl$_3$) δ: 7.99 (1H, d, J=8.6 Hz), 7.75 (1H, d, J=2.0 Hz), 7.68 (1H, s), 7.54 (1H, d, J=2.3 Hz), 7.52 (1H, d, J=2.0 Hz), 7.39-7.33 (1H, m), 7.30-7.26 (1H, m), 6.41 (1H, s), 6.06 (1H, t, J=54.2 Hz), 3.96-3.88 (1H, m), 3.08 (3H, s), 2.71 (3H, s), 2.47 (1H, dd, J=15.4, 4.5 Hz), 2.31 (1H, dd, J=15.6, 8.2 Hz), 2.27 (3H, s), 1.60 (1H, d, J=3.9 Hz), 1.18 (3H, d, J=6.3 Hz).

HRMS (ESI) calcd for $C_{24}H_{26}F_3N_2O_4S$ [M+H]$^+$, required m/z: 495.1565, found 495.1564.

Retention time: 6.9 min chiral HPLC condition: LC1, eluent: hexane-EtOH-MeOH [70:24:6 (v/v/v), isocratic].

Example 31

1-[2-(Difluoromethyl)-4-fluorophenyl]-N-[3-fluoro-4-(methylsulfonyl)phenyl]-5-[(2S)-2-hydroxypropyl]-2-methyl-1H-pyrrole-3-carboxamide

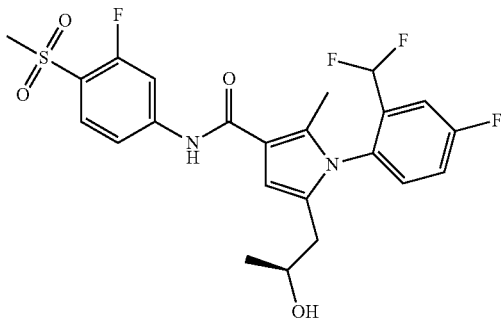 [SMILES: Cc1c(C(=O)Nc2ccc(S(C)(=O)=O)c(F)c2)cc(C[C@H](C)O)n1-c1ccc(F)cc1C(F)F]

The title compound (0.22 g, 96%) was obtained from the compound (0.27 g, 0.47 mmol) of Comparative Example 106 in the process similar to Example 2.

MS (FAB) m/z: 499 [M+H]$^+$.

Retention time: 6.5 min (Example 31—isomer A), 8.5 min (Example 31—isomer B)

chiral HPLC condition: LC1, eluent: hexane-EtOH-MeOH [80:16:4 (v/v/v), isocratic]

Resolution of the isomer was carried out under the following condition.

chiral HPLC condition: LC3, eluent: hexane-EtOH-MeOH [80:16:4 (v/v/v), isocratic]

Example 31—Isomer A $^1$H-NMR (400 MHz, CDCl$_3$) δ: 7.96 (1H, dd, J=12.5, 2.0 Hz), 7.88-7.83 (2H, m), 7.55 (1H, dd, J=8.2, 2.7 Hz), 7.39-7.33 (1H, m), 7.32-7.25 (2H, m), 6.44 (1H, s), 6.10 (1H, t, J=54.2 Hz), 3.90-3.82 (1H, m), 3.22 (3H, s), 2.39-2.35 (2H, m), 2.27 (3H, s), 1.72 (1H, d, J=3.9 Hz), 1.16 (3H, d, J=6.3 Hz).

HRMS (ESI) calcd for $C_{23}H_{23}F_4N_2O_4S$ [M+H]$^+$, required m/z: 499.1315, found 499.1325.

Retention time: 6.5 min chiral HPLC condition: LC1, eluent: hexane-EtOH-MeOH [80:16:4 (v/v/v), isocratic]

[α]$_D^{22}$: +14° (c=1.2, EtOH).

Example 31—Isomer B $^1$H-NMR (400 MHz, CDCl$_3$) δ: 7.97 (1H, dd, J=12.5, 2.0 Hz), 7.87 (1H, dd, J=8.2, 8.2 Hz), 7.81 (1H, s), 7.54 (1H, dd, J=8.2, 2.7 Hz), 7.40-7.34 (1H, m), 7.30-7.26 (2H, m), 6.42 (1H, s), 6.06 (1H, t, J=54.9 Hz), 3.97-3.89 (1H, m), 3.22 (3H, s), 2.47 (1H, dd, J=15.6, 4.3 Hz), 2.31 (1H, dd, J=15.2, 8.2 Hz), 2.27 (3H, s), 1.61 (1H, d, J=3.9 Hz), 1.18 (3H, d, J=6.3 Hz).

HRMS (ESI) calcd for $C_{23}H_{23}F_4N_2O_4S$ [M+H]$^+$, required m/z: 499.1315, found 499.1314.

Retention time: 8.5 min chiral HPLC condition: LC1, eluent: hexane-EtOH-MeOH [80:16:4 (v/v/v), isocratic].

Example 32

1-[2-(Difluoromethoxy)-4-fluorophenyl]-N-[3-fluoro-4-(methylsulfonyl)phenyl]-5-[(2S)-2-hydroxypropyl]-2-methyl-1H-pyrrole-3-carboxamide

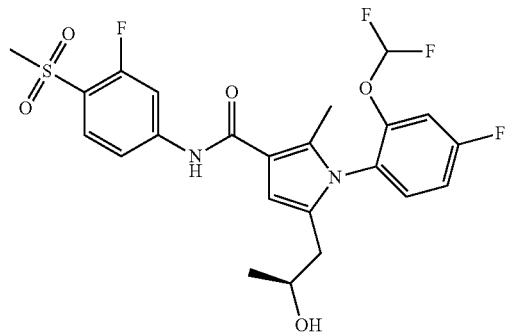 [SMILES: Cc1c(C(=O)Nc2ccc(S(C)(=O)=O)c(F)c2)cc(C[C@H](C)O)n1-c1ccc(F)cc1OC(F)F]

The title compound (0.31 g, 98%) was obtained from the compound (0.37 g, 0.60 mmol) of Comparative Example 107 in the process similar to Example 2.

MS (FAB) m/z: 515 [M+H]$^+$.

Retention time: 6.5 min (Example 32—isomer A), 8.9 min (Example 32—isomer B)

chiral HPLC condition: LC1, eluent: hexane-EtOH-MeOH [80:16:4 (v/v/v), isocratic]

Resolution of the isomer was carried out under the following condition.

chiral HPLC condition: LC3, eluent: hexane-EtOH-MeOH [80:16:4 (v/v/v), isocratic]

Example 32—Isomer A $^1$H-NMR (400 MHz, CDCl$_3$) δ: 7.98 (1H, dd, J=12.5, 2.0 Hz), 7.87 (1H, t, J=8.2 Hz), 7.80 (1H, s), 7.30-7.24 (2H, m), 7.18 (1H, dd, J=8.8, 2.5 Hz), 7.13-7.07 (1H, m), 6.41 (1H, t, J=71.7 Hz), 6.38 (1H, s), 3.88-3.80 (1H, m), 3.22 (3H, s), 2.42 (2H, d, J=6.3 Hz), 2.30 (3H, s), 1.69 (1H, d, J=3.9 Hz), 1.15 (3H, d, J=6.3 Hz).

HRMS (ESI) calcd for $C_{23}H_{22}F_4N_2NaO_5S$ [M+Na]$^+$, required m/z: 537.1083, found 537.1093.

Retention time: 6.5 min chiral HPLC condition: LC1, eluent: hexane-EtOH-MeOH [80:16:4 (v/v/v), isocratic]

[α]$_D^{20}$: −11° (c=1.0, EtOH).

Example 32—Isomer B $^1$H-NMR (400 MHz, CDCl$_3$) δ: 7.98 (1H, dd, J=12.6, 2.0 Hz), 7.86 (1H, dd, J=8.6, 8.2 Hz), 7.81 (1H, s), 7.30-7.26 (2H, m), 7.17 (1H, dd, J=9.0, 2.3 Hz), 7.13-7.07 (1H, m), 6.42 (1H, t, J=71.7 Hz), 6.38 (1H, s), 3.93-3.85 (1H, m), 3.22 (3H, s), 2.48 (1H, dd, J=15.6, 4.3 Hz), 2.37 (1H, dd, J=15.4, 8.4 Hz), 2.30 (3H, s), 1.67 (1H, d, J=3.9 Hz), 1.16 (3H, d, J=6.3 Hz).

HRMS (ESI) calcd for $C_{23}H_{23}F_4N_2O_5S$ [M+H]$^+$, required m/z: 515.1264, found 515.1270.

Retention time: 8.9 min chiral HPLC condition: LC1, eluent: hexane-EtOH-MeOH [80:16:4 (v/v/v), isocratic].

Example 33

N-[3-Fluoro-4-(methylsulfonyl)phenyl]-1-[4-fluoro-2-(trifluoromethyl)phenyl]-5-[(2S)-2-hydroxypropyl]-2-methyl-1H-pyrrole-3-carboxamide

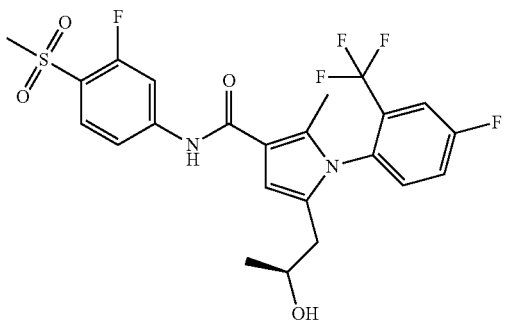 [SMILES: Cc1c(C(=O)Nc2ccc(S(C)(=O)=O)c(F)c2)cc(C[C@H](C)O)n1-c1ccc(F)cc1C(F)(F)F]

The title compound (0.44 g, 90%) was obtained from the compound (0.58 g, 0.96 mmol) of Comparative Example 108 in the process similar to Example 2.

MS (ESI) m/z: 517 [M+H]$^+$

Retention time: 5.4 min (Example 33—isomer A), 8.5 min (Example 33—isomer B)

chiral HPLC condition: LC1, eluent: hexane-EtOH-MeOH [80:16:4 (v/v/v), isocratic]

Resolution of the isomer was carried out under the following condition.

chiral HPLC condition: LC3, eluent: hexane-EtOH-MeOH [80:16:4 (v/v/v), isocratic]

Example 33—Isomer A $^1$H-NMR (400 MHz, CDCl$_3$) δ: 7.98 (1H, dd, J=12.5, 2.0 Hz), 7.90-7.81 (2H, m), 7.60 (1H, dd, J=8.6, 2.7 Hz), 7.48-7.41 (1H, m), 7.32 (1H, dd, J=8.6, 5.1 Hz), 7.29 (1H, dd, J=8.6, 2.0 Hz), 6.40 (1H, s), 3.89-3.79 (1H, m), 3.22 (3H, s), 2.46 (1H, dd, J=15.6, 8.6 Hz), 2.28 (1H, dd, J=15.6, 4.3 Hz), 2.26 (3H, s), 1.76 (1H, brs), 1.16 (3H, d, J=5.9 Hz).

HRMS (ESI) calcd for $C_{23}H_{21}F_5N_2O_4S$ [M+H]$^+$, required m/z: 517.1220, found 517.1192.

Retention time: 5.4 min chiral HPLC condition: LC1, eluent: hexane-EtOH-MeOH [80:16:4 (v/v/v), isocratic]

$[\alpha]_D^{20}$: −3.4° (c=1.0, EtOH).

Example 33—Isomer B $^1$H-NMR (400 MHz, CDCl$_3$) δ: 7.98 (1H, dd, J=12.5, 2.0 Hz), 7.90-7.81 (2H, m), 7.58 (1H, dd, J=8.6, 2.7 Hz), 7.47-7.41 (1H, m), 7.32 (1H, dd, J=8.6, 5.1 Hz), 7.29 (1H, dd, J=8.6, 2.0 Hz), 6.40 (1H, s), 4.09-3.98 (1H, m), 3.22 (3H, s), 2.48 (1H, dd, J=15.6, 8.6 Hz), 2.25 (3H, s), 2.21 (1H, dd, J=15.6, 8.6 Hz), 1.70 (1H, d, J=3.9 Hz), 1.19 (3H, d, J=6.3 Hz).

HRMS (ESI) calcd for $C_{23}H_{21}F_5N_2O_4S$ [M+H]$^+$, required m/z: 517.1220, found 517.1196.

Retention time: 8.5 min chiral HPLC condition: LC1, eluent: hexane-EtOH-MeOH [80:16:4 (v/v/v), isocratic].

Example 34

1-(2-Chloro-4-fluorophenyl)-5-[(2S)-2-hydroxypropyl]-2-methyl-N-[3-methyl-4-(methylsulfonyl)phenyl]-1H-pyrrole-3-carboxamide

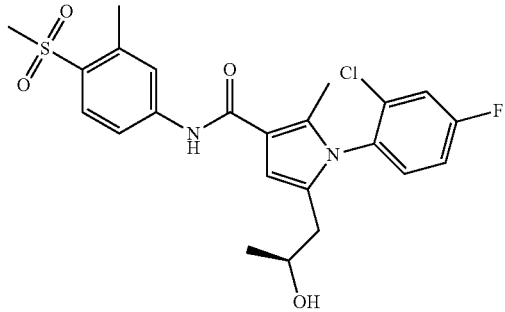 [SMILES: Cc1cc(NC(=O)c2cc(C[C@H](C)O)n(-c3ccc(F)cc3Cl)c2C)ccc1S(C)(=O)=O]

The title compound (0.25 g, 93%) was obtained from the compound (0.32 g, 0.57 mmol) of Comparative Example 99 in the process similar to Example 3. The obtained mixture was optically resolved under the following condition to give a single isomer.

chiral HPLC condition: LC3, eluent: hexane-EtOH-MeOH [70:24:6 (v/v/v), isocratic]

$^1$H-NMR (400 MHz, CDCl$_3$) δ: 8.00 (1H, d, J=8.6 Hz), 7.76 (1H, d, J=2.0 Hz), 7.67 (1H, s), 7.54 (1H, dd, J=8.8, 2.1 Hz), 7.36 (1H, dd, J=7.8, 2.7 Hz), 7.31 (1H, dd, J=8.6, 5.4 Hz), 7.20-7.15 (1H, m), 6.38 (1H, s), 3.87-3.78 (1H, m), 3.08 (3H, s), 2.71 (3H, s), 2.46 (1H, dd, J=15.1, 8.2 Hz), 2.39 (1H, dd, J=15.2, 4.7 Hz), 2.30 (3H, s), 1.69 (1H, d, J=3.6 Hz), 1.17 (3H, d, J=6.2 Hz).

HRMS (ESI) calcd for $C_{23}H_{25}ClFN_2O_4S$ [M+H]$^+$, required m/z: 479.1208, found 479.1200.

Retention time: 6.1 min chiral HPLC condition: LC1, eluent: hexane-EtOH-MeOH [70:24:6 (v/v/v), isocratic]

$[\alpha]_D^{20}$: −26° (c=1.0, EtOH).

Example 35

1-(2-Chloro-4-fluorophenyl)-N-[3-chloro-4-(methylsulfonyl)phenyl]-5-[(2S)-2-hydroxypropyl]-2-methyl-1H-pyrrole-3-carboxamide

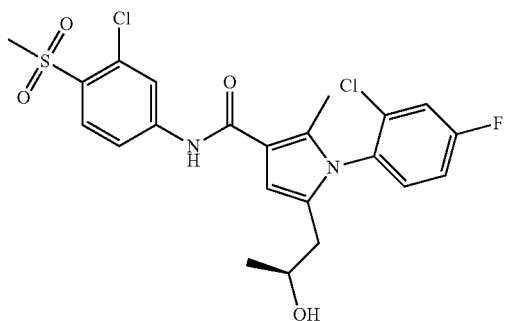

The title compound (0.27 g, 88%) was obtained from the compound (0.36 g, 0.60 mmol) of Comparative Example 105 in the process similar to Example 3. The obtained mixture was optically resolved under the following condition to give a single isomer.

chiral HPLC condition: LC4, eluent: hexane-EtOH [60:40 (v/v), isocratic]

$^1$H-NMR (400 MHz, CDCl$_3$) δ: 8.12 (1H, s), 8.09 (1H, d, J=9.0 Hz), 7.72 (1H, s), 7.55 (1H, d, J=7.6 Hz), 7.37-7.14 (3H, m), 6.38 (1H, s), 3.87-3.79 (1H, m), 3.27 (3H, s), 2.49-2.35 (2H, m), 2.30 (3H, s), 1.66 (1H, d, J=3.6 Hz), 1.17 (3H, d, J=5.9 Hz).

HRMS (ESI) calcd for C$_{22}$H$_{22}$Cl$_2$FN$_2$O$_4$S [M+H]$^+$, required m/z: 499.0728, found 499.0700.

Retention time: 8.5 min chiral HPLC condition: LC2, eluent: hexane-EtOH [60:40 (v/v), isocratic].

Example 36

1-(2-Chloro-4-fluorophenyl)-N-[3-fluoro-4-(methylsulfonyl)phenyl]-5-[(2S)-2-hydroxypropyl]-2-methyl-1H-pyrrole-3-carboxamide

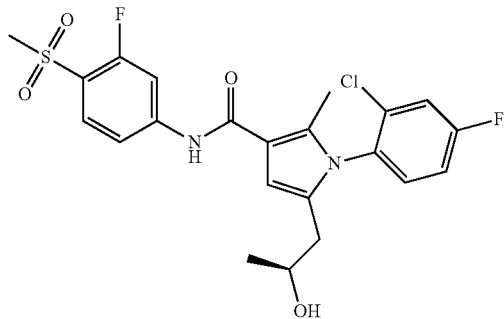 [SMILES: Cc1c(C(=O)Nc2ccc(S(C)(=O)=O)c(Cl)c2)cc(C[C@H](C)O)n1-c1ccc(F)cc1Cl]

The title compound (0.20 g, 98%) was obtained from the compound (0.24 g, 0.42 mmol) of Comparative Example 109 in the process similar to Example 3. The obtained mixture was optically resolved under the following condition to give a single isomer.

chiral HPLC condition: LC3, eluent: hexane-EtOH-MeOH [75:20:5 (v/v/v), isocratic]

$^1$H-NMR (400 MHz, CDCl$_3$) δ: 8.00 (1H, dd, J=12.5, 1.9 Hz), 7.88 (1H, dd, J=8.6, 8.2 Hz), 7.77 (1H, s), 7.36 (1H, dd, J=8.2, 2.7 Hz), 7.32-7.25 (2H, m), 7.20-7.15 (1H, m), 6.38 (1H, s), 3.86-3.79 (1H, m), 3.22 (3H, s), 2.46 (1H, dd, J=15.3, 7.8 Hz), 2.39 (1H, dd, J=15.3, 4.7 Hz), 2.29 (3H, s), 1.67 (1H, d, J=3.5 Hz), 1.17 (3H, d, J=5.9 Hz).

HRMS (ESI) calcd for C$_{22}$H$_{22}$ClF$_2$N$_2$O$_4$S [M+H]$^+$, required m/z: 483.0957, found 483.0941.

Retention time: 6.7 min chiral HPLC condition: LC1, eluent: hexane-EtOH-MeOH [75:20:5 (v/v/v), isocratic]

[α]$_D^{21}$: −25° (c=1.2, EtOH).

Example 37

1-[4-Chloro-2-(trifluoromethyl)phenyl]-5-[(2S)-2-hydroxypropyl]-2-methyl-N-[3-methyl-4-(methylsulfonyl)phenyl]-1H-pyrrole-3-carboxamide

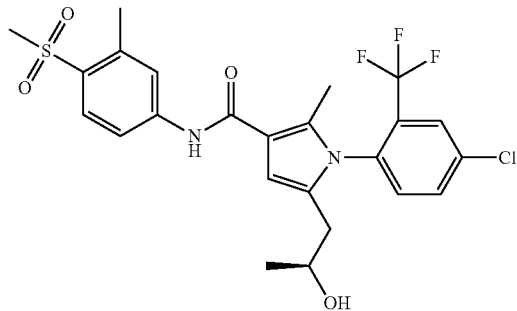 [SMILES: Cc1cc(NC(=O)c2cc(C[C@H](C)O)n(-c3ccc(Cl)cc3C(F)(F)F)c2C)ccc1S(C)(=O)=O]

The title compound (0.45 g, 91%) was obtained from the compound (0.58 g, 0.94 mmol) of Comparative Example 97 in the process similar to Example 3.

MS (ESI) m/z: 529 [M+H]$^+$

Retention time: 4.3 min (Example 37—isomer A), 6.2 min (Example 37—isomer B)

chiral HPLC condition: LC1, eluent: hexane-EtOH-MeOH [70:24:6 (v/v/v), isocratic]

Resolution of the isomer was carried out under the following condition to only isolate Example 37—isomer A.

chiral HPLC condition: LC3, eluent: hexane-EtOH-MeOH [70:24:6 (v/v/v), isocratic]

Example 37—Isomer A $^1$H-NMR (400 MHz, CDCl$_3$) δ: 7.99 (1H, d, J=8.6 Hz), 7.86 (1H, d, J=2.0 Hz), 7.77-7.68 (3H, m), 7.54 (1H, dd, J=8.6, 2.0 Hz), 7.26 (1H, d, J=8.6 Hz), 6.39 (1H, s), 3.89-3.79 (1H, m), 3.07 (3H, s), 2.70 (3H, s), 2.46 (1H, dd, J=15.6, 8.6 Hz), 2.29 (1H, dd, J=15.6, 3.9 Hz), 2.26 (3H, s), 1.73 (1H, brs), 1.16 (3H, d, J=6.3 Hz).

HRMS (ESI) calcd for C$_{24}$H$_{25}$ClF$_3$N$_2$O$_4$S [M+H]$^+$, required m/z: 529.1176, found 529.1160.

Retention time: 4.3 min chiral HPLC condition: LC1, eluent: hexane-EtOH-MeOH [70:24:6 (v/v/v), isocratic]

[α]$_D^{22}$: −3.5° (c=1.0, EtOH).

Example 38

1-[4-Chloro-2-(trifluoromethoxy)phenyl]-5-[(2S)-2-hydroxypropyl]-2-methyl-N-[3-methyl-4-(methylsulfonyl)phenyl]-1H-pyrrole-3-carboxamide

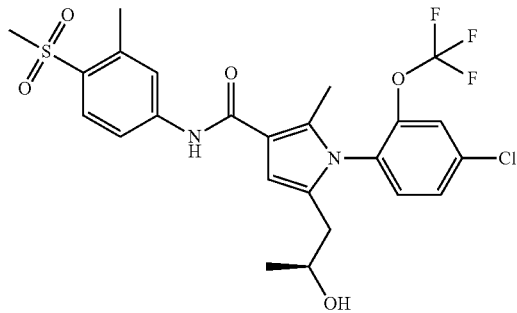 [SMILES: Cc1cc(NC(=O)c2cc(C[C@H](C)O)n(-c3ccc(Cl)cc3OC(F)(F)F)c2C)ccc1S(C)(=O)=O]

The title compound (0.44 g, 86%) was obtained from the compound (0.59 g, 0.93 mmol) of Comparative Example 98 in the process similar to Example 3.

MS (ESI) m/z: 545 [M+H]$^+$

Retention time: 3.9 min (Example 38—isomer A), 5.7 min (Example 38—isomer B)

chiral HPLC condition: LC1, eluent: hexane-EtOH-MeOH [70:24:6 (v/v/v), isocratic]

Resolution of the isomer was carried out under the following condition to only isolate Example 38—isomer A.

chiral HPLC condition: LC3, eluent: hexane-EtOH-MeOH [70:24:6 (v/v/v), isocratic]

Example 38—Isomer A $^1$H-NMR (400 MHz, CDCl$_3$) δ: 7.99 (1H, d, J=8.6 Hz), 7.75 (1H, d, J=2.4 Hz), 7.67 (1H, s), 7.54 (1H, dd, J=8.6, 2.4 Hz), 7.51-7.48 (1H, m), 7.46 (1H, dd, J=8.6, 2.4 Hz), 7.27 (1H, d, J=8.6 Hz), 6.39 (1H, s), 3.87-3.76 (1H, m), 3.07 (3H, s), 2.71 (3H, s), 2.47 (1H, dd, J=15.2, 8.2 Hz), 2.38 (1H, dd, J=15.2, 4.3 Hz), 2.30 (3H, s), 1.67 (1H, brs), 1.16 (3H, d, J=6.3 Hz).

HRMS (ESI) calcd for C$_{24}$H$_{25}$ClF$_3$N$_2$O$_5$S [M+H]$^+$, required m/z: 545.1125, found 545.1107.

Retention time: 3.9 min chiral HPLC condition: LC1, eluent: hexane-EtOH-MeOH [70:24:6 (v/v/v), isocratic]

$[α]_D^{22}$: −8.7° (c=1.0, EtOH).

Example 39

1-[2-(Difluoromethoxy)-4-fluorophenyl]-2-ethyl-5-[(2S)-2-hydroxypropyl]-N-[4-(methylsulfonyl)phenyl]-1H-pyrrole-3-carboxamide

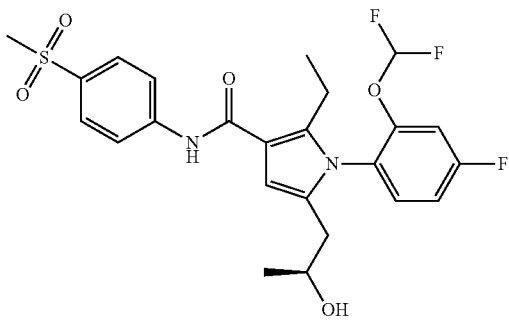 [SMILES: CCc1c(C(=O)Nc2ccc(S(C)(=O)=O)cc2)cc(C[C@H](C)O)n1-c1ccc(F)cc1OC(F)F]

The title compound (0.37 g, 98%) was obtained from the compound (0.44 g, 0.73 mmol) of Comparative Example 110 in the process similar to Example 2. The obtained mixture was optically resolved under the following condition to give a single isomer.

chiral HPLC condition: LC3, eluent: hexane-EtOH-MeOH [85:12:3 (v/v/v), isocratic]

$^1$H-NMR (400MHz, CDCl$_3$) d 7.91 (1H, d, J=9.0 Hz), 7.83 (1H, d, J=9.0 Hz), 7.74 (1H, s), 7.30 (1H, dd, J=8.8, 5.7 Hz), 7.28-7.25 (1H, m), 7.19-7.15 (1H, m), 7.11-7.07 (1H, m), 6.44 (1H, t, J=71.8 Hz), 6.37 (1H, s), 3.88-3.80 (1H, m), 3.05 (3H, s), 2.91-2.82 (1H, m), 2.62-2.53 (1H, m), 2.40 (2H, d, J=6.7 Hz), 1.69 (1H, d, J=3.5 Hz), 1.16 (3H, d, J=6.3 Hz), 1.03 (3H, t, J=7.4 Hz).

HRMS (ESI) calcd for C$_{24}$H$_{26}$F$_3$N$_2$O$_5$S [M+H]$^+$, required m/z: 511.1515, found 511.1503.

Retention time: 6.3 min chiral HPLC condition: LC1, eluent: hexane-EtOH-MeOH [80:16:4 (v/v/v), isocratic]

$[α]_D^{21}$: +2.4° (c=1.1, EtOH).

Example 40

1-(2-Chloro-4-fluorophenyl)-5-[(2S)-2-hydroxypropyl]-2-methyl-N-[4-(methylsulfonyl)phenyl]-1H-pyrrole-3-carboxamide

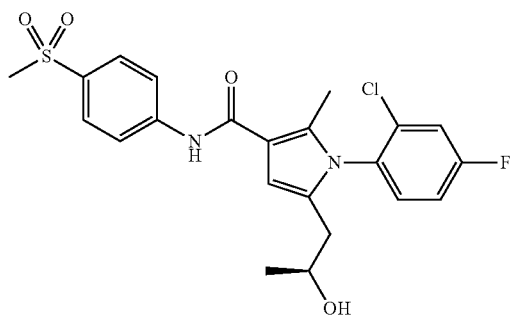 [SMILES: Cc1c(C(=O)Nc2ccc(S(C)(=O)=O)cc2)cc(C[C@H](C)O)n1-c1ccc(F)cc1Cl]

The title compound (2.9 g, 83%) was obtained from the compound (4.2 g, 7.6 mmol) of Comparative Example 91 in the process similar to Example 3.

MS (ESI) m/z: 465 [M+H]$^+$.

Retention time: 8.3 min (Example 40—isomer A), 9.6 min (Example 40—isomer B)

chiral HPLC condition: LC5, eluent: EtOH-MeOH-IPA [45:45:10 (v/v/v), isocratic]

Resolution of the isomer was carried out under the following condition.

chiral HPLC condition: LC6, eluent: EtOH-MeOH-IPA [45:45:10 (v/v/v), isocratic]

Example 40—Isomer A $^1$H-NMR (400 MHz, CDCl$_3$) δ: 7.92 (2H, dd, J=8.8, 1.6 Hz), 7.84 (2H, dd, J=8.8, 1.6 Hz), 7.71 (1H, s), 7.34-7.24 (2H, m), 6.39 (1H, s), 3.86-3.78 (1H, m), 3.06 (3H, s), 2.49-2.36 (2H, m), 2.30 (3H, s), 1.65 (1H, d, J=4.0 Hz), 1.17 (3H, d, J=6.0 Hz).

MS (ESI) m/z: 465 [M+H]$^+$.

Retention time: 8.7 min chiral HPLC condition: LC5, eluent: EtOH-MeOH-IPA [45:45:10 (v/v/v), isocratic].

Example 40—Isomer B $^1$H-NMR (400 MHz, CDCl$_3$) δ: 7.92 (2H, dd, J=8.8, 1.6 Hz), 7.84 (2H, dd, J=8.8, 1.6 Hz), 7.71 (1H, s), 7.34-7.24 (2H, m), 6.39 (1H, s), 3.86-3.78 (1H, m), 3.06 (3H, s), 2.52-2.35 (2H, m), 2.30 (3H, s), 1.65 (1H, d, J=4.0 Hz), 1.17 (3H, d, J=6.0 Hz).

MS (ESI) m/z: 465 [M+H]$^+$.

Retention time: 10.4 min chiral HPLC condition: LC5, eluent: EtOH-MeOH-IPA [45:45:10 (v/v/v), isocratic].

Example 41

1-(4-Chloro-2-methylphenyl)-5-[(2S)-2-hydroxypropyl]-2-methyl-N-[4-(methylsulfonyl)phenyl]-1H-pyrrole-3-carboxamide

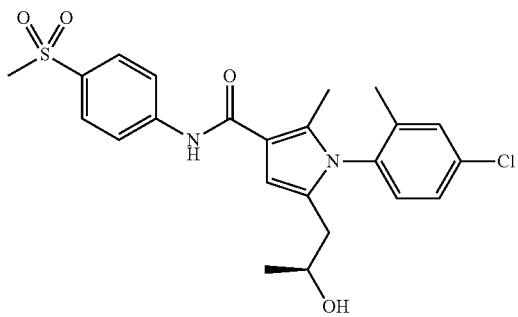 [SMILES: Cc1cc(Cl)ccc1-n1c(C[C@H](C)O)cc(C(=O)Nc2ccc(S(C)(=O)=O)cc2)c1C]

The title compound (1.2 g, 84%) was obtained from the compound (1.7 g, 3.1 mmol) of Comparative Example 92 in the process similar to Example 3.

MS (ESI) m/z: 461 [M+H]$^+$.

Retention time: 6.0 min (Example 41—isomer A), 7.1 min (Example 41—isomer B)

chiral HPLC condition: LC5, eluent: EtOH-MeOH-IPA [45:45:10 (v/v/v), isocratic]

Resolution of the isomer was carried out under the following condition.

chiral HPLC condition: LC6, eluent: EtOH-MeOH-IPA [45:45:10 (v/v/v), isocratic]

Example 41—Isomer A $^1$H-NMR (400 MHz, CDCl$_3$) δ: 7.92 (2H, d, J=8.8 Hz), 7.84 (1H, d, J=8.8 Hz), 7.70 (1H, s), 7.39 (1H, s), 7.33 (1H, d, J=8.4 Hz), 7.09 (1H, d, J=8.8 Hz), 6.38 (1H, s), 3.87-3.79 (1H, m), 3.06 (3H, s), 2.43-2.29 (2H, m), 2.27 (3H, s), 1.94 (3H, s), 1.67.

MS (ESI) m/z: 461 [M+H]$^+$.

Retention time: 6.0 min chiral HPLC condition: LC5, eluent: EtOH-MeOH-IPA [45:45:10 (v/v/v), isocratic].

Example 41—Isomer B $^1$H-NMR (400 MHz, CDCl$_3$) δ: 7.92 (2H, d, J=8.8 Hz), 7.84 (1H, d, J=8.8 Hz), 7.70 (1H, s), 7.39 (1H, s), 7.33 (1H, d, J=8.4 Hz), 7.09 (1H, d, J=8.8 Hz), 6.38 (1H, s), 3.87-3.79 (1H, m), 3.06 (3H, s), 2.43-2.29 (2H, m), 2.27 (3H, s), 1.94 (3H, s), 1.67.

MS (ESI) m/z: 461 [M+H]$^+$.

Retention time: 7.2 min chiral HPLC condition: LC5, eluent: EtOH-MeOH-IPA [45:45:10 (v/v/v), isocratic].

Example 42

1-[4-Chloro-2-(trifluoromethoxy)phenyl]-5-[(2S)-2-hydroxypropyl]-2-methyl-N-[4-(methylsulfonyl)phenyl]-1H-pyrrole-3-carboxamide

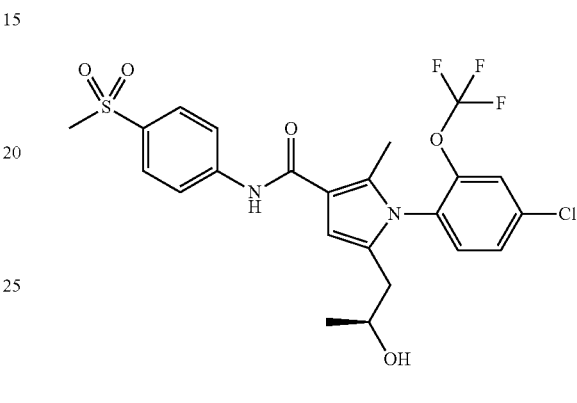

The title compound (1.2 g, 64%) was obtained from the compound (2.2 g, 3.6 mmol) of Comparative Example 93 in the process similar to Example 3.

MS (ESI) m/z: 531 [M+H]$^+$.

Retention time: 7.3 min (Example 42—isomer A), 9.1 min (Example 42—isomer B)

chiral HPLC condition: LC7, eluent: EtOH-MeOH [75:25 (v/v), isocratic]

Resolution of the isomer was carried out under the following condition.

chiral HPLC condition: LC8, eluent: EtOH-MeOH [75:25 (v/v), isocratic]

Example 42—Isomer A $^1$H-NMR (400 MHz, CDCl$_3$) δ: 7.92 (2H, d, J=8.4 Hz), 7.84 (2H, d, J=8.8 Hz), 7.70 (1H, s), 7.52-7.45 (2H, m), 7.31-7.27 (1H, m), 6.39 (1H, s), 4.02-3.92 (1H, m), 3.06 (3H, s), 2.51 (1H, dd, J=15.6, 4.4 Hz), 2.38-2.33 (1H, m), 2.31 (3H, s), 1.60 (1H, d, J=3.6 Hz), 1.19 (3H, d, J=6.4 Hz).

MS (ESI) m/z: 531 [M+H]$^+$.

Retention time: 7.7 min chiral HPLC condition: LC7, eluent: EtOH-MeOH [75:25 (v/v), isocratic].

Example 42—Isomer B $^1$H-NMR (400 MHz, CDCl$_3$) δ: 7.93 (2H, d, J=8.4 Hz), 7.84 (1H, d, J=8.8 Hz), 7.70 (1H, s), 7.39 (1H, s), 7.52-7.45 (2H, m), 6.39 (1H, s), 3.88-3.79 (1H, m), 3.06 (3H, s), 2.52-2.36 (2H, m), 2.31 (3H, s), 1.60 (1H, d, J=4.4 Hz), 1.16 (3H, d, J=6.0 Hz).

MS (ESI) m/z: 531 [M+H]$^+$.

Retention time: 9.2 min chiral HPLC condition: LC7, eluent: EtOH-MeOH [75:25 (v/v), isocratic].

Example 43

1-(2,4-Dichlorophenyl)-5-[(2S)-2-hydroxypropyl]-2-methyl-N-[4-(methylsulfonyl)phenyl]-1H-pyrrole-3-carboxamide

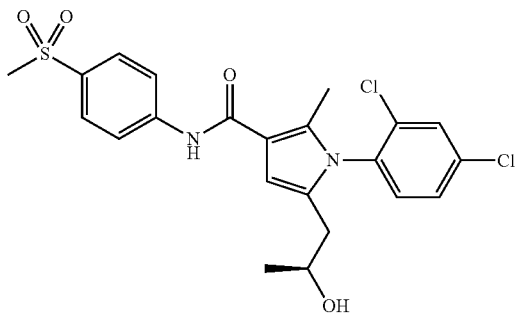 [SMILES: Cc1c(C(=O)Nc2ccc(S(C)(=O)=O)cc2)cc(C[C@H](C)O)n1-c1ccc(Cl)cc1Cl]

The title compound (0.27 g, 80%) was obtained from the compound (0.40 g, 0.7 mmol) of Comparative Example 94 in the process similar to Example 3.

MS (ESI) m/z: 481 [M+H]$^+$.

Retention time: 12.2 min (Example 43—isomer A), 17.0 min (Example 43—isomer B)

chiral HPLC condition: LC5, eluent: EtOH-MeOH [50:50 (v/v), isocratic]

Resolution of the isomer was carried out under the following condition.

chiral HPLC condition: LC6, eluent: EtOH-MeOH [50:50 (v/v), isocratic]

Example 43—Isomer A $^1$H-NMR (400 MHz, CDCl$_3$) δ: 7.92 (2H, m), 7.83 (2H, m), 7.73 (1H, s), 7.63 (1H, d, J=2.4), 7.44 (1H, dd, J=8.4, 2.0 Hz), 7.25 (1H, d, J=8.0), 6.40 (1H, s), 3.85-3.80 (1H, m), 3.06 (3H, s), 2.47 (1H, dd, J=15.6, 8.4 Hz), 2.41 (1H, dd, J=15.2, 4.8 Hz), 2.30 (3H, s), 1.17 (3H, d, J=6.0 Hz).

MS (ESI) m/z: 481 [M+H]$^+$.

Retention time: 12.2 min chiral HPLC condition: LC5, eluent: EtOH-MeOH [50:50 (v/v), isocratic].

Example 43—Isomer B $^1$H-NMR (400 MHz, CDCl$_3$) δ: 7.91 (2H, m), 7.83 (2H, m), 7.75 (1H, s), 7.62 (1H, d, J=2.0), 7.44 (1H, dd, J=8.4, 2.4 Hz), 7.25 (1H, d, J=8.0), 6.40 (1H, s), 3.88-3.84 (1H, m), 3.06 (3H, s), 2.48 (1H, dd, J=15.2, 3.8 Hz), 2.36 (1H, dd, J=15.6, 8.8 Hz), 2.30 (3H, s), 1.17 (3H, d, J=6.0 Hz).

MS (ESI) m/z: 481 [M+H]$^+$.

Retention time: 17.0 min chiral HPLC condition: LC5, eluent: EtOH-MeOH [50:50 (v/v), isocratic].

Example 44

1-(2-Chloro-4-fluorophenyl)-2-ethyl-5-[(2S)-2-hydroxypropyl]-N-[4-(methylsulfonyl)phenyl]-1H-pyrrole-3-carboxamide

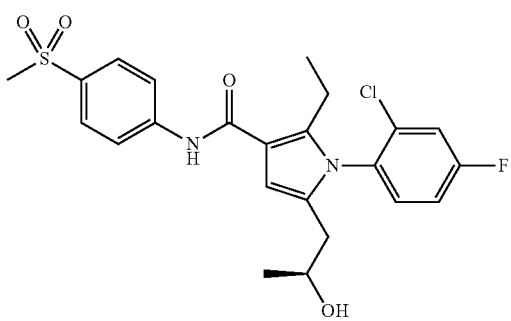 [SMILES: CCc1c(C(=O)Nc2ccc(S(C)(=O)=O)cc2)cc(C[C@H](C)O)n1-c1ccc(F)cc1Cl]

The title compound (1.0 g, 50%) was obtained from the compound (2.3 g, 4.0 mmol) of Comparative Example 111 in the process similar to Example 3.

MS (ESI) m/z: 479 [M+H]$^+$.

Retention time: 10.17 min (Example 44—isomer A), 13.56 min (Example 44—isomer B)

chiral HPLC condition: LC7, eluent: EtOH-MeOH [65:35 (v/v), isocratic].

Resolution of the isomer was carried out under the following condition.

chiral HPLC condition: LC8, eluent: EtOH-MeOH [65:35 (v/v), isocratic].

Example 44—Isomer A $^1$H-NMR (400 MHz, CDCl$_3$) δ: 7.95 (2H, m), 7.85 (2H, m), 7.78 (1H, s), 7.37-7.32 (2H, m), 7.20-7.16 (1H, m), 6.40 (1H, s), 3.92-3.88 (1H, m), 3.06 (3H, s), 2.93-2.83 (1H, m), 2.59-2.50 (1H, m), 2.46 (1H, dd, J=15.2, 3.6 Hz), 2.32 (1H, dd, J=15.2, 8.8 Hz), 1.71 (1H, br s), 1.17 (3H, d, J=6.4 Hz), 1.03 (3H, t, J=7.4 Hz).

MS (ESI) m/z: 479 [M+H]$^+$.

Retention time: 11.17 min.

chiral HPLC condition: LC7, eluent: EtOH-MeOH [65:35 (v/v), isocratic].

Example 44—Isomer B $^1$H-NMR (400 MHz, CDCl$_3$) δ: 7.91 (2H, m), 7.83 (2H, m), 7.74 (1H, s), 7.37-7.32 (2H, m), 7.25-7.15 (1H, m), 6.39 (1H, s), 3.85-3.79 (1H, m), 3.06 (3H, s), 2.88-2.78 (1H, m), 2.66-2.56 (1H, m), 2.45 (1H, dd, J=15.2, 8.2 Hz), 2.32 (1H, dd, J=15.2, 4.0 Hz), 1.67 (1H, d, J=3.2 Hz), 1.16 (3H, d, J=6.4 Hz), 1.03 (3H, t, J=7.4 Hz).
MS (ESI) m/z: 479 [M+H]⁺.
Retention time: 13.56 min.
chiral HPLC condition: LC7, eluent: EtOH-MeOH [65:35 (v/v), isocratic].

Example 45

1-[4-Chloro-2-(4-fluorophenoxy)phenyl]-5-[(2S)-2-hydroxypropyl]-2-methyl-N-[4-(methylsulfonyl)phenyl]-1H-pyrrole-3-carboxamide

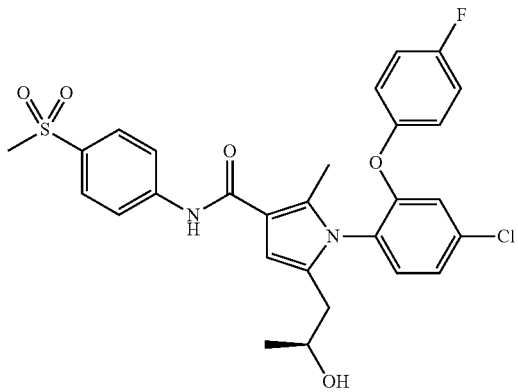 [SMILES: Cc1c(C(=O)Nc2ccc(S(C)(=O)=O)cc2)cc(C[C@H](C)O)n1-c1ccc(Cl)cc1Oc1ccc(F)cc1]

The title compound (0.90 g, 70%) was obtained from the compound (1.5 g, 2.3 mmol) of Comparative Example 95 in the process similar to Example 3.
MS (ESI) m/z: 557 [M+H]⁺.
Retention time: 9.5 min (Example 45—isomer A), 15.8 min (Example 45—isomer B)
chiral HPLC condition: LC5, eluent: EtOH-MeOH [65:35 (v/v), isocratic]
Resolution of the isomer was carried out under the following condition.
chiral HPLC condition: LC6, eluent: EtOH-MeOH [65:35 (v/v), isocratic]
Example 45—Isomer A
MS (ESI) m/z: 557 [M+H]⁺.
Retention time: 9.4 min
chiral HPLC condition: LC5, eluent: EtOH-MeOH [65:35 (v/v), isocratic].
Example 45—Isomer B
MS (ESI) m/z: 557 [M+H]⁺.
Retention time: 15.8 min
chiral HPLC condition: LC5, eluent: EtOH-MeOH [65:35 (v/v), isocratic].

Example 46

1-(2,4-Dichlorophenyl)-2-ethyl-5-[(2S)-2-hydroxypropyl]-N-[4-(methylsulfonyl)phenyl]-1H-pyrrole-3-carboxamide

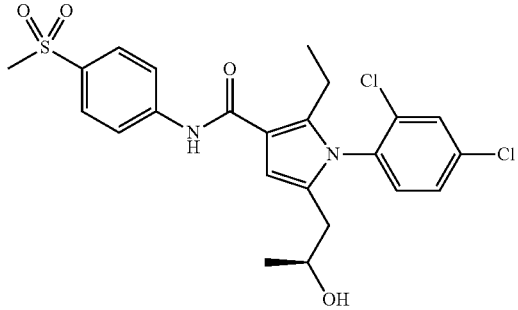 [SMILES: CCc1c(C(=O)Nc2ccc(S(C)(=O)=O)cc2)cc(C[C@H](C)O)n1-c1ccc(Cl)cc1Cl]

The title compound (0.38 g, 84%) was obtained from the compound (0.54 g, 0.92 mmol) of Comparative Example 112 in the process similar to Example 3.
MS (ESI) m/z: 495 [M+H]⁺.
Retention time: 8.1 min (Example 46—isomer A), 12.6 min (Example 46—isomer B)
chiral HPLC condition: LC7, eluent: EtOH-MeOH [65:35 (v/v), isocratic]
Resolution of the isomer was carried out under the following condition.
chiral HPLC condition: LC8, eluent: EtOH-MeOH [65:35 (v/v), isocratic]
Example 46—Isomer A
MS (ESI) m/z: 495 [M+H]⁺.
Retention time: 8.1 min.
chiral HPLC condition: LC7, eluent: EtOH-MeOH [65:35 (v/v), isocratic].
Example 46—Isomer B
MS (ESI) m/z: 495 [M+H]⁺.
Retention time: 12.6 min
chiral HPLC condition: LC7, eluent: EtOH-MeOH [65:35 (v/v), isocratic].

Example 47

1-[4-Chloro-2-(trifluoromethyl)phenyl]-2-ethyl-5-[(2S)-2-hydroxypropyl]-N-[4-(methylsulfonyl)phenyl]-1H-pyrrole-3-carboxamide

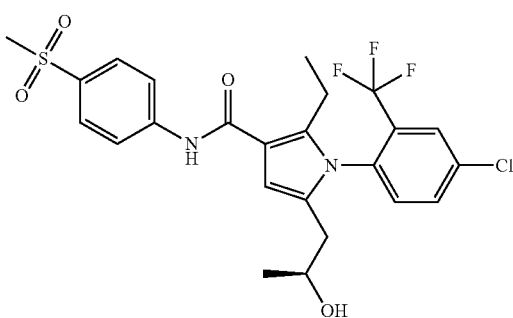 [SMILES: CCc1c(C(=O)Nc2ccc(S(C)(=O)=O)cc2)cc(C[C@H](C)O)n1-c1ccc(Cl)cc1C(F)(F)F]

The title compound (0.68 g, 81%) was obtained from the compound (1.0 g, 1.6 mmol) of Comparative Example 113 in the process similar to Example 3.
MS (ESI) m/z: 529 [M+H]⁺.
Retention time: 9.1 min (Example 47—isomer A), 11.3 min (Example 47—isomer B)
chiral HPLC condition: LC5, eluent: EtOH-MeOH [50:50 (v/v), isocratic]
Resolution of the isomer was carried out under the following condition.
chiral HPLC condition: LC6, eluent: EtOH-MeOH [50:50 (v/v), isocratic]
Example 47—Isomer A
MS (ESI) m/z: 529 [M+H]⁺.
Retention time: 9.1 min
chiral HPLC condition: LC5, eluent: EtOH-MeOH [50:50 (v/v), isocratic].
Example 47—Isomer B
MS (ESI) m/z: 529 [M+H]⁺.
Retention time: 11.3 min chiral HPLC condition: LC5, eluent: EtOH-MeOH [50:50 (v/v), isocratic].

Example 48

2-Ethyl-1-[4-fluoro-2-(trifluoromethyl)phenyl]-5-[(2S)-2-hydroxypropyl]-N-[4-(methylsulfonyl)phenyl]-1H-pyrrole-3-carboxamide

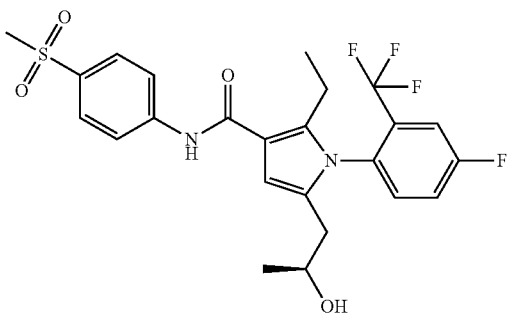 [SMILES: CCc1c(C(=O)Nc2ccc(S(C)(=O)=O)cc2)cc(C[C@H](C)O)n1-c1ccc(F)cc1C(F)(F)F]

The title compound (0.38 g, 34%) was obtained from the compound (1.3 g, 2.2 mmol) of Comparative Example 114 in the process similar to Example 3.

MS (ESI) m/z: 513 [M+H]$^+$.

Retention time: 16.5 min (Example 48—isomer A), 23.8 min (Example 48—isomer B)

chiral HPLC condition: LC5, eluent: EtOH [isocratic]

Resolution of the isomer was carried out under the following condition.

chiral HPLC condition: LC6, eluent: EtOH [isocratic]
Example 48—Isomer A
MS (ESI) m/z: 513 [M+H]$^+$.
Retention time: 16.6 min
chiral HPLC condition: LC5, eluent: EtOH [isocratic].
Example 48—Isomer B
MS (ESI) m/z: 513 [M+H]$^+$.
Retention time: 23.3 min
chiral HPLC condition: LC5, eluent: EtOH [isocratic].

Example 49

N-[4-(Aminosulfonyl)-3-chlorophenyl]-1-(2-chloro-4-fluorophenyl)-5-[(2S)-2-hydroxypropyl]-2-methyl-1H-pyrrole-3-carboxamide

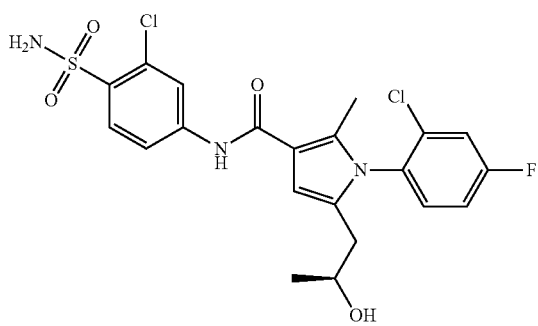 [SMILES: Cc1c(C(=O)Nc2ccc(S(N)(=O)=O)c(Cl)c2)cc(C[C@H](C)O)n1-c1ccc(F)cc1Cl]

The title compound (0.32 g, 47%) was obtained from the compound (0.80 g, 1.4 mmol) of Comparative Example 78 in the process similar to Example 3.

MS (ESI) m/z: 500 [M+H]$^+$.

Retention time: 7.3 min (Example 49—isomer A), 8.9 min (Example 49—isomer B)

chiral HPLC condition: LC5, eluent: EtOH-MeOH [50:50 (v/v), isocratic]

Resolution of the isomer was carried out under the following condition.

chiral HPLC condition: LC6, eluent: EtOH-MeOH [50:50 (v/v), isocratic]
Example 49—Isomer A
$^1$H-NMR (400 MHz, CDCl$_3$) δ: 8.14 (1H, d, J=2.0 Hz), 8.05 (1H, d, J=8.8 Hz), 7.66 (1H, d, J=8.8 Hz), 7.48 (1H, dd, J=8.8, 2.8 Hz), 7.40-7.15 (2H, m), 6.37 (1H, s), 5.06 (2H, s), 3.86-3.77 (1H, m), 2.49-2.32 (2H, m), 2.30 (3H, s), 1.64 (1H, d, J=4.0 Hz), 1.17 (3H, d, J=6.0 Hz).
MS (ESI) m/z: 500 [M+H]$^+$.
Retention time: 8.9 min
chiral HPLC condition: LC5, eluent: EtOH-MeOH [50:50 (v/v), isocratic].
Example 49—Isomer B
$^1$H-NMR (400 MHz, CDCl$_3$) δ: 8.14 (1H, d, J=2.0 Hz), 8.05 (1H, d, J=8.8 Hz), 7.66 (1H, d, J=8.8 Hz), 7.48 (1H, dd, J=8.8, 2.8 Hz), 7.40-7.15 (2H, m), 6.37 (1H, s), 5.06 (2H, s), 3.86-3.77 (1H, m), 2.49-2.32 (2H, m), 2.30 (3H, s), 1.66-1.63 (1H, m), 1.17 (3H, d, J=6.0 Hz).
MS (ESI) m/z: 500 [M−H]$^-$.
Retention time: 7.3 min
chiral HPLC condition: LC5, eluent: EtOH-MeOH [50:50 (v/v), isocratic].

Example 50

1-(5-Chloro-4'-fluorobiphenyl-2-yl)-5-[(2S)-2-hydroxypropyl]-2-methyl-N-[4-(methylsulfonyl)phenyl]-1H-pyrrole-3-carboxamide

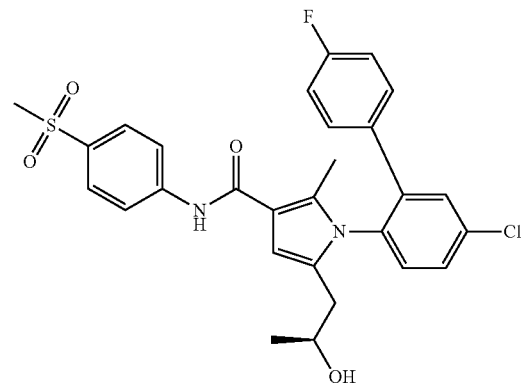 [SMILES: Cc1c(C(=O)Nc2ccc(S(C)(=O)=O)cc2)cc(C[C@H](C)O)n1-c1ccc(Cl)cc1-c1ccc(F)cc1]

The title compound (0.32 g, 47%) was obtained from the compound (0.50 g, 0.79 mmol) of Comparative Example 96 in the process similar to Example 3.

MS (ESI) m/z: 541 [M+H]$^+$.

Retention time: 11.2 min (Example 50—isomer A), 19.8 min (Example 50—isomer B)

chiral HPLC condition: LC7, eluent: EtOH-MeOH [50:50 (v/v), isocratic]

Resolution of the isomer was carried out under the following condition.

chiral HPLC condition: LC8, eluent: EtOH-MeOH [50:50 (v/v), isocratic]

Example 50—Isomer A $^1$H-NMR (400 MHz, CDCl$_3$) δ: 7.91 (2H, d, J=8.4 Hz), 7.82 (2H, d, J=8.8 Hz), 7.64 (1H, s), 7.56 (1H, d, J=2.8 Hz), 7.48 (1H, dd, J=8.4, 2.8 Hz), 7.22 (1H, d, J=9.2 Hz), 6.98-6.96 (4H, m), 6.22 (1H, s), 3.82-3.73 (1H, m), 3.06 (3H, s), 2.33 (3H, s), 2.23-2.19 (2H, m), 1.46 (1H, d, J=4.4 Hz), 1.09 (3H, d, J=6.0 Hz).

MS (ESI) m/z: 541 [M+H]$^+$.

Retention time: 11.2 min chiral HPLC condition: LC7, eluent: EtOH-MeOH [50:50 (v/v), isocratic].

Example 50—Isomer B $^1$H-NMR (400 MHz, CDCl$_3$) δ: 7.91 (2H, d, J=8.4 Hz), 7.82 (2H, d, J=8.8 Hz), 7.63 (1H, s), 7.56 (1H, d, J=2.8 Hz), 7.49 (1H, dd, J=8.4, 2.8 Hz), 7.21 (1H, d, J=9.2 Hz), 6.99-6.97 (4H, m), 6.22 (1H, s), 3.82-3.73 (1H, m), 3.06 (3H, s), 2.32 (3H, s), 2.25-2.21 (2H, m), 1.48 (1H, d, J=3.6 Hz), 1.10 (3H, d, J=6.4 Hz).

MS (ESI) m/z: 541 [M+H]$^+$.

Retention time: 19.8 min chiral HPLC condition: LC7, eluent: EtOH-MeOH [50:50 (v/v), isocratic].

Example 51

1-(4-Chloro-2-methylphenyl)-5-(2-fluoroethyl)-2-methyl-N-[4-(methylsulfonyl)phenyl]-1H-pyrrole-3-carboxamide

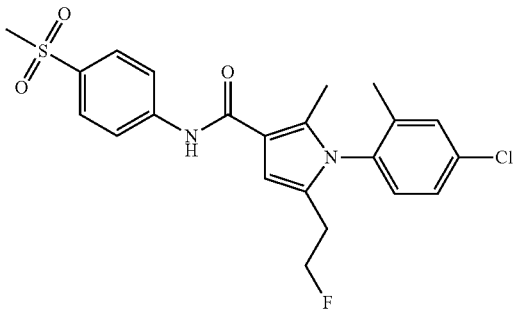 [SMILES: Cc1cc(Cl)ccc1-n1c(CCF)cc(C(=O)Nc2ccc(S(C)(=O)=O)cc2)c1C]

1-(4-Chloro-2-methylphenyl)-5-(2-hydroxyethyl)-2-methyl-N-[4-(methylsulfonyl)phenyl]-1H-pyrrole-3-carboxamide (6.8 g, 92%) was obtained from the compound (8.9 g, 17 mmol) of Comparative Example 67 in the process similar to Example 3. MS (ES+) m/z: 447 [M+H]$^+$.

To a solution of bis(2-methoxyethyl)aminosulfur trifluoride (11 ml, 61 mmol) in dichloromethane (200 ml), a solution of the above 1-(4-chloro-2-methylphenyl)-5-(2-hydroxyethyl)-2-methyl-N-[4-(methylsulfonyl)phenyl]-1H-pyrrole-3-carboxamide (6.8 g, 15 mmol) in dichloromethane (200 ml) was added, and the mixture was stirred at room temperature for 3 hours. The reaction mixture was poured to a saturated aqueous sodium hydrogencarbonate solution cooled to 0° C., and the mixture was stirred at room temperature for 15 minutes. The organic layer was washed with saturated brine, and after it was dried with magnesium sulfate, the solvent was distilled off under reduced pressure. The residue was purified by silica gel column chromatography (hexane-hexane:ethyl acetate=4:1) to give the title compound (3.8 g, 56%) as a solid.

HRMS (ESI) calcd for C$_{22}$H$_{23}$ClFN$_2$O$_3$S [M+H]$^+$, required m/z: 449.1102, found 449.1116.

Retention time: 8.4 min (Example 51—isomer A), 12.8 min (Example 51—isomer B)

chiral HPLC condition: LC, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [70:24:6 (v/v/v), isocratic]

Example 51—Isomer A $^1$H-NMR (500 MHz, CDCl$_3$) δ: 7.84-7.90 (5H, m), 7.39 (1H, s), 7.33 (1H, d, J=8.3 Hz), 7.10 (1H, d, J=8.3 Hz), 6.45 (1H, s), 4.55 (1H, t, J=6.1 Hz), 4.45 (1H, t, J=6.1), 3.05 (3H, s), 2.54-2.73 (2H, m), 2.27 (3H, s), 1.94 (3H, s).

HRMS (ESI) calcd for C$_{22}$H$_{23}$ClFN$_2$O$_3$S [M+H]$^+$, required m/z: 449.1102, found 449.1094.

Retention time: 8.4 min chiral HPLC condition: LC1, eluent: hexane-EtOH-MeOH [70:24:6 (v/v/v), isocratic]

[α]$_D^{22}$: −4.7° (c=1.0, CHCl$_3$).

Example 51—Isomer B $^1$H-NMR (400 MHz, CDCl$_3$) δ: 7.77-7.92 (5H, m), 7.39 (1H, s), 7.34 (1H, d, J=8.2 Hz), 7.10 (1H, d, J=8.2 Hz), 6.41 (1H, s), 4.56 (1H, t, J=6.1 Hz), 4.45 (1H, t, J=6.1), 3.06 (3H, s), 2.53-2.76 (2H, m), 2.27 (3H, s), 1.94 (3H, s).

HRMS (ESI) calcd for C$_{22}$H$_{23}$ClFN$_2$O$_3$S [M+H]$^+$, required m/z: 449.1102, found 449.1120.

Retention time: 12.7 min chiral HPLC condition: LC1, eluent: hexane-EtOH-MeOH [70:24:6 (v/v/v), isocratic]

[α]$_D^{22}$: +4.3° (c=1.0, CHCl$_3$).

Example 52

5-(2-Fluoroethyl)-1-(4-fluoro-2-methylphenyl)-2-methyl-N-[4-(methylsulfonyl)phenyl]-1H-pyrrole-3-carboxamide

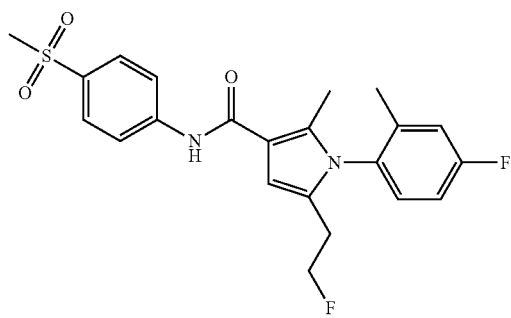 [SMILES: Cc1cc(F)ccc1-n1c(CCF)cc(C(=O)Nc2ccc(S(C)(=O)=O)cc2)c1C]

1-(4-Fluoro-2-methylphenyl)-5-(2-hydroxyethyl)-2-methyl-N-[4-(methylsulfonyl)phenyl]-1H-pyrrole-3-carboxamide (9.6 g, 95%) was obtained from the compound (12 g, 24 mmol) of Comparative Example 66 in the process similar to Example 3. MS (ES+) m/z: 431 [M+H]$^+$.

The title compound (3.7 g, 38%) was prepared from the compound (10 g, 24 mmol) synthesized by the above process in the process similar to Example 51.

HRMS (ESI) calcd for C$_{22}$H$_{23}$F$_2$N$_2$O$_3$S [M+H]$^+$, required m/z: 433.1397, found 433.1397.

Retention time: 8.1 min (Example 52—isomer A), 11.9 min (Example 52—isomer B)

chiral HPLC condition: LC1, eluent: hexane-EtOH-MeOH [70:24:6 (v/v/v), isocratic]

Resolution of the isomer was carried out under the following condition.
chiral HPLC condition: LC3, eluent: hexane-EtOH-MeOH [70:24:6 (v/v/v), isocratic]

Example 52—Isomer A $^1$H-NMR (500 MHz, CDCl$_3$) δ: 7.82-7.91 (5H, m), 7.01-7.17 (3H, m), 6.42 (1H, s), 4.55 (1H, t, J=6.4 Hz), 4.46 (1H, t, J=6.4), 3.05 (3H, s), 2.55-2.73 (2H, m), 2.27 (3H, s), 1.95 (3H, s).
HRMS (ESI) calcd for C$_{22}$H$_{23}$F$_2$N$_2$O$_3$S [M+H]$^+$, required m/z: 433.1397, found 433.1382.
Retention time: 8.1 min
chiral HPLC condition: LC1, eluent: hexane-EtOH-MeOH [70:24:6 (v/v/v), isocratic]
[α]$_D^{20}$: −6.3° (c=1.0, EtOH).

Example 52—Isomer B $^1$H-NMR (500 MHz, CDCl$_3$) δ: 7.83-7.91 (5H, m), 7.02-7.16 (3H, m), 6.42 (1H, s), 4.55 (1H, t, J=6.1 Hz), 4.46 (1H, t, J=6.1), 3.05 (3H, s), 2.53-2.74 (2H, m), 2.27 (3H, s), 1.95 (3H, s).
HRMS (ESI) calcd for C$_{22}$H$_{23}$F$_2$N$_2$O$_3$S [M+H]$^+$, required m/z: 433.1397, found 433.1401.
Retention time: 11.9 min
chiral HPLC condition: LC1, eluent: hexane-EtOH-MeOH [70:24:6 (v/v/v), isocratic]
[α]$_D^{20}$: +6.3° (c=1.0, EtOH).

Example 53

N-[4-(Aminosulfonyl)phenyl]-5-(2-fluoroethyl)-1-[4-fluoro-2-(trifluoromethyl)phenyl]-2-methyl-1H-pyrrole-3-carboxamide

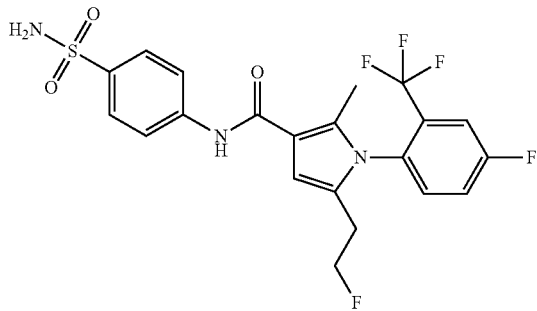 [SMILES: Cc1c(C(=O)Nc2ccc(S(N)(=O)=O)cc2)cc(CCF)n1-c1ccc(F)cc1C(F)(F)F]

N-[4-(Aminosulfonyl)phenyl]-1-[4-fluoro-2-(trifluoromethyl)phenyl]-5-(2-hydroxyethyl)-2-methyl-1H-pyrrole-3-carboxamide (0.27 g, 86%) was obtained from the compound (0.37 g, 0.64 mmol) of Comparative Example 61 in the process similar to Example 2. MS (ES+) m/z: 486 [M+H]$^+$.

The title compound (60 mg, 44%) was obtained from the above compound (87 mg, 0.18 mmol) in the process similar to Example 51.

Retention time: 6.3 min (Example 53—isomer A), 8.7 min (Example 53—isomer B)
chiral HPLC condition: LC1, eluent: hexane-EtOH-MeOH [70:24:6 (v/v/v), isocratic]
Resolution of the isomer was carried out under the following condition.
chiral HPLC condition: LC3, eluent: hexane-EtOH-MeOH [80:16:4 (v/v/v), isocratic]

Example 53—Isomer A
MS (ES+) m/z: 488 [M+H]$^+$.
Retention time: 6.2 min
chiral HPLC condition: LC1, eluent: hexane-EtOH-MeOH [70:24:6 (v/v/v), isocratic].

Example 53—Isomer B $^1$H-NMR (400 MHz, CD$_3$OD) δ: 7.83-7.89 (4H, m), 7.75-7.79 (1H, m), 7.60-7.66 (1H, m), 7.48-7.52 (1H, m), 6.71 (1H, s), 4.61 (1H, t, J=6.3 Hz), 4.49 (1H, t, J=6.5), 2.47-2.80 (2H, m), 2.22 (3H, s).
HRMS (ESI) calcd for C$_{21}$H$_{19}$F$_5$N$_3$O$_3$S [M+H]$^+$, required m/z: 488.1067, found 488.1084.
Retention time: 8.6 min
chiral HPLC condition: LC1, eluent: hexane-EtOH-MeOH [70:24:6 (v/v/v), isocratic].

Example 54

1-[2-(Difluoromethoxy)-4-fluorophenyl]-5-(2-fluoroethyl)-2-methyl-N-[4-(methylsulfonyl)phenyl]-1H-pyrrole-3-carboxamide

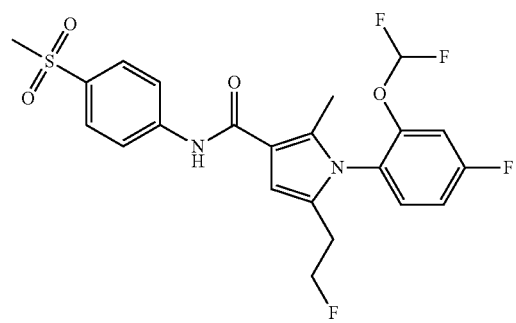 [SMILES: Cc1c(C(=O)Nc2ccc(S(C)(=O)=O)cc2)cc(CCF)n1-c1ccc(F)cc1OC(F)F]

1-[2-(Difluoromethoxy)-4-fluorophenyl]-5-(2-hydroxyethyl)-2-methyl-N-[4-(methylsulfonyl)phenyl]-1H-pyrrole-3-carboxamide (8.9 g, 89%) was obtained from the compound (11 g, 21 mmol) of Comparative Example 68 in the process similar to Example 3. MS (FAB+) m/z: 483 [M+H]$^+$.

The title compound (4.4 g, 49%) was obtained from the above compound (8.9 g, 18 mmol) in the process similar to Example 51.

HRMS (ESI) calcd for C$_{22}$H$_{21}$F$_4$N$_2$O$_4$S [M+H]$^+$, required m/z: 485.1158, found 485.1159.

Retention time: 6.7 min (Example 54—isomer A), 8.1 min (Example 54—isomer B)
chiral HPLC condition: LC1, eluent: hexane-EtOH-MeOH [70:24:6 (v/v/v), isocratic]
Resolution of the isomer was carried out under the following condition.
chiral HPLC condition: LC3, eluent: hexane-EtOH-MeOH [85:12:3 (v/v/v), isocratic]

Example 54—Isomer A $^1$H-NMR (400 MHz, CDCl$_3$) δ: 7.94 (1H, s), 7.83-7.89 (4H, m), 7.26-7.30 (1H, m), 7.16-7.19 (1H, m), 7.06-7.13 (1H, m), 6.44 (1H, s), 6.42 (1H, t, J=72.0 Hz), 4.58 (1H, t, J=6.1 Hz), 4.46 (1H, t, J=6.1 Hz), 3.05 (3H, s), 2.62-2.75 (2H, m), 2.30 (3H, s).
HRMS (ESI) calcd for C$_{22}$H$_{21}$F$_4$N$_2$O$_4$S [M+H]$^+$, required m/z: 485.1158, found 485.1181.
Retention time: 6.6 min
chiral HPLC condition: LC1, eluent: hexane-EtOH-MeOH [70:24:6 (v/v/v), isocratic]
[α]$_D^{22}$: −13.3° (c=1.0, EtOH).

Example 54—Isomer B

¹H-NMR (400 MHz, CDCl₃) δ: 7.91 (2H, d, J=9.0 Hz), 7.83 (2H, d, J=9.0 Hz), 7.73 (1H, s), 7.26-7.30 (1H, m), 7.17-7.20 (1H, m), 7.09-7.13 (1H, m), 6.39 (1H, s), 6.40 (1H, t, J=72.0 Hz), 4.59 (1H, t, J=6.1 Hz), 4.48 (1H, t, J=6.1 Hz), 3.06 (3H, s), 2.63-2.77 (2H, m), 2.31 (3H, s).

HRMS (ESI) calcd for $C_{22}H_{21}F_4N_2O_4S$ $[M+H]^+$, required m/z: 485.1158, found 485.1157.

Retention time: 8.1 min
chiral HPLC condition: LC1, eluent: hexane-EtOH-MeOH [70:24:6 (v/v/v), isocratic]
$[\alpha]_D^{22}$: +12.9° (c=1.0, EtOH).

Example 55

1-[4-Chloro-2-(trifluoromethyl)phenyl]-5-[(2R)-2-fluoropropyl]-2-methyl-N-[4-(methylsulfonyl)phenyl]-1H-pyrrole-3-carboxamide

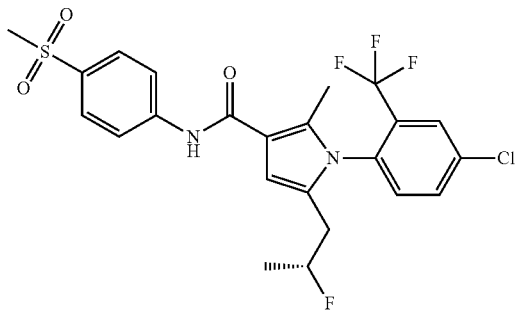 [SMILES: Cc1c(C(=O)Nc2ccc(S(C)(=O)=O)cc2)cc(C[C@@H](C)F)n1-c1ccc(Cl)cc1C(F)(F)F]

The title compound (78 mg, 52%) was obtained from Example 6—isomer A (150 mg, 0.29 mmol) in the process similar to Example 51.

1H-NMR (400 MHz, CDCl₃) δ: 7.91 (2H, d, J=8.6 Hz), 7.86 (1H, d, J=2.2 Hz), 7.83 (2H, d, J=8.6 Hz), 7.77 (1H, s), 7.72 (1H, dd, J=8.4, 2.2 Hz), 7.26 (1H, d, 8.4 Hz), 6.40 (1H, s), 4.64-4.86 (1H, m), 3.05 (3H, s), 2.63-2.77 (1H, m), 2.31-2.45 (1H, m), 2.26 (3H, s), 1.31 (3H, dd, J=23.5, 5.9 Hz).

HRMS (ESI) calcd for $C_{23}H_{22}ClF_4N_2O_3S$ $[M+H]^+$, required m/z: 517.0976, found 517.0993.

Retention time: 5.0 min
chiral HPLC condition: LC1, eluent: hexane-EtOH-MeOH [70:24:6 (v/v/v), isocratic].

Example 56

1-[2-(Difluoromethoxy)-4-fluorophenyl]-5-[(2R)-2-fluoropropyl]-2-methyl[N-[4-(methylsulfonyl)phenyl]-1H-pyrrole-3-carboxamide

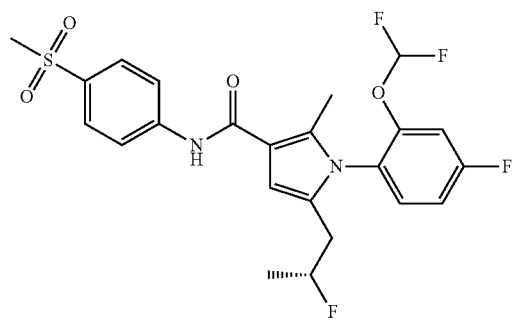 [SMILES: Cc1c(C(=O)Nc2ccc(S(C)(=O)=O)cc2)cc(C[C@@H](C)F)n1-c1ccc(F)cc1OC(F)F]

The title compound (99 mg, 69%) was obtained from Example 9—isomer A (0.14 g, 0.29 mmol) in the process of Example 51.

MS (ES+) m/z: 499 [M+H]⁺.

Retention time: 5.6 min
chiral HPLC condition: LC1, eluent: hexane-EtOH-MeOH [70:24:6 (v/v/v), isocratic].

Example 57

1-[2-(Difluoromethoxy)-4-fluorophenyl]-5-[(2S)-2-fluoropropyl]-2-methyl-N-[4-(methylsulfonyl)phenyl]-1H-pyrrole-3-carboxamide

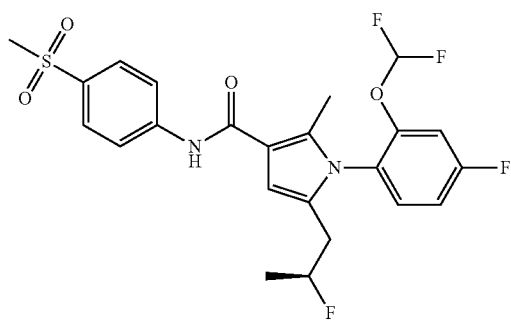 [SMILES: Cc1c(C(=O)Nc2ccc(S(C)(=O)=O)cc2)cc(C[C@H](C)F)n1-c1ccc(F)cc1OC(F)F]

To a solution of Example 9—isomer A (0.33 g, 0.66 mmol) in tetrahydrofuran (10 ml), 4-nitrobenzoic acid (0.17 g, 0.99 mmol) and triphenylphosphine (0.26 g, 0.99 mmol) were added, and the mixture was cooled to 0° C. Thereafter, diisopropyl azodicarboxylate (0.19 mL, 0.99 mmol) was added dropwise, and the mixture was stirred at room temperature for 7 hours. After the reaction mixture was concentrated under reduced pressure, the residue was purified by silica gel column chromatography (hexane-hexane:ethyl acetate=3:1) to give (1R,S)-2-(1-[2-(difluoromethoxy)-4-fluorophenyl]-5-methyl-4-{[4-(methylsulfonyl)phenyl]carbamoyl}-1H-pyrrol-2-yl)-1-methylethyl 4-nitrobenzoate (0.33 g, 78%) as a atropisomeric mixture. MS (ES+) m/z: 646 [M+H]⁺.

The above atropisomeric mixture (0.42 g, 0.65 mmol) was optically resolved under the following condition to give (1R)-2-(1-[2-(difluoromethoxy)-4-fluorophenyl]-5-methyl-4-{[4-(methylsulfonyl)phenyl]carbamoyl}-1H-pyrrol-2-yl)-1-methylethyl 4-nitrobenzoate (0.14 g, 0.22 mmol).

chiral HPLC condition: LC3, eluent: hexane-EtOH-MeOH [80:16:4 (v/v/v), isocratic]
MS (ES+) m/z: 646 [M+H]⁺.
Retention time: 10.0 min
chiral HPLC condition: LC1, eluent: hexane-EtOH-MeOH [75:20:5 (v/v/v), isocratic]

To a solution of the above (1R)-2-(1-[2-(difluoromethoxy)-4-fluorophenyl]-5-methyl-4-{[4-(methylsulfonyl)phenyl]carbamoyl}-1H-pyrrol-2-yl)-1-methylethyl 4-nitrobenzoate (0.14 g, 0.21 mmol) in methanol (3 ml) and dichloromethane (3 ml), a solution of 0.5M sodium methoxide (0.85 ml, 0.42 mmol) in methanol was added dropwise, and the mixture was stirred at room temperature for 2 hours. After the reaction mixture was concentrated under reduced pressure, ethyl acetate and water were added. After the organic layer was washed with a saturated aqueous ammonium chloride solution and saturated brine and it was dried with magnesium sulfate, the solvent was distilled off under reduced pressure. The residue was purified by silica gel column chromatography (hexane:ethyl acetate=3:1-ethyl acetate) to give the title compound (96 mg, 92%) as a solid.

MS (ES+) m/z: 499 [M+H]⁺.

Retention time: 5.7 min chiral HPLC condition: LC1, eluent: hexane-EtOH-MeOH [70:24:6 (v/v/v), isocratic].

Example 58

1-[4-Chloro-2-(difluoromethoxy)phenyl]-5-[(2R)-2-fluoropropyl]-2-methyl-N-[4-(methylsulfonyl)phenyl]-1H-pyrrole-3-carboxamide

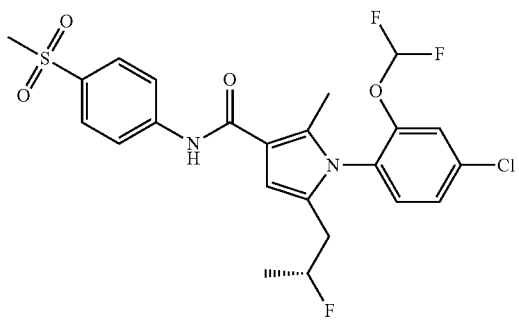 [SMILES: Cc1c(C(=O)Nc2ccc(S(C)(=O)=O)cc2)cc(C[C@@H](C)F)n1-c1ccc(Cl)cc1OC(F)F]

The title compound (62 mg, 62%) was obtained from Example 11—isomer A (95 mg, 0.20 mmol) in the process similar to Example 51.

$^1$H-NMR (500 MHz, CDCl$_3$) δ: 7.89 (2H, d, J=7.8 Hz), 7.84 (1H, s), 7.84 (2H, d, J=7.8 Hz), 7.43 (1H, s), 7.37 (1H, d, J=8.3 Hz), 7.22 (1H, d, J=8.3 Hz), 6.42 (1H, s), 6.39 (1H, t, J=72.0 Hz), 4.63-4.81 (1H, m), 3.05 (3H, s), 2.45-2.74 (2H, m), 2.31 (3H, s), 1.29 (3H, dd, J=24.2, 6.1 Hz).

HRMS (ESI) calcd for C$_{23}$H$_{23}$ClF$_3$N$_2$O$_4$S [M+H]$^+$, required m/z: 515.1019, found 515.1025.

Retention time: 5.8 min chiral HPLC condition: LC1, eluent: hexane-EtOH-MeOH [70:24:6 (v/v/v), isocratic].

Example 59

N-[4-(Aminosulfonyl)phenyl]-1-[4-chloro-2-(trifluoromethyl)phenyl]-5-(2-fluoroethyl)-2-methyl-1H-pyrrole-3-carboxamide

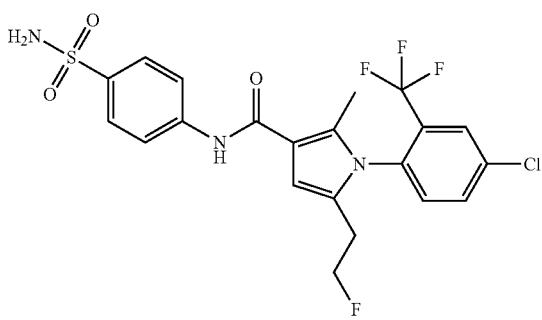 [SMILES: Cc1c(C(=O)Nc2ccc(S(N)(=O)=O)cc2)cc(CCF)n1-c1ccc(Cl)cc1C(F)(F)F]

N-[4-(Aminosulfonyl)phenyl]-1-[4-chloro-2-(trifluoromethyl)phenyl]-5-(2-hydroxyethyl)-2-methyl-1H-pyrrole-3-carboxamide (0.63 g, 86%) was obtained from the compound (0.86 g, 1.5 mmol) of Comparative Example 62 in the process similar to Example 3. MS (ES+) m/z: 502 [M+H]$^+$.

The title compound (0.30 g, 47%) was obtained from the above compound (0.63 g, 1.3 mmol) in the process similar to Example 51.

MS (ES+) m/z: 504 [M+H]$^+$.

Retention time: 6.6 min (Example 59—isomer A), 8.8 min (Example 59—isomer B)

chiral HPLC condition: LC1, eluent: hexane-EtOH-MeOH [70:24:6 (v/v/v), isocratic]

Resolution of the isomer was carried out under the following condition.

chiral HPLC condition: LC3, eluent: hexane-EtOH-MeOH [80:16:4 (v/v/v), isocratic]

Example 59—Isomer A

MS (ES+) m/z: 504 [M+H]$^+$.

Retention time: 6.6 min chiral HPLC condition: LC1, eluent: hexane-EtOH-MeOH [70:24:6 (v/v/v), isocratic].

Example 59—Isomer B

MS (ES+) m/z: 504 [M+H]$^+$.

Retention time: 8.8 min chiral HPLC condition: LC1, eluent: hexane-EtOH-MeOH [70:24:6 (v/v/v), isocratic].

Example 60

1-(2-Chloro-4-fluorophenyl)-5-(2-fluoroethyl)-2-methyl-N-(4-(methylsulfonyl)phenyl)-1H-pyrrole-3-carboxamide

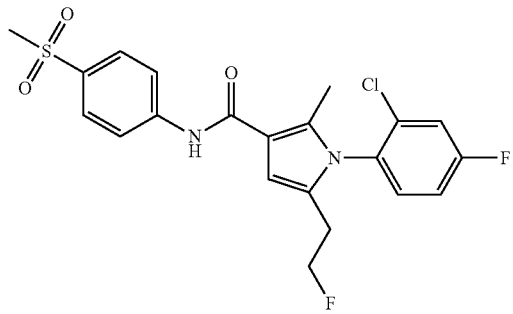 [SMILES: Cc1c(C(=O)Nc2ccc(S(C)(=O)=O)cc2)cc(CCF)n1-c1ccc(F)cc1Cl]

To a solution of the compound (0.90 g, 2.0 mmol) of Example 3 in dichloromethane (20 ml), (diethylamino)sulfur trifluoride (0.32 mL, 2.4 mmol) was added. After the mixture was stirred at room temperature for 20 minutes, the reaction was stopped by a saturated aqueous sodium hydrogencarbonate solution (20 mL), and the mixture was extracted with ethyl acetate. After the organic layer was dried with sodium sulfate, it was filtered and the solvent was distilled off under reduced pressure. The residue was purified by silica gel column chromatography (hexane:ethyl acetate=1:1) to give the title compound (0.36 g, 40%) as a solid.

MS (ESI) m/z: 453 [M+H]$^+$.

Retention time: 10.1 min (Example 60—isomer A), 10.8 min (Example 60—isomer B)

chiral HPLC condition: LC9, eluent: Hex-EtOH [70:30 (v/v), isocratic]

Resolution of the isomer was carried out under the following condition.

chiral HPLC condition: LC10, eluent: Hex-EtOH [70:30 (v/v), isocratic]

Example 60—Isomer A
MS (ESI) m/z: 453 [M+H]+.
Retention time: 10.1 min
chiral HPLC condition: LC9, eluent: Hex-EtOH [70:30 (v/v), isocratic].

Example 60—Isomer B
MS (ESI) m/z: 453 [M+H]+.
Retention time: 10.8 min
chiral HPLC condition: LC9, eluent: Hex-EtOH [70:30 (v/v), isocratic].

Example 61

1-[4-Chloro-2-(trifluoromethyl)phenyl]-5-[2-(dimethylamino)-2-oxoethyl]-2-methyl-N-[4-(methylsulfonyl)phenyl]-1H-pyrrole-3-carboxamide

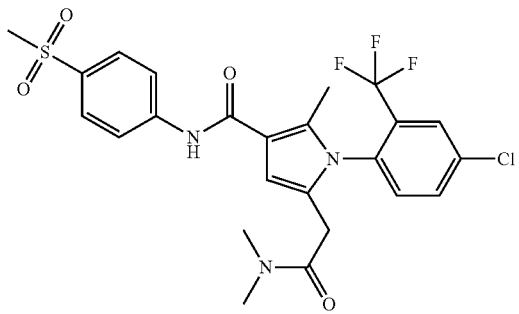 [SMILES: Cc1c(C(=O)Nc2ccc(S(C)(=O)=O)cc2)cc(CC(=O)N(C)C)n1-c1ccc(Cl)cc1C(F)(F)F]

To a solution of the compound (1.0 g, 2.0 mmol) of Example 1 in dichloromethane (10 mL), Dess-Martin reagent (1.3 g, 3.0 mmol) was added at 0° C. The reaction temperature was raised to room temperature, and after the mixture was further stirred for 1 hour, it was diluted with ethyl acetate and the organic layer was washed with an aqueous sodium hydrogencarbonate solution, an aqueous sodium thiosulfate solution, water and saturated brine. After the solution was dried with sodium sulfate, it was filtered and the solvent was distilled off under reduced pressure. The residue was purified by silica gel column chromatography (hexane:ethyl acetate=1:1) to give 1-[4-chloro-2-(trifluoromethyl)phenyl]-2-methyl-N-[4-(methylsulfonyl)phenyl]-5-(2-oxoethyl)-1H-pyrrole-3-carboxamide (0.85 g, 85%).

$^1$H-NMR (400 MHz, CDCl$_3$) δ: 9.57 (1H, t, J=1.6 Hz), 7.91 (2H, d, J=9.0 Hz), 7.86 (1H, d, J=2.7 Hz), 7.83 (2H, d, J=9.0 Hz), 7.79 (1H, s), 7.71 (1H, dd, J=8.6, 2.4 Hz), 7.25 (1H, d, J=8.2 Hz), 6.48 (1H, s), 3.55 (1H, dd, J=18.0, 1.6 Hz), 3.30 (1H, dd, J=18.0, 1.6 Hz), 3.06 (3H, s), 2.28 (3H, s).

MS (ESI) m/z: 499 [M+H+]

To a solution of the above 1-[4-chloro-2-(trifluoromethyl)phenyl]-2-methyl-N-[4-(methylsulfonyl)phenyl]-5-(2-oxoethyl)-1H-pyrrole-3-carboxamide (0.85 g, 1.7 mmol) in tert-butanol (14 mL)-water (3.4 mL), sodium dihydrogenphosphate (0.40 g, 2.6 mmol), 2-methyl-2-butene (0.77 mL, 6.8 mmol) and sodium chlorite (0.85 g, 5.1 mmol) were added, and the mixture was stirred at room temperature for 1 hour. A 10% aqueous sodium hydrogensulfite solution and 1M hydrochloric acid were added to the mixture to stop the reaction, and the mixture was extracted with dichloromethane. The obtained organic layer was washed with saturated brine, and after the solution was dried with sodium sulfate, it was filtered and the solvent was distilled off under reduced pressure. The residue was purified by silica gel column chromatography to give (1-[4-chloro-2-(trifluoromethyl)phenyl]-5-methyl-4-{[4-(methylsulfonyl)phenyl]carbamoyl}-1H-pyrrol-2-yl)acetic acid (0.50 g, 57%).

$^1$H-NMR (400 MHz, CDCl$_3$) δ: 7.93-7.77 (6H, m), 7.69 (1H, dd, J=8.6, 2.4 Hz), 7.31 (1H, d, J=8.2 Hz), 6.52 (1H, s), 3.52 (1H, d, J=17.6 Hz), 3.19 (1H, d, J=17.6 Hz), 3.05 (3H, s), 2.26 (3H, s)

MS (ESI) m/z: 515 [M+H+]

To a solution of the above (1-[4-chloro-2-(trifluoromethyl)phenyl]-5-methyl-4-{[4-(methylsulfonyl)phenyl]carbamoyl}-1H-pyrrol-2-yl)acetic acid (30 mg, 0.518 mmol) in DMF (0.58 mL), 1-hydroxybenzotriazole monohydrate (18 mg, 0.12 mmol) and hydrochloric acid 1-(3-dimethyl-aminopropyl)-3-ethylcarbodiimide (23 mg, 0.12 mmol) were successively added, and the mixture was stirred at room temperature for 1 hour. Thereafter, a 2M dimethylamine/THF solution was added to the mixture, and the mixture was stirred overnight. After the reaction, it was diluted with ethyl acetate, and the organic layer was washed with 1M hydrochloric acid, water and saturated brine. Thereafter, it was dried with sodium sulfate, filtration was carried out, and the solvent was distilled off under reduced pressure. The residue was purified by silica gel column chromatography to give the title compound (17 mg, 54%).

$^1$H-NMR (400 MHz, CDCl$_3$) δ: 7.90 (2H, d, J=9.0 Hz), 7.86 (1H, s), 7.84 (1H, d, J=2.4 Hz), 7.81 (2H, d, J=9.0 Hz), 7.69 (1H, dd, J=8.6, 2.4 Hz), 7.38 (1H, d, J=8.6 Hz), 6.37 (1H, s), 3.52 (1H, d, J=16.4 Hz), 3.14 (1H, d, J=16.4 Hz), 3.05 (3H, s), 2.93 (3H, s), 2.91 (3H, s), 2.26 (3H, s).

HRMS (ESI) calcd for $C_{24}H_{23}ClF_3N_3O_4S$ [M+H]+, required m/z: 542.1128, found 542.1108.

$[α]_D^{22}$: −25.1° (c=1.0, EtOH).

Example 62

1-[4-Fluoro-2-(trifluoromethyl)phenyl]-5-(2-hydroxyethyl)-2-methyl-N-[4-(methylsulfonyl)phenyl]-1H-pyrrole-3-carboxamide 5-[2-(Benzyloxy)ethyl]-1-[4-fluoro-2-(trifluoromethyl)phenyl]-2-methyl-1H-pyrrole-3-carboxylic acid ethyl ester

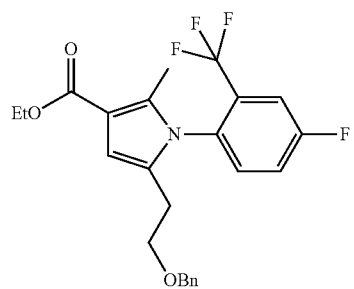 [SMILES: CCOC(=O)c1cc(CCOCc2ccccc2)n(-c2ccc(F)cc2C(F)(F)F)c1C]

A solution of Comparative compound 5 (300 mg, 0.98 mmol) in AcOH (1 mL), 2-amino-5-fluorobenzotrifluoride (179 mg, 0.98 mmol) was added and stirred at 100° C. for 8 hr. The reaction mixture was extracted with AcOEt, the combined organic layers were washed with saturated aq NaHCO$_3$ and brine, dried (Na$_2$SO$_4$), concentrated. The residue was purified over silica gel (AcOEt/n-hexane, 3:7 v/v) to give the atropisomeric mixture of the title compound (332 mg, 75%) as an oil.

$^1$H-NMR (400 MHz, CDCl$_3$) δ: 7.53 (1H, dd, J=8.2, 3.1 Hz), 7.35-7.25 (6H, m), 7.17 (1H, dd, J=8.6, 5.1 Hz), 6.44

(1H, s), 4.45 (2H, s), 4.28 (2H, q, J=7.0 Hz), 3.59 (2H, t, J=7.0 Hz), 2.62-2.55 (1H, m), 2.41-2.34 (1H, m), 2.17 (3H, s), 1.36 (3H, t, J=7.0 Hz).

5-[2-(Benzyloxy)ethyl]-1-[4-fluoro-2-(trifluoromethyl)phenyl]-2-methyl-N-[4-(methylsulfonyl)phenyl]-1H-pyrrole-3-carboxamide

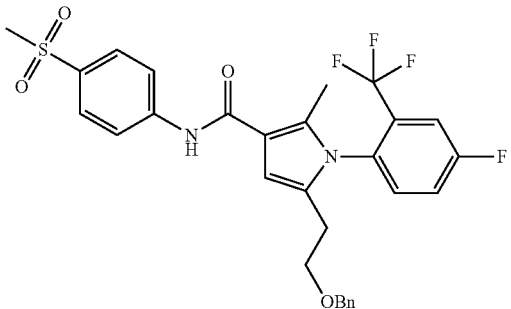 [SMILES: Cc1c(C(=O)Nc2ccc(S(C)(=O)=O)cc2)cc(CCOCc2ccccc2)n1-c1ccc(F)cc1C(F)(F)F]

To a suspension of 5-[2-(benzyloxy)ethyl]-1-[4-fluoro-2-(trifluoromethyl)phenyl]-2-methyl-1H-pyrrole-3-carboxylic acid ethyl ester (332 mg, 0.74 mmol) and 4-(methylsulfonyl)aniline (133 mg, 0.78 mmol) in toluene (3 mL), Me₃Al (0.41 mL, 0.74 mmol, 1.8 M solution in toluene) was added under N₂ atmosphere at room temperature and stirred at 110° C. for 30 min. After the completion of the reaction, it was quenched with 1N HCl, and extracted with AcOEt. The combined organic layers were washed with brine, dried (Na₂SO₄), and concentrated, and the residue was purified over silica gel (AcOEt/n-hexane, 2:3 v/v) to give the atropisomeric mixture of the title compound (220 mg, 52%) as an oil.

¹H-NMR (400 MHz, CDCl₃) δ: 7.92 (2H, d, J=8.8 Hz), 7.82 (2H, d, J=8.8 Hz), 7.66 (1H, s), 7.56 (1H, dd, J=8.1, 2.7 Hz), 7.37-7.26 (6H, m), 7.19 (1H, dd, J=8.8, 4.9 Hz), 6.27 (1H, s), 4.49 (2H, s), 3.63-3.59 (2H, m), 3.06 (3H, s), 2.66-2.60 (1H, m), 2.46-2.40 (1H, m), 2.25 (3H, s).

1-[4-Fluoro-2-(trifluoromethyl)phenyl]-5-(2-hydroxyethyl)-2-methyl-N-[4-(methylsulfonyl)phenyl]-1H-pyrrole-3-carboxamide

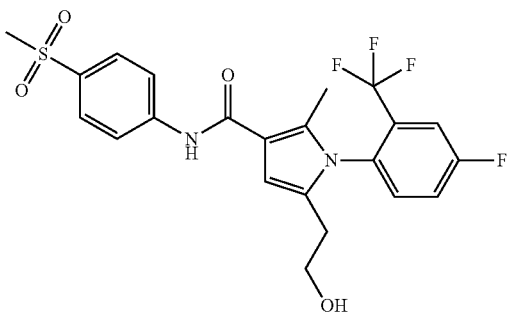 [SMILES: Cc1c(C(=O)Nc2ccc(S(C)(=O)=O)cc2)cc(CCO)n1-c1ccc(F)cc1C(F)(F)F]

To a solution of 5-[2-(benzyloxy)ethyl]-1-[4-fluoro-2-(trifluoromethyl)phenyl]-2-methyl-N-[4-(methylsulfonyl)phenyl]-1H-pyrrole-3-carboxamide (220 mg, 0.38 mmol) in MeOH (3 mL), Pd(OH)₂—C (20 mg) was added and stirred overnight under H₂ atmosphere at room temperature. After the reaction, Pd(OH)₂—C was filtered off and the solvent was evaporated. The residue was purified over silica gel (AcOEt/n-hexane, 9:1 v/v) to give the atropisomeric mixture of the title compound (170 mg, 92%) as a foam.

¹H-NMR (400 MHz, CDCl₃) δ: 7.91 (2H, d, J=8.8 Hz), 7.83 (2H, d, J=8.8 Hz), 7.73 (1H, s), 7.59 (1H, dd, J=8.2, 3.1 Hz), 7.47-7.42 (1H, m), 7.33 (1H, dd, J=8.8, 4.9 Hz), 6.37 (1H, s), 3.82-3.72 (2H, m), 3.06 (3H, s), 2.63-2.56 (1H, m), 2.45-2.39 (1H, m), 2.27 (3H, s), 1.52 (1H, t, J=5.9 Hz).

Retention time: 4.9 min (Example 62—isomer A), 5.7 min (Example 62—isomer B).

chiral HPLC condition: LC2, eluent: EtOH (isocratic)

In the following Test Examples, 1-[2-(trifluoromethyl)phenyl]-2,5-dimethyl-N-[4-(methylsulfonyl)phenyl]-1H-pyrrole-3-carboxamide (Comparative compound A) and 1-[4-fluoro-2-(trifluoromethyl)phenyl]-2,5-dimethyl-N-[4-(methylsulfonyl)phenyl]-1H-pyrrole-3-carboxamide (Comparative compound B) were selected from the compounds described in the prior art (WO 2006/012642) as the most suitable Comparative compounds, and were used.

Comparative compound A

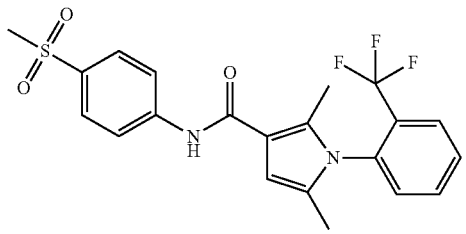

Comparative compound B

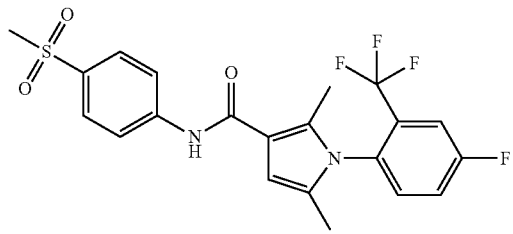

Test Example 1

A plasmid pM-hMR-LBD expressing GAL4-hMR receptor, which has a ligand binding domain (LBD, corresponding to approximately 308 amino acids at the carboxy terminus) of human mineralocorticoid receptor (hMR, NM_000901) bonded to a DNA binding domain of yeast transcription factor GAL4 (corresponding to 147 amino acids at the amino terminus), was prepared. Reporter assay was conducted by using a reporter plasmid (such as plasmid pFR-Luc of STRATAGENE CLONING SYSTEMS) including a luciferase gene, having a sequence (UAS sequence) which binds to the DNA binding domain of GAL4.

The plasmid pM-hMR-LBD and the reporter plasmid as obtained above were gene transferred into renal cell line HEK293 of human fetus by lipofection. On the next day, cells were collected by trypsin treatment, and dispensed with DMEM culture medium containing 5% of FBS treated by activated charcoal, to a white 96-well plate (Costar) with the amount of 95 microliter per well.

The test compounds were used as dissolved in dimethyl sulfoxide at a predetermined concentration, and the test compounds suitably diluted with culture media were added to the cells on the white 96-well plate so that the final concentration becomes 0.1%. When adding the test compounds, they were accompanied with 1 nM aldosterone. The well group of Control group 1 was added with dimethyl sulfoxide, and the well group of Control group 2 was added with 1 nM aldosterone. After the addition, cultivation was carried out overnight.

On the next day, the culture media was removed, and then luciferase substrate (Wako Pure Chemical Industries, Ltd.) was prepared in accordance with the attached document and were added to each well by 50 microliters. Stirring was conducted for approximately 30 minutes, and the amount of luminescence was measured for each well by using Analyst (Molecular Devices), to obtain luciferase activity. A graph which plots relative luciferase activity values, when the luciferase activity value of Control group 1 was taken as 0% and the luciferase activity value of Control group 2 was taken as 100%, for each of the amount of the test compound addition group was made. From the graph, concentration of the test compound which shows the maximum value was calculated as Imax (%), and the concentration which shows Imax/2 was calculated as $ICmax_{50}$ (nM). $ICmax_{50}$ values are shown in Table 15.

(Results)

As shown in the following (Table 15), the atropisomers of the present invention showed significant mineralocorticoid receptor antagonistic action when compared with the corresponding racemic compound.

TABLE 15

| Test Compound | $ICmax_{50}$ (nM) | Imax (%) |
|---|---|---|
| R Reference compound A | 14 | 114 |
| R Reference compound B | 12 | 93 |
| Example 1 | 11 | 110 |
| Example 1 - isomer A | 3.7 | 87 |
| Example 1 - isomer B | >1000 | N.D.[1] |
| Example 3 | 30 | 109 |
| Example 3 - isomer A | 21 | 114 |
| Example 3 - isomer B | >1000 | N.D.[1] |
| Example 5 | 3.9 | 125 |
| Example 5 - isomer A | 3.4 | 119 |
| Example 5 - isomer B | >1000 | N.D.[1] |
| Example 6 | 6.2 | 92 |
| Example 6 - isomer A | 3.1 | 79 |
| Example 6 - isomer B | >1000 | N.D.[1] |
| Example 9 | 41 | 114 |
| Example 9 - isomer A | 18 | 84 |
| Example 9 - isomer B | >1000 | N.D.[11] |
| Example 11 | 13 | 107 |
| Example 11 - isomer A | 7.3 | 89 |
| Example 11 - isomer B | >1000 | N.D.[1] |
| Example 12 | 6.8 | 108 |
| Example 12 - isomer A | 3.1 | 113 |
| Example 12 - isomer B | >1000 | N.D.[1] |
| Example 16 | 7.8 | 94 |
| Example 16 - isomer A | 3.6 | 101 |
| Example 16 - isomer B | >1000 | N.D.[1] |
| Example 22 | 9.1 | 111 |
| Example 22 - isomer A | 6.1 | 99 |
| Example 22 - isomer B | >1000 | N.D.[1] |
| Example 40 | 26 | 112 |
| Example 40 - isomer A | 9.6 | 91 |
| Example 40 - isomer B | >1000 | N.D.[1] |
| Example 42 | 4.8 | 110 |
| Example 42 - isomer A | >1000 | N.D.[1] |
| Example 42 - isomer B | 2.7 | 95 |
| Example 43 | 40 | 100 |
| Example 43 - isomer A | 5.5 | 123 |
| Example 43 - isomer B | >1000 | N.D.[1] |
| Example 44 | 24 | 111 |
| Example 44 - isomer A | >1000 | N.D.[1] |
| Example 44 - isomer B | 12 | 98 |
| Example 45 | 7.1 | 85 |
| Example 45 - isomer A | 1.9 | 105 |
| Example 45 - isomer B | >1000 | N.D.[1] |
| Example 49 | 8.3 | 96 |
| Example 49 - isomer A | >1000 | N.D.[1] |
| Example 49 - isomer B | 4.5 | 104 |
| Example 50 | 2.7 | 114 |
| Example 50 - isomer A | >1000 | N.D.[1] |
| Example 50 - isomer B | 1.2 | 104 |
| Example 51 | 19 | 115 |
| Example 51 - isomer A | 11 | 124 |
| Example 51 - isomer B | >1000 | N.D.[1] |
| Example 54 | 14 | 75 |
| Example 54 - isomer A | 6.5 | 99 |
| Example 54 - isomer B | >1000 | N.D.[1] |
| Example 61 | 5.5 | 115 |

[1]Not determined

Test Example 2

Cynomolgus monkey (male) was used, and it was fasted from the day before administration of the test compound.

Administration samples were prepared by adding a 0.5% MC (methyl cellulose) solution to the Test Compound, so that the dose becomes 3 mg/2 mL/kg. Each of the administration samples was administered intragastrically to the cynomolgus monkey by using a tube. After the samples were administered, approximately 5 mL of 0.5% MC was administered. For each of the administration samples, a group of two cynomolgus monkeys was administered.

With respect to collection of blood, it was conducted by collecting approximately 0.5 mL of blood from crotch vein using a glass syringe treated with heparin, before administration, and 30 minutes, 1, 2, 4, 6, 8, 24 and 48 hours after administration. Blood was centrifuged (1,700×g, 15 min, 4° C.) to obtain plasma. Plasma was stored in a freezer (−20° C.) until pretreatment.

Preparation of standard solution and internal standard (IS) solution: Each of the Test Compounds was dissolved in DMSO (dimethyl sulfoxide) to prepare a solution of 10 mM each. Each of the compound solution was diluted with acetonitrile, and thus standard solution was prepared. Further, niflumic acid (Wako Pure Chemical Industries, Ltd.) was dissolved in DMSO at the concentration of 2 mM, followed by dilution with acetonitrile to prepare an IS solution of 2 μM.

Pretreatment of plasma samples: 20 μL of plasma sample was collected, and then 25 μL of purified water, 100 μL of acetonitrile, and 100 μL of methanol was added. For the preparation of a calibration curve, 25 μL of purified water, 20 μL of each of the standard solutions (acetonitrile solution), 80 μL of acetonitrile, and 100 μL of methanol were added to 20 μL of blank plasma. 40 μL of the acetonitrile solution of IS was added to all of the samples, and then the samples were stirred, filtered by suction using Captiva filter plate (Varian, Inc.), and then the filtrate was used as the sample for LC-MS/MS analysis.

Quantitative Determination of Test Compound: Concentration in plasma was analyzed by LC-MS/MS method for each Test Compound.

[HPLC Analysis Conditions]

HPLC: WATERS 2795 (Waters Corporation);

Column: CAPCELL PAK C8, 2.0 mm I.D.×50 mm, 5 μm (Shiseido Co., Ltd.)

Mobile Phase: A=5 mM ammonium acetate aqueous solution, B=acetonitrile

[MS/MS Analysis Conditions]

MS: Quattro micro API (Waters Corporation)

Ionization Method: Electrospray Ionization (ESI)

Ionization Mode: Positive

Detection Mode: MRM

Analysis: Pharmacokinetic parameter was calculated from concentration of each of the drugs in plasma, by using Win-Nonlin Professional (Ver. 4.0.1, Pharsight Corporation). Here, Noncompartment model was used as the model for parameter calculation.

(Results)

As a result of evaluating Reference compound A and Reference compound B, and the Example compounds listed below, the atropisomer mentioned in Test Example 1 having high activity showed considerably improved concentration in plasma when compared with the Reference drug, as shown in (Table 16). In addition, the compound of Example 62 having 2-hydroxyethyl group as $R^2$, showed considerably improved concentration in plasma, when compared with Reference compound A and Reference compound B which have a methyl group as $R^2$.

TABLE 16

| Test Compound | AUC[1] (μg · h/mL) | Cmax[2] (μg/mL) |
| --- | --- | --- |
| Reference compound A | 0.03 | <0.01 |
| Reference compound B | 0.17 | 0.01 |
| Example 1 - isomer A | 14.11 | 0.99 |
| Example 5 - isomer A | 31.31 | 1.60 |
| Example 6 - isomer A | 30.28 | 1.73 |
| Example 9 - isomer A | 23.95 | 2.35 |
| Example 11 - isomer A | 24.81 | 1.60 |
| Example 16 - isomer A | 13.49 | 1.00 |
| Example 40 - isomer A | 15.11 | 1.30 |
| Example 42 - isomer B | 23.86 | 1.66 |
| Example 43 - isomer A | 14.82 | 1.14 |
| Example 44 - isomer B | 16.92 | 0.94 |
| Example 51 - isomer A | 10.94 | 0.83 |
| Example 54 - isomer A | 11.41 | 0.97 |
| Example 62 | 8.06 | 0.66 |

[1]AUC(ng · h/mL): Area under the plasma concentration (measured by LC-MS/MS method) versus time curve;
[2]Cmax(ng/mL): Maximum concentration

INDUSTRIAL APPLICABILITY

Since the atropisomers of a compound represented by the general formula (I) of the present invention shows pharmacological activities such as particularly good mineralocorticoid receptor antagonistic activity, antihypertensive action, vasodilation action, cardioprotective action, nephropathy inhibitory action, antiarteriosclerotic action and diuretic action, and is high in safety, it is useful as a preventive drug or a therapeutic drug for hypertension, angina cordis, acute coronary syndrome, congestive heart failure, nephropathy, including diabetic nephropathy, arteriosclerosis, cerebral infarction, fibrosis and primary aldosteronism.

We claim:

1. A mineralocorticoid receptor antagonist of general formula (I):

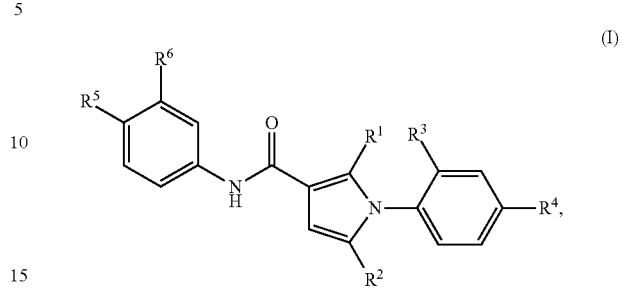

an N-oxide thereof; a diastereomer, racemate, or compound enriched in a diastereomer thereof; an atropisomer, equal mixture of atropisomers, or compound enriched in an atropisomer thereof; or a pharmaceutically acceptable salt of any of the foregoing, wherein, $R^1$ represents a C1-C3 alkyl group;

$R^2$ represents a hydroxy-C1-C4 alkyl group, a fluoro-C1-C4 alkyl group, a carbamoyl-C1-C2 alkyl group, a N-mono(C1-C3 alkyl)carbamoyl-C1-C2 alkyl group or a N,N-di(C1-C3 alkyl)carbamoyl-C1-C2 alkyl group;

$R^3$ represents a halogeno group, a C1-C3 alkyl group, a C1-C3 alkoxy group, a halogeno-C1-C3 alkyl group, a halogeno-C1-C3 alkoxy group, a 4-halogenophenyl group or a 4-halogenophenoxy group;

$R^4$ represents a hydrogen atom, a halogeno group or a C1-C3 alkyl group;

$R^5$ represents a sulfamoyl group or a C1-C3 alkylsulfonyl group; and $R^6$ represents a hydrogen atom, a halogeno group, a C1-C3 alkyl group or a C1-C3 alkoxy group.

2. The compound according to claim 1, wherein $R^1$ is a methyl group or an ethyl group.

3. The compound according to claim 1, wherein $R^1$ is a methyl group.

4. The compound according to claim 1, wherein $R^2$ is a 2-hydroxyethyl group, a 2-hydroxypropyl group, a 2-fluoropropyl group or a 2-fluoroethyl group.

5. The compound according to claim 1, wherein $R^2$ is a 2-hydroxypropyl group.

6. The compound according to claim 1, wherein $R^3$ is a methyl group, a chlorine atom, a halogenomethyl group or a halogenomethoxy group.

7. The compound according to claim 1, wherein $R^3$ is a methyl group, a chlorine atom, a difluoromethyl group, a trifluoromethyl group, a difluoromethoxy group or a trifluoromethoxy group.

8. The compound according to claim 1, wherein $R^3$ is a trifluoromethyl group, a difluoromethoxy group or a trifluoromethoxy group.

9. The compound according to claim 1, wherein $R^4$ is a halogeno group.

10. The compound according to claim 1, wherein $R^4$ is a fluorine atom.

11. The compound according to claim 1, wherein $R^5$ is a sulfamoyl group or a methylsulfonyl group.

12. The compound according to claim 1, wherein $R^5$ is methylsulfonyl group.

13. The compound according to claim 1, wherein $R^6$ is a hydrogen atom, a chlorine atom or a methyl group.

14. The compound according to claim 1, wherein $R^6$ is a hydrogen atom.

15. A compound that is:
1-[4-chloro-2-(trifluoromethyl)phenyl]-5-(2-hydroxyethyl)-2-methyl-N-[4-(methylsulfonyl)phenyl]-1H-pyrrole-3-carboxamide;
1-[4-fluoro-2-(trifluoromethyl)phenyl]-5-[(2S)-2-hydroxypropyl]-2-methyl-N-[4-(methylsulfonyl)phenyl]-1H-pyrrole-3-carboxamide;
1-[4-chloro-2-(trifluoromethyl)phenyl]-5-[(2S)-2-hydroxypropyl]-2-methyl-N-[4-(methylsulfonyl)phenyl]-1H-pyrrole-3-carboxamide;
1-(4-fluoro-2-methylphenyl)-5-[(2S)-2-hydroxypropyl]-2-methyl-N-[4-(methylsulfonyl)phenyl]-1H-pyrrole-3-carboxamide;
1-[2-(difluoromethoxy)-4-fluorophenyl]-5-[(2S)-2-hydroxypropyl]-2-methyl-N-[4-(methylsulfonyl)phenyl]-1H-pyrrole-3-carboxamide;
N-[4-(aminosulfonyl)-3-methylphenyl]-1-[4-fluoro-2-(trifluoromethyl)phenyl]-5-[(2S)-2-hydroxypropyl]-2-methyl-1H-pyrrole-3-carboxamide;
1-[4-chloro-2-(difluoromethoxy)phenyl]-5-[(2S)-2-hydroxypropyl]-2-methyl-N-[4-(methylsulfonyl)phenyl]-1H-pyrrole-3-carboxamide;
N-[4-(aminosulfonyl)-3-chlorophenyl]-1-[4-fluoro-2-(trifluoromethyl)phenyl]-5-[(2S)-2-hydroxypropyl]-2-methyl-1H-pyrrole-3-carboxamide;
1-[4-fluoro-2-(trifluoromethoxy)phenyl]-5-[(2S)-2-hydroxypropyl]-2-methyl-N-[4-(methylsulfonyl)phenyl]-1H-pyrrole-3-carboxamide;
1-[2-(difluoromethoxy)-4-fluorophenyl]-5-[(2S)-2-hydroxypropyl]-2-methyl-N-[3-methyl-4-(methylsulfonyl)phenyl]-1H-pyrrole-3-carboxamide;
1-[2-(difluoromethyl)-4-fluorophenyl]-5-[(2S)-2-hydroxypropyl]-2-methyl-N-[4-(methylsulfonyl)phenyl]-1H-pyrrole-3-carboxamide;
1-(4-fluoro-2-methylphenyl)-5-[(2S)-2-hydroxypropyl]-2-methyl-N-[3-methyl-4-(methylsulfonyl)phenyl]-1H-pyrrole-3-carboxamide;
1-[2-(difluoromethoxy)-4-fluorophenyl]-2-ethyl-5-[(2S)-2-hydroxypropyl]-N-[4-(methylsulfonyl)phenyl]-1H-pyrrole-3-carboxamide;
1-(2-chloro-4-fluorophenyl)-5-[(2S)-2-hydroxypropyl]-2-methyl-N-[4-(methylsulfonyl)phenyl]-1H-pyrrole-3-carboxamide;
1-(4-chloro-2-methylphenyl)-5-[(2S)-2-hydroxypropyl]-2-methyl-N-[4-(methylsulfonyl)phenyl]-1H-pyrrole-3-carboxamide;
1-[4-chloro-2-(trifluoromethoxy)phenyl]-5-[(2S)-2-hydroxypropyl]-2-methyl-N-[4-(methylsulfonyl)phenyl]-1H-pyrrole-3-carboxamide;
1-(2,4-dichlorophenyl)-5-[(2S)-2-hydroxypropyl]-2-methyl-N-[4-(methylsulfonyl)phenyl]-1H-pyrrole-3-carboxamide;
1-(2-chloro-4-fluorophenyl)-2-ethyl-5-[(2S)-2-hydroxypropyl]-N-[4-(methylsulfonyl)phenyl]-1H-pyrrole-3-carboxamide;
1-(2,4-dichlorophenyl)-2-ethyl-5-[(2S)-2-hydroxypropyl]-N-[4-(methylsulfonyl)phenyl]-1H-pyrrole-3-carboxamide;
1-(4-chloro-2-methylphenyl)-5-(2-fluoroethyl)-2-methyl-N-[4-(methylsulfonyl)phenyl]-1H-pyrrole-3-carboxamide;
5-(2-fluoroethyl)-1-(4-fluoro-2-methylphenyl)-2-methyl-N-[4-(methylsulfonyl)phenyl]-1H-pyrrole-3-carboxamide;
1-[2-(difluoromethoxy)-4-fluorophenyl]-5-(2-fluoroethyl)-2-methyl-N-[4-(methylsulfonyl)phenyl]-1H-pyrrole-3-carboxamide;
1-[4-chloro-2-(trifluoromethyl)phenyl]-5-[(2R)-2-fluoropropyl]-2-methyl-N-[4-(methylsulfonyl)phenyl]-1H-pyrrole-3-carboxamide;
1-[4-chloro-2-(difluoromethoxy)phenyl]-5-[(2R)-2-fluoropropyl]-2-methyl-N-[4-(methylsulfonyl)phenyl]-1H-pyrrole-3-carboxamide;
and 1-[4-chloro-2-(trifluoromethyl)phenyl]-5-[2-(dimethylamino)-2-oxoethyl]-2-methyl-N-[4-(methylsulfonyl)phenyl]-1H-pyrrole-3-carboxamide;
or an N-oxide; a diastereomer, racemate, or compound enriched in a diastereomer; an atropisomer, equal mixtures of atropisomers, or compound enriched in an atropisomer thereof; or pharmaceutically acceptable salt of one of the foregoing.

16. A compound that is:
1-[4-fluoro-2-(trifluoromethyl)phenyl]-5-[(2S)-2-hydroxypropyl]-2-methyl-N-[4-(methylsulfonyl)phenyl]-1H-pyrrole-3-carboxamide;
1-[4-chloro-2-(trifluoromethyl)phenyl]-5-[(2S)-2-hydroxypropyl]-2-methyl-N-[4-(methylsulfonyl)phenyl]-1H-pyrrole-3-carboxamide;
1-[2-(difluoromethoxy)-4-fluorophenyl]-5-[(2S)-2-hydroxypropyl]-2-methyl-N-[4-(methylsulfonyl)phenyl]-1H-pyrrole-3-carboxamide;
1-[4-chloro-2-(difluoromethoxy)phenyl]-5-[(2S)-2-hydroxypropyl]-2-methyl-N-[4-(methylsulfonyl)phenyl]-1H-pyrrole-3-carboxamide;
1-[4-fluoro-2-(trifluoromethoxy)phenyl]-5-[(2S)-2-hydroxypropyl]-2-methyl-N-[4-(methylsulfonyl)phenyl]-1H-pyrrole-3-carboxamide;
1-[2-(difluoromethyl)-4-fluorophenyl]-5-[(2S)-2-hydroxypropyl]-2-methyl-N-[4-(methylsulfonyl)phenyl]-1H-pyrrole-3-carboxamide;
1-(2-chloro-4-fluorophenyl)-5-[(2S)-2-hydroxypropyl]-2-methyl-N-[4-(methylsulfonyl)phenyl]-1H-pyrrole-3-carboxamide;
1-[4-chloro-2-(trifluoromethoxy)phenyl]-5-[(2S)-2-hydroxypropyl]-2-methyl-N-[4-(methylsulfonyl)phenyl]-1H-pyrrole-3-carboxamide;
and 1-(2,4-dichlorophenyl)-5-[(2S)-2-hydroxypropyl]-2-methyl-N-[4-(methylsulfonyl)phenyl]-1H-pyrrole-3-carboxamide;
or an N-oxide, a diastereomer, racemate, or compound enriched in a diastereomer; an atropisomer, equal mixtures of atropisomers, or compound enriched in an atropisomer thereof; or pharmaceutically acceptable salt of one of the foregoing.

17. An atropisomer of the compound according to claim 1 that shows stronger mineralocorticoid receptor antagonist activity compared to the other atropisomer(s) of the compound.

18. A pharmaceutical composition comprising the compound according to claim 1 and a pharmacologically acceptable carrier, diluent, or excipient.

19. A method of inhibiting mineralocorticoid receptor activity, the method comprising contacting the mineralocorticoid receptor with an effective inhibiting amount of a compound of claim 1 optionally together with a pharmacologically acceptable carrier, diluent, or excipient.

20. The method according to claim 19 wherein the receptor is in a cell.

21. The method according to claim 20 wherein the cell is within an animal body.

22. The method according to claim 21 wherein the animal is a human.

23. A method of treating a mineralocorticoid receptor-mediated condition or disease in an animal, the method comprising administering to the animal an effective amount of a compound of claim 1 optionally together with a pharmacologically acceptable carrier, diluent, or excipient.

24. The method according to claim 23 wherein the condition or disease is hypertension, angina pectoris, acute coronary syndrome, congestive heart failure, nephropathy, diabetic nephropathy, arteriosclerosis, cerebral infarction, fibrosis, primary aldosteronism or edema.

25. The method according to claim 24 wherein the animal is a human.

26. A method of treating diabetic nephropathy in an animal, the method comprising administering to the animal an effective amount of a compound of claim 1 optionally together with a pharmacologically acceptable carrier, diluent, or excipient.

27. The method according to claim 26 wherein the animal is a human.

* * * * *